US007348359B2

(12) United States Patent
Gardinier et al.

(10) Patent No.: US 7,348,359 B2
(45) Date of Patent: Mar. 25, 2008

(54) RETINOID X RECEPTOR MODULATORS

(75) Inventors: Kevin M. Gardinier, Indianapolis, IN (US); Douglas L. Gernert, Indianapolis, IN (US); Timothy A. Grese, Indianapolis, IN (US); David A. Neel, Zionsville, IN (US); Christopher M. Mapes, San Diego, CA (US); Pierre-Yves Michellys, San Diego, CA (US); Marcus F. Boehm, San Diego, CA (US)

(73) Assignees: Eli Lilly and Company, Indianapolis, IN (US); Ligand Pharmaceuticals, San Diego, CA (US)

( * ) Notice: Subject to any disclaimer, the term of this patent is extended or adjusted under 35 U.S.C. 154(b) by 353 days.

(21) Appl. No.: 10/471,330

(22) PCT Filed: Mar. 14, 2002

(86) PCT No.: PCT/US02/08292

§ 371 (c)(1), (2), (4) Date: Jan. 16, 2004

(87) PCT Pub. No.: WO02/071827

PCT Pub. Date: Sep. 19, 2002

(65) Prior Publication Data

US 2004/0167160 A1    Aug. 26, 2004

Related U.S. Application Data

(60) Provisional application No. 60/275,885, filed on Mar. 14, 2001.

(51) Int. Cl.
  *A61K 31/43*    (2006.01)
  *C07D 307/80*   (2006.01)
  *C07D 307/81*   (2006.01)
(52) U.S. Cl. ........................ 514/469; 549/471
(58) Field of Classification Search ................ 549/471; 514/469
  See application file for complete search history.

(56) References Cited

U.S. PATENT DOCUMENTS 5,801,253 A    9/1998 Klaus et al.

FOREIGN PATENT DOCUMENTS

| EP | 0 909 560 A2 | 4/1999 |
| WO | WO 94/15902 | 7/1994 |
| WO | WO 01/19770 A2 | 3/2001 |

OTHER PUBLICATIONS

Scammells et al, Bioorganic & Medicinal Chemistry vol. 6 p. 1517-1524 (1998).*
Registry No. 37894-25-0, Chem. Abstr. 89:215143 (1978).*

Giguere, Vincent, et al., "Identification of a Receptor for the Morphogen Retinoic Acid," *Nature*, 330: 624-629 (1987).
Petkovich, Martin, et al., "A Human Retinoic Acid Receptor Which Belongs to the Family of Nuclear Receptors," *Nature*, 330: 444-450 (1987).
Evans, Ronald M., "The Steroid and Thyroid Hormone Receptor Superfamily," *Science*, 240: 889-895 (1988).
Heyman, Richard A., et al., "9-Cis Retionic Acid Is a High Affinity Ligand for the Retinoid X Receptor," *Cell*, 68: 397-406 (1992).
Levin, Arthur A., et al., "9-Cis Retinoic Acid Stereoisomer Binds and Activates the Nuclear Receptor RXRα," *Nature*, 355: 359-361 (1992).
Mangelsdorf, David J., et al., "The Retinoid Receptors." In *The Retinoids: Biology, Chemistry and Medicine*, Michael B. Sporn, et al., eds. (NY: Raven Press), pp. 319-349 (1994).
Mangelsdorf, David J., et al., "A Direct Repeat in the Cellular Retinol-Binding Protein Type II Gene Confers Differential Regulation by RXR and RAR," *Cell*, 66: 555-561 (1991).
Mukherjee, R., et al., "Human and Rat Peroxisome Proliferator Activated Receptors (PPARs) Demonstrate Similar Tissue Distribution but Different Responsiveness to PPAR Activators," *J. Steroid Biochem. Molec. Biol.*, 51(3/4): 157-166 (1994).
Jow, Lily and Mukherjee, Ranjan, "The Human Peroxisome Proliferator-Activated Receptor (PPAR) Subtype NUC1 Repress the Activation of hPPARα and Thyroid Hormone Recptors," *J. Biol. Chem.*, 270(7): 3836-3840 (1995).
Sherman, Steven, I., et al., "Central Hypothyroidism Associated with Retinoid X Receptor-Selective Ligands," *N. Engl. J. Med.* 340(14): 1075-1079 (1999).
Tzukerman, Maty T., et al., "Human Estrogen Receptor Transactivational Capacity is Determined by Both Cellular and Promotor Context and Mediated by Two Functionally Distinct Intramolecular Regions," *Mol. Endo.*, 8: 21-30 (1994).
McDonnell, Donald P., et al., "Analysis of Estrogen Receptor Function in Vitro Reveals Three Distinct Classes of Antiestrogens," *Mol. Endo.*, 9: 659-669 (1995).
Casis, Raul, et al., "Synthesis of 4(1H)-Quinolones by Thermolysis of Aryl-Aminomethylene Meldrum's Acid Derivatives," *Synthetic Communications*, 15(2): 125-133 (1985).
Kitamura, Masato, et al., "Asymmetric Synthesis of α-Amino β-Hydroxy Phosphonic Acids Via Binap-Ruthenium Catalyzed Hydrogenation," *Tet. Lett.*, 36(32): 5769-5772 (1995).

* cited by examiner

*Primary Examiner*—Bernard Dentz
(74) *Attorney, Agent, or Firm*—Hamilton, Brook, Smith & Reynolds, P.C.

(57) ABSTRACT

The present invention is directed to compounds represented by Structural Formula (I) and pharmaceutically acceptable salts, solvates and hydrates thereof: (I). The invention is also directed to pharmaceutical compositions, methods of use and methods of making compounds represented by Structural Formula (I) and pharmaceutically acceptable salts, solvates and hydrates thereof.

37 Claims, No Drawings

RETINOID X RECEPTOR MODULATORS

RELATED APPLICATIONS

This application claims the benefit of U.S. 60/275,885 filed 14 Mar. 2001 the entire contents of which are incorporated herein by reference.

BACKGROUND OF THE INVENTION

The vitamin A metabolite, retinoic acid, has long been recognized to induce a broad spectrum of biological effects. For example, retinoic acid-containing products, such as Retin-A® and Accutane®, have found utility as therapeutic agents for the treatment of various pathological conditions. In addition, a variety of structural analogues of retinoic acid have been synthesized that also have been found to be bioactive. Many of these synthetic retinoids have been found to mimic many of the pharmacological actions of retinoic acid, and thus have therapeutic potential for the treatment of numerous disease states.

Medical professionals have become very interested in the therapeutic applications of retinoids. Among their uses approved by the FDA is the treatment of severe forms of acne and psoriasis as well as cancers such as Kaposi's Sarcoma. A large body of evidence also exists that these compounds can be used to arrest and, to an extent, reverse the effects of skin damage arising from prolonged exposure to the sun. Other evidence exists that these compounds have clear effects on cellular proliferation, differentiation and programmed cell death (apoptosis), and thus, may be useful in the treatment and prevention of a variety of cancerous and pre-cancerous conditions, such as acute promyleocytic leukemia (APL), epithelial cancers, squamous cell carcinomas, including cervical and skin cancers and renal cell carcinoma. Furthermore, retinoids may have beneficial activity in treating and preventing diseases of the eye, cardiovascular disease and other skin disorders.

Major insight into the molecular mechanism of retinoic acid signal transduction was gained in 1988, when a member of the steroid/thyroid hormone intracellular receptor superfamily was shown to transduce a retinoic acid signal. V. Giguere et al., Nature, 330:624-29 (1987); M. Petkovich et al., Nature, 330: 444-50 (1987); for a review, see R. M. Evans, Science, 240:889-95 (1988). It is now known that retinoids regulate the activity of two distinct intracellular receptor subfamilies: the Retinoic Acid Receptors (RARs) and the Retinoid X Receptors (RXRs), including their subtypes, RARα, β, γ and RXRα, β, γ. All-trans-retinoic acid (ATRA) is an endogenous low-molecular-weight ligand that modulates the transcriptional activity of the RARs, while 9-cis retinoic acid (9-cis) is the endogenous ligand for the RXRs. R. A. Heyman et al., Cell, 68:397406 (1992); and A. A. Levin et al., Nature, 355:359-61 (1992).

Although both the RARs and RXRs respond to ATRA in vivo, due to the in vivo conversion of some of the ATRA to 9-cis, the receptors differ in several important aspects. First, the RARs and RXRs are significantly divergent in primary structure (e.g., the ligand binding domains of RARα and RXRα have only approximately 30% amino acid homology). These structural differences are reflected in the different relative degrees of responsiveness of RARs and RXRs to various vitamin A metabolites and synthetic retinoids. In addition, distinctly different patterns of tissue distribution are seen for RARs and RXRs. For example, RXRα mRNA is expressed at high levels in the visceral tissues, e.g. liver, kidney, lung, muscle and intestine, while RARα mRNA is not. Finally, the RARs and RXRs have different target gene specificity.

RARs and RXRs regulate transcription by binding to response elements in target genes that generally consist of two direct repeat half-sites of the consensus sequence AGGTCA. It is believed that RAR operates predominantly through a heterodimer complex with RXR. RAR:RXR heterodimers activate transcription by binding to direct repeats spaced by five base pairs (a DR5) or by two base pairs (a DR2). RXRs can also form homodimers. RXR:RXR homodimers bind to a direct repeat with a spacing of one nucleotide (a DR1). D. J. Mangelsdorf et al., "The Retinoid Receptors" in The Retinoids: Biology, Chemistry and Medicine, M. B. Sporn, A. B. Roberts and D. S. Goodman, Eds., Raven Press, New York, N.Y., 2nd Edition (1994). For example, response elements have been identified in the cellular retinal binding protein type II (CRBPII), which consists of a DR1, and in Apolipoprotein AI genes that confer responsiveness to RXR, but not to RAR. Further, RAR has also been shown to repress RXR-mediated activation through the CRBPII RXR response element (D. J. Manglesdorf et al., Cell, 66:555-61 (1991)). RXRs, however, act predominantly as coregulators, which enhance the binding of all-trans retinoic acid, vitamin $D_3$, thyroid hormone, and peroxisome proliferator-activated receptors to their response elements through heterodimerization. Also, RAR specific target genes have been identified, including target genes specific for RARβ (e.g., βRE), that consist of a DR5. These data indicate that two retinoic acid responsive pathways are not simply redundant, but instead manifest a complex interplay.

RXR agonists in the context of an RXR:RXR homodimer display unique transcriptional activity in contrast to the activity of the same compounds through an RXR heterodimer. Activation of a RXR homodimer is a ligand dependent event, i.e., the RXR agonist must be present to bring about the activation of the RXR homodimer. In contrast, RXR working through a heterodimer (e.g., RXR:RAR, RXR:VDR) is often the silent partner, i.e., no RXR agonist will activate the RXR-containing heterodimer without the corresponding ligand for the heterodimeric partner. However, for other heterodimers, (e.g., PPAR:RXR) a ligand for either or both of the heterodimer partners can activate the heterodimeric complex. Furthermore, in some instances, the presence of both an RXR agonist and the agonist for the other heterodimeric partner (e.g., gemfibrizol for PPARα and TTNPB for RARα) leads to at least an additive, and often a synergistic enhancement of the activation pathway of the other IR of the heterodimer pair (e.g., the PPARα pathway). See e.g., WO 94/15902, published Jul. 21, 1994; R. Mukherjee et al., J. Steroid Biochem. Molec. Biol., 51:157-166 (1994); and L. Jow and R. Mukherjee, J. Biol. Chem., 270:3836-40 (1995).

RXR modulators which have been identified so far have exhibited significant therapeutic utility, but they have also exhibited some undesirable side effects. For instance, retinoids have been shown to elevate triglycerides and suppress the thyroid hormone axis (see, e.g., Sherman, S. I. et al., N. Engl. J. Med. 340(14):1075-1079 (1999). In addition, many retinoids have undesirable side effects such as skin irritation, lipid and bone toxicity, visual effects (including night blindness and dry eye) and teratogenicity. Therefore, development of new compounds that modulate RXR homo- and heterodimer activity while exhibiting fewer side effects is desirable.

SUMMARY OF THE INVENTION

RXR modulators bind to RXR homo- or heterodimers and either increase or decrease their ability to activate transcription of genes that control cellular differentiation and proliferation. Conditions mediated by retinoid X receptors include diabetes, dermatologic diseases, inflammatory diseases, neurodegenerative diseases, obesity, cardiovascular diseases, cancer and other proliferative diseases, such as atherosclerosis, uterine leiomyomata. In addition, RXR modulators can be used to promote wound healing or to stimulate hair growth.

The present invention is directed to a class of compounds that are RXR modulators. The compounds of the invention can be represented by Structural Formula I and pharmaceutically acceptable salts, solvates and hydrates thereof:

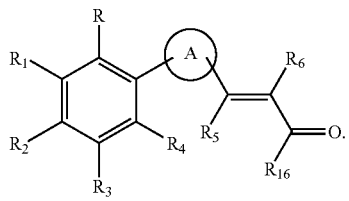

I

In Structural Formula I, R is selected from the group of hydrogen, F, Cl, Br, I, $C_1$-$C_3$ alky, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;

$R_1$ and $R_2$ are each, independently, H, a halo, a $C_1$-$C_{10}$ alkyl, a $C_3$-$C_{10}$ cycloalyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alky, $C_1$-$C_3$ haloalkyl or $C_1$-$C_3$ alkoxy; or $R_1$ and $R_2$ taken together with the carbon atoms to which they are attached form a five or six membered carbocyclic ring which is optionally substituted with one or more halo or $C_1$-$C_6$ alkyl groups. $R_{14}$ and $R_{15}$ are each, independently, H, a $C_1$-$C_6$ alkyl, or taken together with the nitrogen they are attached to can form a 5 to 8 heterocycle.

Alternatively, R and $R_1$ taken together with the carbon atoms to which they are attached form an aryl, a heteroaryl, a $C_5$-$C_8$ cycloalkyl or $C_5$-$C_8$ cycloalkenyl ring in which the aryl, heteroaryl, $C_5$-$C_8$ cycloalkyl or $C_5$-$C_8$ cyclolkenyl are optionally substituted with one or more halo, $C_1$-$C_3$ allyl, $C_1$-$C_3$ haloalkyl or $C_1$-$C_3$ alkoxy substituents. Preferably, when R and $R_1$ together with the carbon atoms to which they are attached form an aryl or a heteroaryl, the aryl and heteroaryl have from five to six atoms.

$R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy.

$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl, and alkoxy are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$. Preferably, the aryl and the heteroaryl substituents each, independently, have from five to ten atoms.

Alternatively, $R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents. Preferably, when $R_3$ and $R_4$ together with the carbon atoms to which they are attached form an aryl or a heteroaryl, the aryl and heteroaryl have from five to ten atoms.

$R_5$ is H, a halo, or a $C_1$-$C_3$ alkyl group which is optionally substituted with one or more halo.

$R_6$ is H or halo.

$R_{16}$ is $OR_{17}$, $OCH(R_{17})OC(O)R_{18}$, $-NR_{19}R_{20}$, or an aminoalkyl.

$R_{17}$, $R_{19}$ and $R_{20}$ are each, independently, H or a $C_1$-$C_6$ alkyl.

$R_{18}$ is a $C_1$-$C_6$ alkyl.

Ring A is a heteroaryl group represented by the following structural formula:

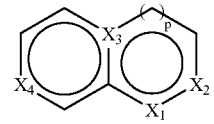

In ring A, $X_1$ and $X_2$ are each, independently, O, S, N, NH, or CH.

$X_3$ is N or C.

$X_4$ is CH or N.

p is 0 or 1.

However, when $X_1$ is O or S, then $X_2$ is CH or N and p is 0.

Ring A is optionally substituted with one or more substituents selected from a halo, a $C_1$-$C_6$ alkyl, or a $C_1$-$C_6$ alkoxy.

In one embodiment, the present invention relates to a method of modulating retinoid X receptor activity in a mammal by administering to the mammal a pharmaceutically effective amount of at least one compound represented by Structural Formula I, or pharmaceutically acceptable salts, solvates and hydrates thereof.

In another embodiment, the present invention relates to a method of modulating RXRα:PPARα heterodimer activity in a mammal by administering to the mammal a pharmaceutically effective amount of at least one compound represented by Structural Formula I, or pharmaceutically acceptable salts, solvates and hydrates thereof.

In another embodiment, the present invention relates to a method of modulating RXRα:PPARγ heterodimer activity in a mammal by administering to the mammal a pharmaceutically effective amount of at least one compound represented by Structural Formula I, or pharmaceutically acceptable salts, solvates and hydrates thereof.

In another embodiment, the present invention relates to a method of lowering blood glucose levels without altering serum triglyceride levels in a mammal by administering to the mammal a pharmaceutically effective amount of at least one compound represented by Structural Formula I, or pharmaceutically acceptable salts, solvates and hydrates thereof.

In another embodiment, the present invention relates to a method of increasing HDL cholesterol levels and reducing triglyceride levels in a mammal by administering to the mammal a pharmaceutically effective amount of at least one compound represented by Structural Formula I, or pharmaceutically acceptable salts, solvates and hydrates thereof.

In another embodiment, the present invention relates to a method of modulating lipid metabolism in a mammal by administering to the mammal a pharmaceutically effective amount of at least one compound represented by Structural Formula I, or pharmaceutically acceptable salts, solvates and hydrates thereof.

In another embodiment, the present invention relates to a method of treating or preventing a disease or condition in a mammal, wherein the disease or condition are selected from the group consisting of syndrome X, non-insulin dependent diabetes mellitus, cancer, photoaging, acne, psoriasis, obesity, cardiovascular disease, atherosclerosis, uterine leiomyomata, inflamatory disease, neurodegenerative diseases, wounds and baldness. The method involves administering to the mammal a pharmaceutically effective amount of at least one compound represented by Structural Formula I, or pharmaceutically acceptable salts, solvates and hydrates thereof.

In another embodiment, the present invention also relates to pharmaceutical compositions which include a pharmaceutically acceptable carrier and at least one compound represented by Structural Formula I, or pharmaceutically acceptable salts, solvates and hydrates thereof.

In yet another embodiment, the present invention relates to a method of making a compound represented by Structural Formula I.

Compounds of the present invention and pharmaceutically acceptable salts, solvates and hydrates thereof are expected to be effective in treating diseases or conditions that are mediated by retinoid X receptors or heterodimers of retinoid X receptors. Therefore, compounds of the invention and pharmaceutically acceptable salts, solvates and hydrates thereof are believed to be effective in treating syndrome X, non-insulin dependent diabetes mellitus, cancer, photoaging, acne, psoriasis, obesity, cardiovascular disease, atherosclerosis, uterine leiomyomata, inflamatory disease, neurodegenerative diseases, wounds and baldness. In addition, compounds of the invention exhibit fewer side effects than compounds currently used to treat these conditions.

DETAILED DESCRIPTION OF THE INVENTION

As used herein, unless otherwise specified, alkyl groups include straight chained or branched $C_1$-$C_{10}$ hydrocarbons, which are completely saturated. Preferably, an alkyl group has from 1 to 6 carbon atoms.

The term "alkenyl" means a straight-chain or branched-chain hydrocarbon radical having one or more carbon-carbon double-bonds and having from 2 to about 10 carbon atoms. Examples of alkenyl radicals include ethenyl, propenyl, 1,4-butadienyl and the like. Preferably, an alkenyl group has from 1 to 6 carbon atoms.

The term "alkynyl" means a straight-chain or branched-chain hydrocarbon radical having one or more carbon-carbon triple-bonds and having from 2 to about 10 carbon atoms. Examples of alkynyl radicals include ethynyl, propynyl, butynyl and the like. Preferably, an alkynyl group has from 1 to 6 carbon atoms.

An alkoxy group is a $C_1$-$C_6$ alkyl which is linked to a compound of the invention by an oxygen. The alkyl portion of the $C_1$-$C_6$ alkoxy group can be straight chained or branched and is completely saturated. Examples of alkoxy radicals include methoxy, ethoxy, n-propoxy, iso-propoxy, n-butoxy, iso-butoxy, sec-butoxy, tert-butoxy and the like.

Cycloalkyl groups, as used herein, include $C_3$-$C_8$ hydrocarbons, which are completely saturated.

The term "cycloalkenyl" includes optionally substituted $C_5$-$C_8$ carbocyclic structures which have one or more double bond but are not aromatic.

The terms "haloalkyl", "haloalkenyl" and "haloalkynyl" include $C_1$-$C_{10}$ alkyl, $C_1$-$C_{10}$ alkenyl and $C_1$-$C_{10}$ alkynyl structures, as described above, that are substituted with one or more F, Cl, Br or I, or with combinations thereof The term "carbocyclic" means a cycloalkyl, cycloalkenyl or aryl wherein the cyclic moiety is composed of carbon atoms.

The term "heterocycle" includes optionally substituted, saturated, unsaturated, or aromatic three- to eight-membered cyclic structures wherein the cyclic moiety includes one to four heteroatoms selected from oxygen, nitrogen, sulfur, or combinations thereof.

As used herein, aryl groups have from one to ten carbon atoms and include monocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl).

Heteroaryl groups, as used herein, are aromatic ring systems having from five to ten atoms wherein from one to four of the atoms are heteroatoms selected from nitrogen, sulfur or oxygen and the remaining atoms are carbon atoms. Heteroaryl groups include thienyl, benzo[b]furanyl, benzo[b]thienyl, indolyl, thieno[2,3-c]pyridinyl, benzo[d]isoxazolyl, indazolyl, imidazo[1,2-a]pyridinyl, isoquinolinyl, quinolinyl, pyridyl, pyrrolyl, isoxazolyl, and pyrimidinyl.

An aryl-$C_1$-$C_6$-alkyl group, as used herein, is an aryl substituent that is linked to a compound by an alkyl group having from one to six carbon atoms.

An aminoalkyl group is an alkyl group having from one to six carbon atoms which is substituted with at least one amine represented by —$NR_{19}R_{20}$, in which $R_{19}$ and $R_{20}$ are each, independently, hydrogen, a $C_1$-$C_6$ alkyl or $R_{19}$ and $R_{20}$ taken together with the nitrogen to which they are attached form a five or six membered heterocycloalkyl.

A heterocycloalkyl is a non-aromatic ring which contains from one to four heteroatoms selected from oxygen, nitrogen or sulfur (e.g., morpholine, piperidine, piperazine, pyrrolidine, and thiomorpholine). Preferred heterocycloalkyl groups are morpholine and piperidine.

The term "halo" includes to F, Cl, Br or I.

A carbonyl group is an aldehyde group represented by —CHO or a ketone group represented by —C(O)—$C_1$-$C_6$-alkyl.

Phenol and amino protecting groups are known to those skilled in the art. For examples of amino protecting groups see Greene, et al., *Protective Groups in Organic Synthesis* (1991), John Wiley & Sons, Inc., pages 309-405, the teachings of which are incorporated herein by reference in their entirety. Preferably, amines are protected as amides, carbamates or a phenylsulfonamide. For examples of phenol protecting groups see Id., pages 143-174, the teachings of which are incorporated herein by reference in their entirety. A preferred phenol protecting group is a methoxymethyl group.

The substituents of an "optionally substituted" structure may include, but are not limited to, one or more of the following preferred substituents: F, Cl, Br, I, CN, $NO_2$, $NH_2$, NHCH$_3$, N(CH$_3$)$_2$, SH, SCH$_3$, OH, OCH$_3$, OCF$_3$, CH$_3$, CF$_3$, a C$_1$-C$_6$ alkyl, halo, a C$_1$-C$_6$ alkoxy, a C$_1$-C$_6$ alkyl group which is substituted with from one to thirteen halo substituents, or a C$_1$-C$_6$ alkoxy group which is substituted with from one to thirteen halo substituents. The maximum number of substituents that a structure can have is dependent on the particular structure. A person skilled in the art would be able to determine the maximum number of substituents that a particular structure could have by examining the structure of the structure. For example, a phenyl group which is attached to a compound of the invention by one bond can have from one to five substituents, whereas an indolyl group which is attached to a compound of the invention by two bonds can have from one to five substituents.

The term RXR modulator refers to a compound that binds to one or more retinoid X receptors and modulates (i.e., increases or decreases the transcriptional activity and/or biological properties of the given receptor dimer) the transcriptional activity of an RXR homodimer (i.e., RXR:RXR) and/or RXR in the context of a heterodimer, including but not limited to heterodimer formation with peroxisome proliferator activated receptors (e.g., RXR:PPARα,β,γ1 or γ2), thyroid receptors (e.g., RXR:TRα or β), vitamin D receptors (e.g., RXR:VDR), retinoic acid receptors (e.g., RXR:RARα,β or γ), NGFIB receptors (e.g., RXR:NGFIB), NURR1 receptors (e.g., RXR:NURR1) LXR receptors (e.g., RXR:LXRα,β), DAX receptors (e.g., RXR:DAX), as well as other orphan receptors that form heterodimers with RXR, as either an agonist, partial agonist and/or antagonist. The particular effect of an RXR modulator as an agonist, partial agonist and/or antagonist will depend upon the cellular context as well as the heterodimer partner in which the modulator compounds acts.

In a first preferred embodiment, compounds of the present invention and pharmaceutically acceptable salts, solvates and hydrates thereof, separately or with their respective pharmaceutical compositions, have a benzo[b]furanyl ring A. This group of compounds can be represented by Structural Formula II:

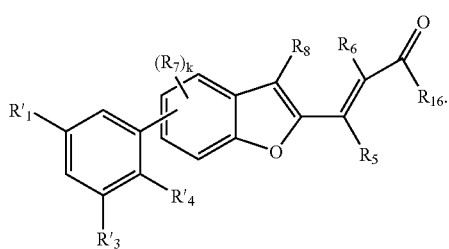

II

In Structural Formula II, R$_5$, R$_6$, and R$_{16}$, are as defined for Structural Formula I.

R$_1$' and R$_3$' are each, independently, H, a halo, a C$_1$-C$_{10}$ alkyl, a C$_3$-C$_{10}$ cycloalkyl, a C$_5$-C$_{10}$ cycloalkenyl, a 6 to 10 membered aryl, a 5 to 10 membered heteroaryl, an aryl-C$_1$-C$_6$-alkyl or an amino group represented by the formula NR$_{14}$R$_{15}$, wherein the alkyl, cycloalkyl, cycloalkenyl, aryl, heteroaryl and arylalkyl are optionally substituted with one or more halo, C$_1$-C$_3$ alkyl, C$_1$-C$_3$ haloalkyl or C$_1$-C$_3$ alkoxy.

R$_4$' is H, a halo, an aryl-C$_1$-C$_6$-alkyl, a C$_1$-C$_{10}$ alkyl or a C$_1$-C$_{10}$ alkoxy group wherein the arylalkyl, alkyl and alkoxy groups are optionally substituted with one or more substituents selected from halo, C$_1$-C$_6$ alkyl, aryl, heteroaryl, a C$_1$-C$_6$ alkoxy, an amino group represented by the formula NR$_{14}$R$_{15}$.

Each R$_7$ is, independently, a halo or a C$_1$-C$_6$ alkyl group.
R$_8$ is H, a halo or a C$_1$-C$_6$ alkyl group.
k is 0, 1, 2 or 3.

Examples of compounds having Structural Formula II include, for instance, the compounds described in Examples 1-7, 9-10 and 22.

In a second preferred embodiment, compounds of the present invention and pharmaceutically acceptable salts, solvates and hydrates thereof, separately or with their respective pharmaceutical compositions, have a benzo[b]thienyl ring A. This group of compounds can be represented by Structural Formula III:

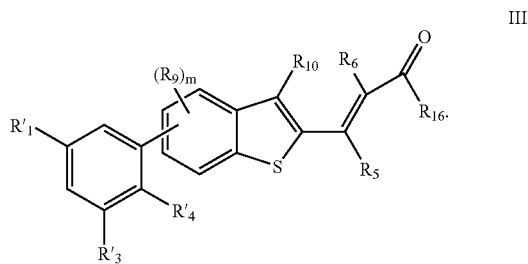

III

In Structural Formula III, R$_5$, R$_6$, and R$_{16}$, are as defined for Structural Formula I and R$_1$', R$_3$', and R$_4$' are defined as in Structural Formula II.

Each R$_9$ is, independently, a halo or a C$_1$-C$_6$ alkyl group;
R$_{10}$ is H, a halo or a C$_1$-C$_6$ alkyl group; and
m is 0, 1, 2 or 3.

Examples of compounds having Structural Formula III include, for instance, the compounds described in Examples 12, 14-21, 23-33 and 35-47.

In a third preferred embodiment, compounds of the present invention and pharmaceutically acceptable salts, solvates and hydrates thereof, separately or with their respective pharmaceutical compositions, have an indolyl ring A. This group of compounds can be represented by Structural Formula IV:

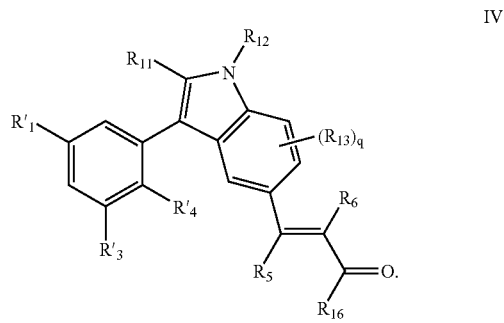

IV

In Structural Formula IV, R$_5$, R$_6$, and R$_{16}$, are as defined for Structural Formula I and R$_1$', R$_3$', and R$_4$' are defined as in Structural Formula II.

R$_{11}$ is H, a halo or a C$_1$-C$_6$ alkyl.
R$_{12}$ is H or a C$_1$-C$_6$ alkyl.
Each R$_{13}$ is, independently, a halo or a C$_1$-C$_6$ alkyl group.
q is 0, 1, 2 or 3

Examples of compounds having Structural Formula IV include, for instance, the compounds described in Examples 48-52 and 63-65.

Compounds of the present invention include, but are not limited to, the following group of compounds:

3-[5-(2-hydroxy-3-tert-butyl-5-ethylphenyl)-benzo[b]furan-2-yl]-but-2-enoic acid;

2-fluoro-3-[5-(2-methoxy-3,5-di-iso-propylphenyl)-benzo[b]furan-2-yl]-but-2-enoic acid;

2-fluoro-3-[7-(2-propoxy-3-tert-butyl-5-ethylphenyl)-benzo[b]furan-2-yl]-but-2-enoic acid ethyl ester;

3-[7-(2-ethoxy-3,5-di-tert-butylphenyl)-benzo[b]furan-2-yl]-but-2-enoic acid;

3-[7-(2-ethoxy-3,5-di-iso-propylphenyl)-benzo[b]furan-2-yl]-but-2-enoic acid;

3-[7-(2-propoxy-3,5-di-iso-propylphenyl)-benzo[b]furan-2-yl]-but-2-enoic acid;

3-{7-[2-(3-fluoropropoxy)-3,5-di-iso-propylphenyl]-benzo[b]furan-2-yl}-but-2-enoic acid;

ethyl-2-carboxylate-7-(2-ethoxy-3,5-diisopropylbenzene)-benzo[b]thiophene;

3-{7-[2-(2,2-difluoroethoxy)-3,5-di-iso-propylphenyl]-benzo[b]furan-2-yl}-but-2-enoic acid;

(E)-2-fluoro-3-{7-[2-(2,2-difluoroethoxy)-3,5-di-iso-propylphenyl]-benzo[b]furan-2-yl}-but-2-enoic acid;

(E)-3-{7-[5,5,8,8,-tetramethyl-3-ethoxy-5,6,7,8-tetrahydronaphth-2-yl]-benzo[b]furan-2-yl}-but-2-enoic acid;

3-[7-(2-ethoxy-3,5-di-iso-propylphenyl)-benzo[b]thien-2-yl]-but-2-enoic acid;

2-carboxy-4-(2-propoxy-3,5-di-tert-butylphenyl)-benzo[b]thiophene;

3-{4-[2-(2,2-difluoroethoxy)-3,5-di-tert-butylphenyl]-benzo[b]thien-2-yl}-but-2-enoic acid;

(E)-3-[4-(2-propoxy-3,5-di-iso-propylphenyl)-benzo[b]thien-2-yl]-but-2-enoic acid;

(E)-3-[4-(2-ethoxy-3,5-di-iso-propylphenyl)-benzo[b]thien-2-yl]-but-2-enoic acid;

(E)-3-[4-(2-n-butoxy-3,5-di-iso-propylphenyl)-benzo[b]thien-2-yl]-but-2-enoic acid;

(E)-3-[4-(2-n-butoxy-3,5-di-iso-propylphenyl)-5-fluorobenzo[b]thien-2-yl]-but-2-enoic acid;

(E) 2-fluoro-3-[4-(2-n-propoxy-3,5-di-iso-propylphenyl)-benzo[b]thien-2-yl]-prop-2-enoic acid;

(E) 3-[4-(2-propyloxy-3,5-di-iso-propylphenyl)benzo[b]thien-2-yl]prop-2-enoic acid;

3-{4-[2-(2,2,2-trifluoroethoxy)-3,5-di-iso-propylphenyl]benzo[b]thien-2-yl}-but-2-enoic acid;

3-{4-[2-(2,2,2-trifluoroethoxy)-3,5-di-iso-propylphenyl]benzo[b]furan-2-yl}-but-2-enoic acid;

3-{4-[2-(2,2,2-trifluoroethoxy)-3-tert-butyl-5-methylphenyl]benzo[b]thien-2-yl}but-2-enoic acid;

(E) 3-{4-[2-(2,2,2-trifluoroethoxy)-3,5-di-tert-butylphenyl]-benzo[b]thien-2-yl}but-2-enoic acid;

(E) 3-{4-[2-(2,2,2-trifluoroethoxy)-3-tert-butyl-5-ethylphenyl]-benzo[b]thien-2-yl}but-2-enoic acid;

(E) 3-{4-[2-(3-fluoropropoxy)-3-tert-butyl-5-ethylphenyl]-benzo[b]thien-2-yl}but-2-enoic acid;

(E) 3-{4-[2-(2,2-difluoroethoxy)-3-(adamant-1-yl)-5-methylphenyl]benzo[b]thien-2-yl}but-2-enoic acid;

(E) 3-{4-[2-(3,3-difluoropropoxy)-3-tert-butyl-5-ethylphenyl]-benzo[b]thien-2-yl}but-2-enoic acid;

(E) 3-{4-[2-(2,2-difluoroethoxy)-3-propyl-5-tert-butylphenyl]-benzo[b]thien-2-yl}but-2-enoic acid;

(E) 3-{4-[2-(3,3-difluoropropoxy)-3-propyl-5-phenylphenyl]-benzo[b]thien-2-yl}but-2-enoic acid;

(E) 3-{4-(2-(2,2,2-trifluoroethoxy)-3-phenyl-5-methylphenyl]-benzo[b]thienyl}but-2-enoic acid;

(E) 3-{4-[2-(2-methylpropoxy)-3-tert-butyl-5-ethylphenyl]-benzo[b]thien-2-yl}but-2-enoic acid;

(E) 3-{4-[2-(2,2,2-trifluoroethoxy)-4-tert-butylphenyl]-benzo[b]thien-2-yl}but-2-enoic acid;

(E) 3-[4-(5-(2,2,2-trifluoroethoxy)-6-tert-butylindan-4-yl)-benzo[b]thien-2-yl]but-2-enoic acid;

(E) 3-[4-(3,5-di-tert-butylphenyl)-benzo[b]thien-2-yl]but-2-enoic acid;

(E) 3-{4-[3,5-di-iso-propyl-2-(2,2,2-trifluoroethoxy)phenyl]-5-fluoro-benzo[b]thien-2-yl}but-2-enoic acid;

(E) 3-{4-[2-(3-methylbutoxy)-3,5-di-tert-butylphenyl]-benzo[b]thien-2-yl}but-2-enoic acid;

(E) 3-{4-[2-(3,3,3-difluoropropoxy)-3,5-di-tert-butylphenyl]-benzo[b]thien-2-yl}but-2-enoic acid;

(E) 3-{4-[2-(2-methylpropoxy)-3,5-di-tert-butylphenyl]-benzo[b]thien-2-yl}but-2-enoic acid;

(E) 3-{4-[2-(2,2,2-trifluoroethoxy)-3,5-di-(1,1-dimethylpropyl)-phenyl]-benzo[b]thien-2-yl}but-2-enoic acid;

(E) 3-{4-[2-(2,2-difluoroethoxy)-3,5-di-(1,1-diethylpropyl)phenyl]-benzo[b]thien-2-yl}but-2-enoic acid;

(E) 3-{4-[2-(3-fluoropropoxy)-3,5-di-(1,1-dimethylpropyl)phenyl]-benzo[b]thien-2-yl}but-2-enoic acid;

(E) 3-{4-[2-(3-methylbutoxy)-3,5-di-(1,1-dimethylpropyl)phenyl]-benzo[b]thien-2-yl}but-2-enoic acid;

(E) 3-{4-[2-(3,3-difluoropropoxy)-3,5-di-(1,1-dimethylpropyl)-phenyl]-benzo[b]thiophene]but-2-enoic acid;

(E) 3-{4-[2-(2,2-difluoroethoxy)-3,5-di-(dimethylphenylmethyl)phenyl]-benzo[b]thien-2-yl}but-2-enoic acid;

(E) 3-{4-[2-(2,2-difluoroethoxy)-3-tert-butyl-5-phenylphenyl]-benzo[b]thien-2-yl]but-2-enoic acid;

(E) 3-{5-[2-(2,2-difluoroethoxy)-3-phenyl-5-tert-butylphenyl]-benzo[b]thien-2-yl}but-2-enoic acid;

3-[3-(2-butoxy-3,5-di-iso-propylphenyl)-1H-indol-5-yl]-but-2-enoic acid;

3-[3-(2-butoxy-3,5-di-iso-propylphenyl)-1-methyl-1H-indol-5-yl]-but-2-enoic acid;

3-[3-(2-ethoxy-3,5-di-iso-propyl-phenyl)-1H-indol-5-yl]-but-2-enoic acid;

3-[3-(2-butoxy-3,5-di-tert-butyl-phenyl)-1H-indol-5-yl]-but-2-enoic acid;

3-[4-(2-butoxy-3,5-di-iso-propylphenyl)-1H-indol-2-yl]-but-2-enoic acid;

3-[1-(2-butoxy-3,5-di-iso-propyl-phenyl)-isoquinolin-7-yl]-but-2(E)-enoic acid;

3-[4-(2-butoxy-3,5-di-iso-propyl-phenyl)-quinolin-6-yl]-but-2(E)-enoic acid;

3-{3-[2-(3-fluoropropoxy)-3,5-di-iso-propylphenyl]-benzo[b]thien-5-yl}-but-2-enoic acid;

3-[3-(2-hydroxy-3,5-di-iso-propylphenyl)-benzo[b]thien-5-yl]-but-2-enoic acid;

3-[3-(3,5-di-iso-propyl-2-methoxyphenyl)-benzo[b]thien-5-yl]-but-2-enoic acid;

3-[3-(2-ethoxy-3,5-di-iso-propyl-phenyl)-thieno[2,3-c]pyridin-5-yl]-but-2-enoic acid;

3-[3-(2-ethoxy-3,5-di-iso-propyl-phenyl)-benzo[d]isoxazol-5-yl]-but-2-enoic acid;

3-[3-(2-ethoxy-3,5-di-iso-propyl-phenyl)-1H-indazol-5-yl]-but-2-enoic acid;

3-[3-(2-ethoxy-3,5-di-iso-propyl-phenyl)-imidazo[1,2-a]pyridin-6-yl]-but-2-enoic acid;

3-[3-(2-ethoxy-3,5-di-iso-propyl-phenyl)-imidazo[1,2-a]pyridin-6-yl]-acrylic acid;

3-[3-(3,5-di-tert-butyl-2-propoxy-phenyl)-1H-indol-5-yl]-but-2-enoic acid;

3-{3-[3,5-di-tert-butyl-2-(2,2-difluro-ethoxy)-phenyl]-1H-indol-5-yl}-but-2-enoic acid;

3-{3-[3,5-di-tert-butyl-2-(2,2,2-trifluoro-ethoxy)-phenyl]-1H-indol-5-yl}-but-2-enoic acid, and pharmaceutically acceptable salts, solvates and hydrates thereof.

In one embodiment, ring A of compounds of the present invention is a benzo[b]furanyl. These compounds include, but are not limited to, the following group of compounds:

3-[5-(2-hydroxy-3-tert-butyl-5-ethylphenyl)-benzo[b]furan-2-yl]-but-2-enoic acid;

2-fluoro-3-[5-(2-methoxy-3,5-diisopropylphenyl)-benzo[b]furan-2-yl]-but-2-enoic acid;

2-fluoro-3-[7-(2-propoxy-3-tert-butyl-5-ethylphenyl)-benzo[b]furan-2-yl]-but-2-enoic acid ethyl ester;

3-[7-(2-ethoxy-3,5-di-tert-butylphenyl)-benzo[b]furan-2-yl]-but-2-enoic acid;

3-[7-(2-ethoxy-3,5-diisopropylphenyl)-benzo[b]furan-2-yl]-but-2-enoic acid;

3-[7-(2-propoxy-3,5-diisopropylphenyl)-benzo[b]furan-2-yl]-but-2-enoic acid;

3-{7-[2-(3-fluoropropoxy)-3,5-diisopropylphenyl]-benzo[b]furan-2-yl}-but-2-enoic acid;

3-{7-[2-(2,2-difluoroethoxy)-3,5-diisopropylphenyl]-benzo[b]furan-2-yl}-but-2-enoic acid;

(E)-2-fluoro-3-{7-[2-(2,2-difluoroethoxy)-3,5-diisopropylphenyl]-benzo[b]furan-2-yl}-but-2-enoic acid;

(E)-3-{7-[5,5,8,8,-tetramethyl-3-ethoxy-5,6,7,8-tetrahydronaphth-2-yl]-benzo[b]furan-2-yl}-but-2-enoic acid;

3-{4-[2-(2,2,2-trifluoroethoxy)-3,5-di-iso-propylphenyl]-benzo[b]furan-2-yl}-but-2-enoic acid; and pharmaceutically acceptable salts, solvates and hydrates thereof.

In another embodiment, ring A of compounds of the present invention is a benzo[b]thienyl. These compounds include but are not limited to the following group of compounds:

ethyl-2-carboxylate-7-(2-ethoxy-3,5-di-iso-propylbenzene)-benzo[b]thiophene;

3-[7-(2-ethoxy-3,5-di-iso-propylphenyl)-benzo[b]thien-2-yl]-but-2-enoic acid;

2-carboxy-4-(2-propoxy-3,5-di-tert-butylphenyl)-benzo[b]thiophene;

(E)-3-[4-(2-propoxy-3,5-di-iso-propylphenyl)-benzo[b]thien-2-yl]-but-2-enoic acid;

(E)-3-[4-(2-ethoxy-3,5-di-iso-propylphenyl)-benzo[b]thien-2-yl]-but-2-enoic acid;

(E)-3-[4-(2-n-butoxy-3,5-di-iso-propylphenyl)-benzo[b]thien-2-yl]-but-2-enoic acid;

(E)-3-[4-(2-n-butoxy-3,5-di-iso-propylphenyl)-5-fluorobenzo[b]thien-2-yl]-but-2-enoic acid;

2-fluoro-3-[4-(3,5-di-iso-propyl-2-propyloxyphenyl)-benzo[b]thien-2-y]but-2-enoic acid 3-[4-(3,5-di-iso-propyl-2-propyloxyphenyl)-benzo[b]thien-2-yl]but-2-enoic acid;

3-{4-[2-(2,2,2-trifluoroethoxy)-3,5-di-iso-propylphenyl]benzo[b]thien-2-yl}-but-2-enoic acid;

(E) 2-{4-[2-(2,2,2-trifluoroethyloxy)-3-tert-butyl-5-methylphenyl]-benzo[b]thien-2-yl}but-2-enoic acid;

(E) 3-{4-[2-(2,2,2-trifluoroethyloxy)-3,5-di-tert-butylphenyl]-benzo[b]thien-2-yl}but-2-enoic acid;

(E) 3-{4-[2-(2,2,2-trifluoroethyloxy)-3-tert-butyl-5-ethylphenyl]-benzo[b]thien-2-yl}but-2-enoic acid;

(E) 3-{4-[2-(3-fluoropropyloxy)-3-tert-butyl-5-ethylphenyl]-benzo[b]thien-2-yl}but-2-enoic acid;

(E) 3-{4-[2-(2,2-difluoroethyloxy)-3-(adamant-1-yl)-5-methylphenyl]-benzo[b]thien-2-yl}but-2-enoic acid;

(E) 3-{4-[2-(3,3-difluoropropyloxy)-3-tert-butyl-5-ethylphenyl]-benzo[b]thien-2-yl}but-2-enoic acid;

(E) 3-{4-[2-(2,2-difluoroethyloxy)-3-propyl-5-tert-butylphenyl]benzo[b]thien-2-yl}but-2-enoic acid;

(E) 3-{4-[2-(3,3-difluoropropyloxy)-3-propyl-5-phenylphenyl]-benzo[b]thien-2-yl}but-2-enoic acid;

(E) 3-{4-[2-(2,2,2-trifluoroethyloxy)-3-phenyl-5-methylbenzene]-benzo[b]thien-2-yl}but-2-enoic acid;

(E) 3-{4-[2-(2-methylpropyloxy)-3-tert-butyl-5-ethylphenyl]benzo[b]thien-2-yl}-but-2-enoic acid;

(E) 3-{4-[2-(2,2,2-trifluoroethyloxy)-4-tert-butylphenyl]-benzo[b]thien-2-yl}but-2-enoic acid; and pharmaceutically acceptable salts, solvates and hydrates thereof.

In another embodiment, ring A of compounds of the present invention is an indolyl. These compounds include, but are not limited to, the following group of compounds:

3-[3-(2-butoxy-3,5-di-iso-propyl-phenyl)-1H-indol-5-yl]-but-2-enoic acid;

3-[3-(2-butoxy-3,5-di-iso-propylphenyl)-1-methyl-1H-indol-5-yl]-but-2-enoic acid;

3-[3-(2-ethoxy-3,5-di-iso-propyl-phenyl)-1H-indol-5-yl]-but-2-enoic acid;

3-[3-(2-butoxy-3,5-tert-butyl-phenyl)-1H-indol-5-yl]-but-2-enoic acid;

3-[4-(2-butoxy-3,5-di-iso-propylphenyl)-1H-indol-2-yl]-but-2-enoic acid;

3-[3-(3,5-di-tert-butyl-2-propoxy-phenyl)-1H-indol-5-yl]-but-2-enoic acid;

3-{3-[3,5-di-tert-butyl-2-(2,2-difluro-ethoxy)-phenyl]-1H-indol-5-yl}-but-2-enoic acid;

3-{3-[3,5-di-tert-butyl-2-(2,2,2-trifluoro-ethoxy)-phenyl]-1H-indol-5-yl}-but-2-enoic acid;

and pharmaceutically acceptable salts, solvates and hydrates thereof.

In a fourth preferred embodiment, compounds represented by Structural Formula I have a ring A that is selected from the group consisting of an optionally substituted benzofuranyl, an optionally substituted benzo[b]thiophenyl, an optionally substituted indolyl, an optionally substituted thieno[2,3-c]pyridinyl, an optionally substituted benzo[d]isoxazolyl, an optionally substituted indazolyl, an optionally substituted imidazo[1,2-a]pyridinyl, an optionally substituted isoquinolinyl, or an optionally substituted quinolinyl.

In a fifth preferred embodiment, compounds represented by Structural Formula I have a ring A that is selected from the following groups:

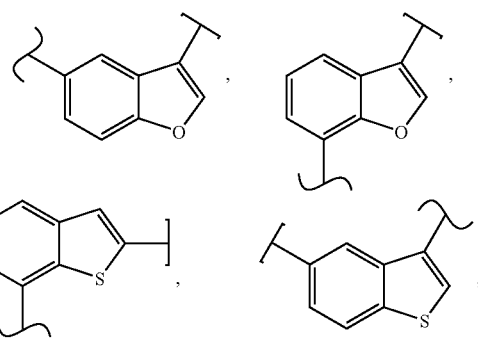

-continued

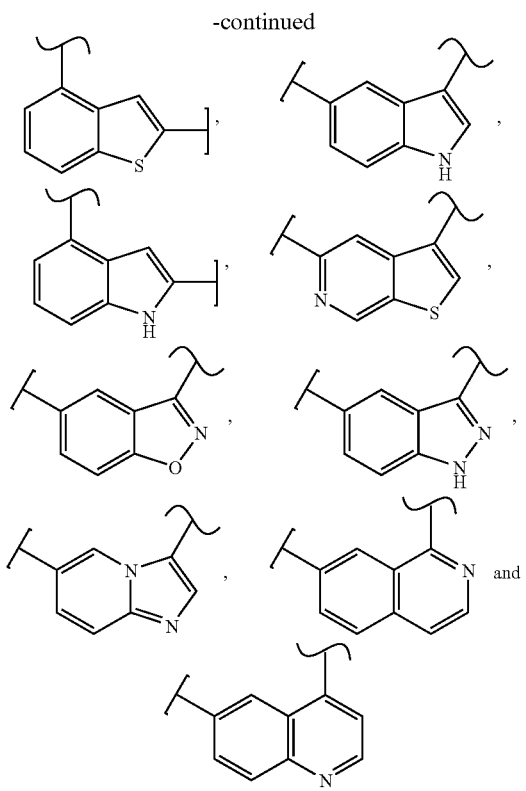

The symbol "⌒" indicates a single bond connecting ring A to the phenyl group, and the symbol "[" indicates a single bond connecting ring A to the α,β-unsaturated carbonyl group.

In another embodiment, $R_4$ of Structural Formula I or $R_4$ of preferred embodiments four and five is a $C_2$-$C_5$ alkoxy group which is optionally substituted with one or more fluoro.

In another embodiment, $R_4'$ of preferred embodiments one, two and three is a $C_2$-$C_5$ alkoxy group which is optionally substituted with one or more fluoro.

In another embodiment, $R_5$ is methyl and $R_6$ is H in anyone of the previous embodiments.

In another embodiment, $R_5$ is methyl and $R_6$ is fluoro in anyone of the previous embodiments.

In another embodiment, $R_1$ and $R_3$ in anyone of the previous embodiments in which they occur are the same.

In another embodiment, $R_1$ and $R_3$ in anyone of the previous embodiments in which they occur are the same and are iso-propyl or tert-butyl.

In another embodiment, $R_1'$ and $R_3'$ in anyone of the previous embodiments in which they occur are the same.

In another embodiment, $R_1'$ and $R_3'$ in anyone of the previous embodiments in which they occur are the same and are iso-propyl or tert-butyl.

Compounds of Formula I are differentiated from previously disclosed RXR modulators that have insulin sensitizing activity, in that they cause little or no suppression of the thyroid axis and little or no elevation of triglycerides. These compounds are heterodimer selective modulators of RXR activity. They bind to RXR with high affinity ($K_i$<500 nM) and produce potent synergistic activation of the RXR:PPARγ heterodimer, but preferably do not synergize with RAR agonists at the RXR:RAR heterodimer. This synergistic activation of PPARγ in vitro is contemplated to be a major determinant of the antidiabetic efficacy of compounds in vivo.

Compounds of the present invention possess particular application as RXR modulators and in particular as dimer-selective RXR modulators including, but not limited to, RXR homodimer antagonists, and agonists, partial agonists and antagonists of RXRs in the context of a heterodimer.

In a second aspect, the present invention provides a method of modulating processes mediated by RXR homodimers and/or RXR heterodimers comprising administering to a patient an effective amount of a compound of the invention as set forth above. Compounds of the present invention also include all pharmaceutically acceptable salts, as well as esters, and amides. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

Compounds of the present invention are useful in the modulation of transcriptional activity through RXR in the context of heterodimers other than RXR:RARα,β,γ (e.g., RXR:PPARα,β,γ; RXR:TR; RXR:VDR; RXR:NGFIB; RXR:NURR1; RXR:LXRα,β, RXR:DAX), including any other intracellular receptors (IRs) that form a heterodimer with RXR. For example, application of compounds of the present invention to modulate a RXRα:PPARα heterodimer is useful to increase, HDL cholesterol levels and reduce triglyceride levels. Application of many of the same compounds of the present invention to a RXRα:PPARγ heterodimer modulates a distinct activity, i.e., modulation of adipocyte biology, including effects on the differentiation and apoptosis of adipocytes, which will have implications in the treatment and/or prevention of diabetes and obesity. In addition, use of the modulator compounds of the present invention with activators of the other heterodimer partner (e.g., fibrates for PPARα and thiazolidinediones for PPARγ) can lead to a synergistic enhancement of the desired response. Likewise, application of the modulator compounds of the present invention in the context of a RXRα:VDR heterodimer will be useful to modulate skin related processes (e.g., photoaging, acne, psoriasis), malignant and pre-malignant conditions and programmed cell death (apoptosis). Further, it will be understood by those skilled in the art that the modulator compounds of the present invention will also prove useful in the modulation of other heteromer interactions that include RXR, e.g., trimers, tetramers and the like.

In the context of an RXR homodimer, compounds of the present invention function as partial agonists. Further, when the modulator compounds of the present invention are combined with a corresponding modulator of the other heterodimeric partner, a surprising synergistic enhancement of the activation of the heterodimer pathway can occur. For example, with respect to a RXRα:PPARα heterodimer, the combination of a compound of the present invention with clofibric acid or gemfibrozil unexpectedly leads to a greater than additive (i.e. synergistic) activation of PPARα responsive genes, which in turn is useful to modulate serum cholesterol and triglyceride levels and other conditions associated with lipid metabolism.

Whether acting on an RXR heterodimer pathway, or the RXR homodimer pathway, it will also be understood by those skilled in the art that the dimer-selective RXR modulator compounds of the present invention will prove useful in any therapy in which agonists, partial agonists and/or full antagonists of such pathways will find application. Importantly, because compounds of the present invention can differentially activate RXR homodimers and RXR heterodimers, their effects will be tissue and/or cell type specific, depending upon the cellular context of the different tissue types in a given patient. For example, compounds of the present invention will exert an RXR antagonist effect in tissues where RXR homodimers prevail, and partial agonist or full agonist activity on the PPAR pathway where RXRα:PPARα heterodimers prevail (e.g., in liver tissue). Thus, compounds of the present invention will exert a differential effect in various tissues in an analogous fashion to the manner in which various classes of estrogens and antiestrogens (e.g. Estrogen, Tamoxifen, Raloxifen) exert differential effects in different tissue and/or cell types (e.g., bone, breast, uterus). See e.g., M. T. Tzukerman et al., *Mol. Eudo*, 8:21-30 (1994); D. P. McDonnell et al., *Mol. Endo.*, 9:659-669 (1995). However, in the present case, it is believed that the differential effects of compounds of the present invention are based upon the particular dimer pair through which the compound acts, rather than through different transactivating regions of the estrogen receptor in the case of estrogens and antiestrogens. However, it is possible that they also function, in part, by tissue selectivity.

The particular conditions that may be treated with compounds of the present invention include, but are not limited to, skin-related diseases, such as actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin pigmentation agents and to treat and reverse the effects of age and photo damage to the skin. With respect to the modulation of malignant and pre-malignant conditions, compounds may also prove useful for the prevention and treatment of cancerous and pre-cancerous conditions, including, premalignant and malignant hyperproliferative diseases and cancers of epithelial origin such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposis sarcoma. In addition, the present compounds may be used as agents to treat and prevent various cardiovascular diseases, including, without limitation, diseases associated with lipid metabolism such as dyslipidemias, prevention of restenosis and as an agent to increase the level of circulating tissue plasminogen activator (TPA), metabolic diseases such as obesity and diabetes (i.e., non-insulin dependent diabetes mellitus and insulin dependent diabetes mellitus), the modulation of differentiation and proliferation disorders, as well as the prevention and treatment of neurodegenerative diseases such as Alzheimer's disease, Parkinson's disease and Amyotrophic Lateral Sclerosis (ALS), and in the modulation of apoptosis, including both the induction of apoptosis and inhibition of T-Cell activated apoptosis.

Furthermore, it will be understood by those skilled in the art that compounds of the present invention, including pharmaceutical compositions and formulations containing these compounds, can be used in a wide variety of combination therapies to treat the conditions and diseases described above. Thus, compounds of the present invention can be used in combination with modulators of the other heterodimeric partner with RXR (ie., in combination with PPARα modulators, such as fibrates, in the treatment of cardiovascular disease, and in combination with PPARγ modulators, such thiazolidinediones, in the treatment of diabetes, including non-insulin dependent diabetes mellitus and insulin dependent diabetes mellitus, and with agents used to treat obesity) and with other therapies, including, without limitation, chemotherapeutic agents such as cytostatic and cytotoxic agents, immunological modifiers such as interferons, interleukins, growth hormones and other cytokines, hormone therapies, surgery and radiation therapy.

By utilizing compounds of the present invention with modulators of the other heterodimeric partner one is able to utilize lower dosages of either or both modulators, thereby leading to a significant decrease in the side-effects associated with such modulators when employed alone at the strengths required to achieve the desired effect. Thus, the modulator compounds of the present invention, when utilized in combination therapies, provide an enhanced therapeutic index (i.e., significantly enhanced efficacy and/or decrease side-effect profiles) over utilization of compounds by themselves.

Prodrugs are compounds of the present invention, which have chemically or metabolically cleavable groups and become by solvolysis or under physiological conditions compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on compounds of this invention are preferred prodrugs. In some cases it is desirable to prepare double ester type prodrugs such as (acyloxy) alkyl esters or ((alkoxycarbonyl) oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of Formula I in a medium such as methanol with an acid or base esterification catalyst (e.g., NaOH, $H_2SO_4$). Ethyl ester prodrugs are prepared in similar fashion using ethanol in place of methanol.

Morpholinylethyl ester prodrugs may be prepared by reaction of the sodium salt of a compound of Structural Formula I (in a medium such as dimethylformamide) with 4-(2-chloroethyl)morphine hydrochloride (available from Aldrich Chemical Co., Milwaukee, Wis. USA, Item No. C4,220-3).

The term "pharmaceutically acceptable" means that the carrier, diluent, excipients and salt must be compatible with the other ingredients of the formulation, and not deleterious to the recipient thereof. Pharmaceutical formulations of the present invention are prepared by procedures known in the art using well known and readily available ingredients.

"Preventing" refers to reducing the likelihood that the recipient will incur or develop any of the pathological conditions described herein.

By virtue of its acidic moiety, a compound of Structural Formula I forms salts with pharmaceutically acceptable bases. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts, zinc salts, and ammonium salts, as well as salts made from physiologically acceptable organic bases such as methylamine, dimethylamine, trimethylamine, ethylamine, diethylamine, triethylamine, morpholine, pyridine, piperidine, piperazine, picoline, nicotinamide, urea, tris(hydroxymethyl)aminomethane, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, cinnamates, picrate, formate, fumarates, tartrates [e.g. (+)-tartrates, (−)-tartrates or mixtures thereof including racemic mixtures], succinates, benzoates and salts with amino acids such as glutamic acid.

Certain compounds of Structural Formula I and their salts may also exist in the form of solvates, for example hydrates, and the present invention includes each solvate and mixtures thereof.

Certain compounds of Structural Formula I may exist in different tautomeric forms or as different geometric isomers, and the present invention includes each tautomer and/or geometric isomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may exist in more than one crystal form. Polymorphs of compounds represented by Structural Formula I form part of this invention and may be prepared by crystallization of a compound of Structural Formula I under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of Structural Formula I followed by gradual or fast cooling. The presence of polymorphs may be determined by solid probe nmr spectroscopy, ir spectroscopy, differential scanning calorimetry, powder X-ray diffraction or such other techniques.

The language a "therapeutically effective amount" or "pharmaceutically effective amount" is intended to include an amount which is sufficient to mediate a disease or condition and prevent its further progression or ameliorate the symptoms associated with the disease or condition. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate one or more retinoid X receptor, such as RXR α, RXR β, and/or RXR γ, which mediates a disease or condition. Conditions mediated by retinoid X receptors include diabetes, dermatologic diseases, inflammatory diseases, neurodegenerative diseases, obesity, cardiovascular, diseases, cancer and other proliferative diseases, such as atherosclerosis, uterine leiomyomata. In addition, RXR modulators can be used to promote wound healing or to stimulate hair growth.

Compounds of Structural Formula I, and the pharmaceutically acceptable salts, solvates and hydrates thereof, have valuable pharmacological properties and can be used in pharmaceutical preparations containing the compound or pharmaceutically acceptable salts, esters or prodrugs thereof, in combination with a pharmaceutically acceptable carrier or diluent. They are useful as therapeutic substances in preventing or treating diabetes, dermatologic diseases, inflammatory diseases, neurodegenerative diseases, obesity, cardiovascular diseases, cancer, atherosclerosis, uterine leiomyomata, wounds or hair loss in human or non-human animals. Suitable pharmaceutically acceptable carriers include inert solid fillers or diluents and sterile aqueous or organic solutions. The active compound will be present in such pharmaceutical compositions in amounts sufficient to provide the desired dosage amount in the range described herein.

For oral administration, the compound or salts thereof can be combined with a suitable solid or liquid carrier or diluent to form capsules, tablets, pills, powders, syrups, solutions, suspensions and the like.

The tablets, pills, capsules, and the like may also contain a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The active compounds can also be administered intranasally as, for example, liquid drops or spray.

For parental administration compounds of the present invention, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of compounds. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, ethanol, polyol (e.g. glycerol, propylene glycol and liquid polyethylene glycol), propylene glycol and liquid polyethylene glycol), suitable mixtures thereof, and vegetable oils. The injectable solutions prepared in this manner can then be administered intravenously, intraperitoneally; subcutaneously, or intramuscularly, with intramuscular administration being preferred in humans.

The effective dosage of active ingredient employed may vary depending on the particular compound employed, the mode of administration, the condition being treated and the severity of the condition being treated.

Preferably compounds of the invention or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Structural Formula I or salts thereof) in a unit dose of composition is a therapeutically effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Pharmaceutical formulations of the invention are prepared by combining (e.g., mixing) a therapeutically effective amount of a compound of the invention together with a pharmaceutically acceptable carrier or diluent. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. Compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection compounds of the invention may be dissolved in at a concentration of about 0.05 to about 5.0 mg/mL in a 4% dextrose/0.5% Na citrate aqueous solution.

Solid form formulations include powders, tablets and capsules. A solid carrier can be one or more substance which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Powders and tablets preferably contain from about 1 to about 99 weight percent of the active ingredient which is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

The following pharmaceutical formulations 1 through 8 are illustrative only and are not intended to limit the scope of the invention in any way. "Active Ingredient", refers to a compound according to Structural Formula I or salts thereof.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight |
|---|---|
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4
Tablets, each containing 60 mg of Active ingredient, are made as follows:

| Active Ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5
Capsules, each containing 80 mg of Active Ingredient, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6
Suppositories, each containing 225 mg of Active Ingredient, are made as follows:

| Active Ingredient | 225 mg |
|---|---|
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions, each containing 50 mg of Active Ingredient per 5 mL dose, are made as follows:

| Active Ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8
An intravenous formulation may be prepared as follows:

| Active Ingredient | 100 mg |
|---|---|
| Isotonic saline | 1,000 mL |

The solution of the above materials generally is administered intravenously to a subject at a rate of 1 mL per minute.

Synthesis

In general, compounds of the invention can be prepared by heating a triflate or halo substituted heteroaromatic compound (IX) in an organic solvent with about 1 eq. to about 2 eq. of a substituted phenylboronic acid (X) in the presence of about 0.01 eq. to about 0.1 eq. of tetrakis(triphenylphosphine) palladium(0) and a base, such as sodium carbonate, to form a phenyl substituted heteroaromatic compound (XI) (see Scheme I). The organic solvent used is typically toluene or a mixture of toluene and an alcohol, and reaction mixture is typically heated to about 60° C. to about 110° C. for about 3 h to about 16 h.

Scheme I:
Method of preparing a (substituted phenyl)-heteroaromatic compound (XI).

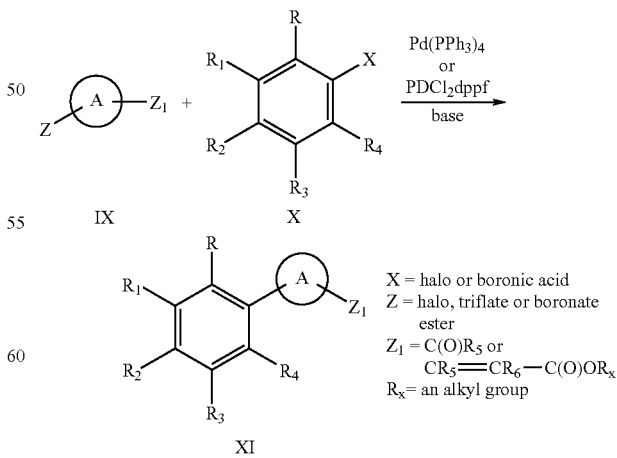

Alternatively, $R_4$ can be replaced by a protected phenolic hydroxy group in compounds X and XI of Scheme I. In this case, after addition of the substituted phenyl group to ring A, the protecting group can be removed to form a phenolic hydroxy. The phenolic hydroxy can then be reacted with an optionally substituted $C_1$-$C_9$ alkyl iodide or an optionally substituted $C_1$-$C_9$ alkyl bromide in the presence of cesium fluoride or cesium carbonate to form a compound represented by Formula XI in which $R_4$ is an optionally substituted $C_1$-$C_9$ alkoxy group.

When $Z_1$ is a ketone or an aldehyde, the ketone or aldehyde substituent of the (substituted phenyl)-heteroaromatic ketone (XII) is converted to a α,β-unsaturated ester via a Homer-Emmons condensation with a trialkyl phosphonoacetate (XIII) (see Scheme II). The reaction is typically carried out by treating a solution of a trialkyl phosphonoacetate (XI) in an aprotic solvent such as dimethyl formamide (DMF) that has been cooled to about –20° C. to about 10° C., with a strong base, such as sodium hydride, for about 15 minutes to about 30 minutes to form an enol anion. The anion is then added to a solution of the phenyl substituted heteroaromatic ketone or aldehyde (XII) followed by heating the solution to about 20° C. to about 60° C. for about 3 h to about 7 h. The reaction is then quenched with water or saturated ammonium chloride solution to form a (substituted phenyl)-heteroaromatic α,β-unsaturated ester (XIV).

The (substituted phenyl)-heteroaromatic α,β-unsaturated ester (XIV) is converted to a (substituted phenyl)-heteroaromatic α,β-unsaturated carboxylic acid (XV) by a saponification reaction wherein the α,β-unsaturated ester (XIV) is treated with an aqueous solution of an alkali metal hydroxide base, such as lithium hydroxide. A water miscible organic solvent, such as tetrahydrofuran, dioxane, and alcohols, can also be present in the reaction mixture. Typically, the reaction is heated to about 50° C. to about 80° C. for about 1 h to about 4 h. When the reaction is complete the reaction mixture is acidified with an aqueous solution of HCl to a pH of about 1 to about 2, then the product is extracted into an organic solvent.

Scheme II:
Addition of α,β-unsaturated carboxylic acid group to a (substituted phenyl)-heteroaromatic ketone (XII).

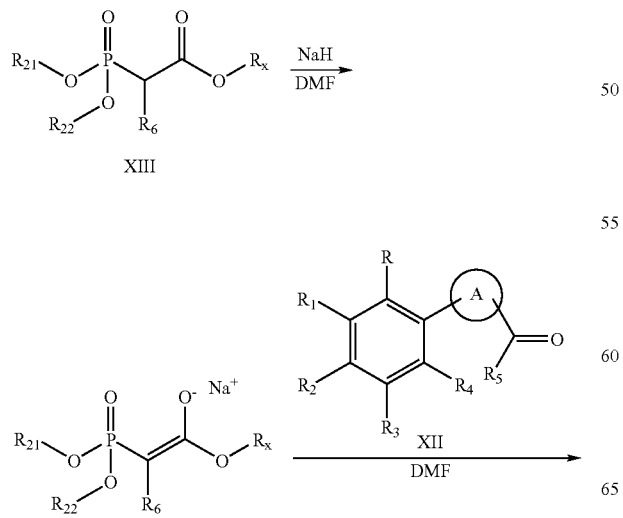

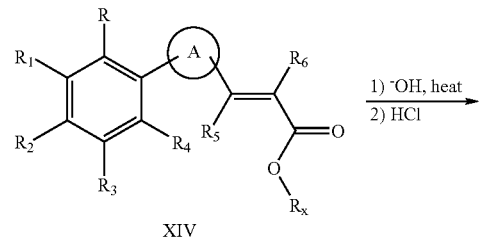

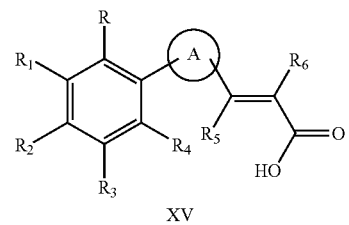

$R_{21}$ and $R_{22}$ are each, independently, an alkyl

Alternatively, the α,β-unsaturated carboxylic ester group can be added to the heteroaromatic compound before it has been coupled with the substituted phenylboronic acid compound (i.e., $Z_1$ in Scheme I is an α,β-unsaturated ester represented by $CR_5$=$CR_6$—C(O)OR$_x$). The starting material in this embodiment is a halo substituted heteroaromatic compound (XVI) that also has a substituent, such as a hydroxy or a keto group, that can be converted into a triflate. The substituted heteroaromatic compound (XVI) is reacted with an excess amount of α,β-unsaturated ester (XVII) (about 2 eq. to about 5 eq.) in an aprotic organic solvent in the presence of a catalytic amount of palladium acetate (about 0.01 eq. to about 0.1 eq.) and an aprotic base, such as a trialkyl amine (see Scheme III). The reaction is typically heated for about 16 h to about 30 h at about 70° C. to about 110° C. to form a heteroaromatic α,β-unsaturated ester (XVII). The hydroxy or ketone group can then be converted to a triflate by reaction with trifluoromethanesulfonic anhydride to form a triflate substituted heteroaromatic compound (IX) which can be used reacted with a substituted phenylboronic acid as shown in Scheme I.

Scheme III:
Addition of α,β-unsaturated ester group to a halo substituted heteroaromatic compound (XVI).

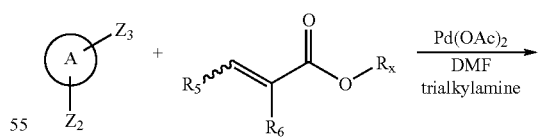

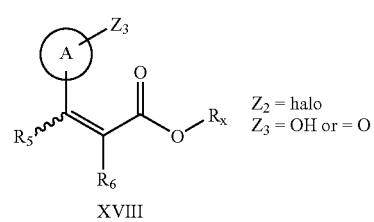

A substituted phenyl boronic acid (X) can be prepared from a substituted 2-iodophenol by forming a solution of the substituted 2-iodophenol (XIX), a base (e.g., potassium carbonate or cesium carbonate) and an alkyl halide, alkyl mesylate, or alkyl tosylate (XX) in a solvent (e.g., DMF or an alcohol) (see Scheme IV). The solution contains with respect to the substituted 2-iodophenol (XIX) about 1 eq. to about 2 eq. of the alkyl halide, alkyl mesylate, or alkyl tosylate (XX) and about 1.5 eq. to about 2.5 eq. of the base. The solution is stirred for about 2 h to about 6 h at about room temperature to about 100° C. to form a 2-alkoxy-1-iodobenzene (XXI).

A solution of an alkyl lithium is added to solution of the 2-alkoxy-1-iodobenzene (XXI) in a polar, aprotic solvent which is kept at about −50° C. to about −100° C. The alkyl lithium compound is present in about 1.2 eq. to about 2.5 eq. with respect to the 2-alkoxy-1-iodobenzene (XXI). The suspension which forms on addition of the alkyl lithium is stirred for about 30 min. to about 1 h before adding about 2 eq. with respect to the alkyl lithium of a trialkyl borate (e.g., trimethyl borate). The reaction is allowed to warm to about −75° C. to about 0° C. over a period of about 10 h to about 20 h. About 1 eq. to about 1.5 eq. with respect to the alkyl lithium of an acid, such as sulfuric acid or hydrochloric acid, was added, and the reaction was stirred for an additional period of about 20 min. to about 1 h to yield the substituted phenyl boronic acid (X).

Scheme IV:
Preparation of a substituted phenylboronic acid.

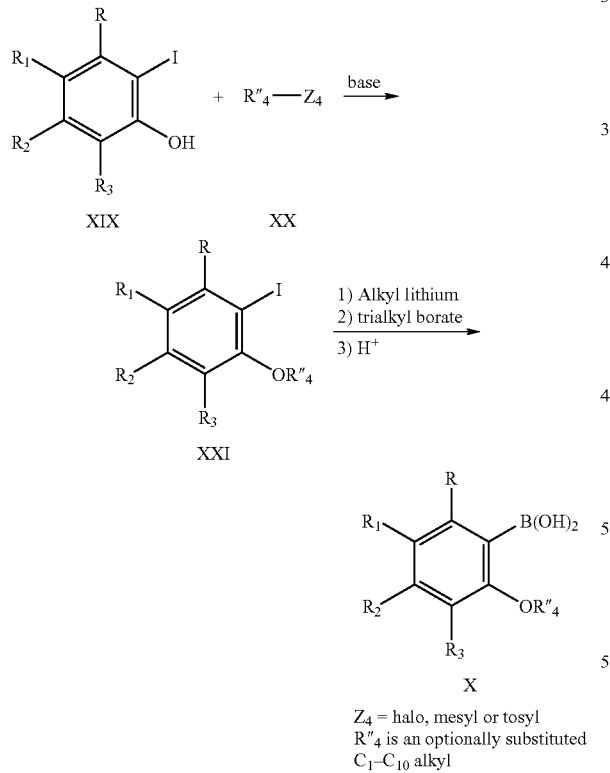

$Z_4$ = halo, mesyl or tosyl
$R''_4$ is an optionally substituted $C_1$–$C_{10}$ alkyl A compound in which ring A is a benzo[b]furanyl can be synthesized from a triflate or halo substituted benzo[b]furan using the method disclosed in Scheme I, or alternatively, it can be synthesized by reacting a triflate or halo substituted salicylaldehyde (XXII) with a substituted phenylboronic acid (X) (see Scheme V). In this embodiment, the salicylaldehyde (XXII) and about 0.01 eq. to about 0.1 eq. of palladium triphenyl phosphine is dissolved in an organic solvent, such as toluene, benzene or xylene, to form a salicylaldehyde solution having a concentration of about 0.1 M to about 0.15 M. A solution having a concentration of about 0.3 M to about 0.8 M of phenyl boronic acid (X) in alcohol, such as ethanol, is added to the salicylaldehyde solution (about 1.5 to about 2.5 molar equivalents of phenyl boronic acid is added with respect to salicylaldehyde). Then a 2 N aqueous solution of sodium carbonate is added (about 1 eq. to about 1.5 eq. with respect to the phenyl boronic acid), and the reaction is refluxed for about 1 h to about 5 h to form a 2-hydroxy-(substituted-phenyl)-benzaldehyde (XXIII).

The furanyl ring of the benzo[b]furanyl ring is formed by dissolving the 2-hydroxy-(substituted-phenyl)-benzaldehyde (XXIII), about 1 eq. to about 1.5 eq. of an α-halocarbonyl compound represented by Formula XXIV and about 1.2 eq. to about 1.8 eq. of cesium carbonate in an aprotic organic solvent, such as dimethyl formamide (DMP). The solution is heated to about 50° C. to about 70° C. for about 10 h to about 20 h to form a (substituted phenyl)-2-carbonylbenzo[b]furan (XXV). An α,β-unsaturated carboxylic acid group can be added to the (substituted phenyl)-2-carbonylbenzo[b]furan (XXV) by the method depicted in Scheme II.

Scheme V:
Synthesis of a (substituted phenyl)-2-carbonylbenzo[b]furan (XXV) which can be used to prepare a compound represented by Formula I in which ring A is benzo[b]furanyl.

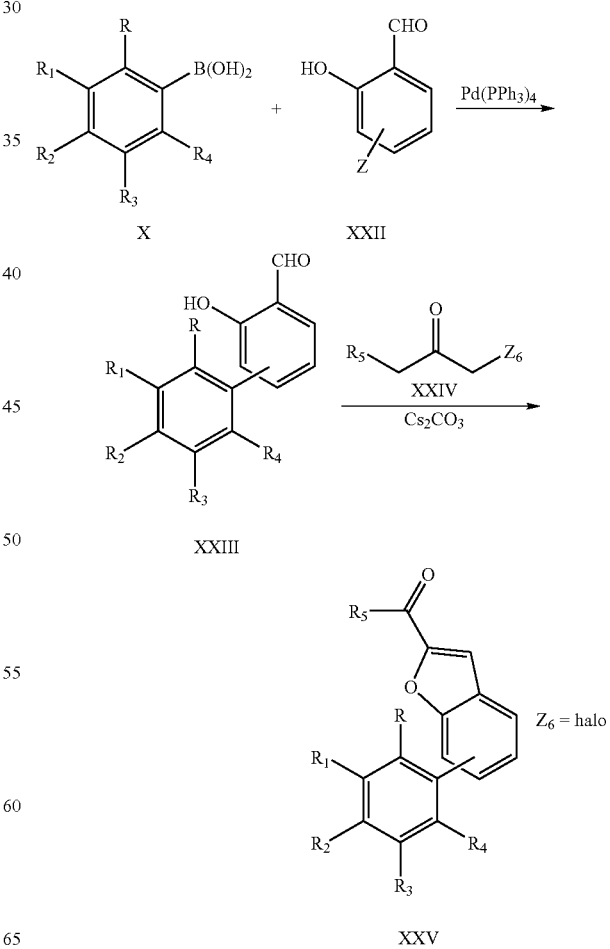

A compound in which ring A is a benzo[b]thienyl can be synthesized from a triflate or halo substituted benzo[b]thienyl using the method disclosed in Scheme I or, alternatively, it can be synthesized from a fluorocarbonylbenzene (XXVI) (see Scheme VI). In this embodiment, sodium hydride is added to a solution of an alkyl thioglycolate (XXVII) in an aprotic solvent (e.g., DMF or an ether) that has been cooled to about −20° C. to about 10° C. About 5 min. to about 20 min. after addition of the sodium hydride, fluorocarbonylbenzene (XXVI) is added to the reaction mixture, and it is allowed to warm up to room temperature. Typically, the alkyl thioglycolate (XXVII) is present in the reaction mixture in an excess with respect to the fluorocarbonylbenzene (XXVI). The reaction is complete in about 1 h to about 3 h to give a thiophenyl-acetic acid alkyl ester (XXVIII).

The thiophenyl-acetic acid alkyl ester (XXVIII) is converted to a thiophenyl-acetic acid (XXIX) via the saponification method described for the third step of Scheme II. The thiophenyl-acetic acid (XXIX) is then converted to an acid chloride via treatment with thionyl chloride followed by a Friedel-Crafts acylation to form a benzo[b]thien-3-one (XXX). In this reaction, a solution of thiophenyl-acetic acid (XXIX) in an aprotic solvent (e.g., methylene chloride or dichloroethane) at room temperature is treated with about 1.5 eq. to about 2.5 eq. of thionyl chloride. Preferably, one drop of DMF is also added to the reaction. The reaction mixture is heated to about 30° C. to about 70° C. for about 20 min. to about 1 h, then cooled to room temperature. Preferably, after the reaction to form the acid chloride is complete, dry nitrogen is bubbled through the reaction mixture for about 5 min. to about 20 min. to remove traces of HCl gas. About 0.1 eq. to about 0.5 eq. of a Friedel-Crafts catalyst is added to the reaction mixture, and the reaction is heated to about 30° C. to about 50° C. for about 1 h to about 3 h to form a benzo[b]thien-3-one (XXXI). Friedel-Crafts catalysts include aluminum trichloride, aluminum tribromide, boron trifluoride, ferric chloride, and zinc chloride. Aluminum trichloride is a preferred Friedel-Crafts catalyst.

The benzo[b]thien-3-one (XXXI) is converted to a trifluoromethanesulfonic acid benzo[b]thien-3-yl ester (XXXII) by treating the benzo[b]thien-3-one (XXXI) in an aprotic solvent that has been cooled to about −50° C. to about −100° C. with a base such as lithium diisopropyl amine (LDA). About 20 min. to about 45 min. after addition of the LDA, N-phenyltrifluoromethanesulfonimide is added, and the reaction mixture is allowed to warm up to room temperature. The reaction is complete after about 45 min. to about 1.5 h to form the trifluoromethanesulfonic acid benzo[b]thien-3-yl ester (XXXII).

The the triflate group and the carbonyl group of the trifluoromethanesulfonic acid benzo[b]thien-3-yl ester (XXXII) can be further reacted to form compounds of the invention. The triflate group can be reacted with a substituted phenylboronic acid to form a 3-(substituted phenyl)-benzo[b]thiophene via the method depicted in Scheme I, and the carbonyl group can be converted to an α,β-unsaturated carboxylic acid group via the method depicted in Scheme II.

Scheme VI:
Synthesis of a 3-(substituted phenyl)-benzo[b]thiophene (XXXI) which can be used to prepare compounds represented by Formula I in which ring A is benzo[b]thienyl.

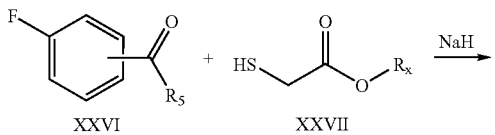

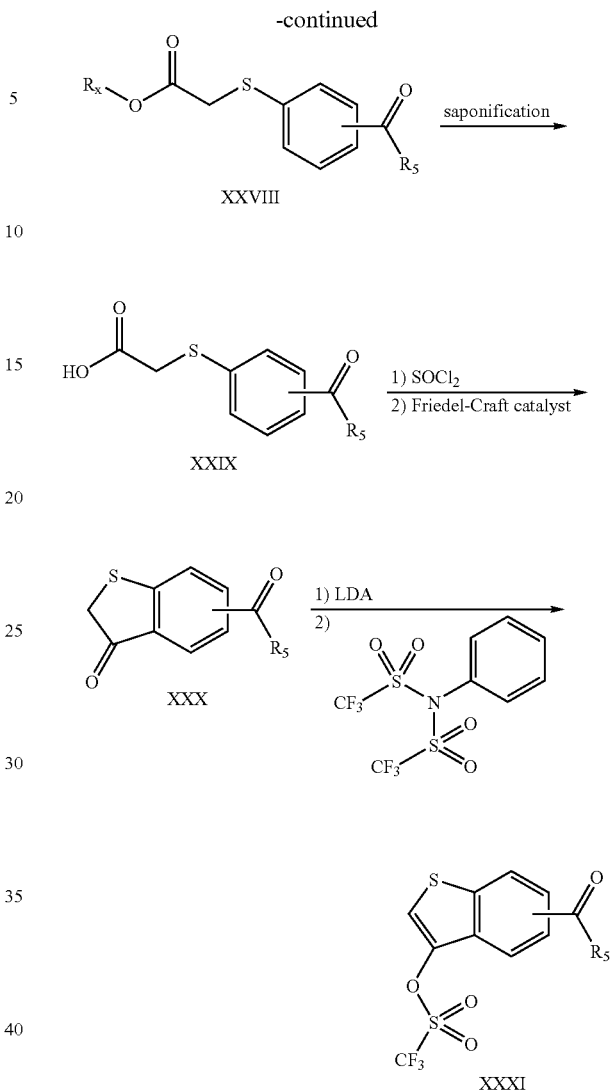

A 3-(substituted phenyl)-(α,β-unsaturated carboxy)-indole (XXXVI) can be prepared from an haloindole in which the amino group has been protected with an amino protecting group, such as a phenylsulfonamide or a carbamate (see Scheme VII). The 1-protected-haloindole (XXXII) is converted into a 1-protected-(α,β-unsaturated carboxylic ester)-indole (XXXIV) by treatment with a large excess (e.g., about 5 eq. to about 10 eq.) of an α,β-unsaturated ester (XXXIII) in the presence of a palladium acetate catalyst and a base as described in Scheme III.

A solution in an organic solvent of the 1-protected-(α,β-unsaturated carboxylic ester)-indole (XXXIV), N-iodosuccinamide (NIS) and an acid catalyst, such as p-toluenesulfonic acid, is stirred for about 3 h to about 6 h at room temperature to form a 1-protected-3-iodo-(α,β-unsaturated carboxylic ester)-indole (XXXV). About 1.5 eq. to about 2.5 eq. of N-iodosuccinamide and about 0.1 eq. to about 0.2 eq of the acid catalyst is present in the solution.

The iodo group can be reacted with a substituted phenylboronic acid to form a 1-protected-3-(substituted phenyl)-(α,β-unsaturated carboxylic ester)-indole via the method depicted in Scheme I. The ester group of the 1-protected- 3-(substituted phenyl)-(α,β-unsaturated carboxylic ester)-indole can be converted to a carboxylic acid group via a saponification reaction, and the indole nitrogen can be deprotected to form a 3-(substituted phenyl)-(α,β-unsaturated carboxy)-indole (XXXVI).

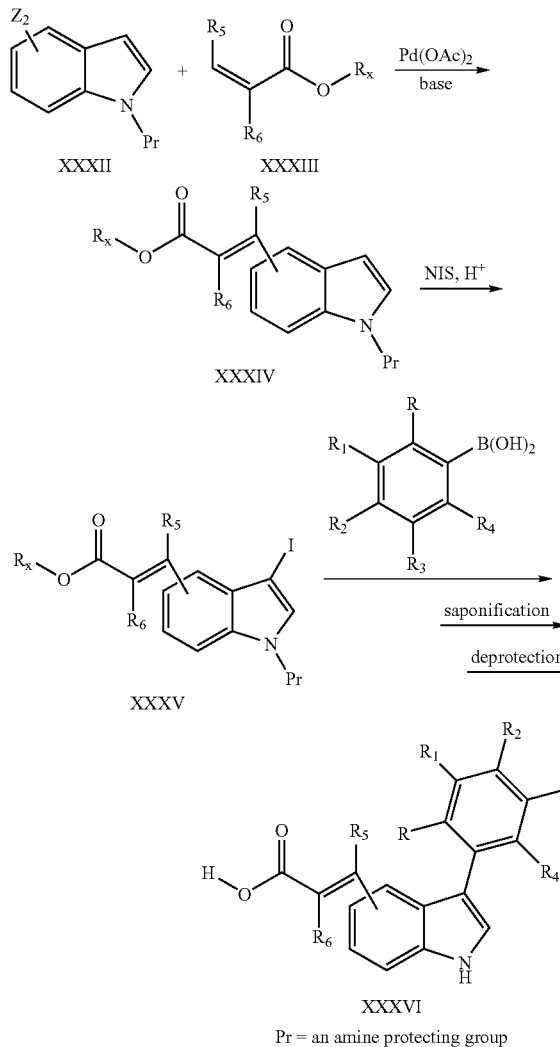

Scheme VII:
Preparation of 3-(substituted phenyl)-(α,β-unsaturated carboxy)-indoles.

Pr = an amine protecting group

A 2-(substituted phenyl)-(α,β-unsaturated carboxy)-indole (XLI) can also be prepared from a 1-protected-haloindole (XXXVII) (see Scheme VIII). A base, such as LDA, is added to a solution of the 1-protected-haloindole (XXXVII) in an aprotic solvent, such as an ether, which is maintained at about −50° C. to about −100° C. About 1 h to about 2 h after the addition of the LDA, the solution is allowed to warm up to about −20° C. to about 10° C. over a period of about 30 min. to about 1 h. The solution is then cooled back down to about −50° C. to about −100° C., then canulated into a solution of chlorotrimethylsilane (TMSCI) in an aprotic solvent which is also maintained at about −50° C. to about −100° C. The reaction is allowed to warm to room temperature and is continued for about 10 h to about 16 h to form a 1-protected-2-trimethylsilyl-haloindole (XXXVIII).

The trimethylsilyl group of the 1-protected-2-trimethylsilyl-haloindole (XXXVIII) is converted into a carbonyl group via a Friedel-Crafts acylation reaction. The Friedel-Crafts acylation is carried out by adding an anhydride or an acid halide (XXXIX) to a mixture of a Friedel-Crafts catalyst in an anhydrous solvent. After about 15 min. to about 30 min., the mixture is cooled to about 10° C. to about −10° C., then the 1-protected-2-trimethylsilyl-haloindole (XXXVIII) is added and the reaction. About 5 eq. to about 7 eq. of the Friedel-Crafts catalyst and about 2.5 eq. to about 3.5 eq. of the anhydride or acid chloride with respect to the 1-protected-2-trimethylsilyl-haloindole (XXXVIII) are present in the reaction mixture. The reaction is allowed to warm to room temperature and continued for about 45 min. to about 2 h to form a 1-protected-2-(carbonyl)-haloindole (XL).

The the halo group and the alkyl ketone group of the 1-protected-2-(carbonyl)-haloindole (XL) can be further reacted to form compounds of the invention. The halo group can be reacted with a substituted phenylboronic acid to form a 1-protected-2-(carbonyl)-(substituted phenyl)-indole via the method depicted in Scheme I, and the carbonyl group can be converted to an α,β-unsaturated carboxylic acid group via the method depicted in Scheme II. Finally, the amino group is deprotected to form a 2-(α,β-unsaturated carboxy)-(substituted phenyl)-indole (XLI).

Scheme VIII:
Preparation of 2-(α,β-unsaturated carboxy)-(substituted phenyl)-indoles (XLI) which can be used to prepare a compound of Formula I in which ring A is an indole.

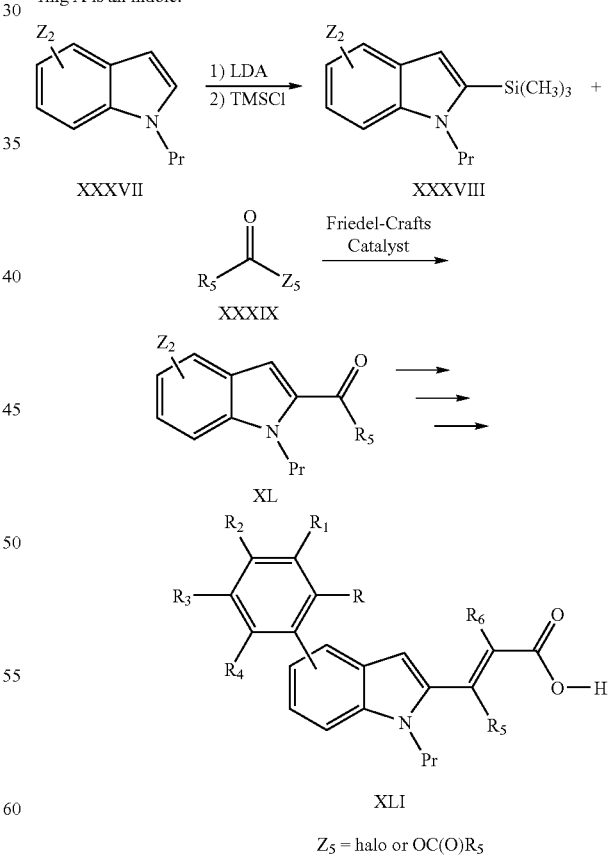

$Z_5$ = halo or OC(O)$R_5$

Compounds of Formula I in which ring A is a isoquinoline or an quinoline can be prepared from a halo-isoquinolin-1-one (XLII) or a carbonyl-quinolin-4-one, respectively (see Scheme IXa which depicts the method for the conversion of halo-isoquinolin-1-one and IXb which depicts the method for the conversion of carbonyl-quinolin-4-one). The halo group of the halo-isoquinolin-1-one (XLII) is converted to an α,β-unsaturated carboxylic ester (XVII) via the method depicted in Scheme III to form an (α,β-unsaturated carboxylic ester)-isoquinolin-1-one (XLIV). The carbonyl group of the (α,β-unsaturated carboxylic ester)-isoquinolin-1-one (XLIV) is converted to a triflate group by adding about 1.1 eq. to about 1.5 eq. trifluoromethane-sulfonic anhydride (Tf$_2$O) to a basic solution of the (α,β-unsaturated carboxylic ester)-isoquinolin-1-one (XLIV) which is maintained at about 0° C. The reaction is complete in about 1 h to about 3 h to form a 1-trifluoromethanesulfonyloxy-(α,β-unsaturated carboxylic ester)-isoquinoline (XLV). The triflate group can be reacted with a substituted phenylboronic acid via the method depicted in Scheme I to form a compound of Formula I in which ring A is an isoquinoline.

Scheme IXa:
Preparation of 4-trifluoromethanesulfonyloxy-(a,b-unsaturated carboxylic ester)-isoquinoline (XLV) which can be used to prepare a compound of Formula I in which ring A is an isoquinoline.

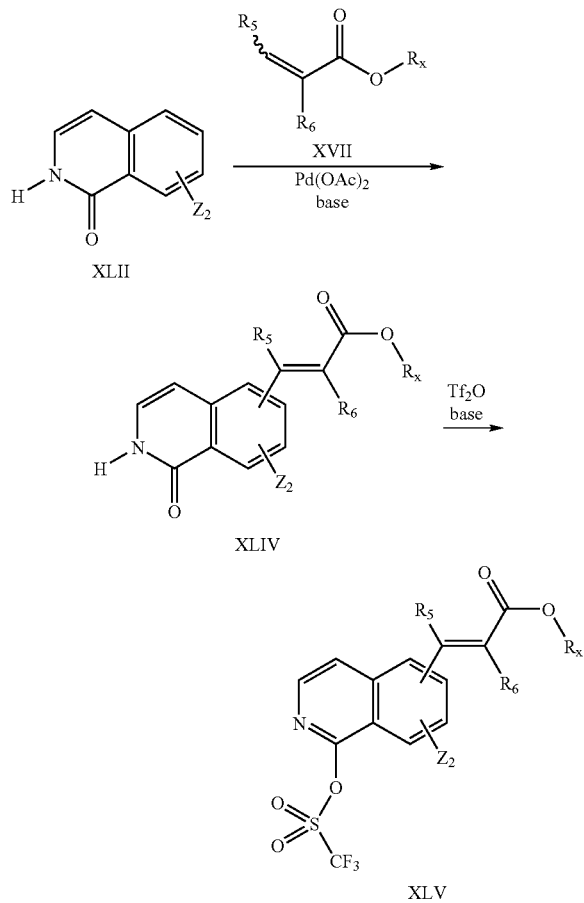

romethanesulfonyloxy-carbonyl-quinoline (LXX). The triflate group can be reacted with a substituted phenylboronic acid (X) via the method depicted in Scheme I to form a (substituted phenyl)-carbonyl-quinoline (LXXI). The carbonyl group of the (substituted phenyl)-carbonyl-quinoline (LXXI) can be converted to an α,β-unsaturated carboxylic ester by adding the (substituted phenyl)-carbonyl-quinoline (LXXI) to a solution of 2-lithio-1,1-diflouroethene (prepared by combining an alkyl lithium with 1,1-difluoroethene at about −78° C.) while maintaining a temperature below −78° C. The resulting alcohol is isolated and immediately treated with methanol and H$_2$SO$_4$ to give a compound of Formula I in which ring A is a quinoline (LXXII).

Scheme IXb:
Preparation of a compound of Formula I in which ring A is a quinoline.

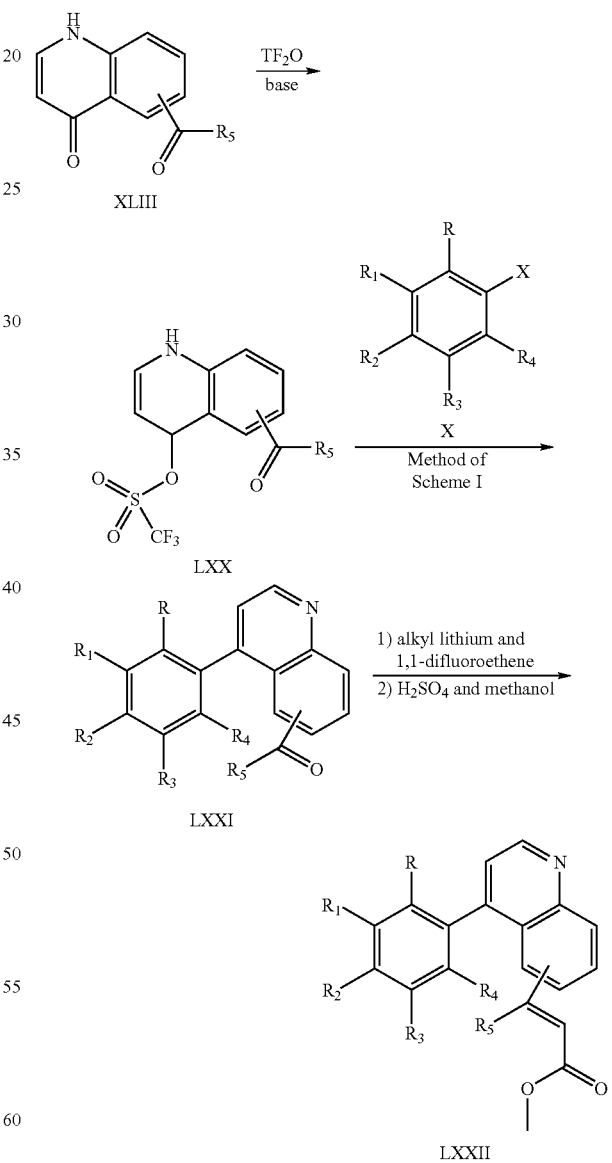

Compounds of Formula I in which ring A is a quinoline can be prepared from a carbonyl-quinolin-1-one (XLM) via the method depicted in Scheme IXb. The carbonyl-quinolin-4-one (XLI) is converted to a triflate group by adding about 1.1 eq. to about 1.5 eq. trifluoromethanesulfonic anhydride (Tf$_2$O) to a basic solution of the carbonyl-quinolin-1-one (XLIII) which is maintained at about 0° C. The reaction is complete in about 1 h to about 3 h to form a 1-trifluo- Compounds of Formula I in which ring A is a thieno[2,3-c]pyridinyl can be prepared from a 2,3-thiophenedicarboxaldehyde (XLVI) (see Scheme X). The pyridinyl ring is formed by cooling a solution of the 2,3-thiophenedicarboxaldehyde (XLVI) in an organic solvent to about −10° C. to about 10° C., then adding about 1 eq. to about 1.5 eq. of (1-acetylamino-2-oxo-propyl)-phosphonic acid dimethyl ester (XLVII) and about 1 eq. to about 1.5 eq of a hindered aprotic base such as 1,8-diazabicyclo[5.4.0]undec-7-ene (DBU). The solution is allowed to come to room temperature and is stirred for about 8 h to about 20 h to form 1-thieno[2,3-c]pyridin-5-yl-ethanone (XLVIII).

The 1-thieno[2,3-c]pyridin-5-ylthanone (XLVIII) dissolved in a mixture of an organic solvent and a saturated bicarbonate solution and treated with about 2 eq. to about a 4 eq. of bromine. After stirring the mixture overnight at room temperature, 1-(3-bromo-thieno[2,3-c]pyridin-5-yl)-ethanone (XLIX) was formed.

A substituted phenyl and a α,β-unsaturated carboxylic acid group can be added to the 1-(3-bromo-thieno[2,3-c]pyridin-5-yl)-ethanone by the method decribed in Scheme I and Scheme II, respectively.

Scheme X:
Preparation of 1-(3-bromo-thieno[2,3-c]pyridin-5-yl)-ethanone (XLIX) which can be used to prepare a compound of Formula I in which ring A is a thieno[2,3-c]pyridine.

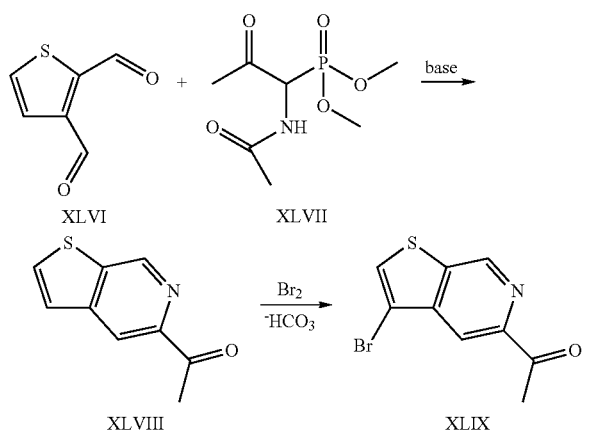

Compounds of Formula I in which ring A is a benzo[d]isoxazole can be prepared from a substituted halobenzene or a substituted trifluoromethanesulfonyloxybenzene (L) (see Scheme XI). The substituted halobenzene or a substituted trifluoromethanesulfonyloxybenzene (L) is dissolved in an aprotic solvent, such as an ether, and then cooled to about −50° C. to bout −100° C. About 1.5 eq. to about 2.5 eq. of an alkyl lithium compound, such as t-butyl lithium, s-butyl lithium or n-butyl lithium, is added, and the reaction is allowed to stir for about 15 min. to about 1 h before a halo-2-fluorobenzaldehyde (LI) is added to the reaction mixture. The reaction is allowed to warm to room temperature and stirred for about 8 h to about 20 h to form a halo-2-fluoro-phenyl)-(substituted phenyl) methanol (LII).

The alcohol group of the (halo-2-fluoro-phenyl)-(substituted phenyl) methanol (LII) is oxidized to a ketone by adding a solution of the (halo-2-fluoro-phenyl)-(substituted phenyl) methanol (LII) in an organic solvent to a suspension of about 1 eq. to about 1.5 eq. of pyridinium chlorochromate (PCC) at room temperature. After about 3 h to about 6 h, a (halo-2-fluoro-phenyl)-(substituted phenyl) methanone (LIII) is formed.

To form the benzo[d]isoxazole ring, about 1 eq. of an oxime, such as acetone oxime (LIV), is added to a mixture of about 1 eq. of a hindered base, such as potassium t-butoxide in an ether. After the mixture is stirred for about 15 min. to about 1 h at room temperature, about 0.7 eq. to about 1 eq. of the (halo-2-fluoro-phenyl)-(substituted phenyl) methanone (LIII) is added, and the reaction is stirred for about 1 h to about 3 h. The reaction is quenched with ammonium chloride, then extracted with an organic solvent. The organic layer is dried over a drying agent such as magnesium sulfate, then filtered and evaporated to a residue. The residue is dissolved in a solution of 1:1 (vol:vol) alcohol/N HCl and refluxed for about 0.5 h to about 2 h to form a halo-3-(2-ethoxy-3,5-diisopropyl-phenyl)-benzo[d]isoxazole (LV).

A α,β-unsaturated carboxylic acid group can be added to the halo-3-(substituted phenyl)-benzo[d]isoxazole (LV) by the method described in Scheme III to form a compound represented by Formula I in which ring A is a benzo[d]isoxazole.

Scheme XI:
Preparation of a halo-3-(substituted phenyl)-benzo[d]isoxazole (LV) which can be used to prepare a compound of Formula I in which ring A is a benzo[d]isoxasole.

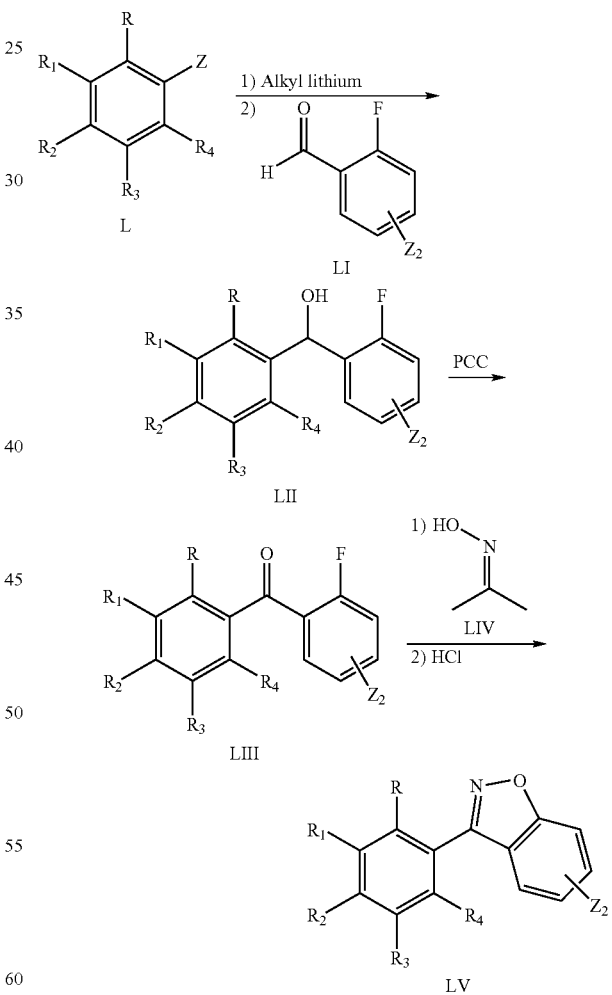

Compounds of Formula I in which ring A is an indazole can be prepared from a (halo-2-fluoro-phenyl)-(substituted phenyl) methanone (LIII) (see Scheme XII). A hydrazone, such as benzophenone hydrazone (LVI), is added to a solution of a hindered base, such as potassium t-butoxide, in a polar organic solvent, such as an ether. The hydrazone and the base are present in the solution in about equal molar amounts. After stirring the mixture for about 15 min. to about 1 h, about 0.7 eq. to about 1 eq. of the (halo-2-fluorophenyl)-(substituted phenyl) methanone (LIII) is added and the mixture is stirred for about 8 h to about 20 h at room temperature. The reaction is quenched with ammonium chloride, then extracted with an organic solvent. The organic layer is dried over a drying agent, such as magnesium sulfate, then filtered and evaporated to a residue. The residue is dissolved in a solution of 1:1 (vol:vol) alcohol/1N HCl and refluxed for about 0.5 h to about 2 h to form a halo-3-(substituted phenyl)-indazole (LVII).

A α,β-unsaturated carboxylic acid group can be added to the halo-3-(substituted phenyl)-indazole (LVII) by the method described in Scheme III to form a compound represented by Formula I in which ring A is an indazole.

Scheme XII:
Preparation of a halo-3-(substituted phenyl)-indazole (LVII) which can be used to prepare a compound of Formula I in which ring A is an indazole.

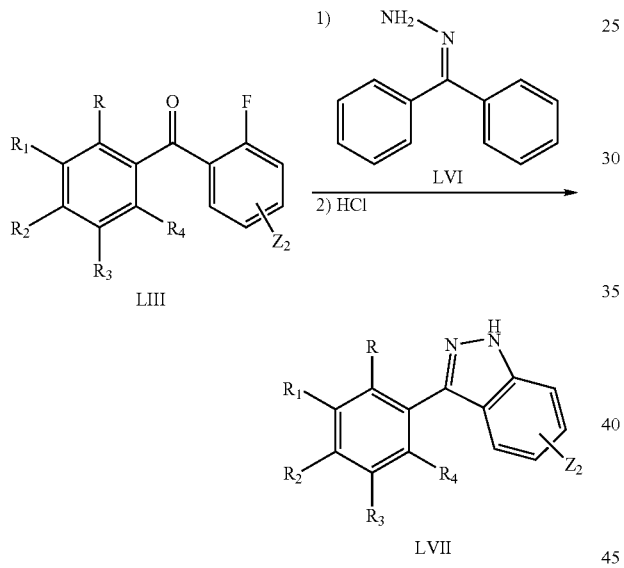

Compounds of Formula I in which ring A is an imidazo[1,2-a]pyridine can be prepared from a 2-amino-halo-pyridine (LVIII) (see Scheme XIII). The halo group of the 2-amino-halo-pyridine can be substituted with an α,β-unsaturated carboxylic ester group via the method depicted in Scheme III to form a 2-amino-(α,β-unsaturated carboxylic ester)-pyridine (LIX).

A haloacetaldehyde dialkyl acetal is refluxed in an aqueous HCl solution to form haloacetaldehyde (LX). After about 15 min. to about 1 h, the reaction is cooled to room temperature and sodium bicarbonate is added until the reaction mixture is basic. About 0.7 eq. to about 1 eq. of 2-amino-(α,β-unsaturated carboxyl ester)-pyridine (LIX) is added to the reaction mixture, and the reaction is allowed to stir for about 8 h to about 20 h to form an (α,β-unsaturated carboxyl ester)-imidazo[1,2-a]pyridine (LXI).

The (α,β-unsaturated carboxyl ester)-imidazo[1,2-a]pyridine (LXI) is dissolved in an organic solvent, and the mixture is cooled to about −10° C. to about 10° C. About 1 eq. to about 1.5 eq. of N-iodosuccinimide (NIS) is added to the reaction mixture. After about 0.5 to about 2 h, 3-iodo-(α,β-unsaturated carboxyl ester)-imidazo[1,2-a]pyridine (LXII) is formed.

The iodo group of the 3-iodo-(α,β-unsaturated carboxyl ester)-imidazo[1,2-a]pyridine (LXII) can be converted to a substituted phenyl group by the method described in Scheme I to form a compound represented by Formula I in which ring A is an imidazo[1,2-a]pyridine.

Scheme XIII:
Preparation of a 3-iodo-(α,β-unsaturated carboxyl ester)-imidazo[1,2-a]pyridine (LXII) which can be used to prepare a compound of Formula I in which ring A is an imidazo[1,2-a]pyridine.

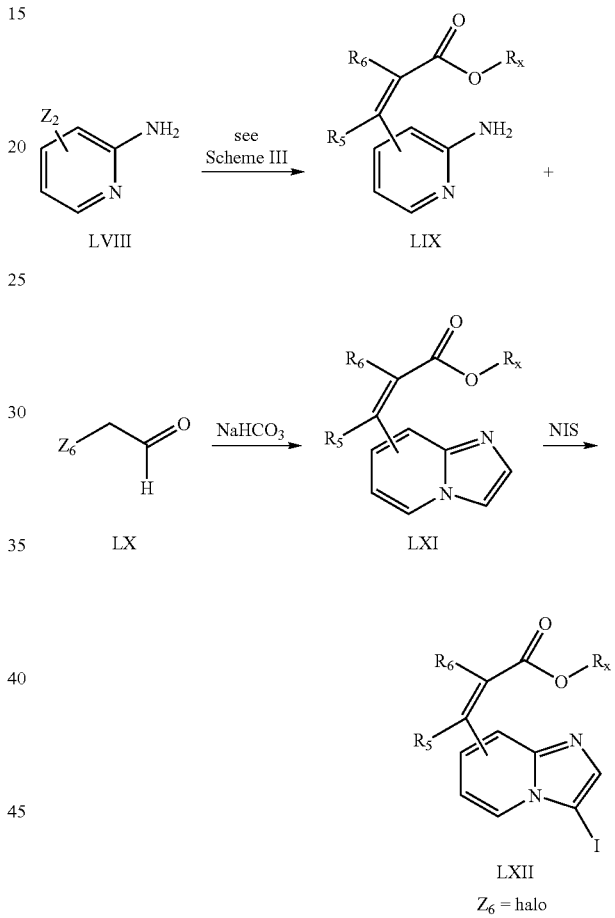

m

Alternatively, compounds of Formula I in which ring A is an imidazo[1,2-a]pyridine can be prepared from a 2-amino-carboxyl-pyridine (LXIII) (see Scheme XIV). A haloacetaldehyde dialkyl acetal is refluxed in an aqueous HCl solution to form haloacetaldehyde (LX). After about 15 min. to about 1 h, the reaction is cooled to room temperature and sodium bicarbonate is added until the reaction mixture is basic. About 0.7 eq. to about 1 eq. of 2-amino-carboxyl-pyridine (LXIII) is added to the reaction mixture and the reaction is allowed to stir for about 8 h to about 20 h to form a carboxy-imidazo[1,2-a]pyridine (LXIV).

A solution of 1 eq. of the carboxy-imidazo[1,2-a]pyridine (LXIV), about 2.5 eq. to about 3.5 eq. cesium carbonate and about 1 eq. to about 2 eq. of iodoalkane in an organic solvent is stirred at room temperature for about 8 h to about 20 h to form a (carboxylic ester)-imidazo[1,2-a]pyridine (LXV).

The (carboxylic ester)-imidazo[1,2-a]pyridine (LXV) is dissolved in an organic solvent, and the mixture is cooled to about −10° C. to about 10° C. About 1 eq. to about 1.5 eq. of N-iodosuccinimide (NIS) is added to the reaction mixture. After about 0.5 to about 2 h, 3-iodo-(carboxylic ester)-imidazo[1,2-a]pyridine (LXVI) is formed.

The iodo group of the 3-iodo-(carboxylic ester)-imidazo[1,2-a]pyridine (LXVI) can be replaced with a substituted phenyl group by the method described in Scheme I to form a 3-(substituted phenyl)-(carboxylic ester)-imidazo[1,2-a]pyridine (LXVII).

The carboxylic ester group of the 3-(substituted phenyl)-(carboxylic ester)-imidazo[1,2-a]pyridine (LXVII) is reduce to an alcohol by treating a solution of 3-(substituted phenyl)-(carboxylic ester)-imidazo[1,2-a]pyridine (LXVII) in an aprotic organic solvent at about −50° C. to about −100° C. with about 2.5 eq. to about 3.5 eq. of diisobutylaluminum hydride (DIBAL-H). After about 3 h to about 6 h, 3-(substituted phenyl)-(hydroxymethyl)-imidazo[1,2-a]pyridine (LXVI is formed.

The hydroxy group of 3-(substituted phenyl)-(hydroxymethyl)-imidazo[1,2-a]pyridine (LXVIII) is oxidized to an aldehyde by treating a solution of the 3-(substituted phenyl)-(hydroxymethyl)-imidazo[1,2-a]pyridine (LXVIII) in an organic solvent with about 1 eq. to about 2 eq. of 4-methylmorpholine N-oxide (NMO) and a catalytic amount (about 0.01 eq. to about 0.1 eq.) of tetrapropylammonium perruthenate (TRAP). The reaction is stirred at room temperature for about 2 h to about 4 h to form of 3-(substituted phenyl)-(aldehyde)-imidazo[1,2-a]pyridine (LXIX).

A α,β-unsaturated carboxylic acid group can be added to the 3-(substituted phenyl)-(aldehyde)-imidazo[1,2-a]pyridine (LXIX) by the method described in Scheme II to form a compound represented by Formula I in which ring A is an imidazo[1,2-a]pyridine.

Scheme XIV:
Preparation of a 3-(substituted phenyl)-(aldehyde)-imidazo[1,2-a]pyridine (LXIX) which can be used to prepare a compound of Formula I in which ring A is an imidazo[1,2-a]pyridine.

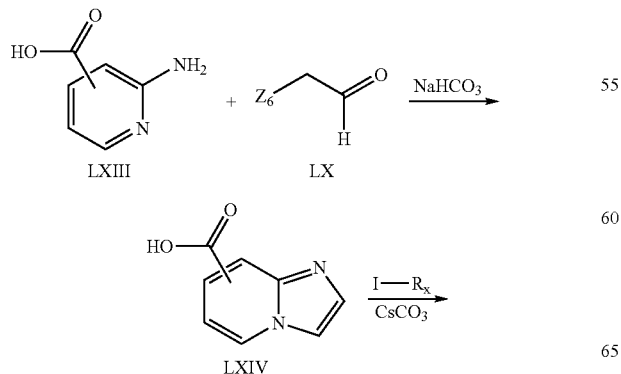

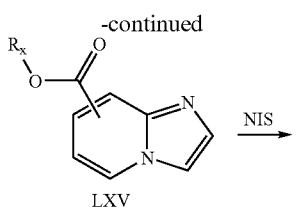

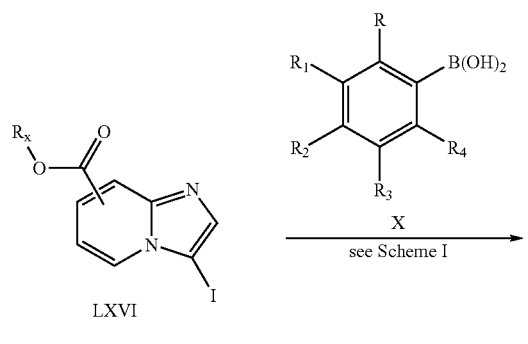

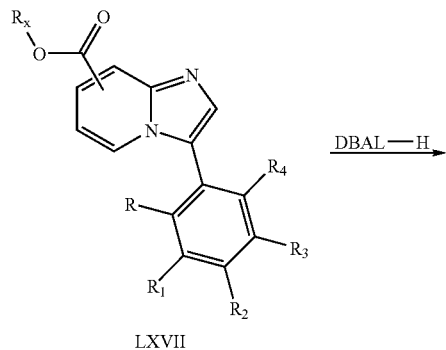

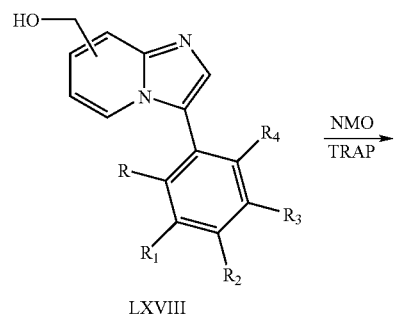

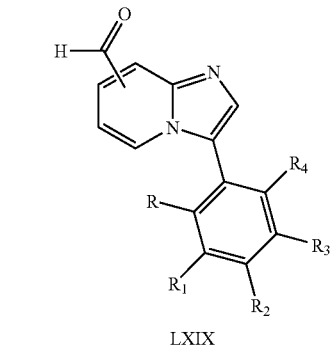

EXAMPLES

Example 1

3-[5-(2-Hydroxy-3-tert-butyl-5-ethylphenyl)-benzo[b]furan-2-yl]-but-2-enoic acid

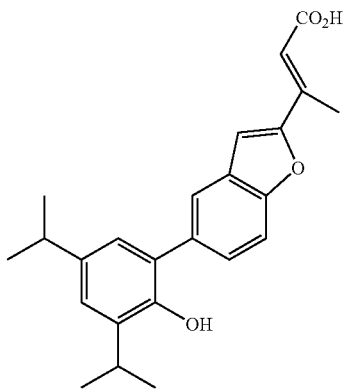

A. 2-Hydroxy-5-(5-ethyl-3-tert-butyl-2-methoxymethoxyphenyl)-benzaldehyde

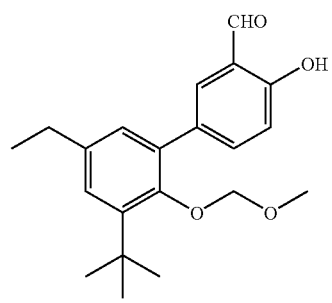

To a mixture of 91 mg (0.078 mmol, 5%) of Pd(PPh₃)₄ and 252 mg (1.26 mmol) of 5-bromo salicylaldehyde in 10 mL of dry toluene was added 685 mmol (2.5 mmol, 2 equivalents) of 2-methoxymethoxy-3-tert-butyl-5-ethyl phenylboronic acid diluted in 5 mL of ethanol followed by 1.3 mL of a 2N aqueous solution of Na₂CO₃. The mixture was stirred at reflux for 3 hours and after cooling extracted with ethyl acetate. The organic layer was dried over MgSO₄ and evaporated under reduced pressure. The residual oil was purified over silica gel (eluent: ethyl acetate/hexane: 10/90) to give 333 mg (0.969 mmol, yield: 77%) of 2-hydroxy-5-(5-ethyl-3-tert-butyl-2-methoxymethoxyphenyl)-benzaldehyde a pale brownb oil. ¹H NMR (CDCl₃), δ: 11.04 (s, 1H), 9.95 (s, 1H), 7.75 (dd, J=8.9, 2.1 Hz, 1H), 7.74 (d, J=2.1 Hz, 1H), 7.19 (d, J=2.1 Hz, 1H), 7.06 (d, J=8.9 Hz, 1H), 6.98 (d, J=1.9 Hz, 1H), 4.52 (s, 2H), 3.29 (s, 3H), 2.64 (dd, J=15.2, 7.6 Hz, 2H), 1.47 (s, 9H), 1.26 (t, J=7.4 Hz, 3H).

B. 2-Acetyl-5-(5-ethyl-3-tert-butyl-2-methoxymethoxyphenyl)-benzo[b]furan

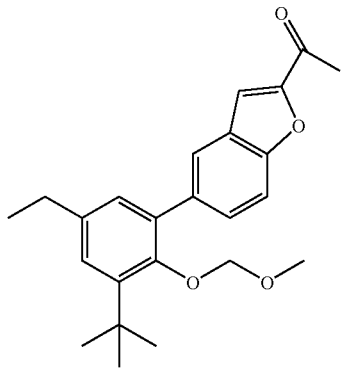

A mixture of 333 mg (0.969 mmol) of 2-hydroxy-5-(5-ethyl-3-tert-butyl-2-methoxymethoxyphenyl)-benzaldehyde, 116 mg (1.26 mmol, 0.1 mL) of chloroacetone and 473 mg (1.45 mmol, 1.5 equivalents) of Cs₂CO₃ in 5 mL of dry DMF was heated to 60° C. overnight. After cooling, water was added (15 mL) and the solution was extracted with ethyl acetate. The organic layer was washed with water and brine, then dried over MgSO₄. Evaporation of the solvents followed by purification over a short silica plug afforded 2-acetyl-5-(5-ethyl-3-tert-butyl-2-methoxymethoxyphenyl)-benzo[b]furan as a clear yellow oil (200 mg, 0526 mmol, yield: 54%). ¹H NMR(CDCl₃), δ:7.85 (d, J=1.4 Hz, 1H), 7.68 (dd, J=8.7, 1.7 Hz, 1H), 7.62 (d, J=8.7 Hz, 1H), 7.19 (d, J=2.1 Hz, 1H), 7.02 (d, J=2.3 Hz, 1H), 4.44 (s, 2H), 3.21 (s, 3H), 2.65 (m, 2H), 2.63 (s, 3H), 1.48 (s, 9H), 1.27 (t, J=7.7 Hz, 3H).

C. 3-[5-(2-Methoxymethoxy-3-tert-butyl-5-ethylphenyl)-benzo[b]furan-2-yl]-but-2-enoic acid ethyl ester

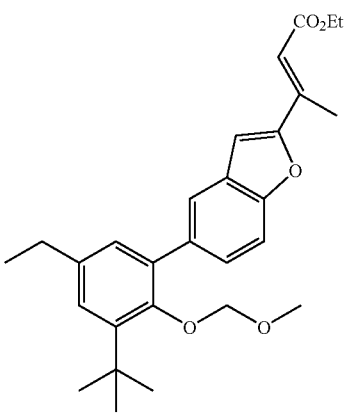

To a mixture of 73 mg (1.52 mmol) of NaH in 2 mL of dry DMF was added 287 mg (1.3 mmol, 0.25 mL) of triethylphosphonoacetate diluted in 1 mL of dry DMF at 0° C. After the gas evolution ceased, the solution was stirred at this temperature for 15 minutes and 195 mg (0.512 mmol) of 2-acetyl-5-(5-ethyl-3-tert-butyl-2-methoxymethoxyphenyl)-benzo[b]furan diluted in 1 mL of dry DMF was added dropwise. The reddish solution was heated to 40° C. until completion (TLC monitoring). After cooling, water was added and the mixture as extracted with ethyl acetate. The organic layer was washed with water and brine and dried over MgSO$_4$. The solvents were evaporated under reduced pressure, and the residual oil was purified over silica gel (eluent: ethyl acetate/hexane: 5/95) to afford 58 mg (0.129 mmol, yield: 25%) of 3-[5-(2-methoxymethoxy-3-tert-butyl-5-ethylphenyl)-benzo[b]furan-2-yl]-butenoic acid ethyl ester as a clear yellow oil. $^1$H NMR (CDCl$_3$), δ: 7.72 (d, J=1.1 Hz, 1H), 7.53 (dd, J=8.5, 1.7 Hz, 1H), 7.49 (d, J=8.5 Hz, 1H), 7.18 (d, J=2.1 Hz, 1H), 6.77 (broad s, 1H), 4.44 (s, 2H), 4.24 (dd, J=14.4, 7.2 Hz, 2H), 3.22 (s, 3H), 2.64 (dd, J=15.1, 7.5 Hz, 2H), 2.56 (s, 3H), 1.48 (s, 9H), 1.34 (t, J=7.2 Hz, 3H), 1.26 (t, J=7.7 Hz, 3H).

D. 3-[5-(2-Methoxymethoxy-3-tert-butyl-5-ethylphenyl)-benzo[b]furan-2-yl]-but-2-enoic acid

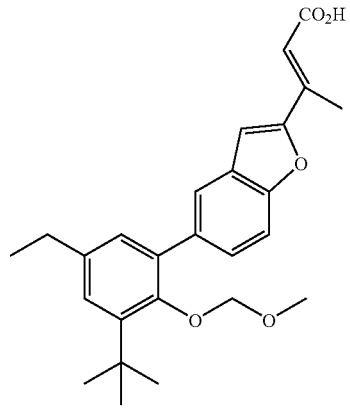

A mixture of 50 mg (0.111 mmol) of 3-[5-(2-methoxymnethoxy-3-tert-butyl-5-ethylphenyl)-benzo[b]furan-2-yl]-but-2-enoic acid ethyl ester in 1 mL of TIF, 1 mL of methanol and 0.5 mL of 2N aqueous LiOH solution was heated to 60° C. until completion (TLC monitoring). After cooling to room temperature the solvents are evaporated, the mixture was acidified with 2N aqueous HCl to pH=1-2 and extracted with ethyl acetate. The organic layer was dried over MgSO$_4$ and the solvents were removed under reduced pressure. The crude acid is directly recrystallized from petroleum ether to give 10 mg (0.023 mmol, yield: 21%) of 3-[5-(2-methoxymethoxy-3-tert-butyl-5-ethylphenyl)-benzo[b]furan-2-yl]-but-2-enoic acid as a yellow powder. $^1$H NMR (CDCl$_3$), δ: 7.73 (broad s, 1H), 7.56 (dd, J=8.5, 1.7 Hz, 1H), 7.50 (d, J=8.5 Hz, 1H), 7.17 (d, J=2.1 Hz, 1H), 7.08 (broad s, 1H), 7.01 (d, J=1.9 Hz, 1H), 6.70 (s, 1H), 4.45 (s, 2H), 3.22 (s, 3H), 2.64 (dd, J=15.2, 7.6 Hz, 2H), 2.58 (s, 3H), 1.48 (s, 9H), 1.26 (t, J=7.6 Hz, 3H).

E. 3-[5-(2-Hydroxy-3-tert-butyl-5-ethylphenyl)-benzo[b]furan-2-yl]-but-2-enoic acid A mixture of 9 mg (0.021 mmol) of 3-[5-(2-methoxymethoxy-3-tert-butyl-5-ethylphenyl)-benzo[b]furan-2-yl]-but-2-enoic acid in 0.5 mL of THF, 0.5 mL of methanol and 2 mL of 6 N aqueous HCL was heated to 40° C. overnight. The solvents were evaporated and the aqueous layer was extracted with ethyl acetate. The organic layer was dried over MgSO$_4$ and the solvents were removed under reduced pressure. The crude acid is directly recrystallized from acetonitrile to afford 5 mg (0.013 mmol, yield: 62%) of 3-[5-(2-hydroxy-3-tert-butyl-5-ethylphenyl)-benzo[b]furan-2-yl]-but-2-enoic acid as a white solid. $^1$H NMR (CDCl$_3$), δ: 7.67 (s, 1H), 7.59 (dd, J=8.4, 2.0 Hz, 1H), 7.43 (d, J=8.4 Hz, 1H), 7.14 (s, 1H), 7.09 (s, 1H), 6.94 (s, 1H), 6.73 (s, 1H), 3.80 (broad s, 1H), 2.64 (dd, J=15.2, 7.4 Hz, 2H), 2.59 (s, 3H), 1.45 (s, 9H), 1.25 (t, J=7.5 Hz, 3H).

Example 2

2-Fluoro-3-[5-(2-methoxy-3,5-diisopropylphenyl)-benzo[b]furan-2-yl]-but-2-enoic acid

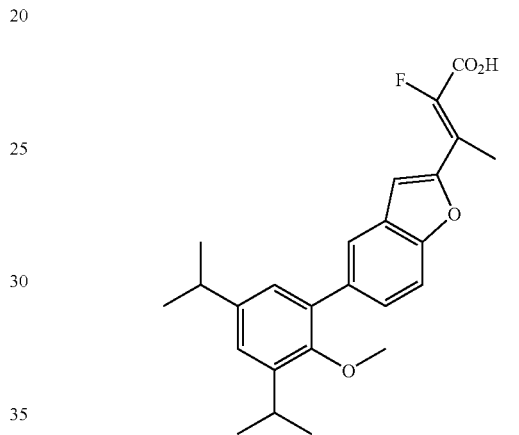

A. 2-Acetyl-5-bromo benzo[b]furan

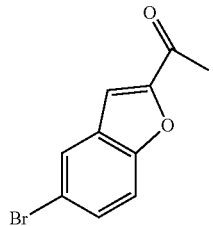

A mixture of 5.0 g (24.9 mmol) of 5-bromo-salicylaldehyde, 3.0 g (32.3 mmol, 2.6 mL) of chloroacetone and 12 g (37.2 mmol) of Cs$_2$CO$_3$ in 30 mL of dry DMF was heated to 60° C. overnight. After cooling at room temperature, water (100 mL) was added and the mixture was extracted with ethyl acetate. The organic layer was dried over MgSO$_4$ and the solvents were removed under reduced pressure. The crude product was directly recrystallized from hexane to afford 4.14 g (17.3 mmol, yield: 70%) of 2-acetyl-5-bromo benzo[b]furan as a pale orange crystal. $^1$H NMR (CDCl$_3$), δ: 7.84 (d, J=1.9 Hz, 1H), 7.56 (dd, J=9.0, 2.1 Hz, 1H), 7.45 (d, J=8.9 Hz, 1H), 7.42 (s, 1H), 2.60 (s, 3H).

B. 2-Acetyl-5-[(2-methoxy-3,5-diisopropyl)-phenyl]benzo[b]furan

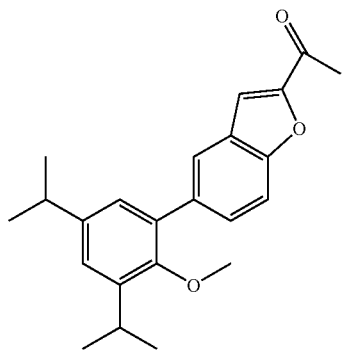

To a mixture of 57 mg (0.049 mmol, 5%) of Pd(PPh$_3$)$_4$, 362 mg (1.26 mmol) of 2-acetyl-5-bromobenzo[b]furan and 297 mg (2.52 mmol) of 2-methoxy-3,5-diisopropyl phenylboronic acid in 10 mL of toluene, and 5 mL of ethanol was added 1.3 mL of a 2N Na$_2$CO$_3$ aqueous solution. The mixture was heated to reflux for 3 hours and after cooling (room temperature) extracted with ethyl acetate. The organic layer was dried over MgSO$_4$ and the solvents were removed under reduced pressure. The crude product was filtrated over a short silica plug (eluent: ethyl acetate/hexane: 10/90) and recrystallized from hexane to afford 309 mg (0.882 mmol, yield: 70%) of 2-acetyl-5-[(2-methoxy-3,5-diisopropyl)-phenyl]benzo[b]furan as a white solid.

$^1$H NMR (CDCl$_3$), δ: 7.91 (s, 1H), 7.74 (d, J=8.6 Hz, 1H), 7.62 (d, J=8.6 Hz, 1H), 7.55 (s, 1H), 7.13 (d, J=1.3 Hz, 1H), 7.05 (d, J=1.3 Hz, 1H), 3.40 (ddd, J=13.8, 6.8, 6.8 Hz, 1H), 3.30 (s, 3H), 2.92 (ddd., J=13.7, 6.9, 6.9 Hz, 1H), 2.63 (s, 3H), 1.29 (m, 6H).

C. 2-Fluoro-3-[5-(2-methoxy-3,5-diisopropylphenyl)-benzo[b]furan-2-yl]-but-2-enoic acid ethyl ester

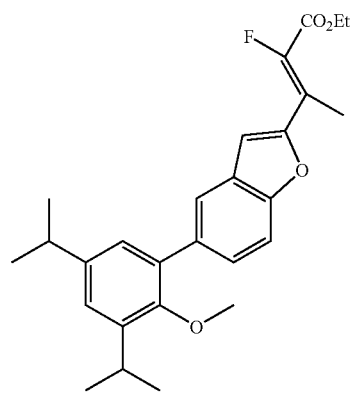

To a mixture of 43 mg (0.89 mmol) of NaH in 1 mL of dry DMF was added 216 mg (0.89 mmol, 0.15 mL) of triethyl 2-fluoro-2-phosphonoacetate diluted in 1 mL of dry DMF at 0° C. After the gas evolution ceased, the solution was stirred at this temperature for 15 minutes and 103 mg (0.296 mmol) of 2-acetyl-5-[(2-methoxy-3,5-diisopropyl)-phenyl]benzo[b]furan diluted in 1 mL of dry DMF was added dropwise. The reddish solution was stirred to 0° C. until completion (TLC monitoring). After cooling, water was added and the mixture as extracted with ethyl acetate. The organic layer was washed with water and brine and dried over MgSO$_4$. The solvents were evaporated under reduced pressure, and the residual oil was purified over silica gel (eluent: ethyl acetate/hexane: 5/95) to afford 67 mg (0.157 mmol, yield: 53%) of 2-fluoro-3-[5-(2-methoxy-3,5-diisopropylphenyl)-benzo[b]furan-2-yl]-but-2-enoic acid ethyl ester (ratio E/Z=1/2) as a clear yellow oil. $^1$H NMR (CDCl$_3$), δ: 7.80 (s, 1H), 7.59 (d, J=8.6 Hz, 1H), 7.49 (m, 1H), 7.29 (d, J=2.9 Hz, 1H), 7.15 (m, 2H), 4.33 (dd, J=14.2, 7.1 Hz, 2H), 3.38 (m, 1H), 3.30 (s, 3H), 2.90 (m, 1H), 2.42 (d, J=3.2 Hz, 3H), 1.40 (t, J=7.1 Hz, 3H), 1.28 (m, 12H).

D. 2-Fluoro-3-[5-(2-methoxy-3,5-diisopropylphenyl)-benzo[b]furan-2-yl]-but-2-enoic acid A mixture of 60 mg (0.136 mmol) of 2-fluoro-3-[5-(2-methoxy-3,5-diisopropylphenyl)-benzo[b]furan-2-yl]-but-2-enoic acid ethyl ester diluted in 1 mL of THF, 1 mL of methanol and 0.5 mL of 2 N aqueous LiOH was heated to 40° C. until complete consumption of the ester. The solvents were evaporated and the aqueous layer was extracted with ethyl acetate. The organic layer was dried over MgSO$_4$ and the solvents were removed under reduced pressure. The crude acid is directly purified over preparative HPLC (eluent: methanol/water+0.1% TFA: 10/90) to afford 10 mg (0.024 mmol, yield: 18%) of the corresponding acid, 2-fluoro-3-[5-(2-methoxy-3,5-diisopropylphenyl)-benzo[b]furan-2-yl]-but-2-enoic acid (30 mg −0.073 mmol, yield: 54% of the E isomer was also isolated) as a pasty oil.

$^1$H NMR (CDCl$_3$), δ: 7.83 (s, 1H), 7.62 (d, J=8.8 Hz, 1H), 7.55 (d, J=8.6 Hz, 1H), 7.38 (d, J=3.8 Hz, 1H), 7.11 (d, J=1.7 Hz, 1H), 7.06 (d, J=1.7 Hz, 1H), 4.33 (dd, J=14.2, 7.1 Hz, 2H), 3.40 (m, 1H), 3.31 (s, 3H), 2.92 (m, 1H), 2.63 (d, J=3.1 Hz, 3H), 1.31 (m, 12H).

Example 3

2-Fluoro-3-[7-(2-propoxy-3-tert-butyl-5-ethylphenyl)-benzo[b]furan-2-yl]-but-2-enoic acid ethyl ester

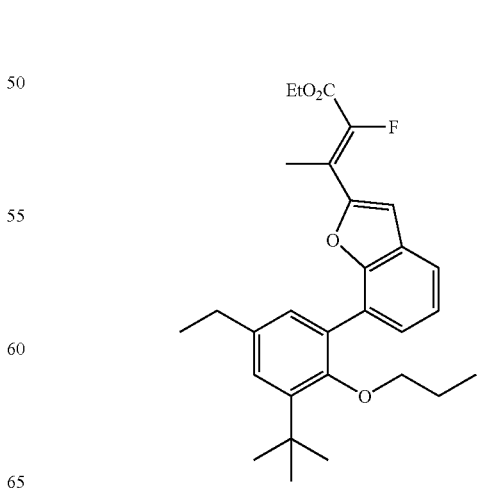

A. 2-Acetyl-7-bromo benzo[b]furan

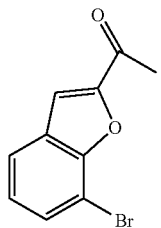

A mixture of 5.0 g (24.9 mmol) of 3-bromo-salicylaldehyde, 3.0 g (32.3 mmol, 2.6 mL) of chloroacetone and 12 g (37.2 mmol) of $Cs_2CO_3$ in 30 mL of dry DMF was heated to 60° C. overnight. After cooling at room temperature, water (100 mL) was added and the mixture was extracted with ethyl acetate. The organic layer was dried over $MgSO_4$ and the solvents were removed under reduced pressure. The crude product was directly recrystallized from hexane to afford 2-acetyl-7-bromo benzo[b]furan as a pale orange crystal.

B. 2-Acetyl-7-(2-propoxy-3-tert-butyl-5-ethylphenyl) benzo[b]furan

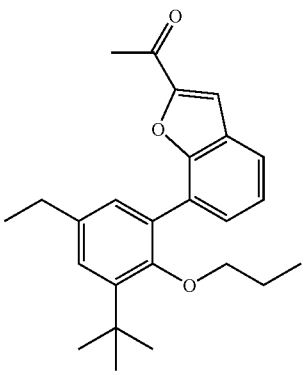

To a mixture of 57 mg (0.049 mmol, 5%) of $Pd(PPh_3)_4$, 362 mg (1.26 mmol) of 2-acetyl-7-bromobenzo[b]furan and 2.52 mmol of 2-propoxy-3-tert-butyl-5-ethyl phenylboronic acid in 10 mL of toluene, and 5 mL of ethanol was added 1.3 mL of a 2N $Na_2CO_3$ aqueous solution. The mixture was heated to reflux for 3 hours and after cooling (room temperature) extracted with ethyl acetate. The organic layer was dried over $MgSO_4$ and the solvents were removed under reduced pressure. The crude product was filtrated over a short silica plug (eluent: ethyl acetate/hexane: 10/90) and recrystallized from hexane to afford 2-acetyl-7-(2-propoxy-3-tert-butyl-5-ethylphenyl)benzo[b]furan as a white solid.

C. 2-Fluoro-3-[7-(2-propoxy-3-tert-butyl-5-ethylphenyl)-benzo[b]furan-2-yl]-but-2-enoic acid ethyl ester To a mixture of 43 mg (0.89 mmol) of NaH in 1 mL of dry DMF was added 216 mg (0.89 mmol, 0.15 mL) of triethyl 2-fluoro-2-phosphonoacetate diluted in 1 mL of dry DMP at 0° C. After the gas evolution ceased, the solution was stirred at this temperature for 15 minutes and 0.296 mmol of 2-acetyl-7-(2-propoxy-3-tert-butyl-5-ethylphenyl) benzo[b]furan diluted in 1 mL of dry DMF was added dropwise. The reddish solution was stirred to 0° C. until completion (TLC monitoring). After cooling, water was added and the mixture as extracted with ethyl acetate. The organic layer was washed with water and brine and dried over $MgSO_4$. The solvents were evaporated under reduced pressure, and the residual oil was purified over silica gel (eluent: ethyl acetate/hexane: 5/95) to afford 2-fluoro-3-[7-(2-propoxy-3-tert-butyl-5-ethylphenyl)-benzo[b]furan-2-yl]-but-2-enoic acid ethyl ester as a clear yellow oil. $^1$H NMR (CDCl$_3$), δ: 7.52 (d, J=7.8 Hz, 1H), 7.52 (d, J=7.2 Hz, 1H), 7.39 (d, J=3.4 Hz, 1H), 7.33 (t, J=7.6 Hz, 1H), 7.22 (d, J=2.1 Hz, 1H), 7.17 (d, J=2.2 Hz, 1H), 3.27 (t, J=6.2 Hz, 2H), 2.66 (dd, J=15.1, 7.5 Hz, 1H), 2.54 (d, J=3.4 Hz, 3H), 1.46 (s, 9H), 1.27 (t, J=7.7 Hz, 3H), 1.19 (m, 2H), 0.50 (t, J=7.4 Hz, 3H).

Example 4

3-[7-(2-Ethoxy-3,5-di-tert-butylphenyl)-benzo[b]furan-2-yl]-but-2-enoic acid

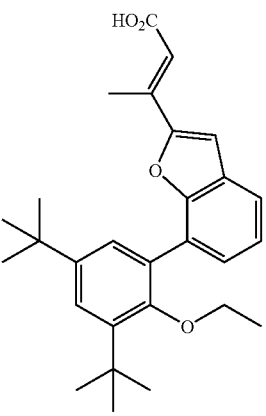

A. 2-Acetyl-7-trifluoromethanesulfonate benzo[b]furan

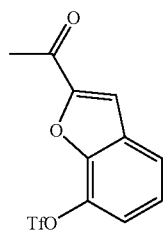

To a mixture of 4.84 g (27.5 mmol) of 2-acetyl-7-hydroxy benzo[b]furan in 40 mL of dry $CH_2Cl_2$ and 10 mL of dry triethylamine was added 10.9 g (30.5 mmol) of phenyltriflimide at room temperature. The mixture was stirred at room temperature until complexion (TLC monitoring) and water was added. The aqueous layer was extracted with $CH_2Cl_2$ and the organic layer was dried over $MgSO_4$. Evaporation of the solvents gave the crude triflate which was recrystallized from hexane to afford 8.0 g (26 mmol, yield: 95%) of 2-acetyl-7-trifluoromethanesulfonate benzo[b]furan as a white solid. $^1$H NMR (CDCl$_3$), δ: 7.74 (d, J=7.7 Hz, 1H), 7.56 (s, 1H), 7.43 (d, J=8.0 Hz, 1H), 7.37 (t, J=8.0 Hz, 1H), 2.65 (s, 3H).

B. 2-Acetyl-7-(3,5-di-tert-butyl-2-ethoxyphenyl)-benzo[b]furan

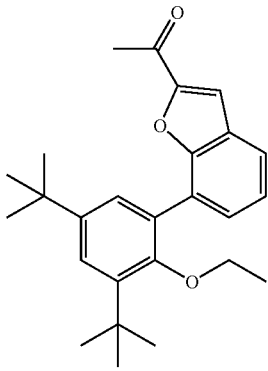

A mixture of 300 mg (1.08 mmol) of 3,5-di-tert-butyl-2-ethoxy phenylboronic acid, 498 mg (1.62 mmol) of 2-acetyl-7-trifluoromethanesulfonate benzo[b]furan and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 395 mg (1.00 mmol, yield: 93%/boronic acid) of 2-acetyl-7-(3,5-di-tert-butyl-2-ethoxyphenyl)-benzo[b]furan as a clear yellow pasty solid. $^1$H NMR (CDCl$_3$), δ: 7.72 (d, J=7.4 Hz, 1H), 7.68 (d, J=7.8 Hz, 1H), 7.56 (s, 1H), 7.42 (s, 2H), 7.38 (d, J=7.6 Hz, 1H), 3.35 (dd, J=13.9, 7.0 Hz, 2H), 2.58 (s, 3H), 1.48 (s, 9H), 1.36 (s, 9H), 0.86 (t, J=7.0 Hz, 3H).

C. 3-[7-(2-Ethoxy-3,5-di-tert-butylphenyl)-benzo[b]furan-2-yl]-but-2-enoic acid ethyl ester

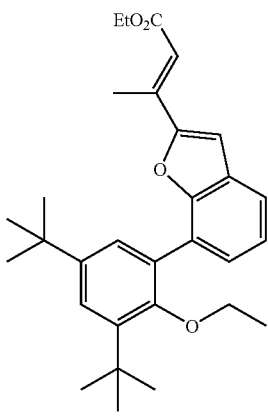

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 200 mg (0.51 mmol) of 2-acetyl-7-(3,5-di-tert-butyl-2-ethoxyphenyl)-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 220 mg (0.476 mmol, yield: 93%) of 3-[7-(2-ethoxy-3,5-di-tert-butylphenyl)-benzo[b]furan-2-yl]-but-2-enoic acid ethyl ester as a pale yellow oil. $^1$H NMR (CDCl$_3$), δ: 7.61 (d, J=7.4 Hz, 1H), 7.55 (d, J=7.6 Hz, 1H), 7.46 (d, J=2.4 Hz, 1H), 7.41 (d, J=2.4 Hz, 1H), 7.29 (t, J=7.6 Hz, 1H), 7.03 (s, 1H), 6.62 (s, 1H), 4.17 (dd, J=14.4, 7.2 Hz, 2H), 3.37 (dd, J=13.9, 7.0 Hz, 2H), 2.54 (s, 3H), 1.49 (s, 9H), 1.36 (s, 9H), 0.89 (t, J=6.9 Hz, 3H).

D. 3-[7-(2-Ethoxy-3,5-di-tert-butylphenyl)-benzo[b]furan-2-yl]-but-2-enoic acid

A mixture of 210 mg (0.450 mmol) of 3-[7-(2-ethoxy-3,5-di-tert-butylphenyl)-benzo[b]furan-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[7-(2-Ethoxy-3,5-di-tert-butylphenyl)-benzo[b]furan-2-yl]-but-2-enoic acid was isolated as a white solid.

$^1$H NMR (CDCl$_3$), δ: 7.62 (d, J=7.4 Hz, 1H), 7.56 (d, J=7.6Hz, 1H), 7.44 (d, J=2.1 Hz, 1H), 7.41 (d, J=2.3 Hz, 1H), 7.31 (t, J=7.8 Hz, 1H), 7.10 (s, 1H), 6.63 (s, 1H), 3.37 (dd, J=13.8, 6.9 Hz, 2H), 2.56 (s, 3H), 1.48 (s, 9H), 1.37 (s, 9H), 0.88 (t, J=6.9 Hz, 3H).

Example 5

3-[7-(2-Ethoxy-3,5-diisopropylphenyl)-benzo[b]furan-2-yl]-but-2-enoic acid

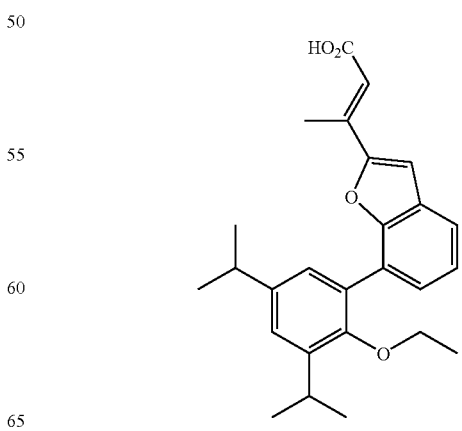

A. 2-Ethoxy-1-iodo-3,5-diiosopropyl-benzene

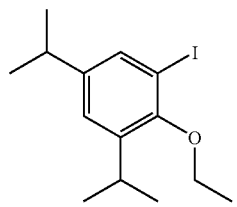

2-Iodo-4,6-diisopropyl-phenol (6.08 g, 20 mmol), cesium carbonate (13 g, 40 mmol) and iodoethane (2.43 ml, 30 mmol) were reacted in dimethylformamide (100 mL) at room temperature. The reaction was diluted with water (100 mL)/hexane (30 mL). The solids were dissolved and the water layer separated and extracted with hexane (15 mL). The hexane portions were combined, dried ($Na_2SO_4$), and concentrated in vacuo to provide (6.50 g, 98%) of a yellow oil. $^1$H NMR (250 MHz, $CDCl_3$): δ 7.46 (d, 1H, J=2.1), 7.05 (d, 1H, J=2.1), 3.83, (t, 2H, J=6.6), 3.31 (sep, 1H, J=6.9), 2.81 (sep, 1H, J=6.9), 1.82 (m, 21), 1.55 (m, 2H), 1.22 (d, 6H, J=6.9), 1.21 (d, 6H, J=6.9).

B. (2-Ethoxy-3,5-diisopropylphenyl)-boronic acid

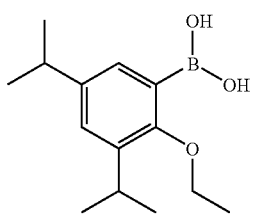

2-Ethoxy-1-iodo-3,5-diiosopropyl-benzene (56 mmol) was dissolved in anhydrous THF (250 mL) under nitrogen and cooled to −75° C. to in a dry ice/acetone bath. t-Butyl lithium (72.6 mL, 123 mmol, 1.7 M in pentane) was added over 21 min at −73° C. and the suspension was stirred for 40 min. Trimethyl borate (27.6 mL, 246 mmol) was added at −73° C. The dry ice bath was left in place and the reaction allowed to warm to 12° C. overnight. The reaction was stirred 30 min with 1N $H_2SO_4$ (125 mL) and then diluted into water (125 mL)/EtOAc (175 mL). The organic phase was separated and washed with 10% aqueous $NaHCO_3$, dried ($Na_2SO_4$) and concentrated in vacuo to provide 15.7 g of a viscous yellow oil. The oil was passed over a large silica pad with a gradient elution of hexane, (95:5) hexane:ethyl acetate, (9:1) hexane:ethyl acetate and (4:1) hexane:ethyl acetate. The product came off in (95:5) and (9:1) hexane:ethyl acetate providing (54.8 g, 70%) as a yellow solid. Mp: 86-89° C. $^1$H NMR (250 MHz, $CDCl_3$): δ 7.52 (d, 1H, J=2.4), 7.24 (d, 1H, J=2.4), 6.27 (s, 2H), 3.89 (q, 2H, J=7.0), 3.26 (sep, 1H, J=6.9), 2.90 (sep, 1H, J=6.9), 1.46 (t, 3H, J=7.0), 1.26 (d, 6H, J=6.9), 1.25 (d, 6H, J=6.9).

C. 2-Acetyl-7-(3,5-diisopropyl-2-ethoxyphenyl)-benzo[b]furan

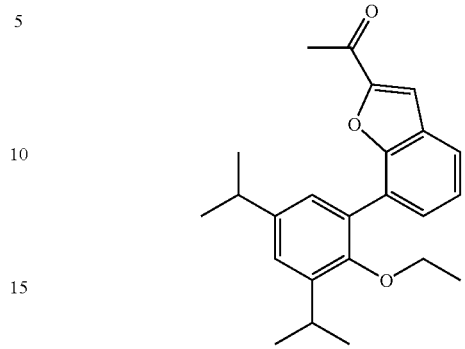

A mixture of 1.08 mmol of 3,5-diisopropyl-2-ethoxy phenylboronic acid, 498 mg (1.62 mmol) of 2-acetyl-7-trifluoromethanesulfonate benzo[b]furan (see Example 4, step A) and 62 mg (0.05 mmol) of $Pd(PPh_3)_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over $MgSO_4$ and after evaporation of the solvents, the crude oil was purified over a short silica plug (eluent: 10/90=ethyl acetate/hexane) to afford 2-acetyl-7-(3,5-diisopropyl-2-ethoxyphenyl)-benzo[b]furan as a clear yellow pasty solid.

D. 3-[7-2-Ethoxy-3,5-diisopropylphenyl)-benzo[b]furan-2-yl]-but-2-enoic acid ethyl ester

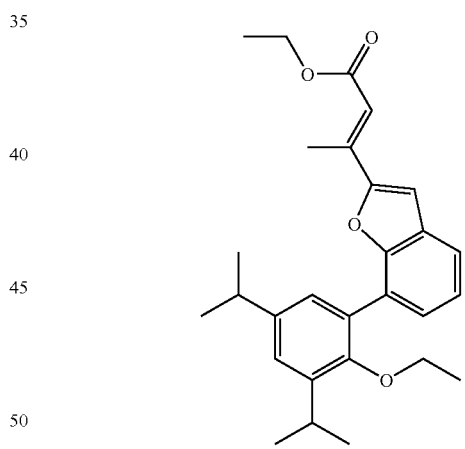

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMN) at 0° C. After the gas evolution has ceased, 0.51 mmol of 2-acetyl-7-(3,5-diisopropyl-2-ethoxyphenyl)-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over $MgSO_4$. After evaporation of the solvents, the crude oil is purified over a short plug of silica gel (eluent: 95/5 hexane/ ethyl acetate) to afford 3-[7-(2-ethoxy-3,5-diisopropylphenyl)-benzo[b]furan-2-yl]-but-2-enoic acid ethyl ester as a pale yellow oil.

E. 3-[7-(2-Ethoxy-3,5-diisopropylphenyl)-benzo[b]furan-2-yl]-but2-enoic acid A mixture of 0.450 mmol of 3-[7-(2-ethoxy-3,5-diisopropylphenyl)-benzo[b]furan-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[7-(2-Ethoxy-3,5-diisopropylphenyl)-benzo[b]furan-2-yl]-but-2-enoic acid was isolated as a white solid. $^1$H-NMR (CDCl$_3$), δ: 7.65 (d, J=7.5 Hz, 1H, Ar—H), 7.56 (d, J=7.7 Hz, 1H, Ar—H), 7.33 (d, J=2.0 Hz, 1H, Ar—H), 7.29 (t, J=7.6 Hz, 1H, Ar—H), 7.16 (d, J=2.0 Hz, 1H, Ar—H), 7.11 (s, 1H, furan-H), 6.60 (s, 1H, C=C—H), 3.43 (m, 3H, CH$_3$—CH—CH$_3$, O—CH$_2$—CH$_3$), 2.95 (m, 1H, CH$_3$—CH—CH$_3$), 2.57 (s, 3H, C=C—CH$_3$), 1.31 (d, J=6.9 Hz, 12H, CH$_3$—CH—CH$_3$), 0.97 (t, J=7.0 Hz, 3H, O—CH$_2$—CH$_3$).

Example 6

3-[7-(2-propoxy-3,5-diisopropylphenyl)-benzo[b]furan-2-yl]-but-2-enoic acid

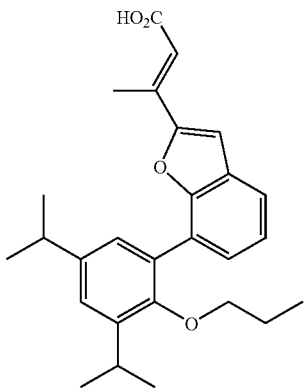

A. 2-Acetyl-7-(3,5-diisopropyl-2-propoxyphenyl)-benzo[b]furan

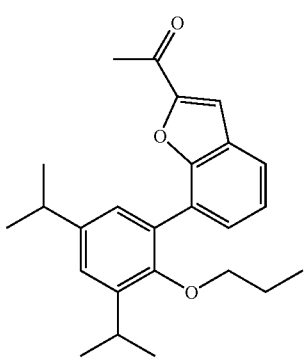

A mixture of 1.08 mmol of (3,5-diisopropyl-2-propoxyphenyl)-boronic acid, 498 mg (1.62 mmol) of 2-acetyl-7-trifluoromethanesulfonate benzo[b]furan (see Example 4, step A) and 62 mg (0.05 mmol) of Pd(Ph$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-acetyl-7-(3,5-diisopropyl-2-propoxyphenyl)-benzo[b]furan as a clear yellow pasty solid.

B. 3-[7-(2-Propoxy-3,5-diisopropylphenyl)-benzo[b]furan-2-yl]-but-2-enoic acid ethyl ester

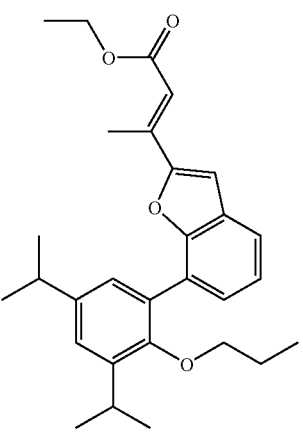

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-7-(3,5-di-isopropyl-6-propoxybenzene)-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 3-[7-(2-propoxy-3,5-diisopropylphenyl)-benzo[b]furan-2-yl]-but-2-enoic acid ethyl ester as a pale yellow oil.

C. 3-[7-(2-Propoxy-3,5-diisopropylphenyl)-benzo[b]furan-2-yl]-but-2-enoic acid A mixture of 0.450 mmol of 3-[7-(2-propoxy-3,5-diisopropylphenyl)-benzo[b]furan-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[7-(2-Propoxy-3,5-diisopropylphenyl)-benzo[b]furan-2-yl]-but-2-enoic acid was isolated as a white solid. $^1$H-NMR (CDCl$_3$), δ: 7.61 (d, J=7.1 Hz, 1H, Ar—H), 7.56 (d, J=7.8 Hz, 1H, Ar—H), 7.28 (m, 2H, Ar—H, Ar—H), 7.16 (d, J=2.2 Hz, 1H, Ar—H), 7.10 (s, 1H, furan-H), 6.60 (s, 1H, C=C—H), 3.43 (m, 1H, CH$_3$—CH—CH$_3$), 3.30 (t, J=6.4 Hz, 2H, O—CH$_2$—CH$_2$—CH$_3$), 2.95 (m, 1H, CH$_3$—CH—CH$_3$, 2.56 (s, 3H, C=C—CH₃), 1.32 (m, 14, CH₃—CH—CH₃, O—CH₂—CH₂—CH₃), 0.64 (t, J=7.4 Hz, 3H, O—CH₂—CH₂—CH₃).

Example 7

3-{7-[2-(3-Fluoropropoxy)-3,5-diisopropylphenyl]-benzo[b]furan-2-yl}-but-2-enoic acid

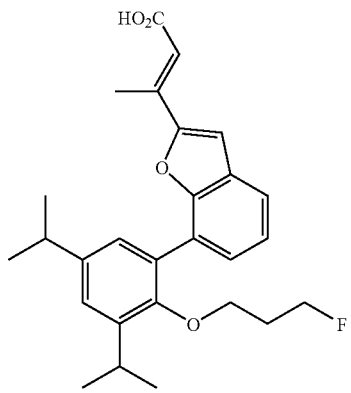

A. Acetyl-7-[3,5-diisopropyl-2-(3-fluoropropoxy)phenyl]-benzo[b]furan

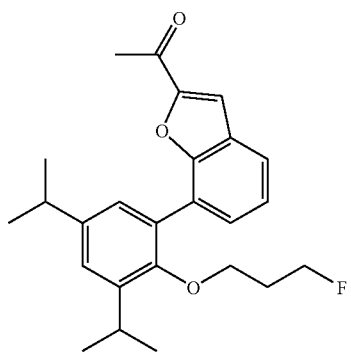

A mixture of 1.08 mmol of 3,5-diisopropyl-2-(3-fluoropropoxy) phenylboronic acid, 498 mg (1.62 mmol) of 2-acetyl-7-trifluoromethanesulfonate benzo[b]furan (see Example 4, step A) and 62 mg (0.05 mmol) of Pd(PPh₃)₄, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO₄ and after evaporation of the solvents, the crude oil was purified over a short silica plug (eluent: 10/90=ethyl acetate/hexane) to afford 2-acetyl-7-[3,5-diisopropyl-2-(3-fluoropropoxy)phenyl]-benzo[b]furan as a clear yellow pasty solid.

B. 3-{7-[2-(3-Fluoropropoxy)-3,5-diisopropylphenyl]-benzo[b]furan-2-yl}-but-2-enoic acid ethyl ester

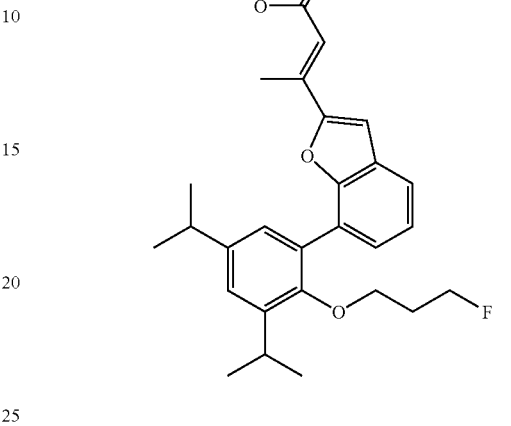

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-7-[3,5-diisopropyl-2-(3-fluoropropoxy)phenyl]-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO₄. After evaporation of the solvents, the crude oil is purified over a short plug of silica gel (eluent: 95/5 hexane/ethyl acetate) to afford 3-{7-[2-(3-fluoropropoxy)-3,5-diisopropylphenyl]-benzo[b]furan-2-yl}-but-2-enoic acid ethyl ester as a pale yellow oil.

C. 3-{7-[2-(3-Fluoropropoxy)-3,5-diisopropylphenyl]-benzo[b]furan-2-yl}-but-2-enoic acid A mixture of 0.450 mmol of 3-{7-[2-(3-fluoropropoxy)-3,5-diisopropylphenyl]-benzo[b]furan-2-yl}-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO₄ and after evaporation of the solvents, the crude acid was recrystallized from acetonitrile. 3-{7-[2-(3-Fluoropropoxy)-3,5-diisopropylphenyl]-benzo[b]furan-2-yl}-but-2-enoic acid was isolated as a white solid. ¹H-NMR (CDCl₃),: 7.58 (d, J=6.7 Hz, 1H, Ar—H), 7.56 (d, J=6.2 Hz, 1H, Ar—H), 7.29 (t, J=7.6 Hz, 1H, Ar—H), 7.28 (d, J=2.2 Hz, 1H, Ar—H), 7.17 (d, J=2.1 Hz, 1H, Ar—H), 7.11 (s, 1H, furan-H), 6.59 (s, 1H, C=C—H), 4.25 (dt, J=47.1 Hz, J=6.1 Hz, 2H, O—CH₂—CH₂—CH₂F), 3.46 (t, J=5.9 Hz, 2H, O—CH₂—CH₂—CH₂F), 3.38 (m, 1H, CH₃—CH—CH₃), 2.95 (m, 1H, CH₃—CH—CH₃), 2.56 (s, 3H, C=C—CH₃), 1.70 (m, 2H, O—CH₂—CH₂—CH₂F), 1.32 (d, J=5.7 Hz, 6H, CH₃—CH—CH₃), 1.30 (d, J=6.6 Hz, 6H, CH₃—CH—CH₃).

Example 8

Ethyl-2-carboxylate-7-(2-ethoxy-3,5-diisopropylbenzene)-benzo[b]thiophene

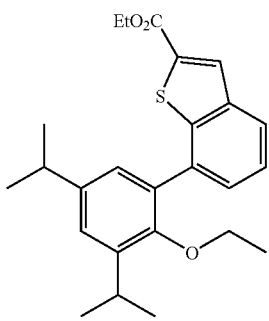

A mixture of 300 mg (1.2 mmol) of 2-ethoxy-3,5-diisopropylphenylboronic acid, 265 mg (0.8 mmol) of ethyl-2-carboxylate-7-iodo benzo[b]thiophene, 46 mg (0.04 mmol) Pd(PPh$_3$)$_4$, 6 mL of toluene, 3 mL of absolute ethanol and 0.8 mL of a 2N Na$_2$CO$_3$ aqueous solution was refluxed for 5 hours. After cooling at room temperature, water was added and the mixture was extracted with ethyl acetate. The organic layer were dried over MgSO$_4$ and after evaporation, the crude oil was purified over silica gel (eluent: 10/90 ethyl acetate/hexane) to afford 284 mg (0.692 mmol, yield=86%) of ethyl-2-carboxylate-7-(2-ethoxy-3,5-diisopropylbenzene)-benzo[b]thiophene. $^1$H-NMR (CDCl$_3$), δ: 8.12 (s, 1H), 7.85 (dd, J=7.8, 0.9 Hz, 1H), 7.55 (d, J=6.6 Hz, 1H), 7.47 (t, J=7.6 Hz, 1H), 7.19 (d, J=2.2 Hz, 1H), 7.17 (d, J=2.2 Hz, 1H), 4.38 (dd, J=14.1, 7.0 Hz, 2H), 3.43 (dt, J=13.8, 6.9 Hz, 1H), 3.33 (dd, J=14.0, 7.0 Hz, 2H), 2.92 (dt, J=13.8, 6.9 Hz, 1H), 1.38 (t, J=7.2 Hz, 3H), 1.28 (m, 12H), 0.88 (t, J=7.1 Hz, 3H).

Example 9

3-{7-[2-(2,2-Difluoroethoxy)-3,5-diisopropylphenyl]-benzo[b]furan-2-yl}-but-2-enoic acid

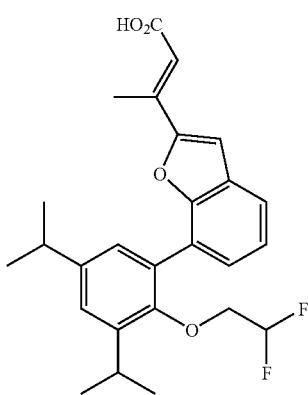

A. 2-Acetyl-7-[3,5-diisopropyl-2-(2,2-difluoroethoxy)phenyl]-benzo[b]furan

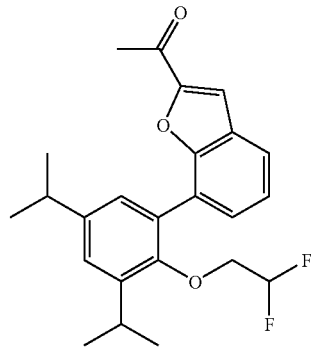

A mixture of 1.08 mmol of 3,5-diisopropyl-2-(2,2-difluoroethoxy) phenylboronic acid, 498 mg (1.62 mmol) of 2-acetyl-7-trifluoromethanesulfonate benzo[b]furan (see Example 4, step A) and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-acetyl-7-[3,5-diisopropyl-2-(2,2-difluoroethoxy)phenyl]-benzo[b]furan as a clear yellow pasty solid.

B. 3-{7-[2-(2,2-Difluoroethoxy)-3,5-diisopropylphenyl]-benzo[b]furan-2-yl}-but-2-enoic acid ethyl ester

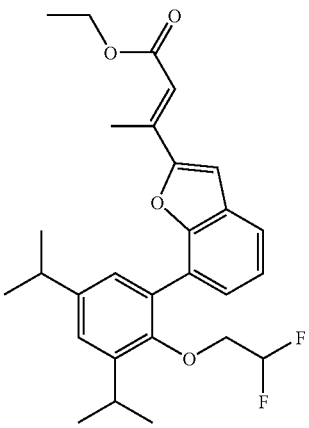

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-7-[3,5-diisopropyl-2-(2,2-difluoroethoxy)phenyl]-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO₄. After evaporation of the solvents, the crude oil is purified over a short plug of silica gel (eluent: 95/5 hexane/ethyl acetate) to afford 3-{7-[2-(2,2-difluoroethoxy)-3,5-diisopropylphenyl]-benzo[b]furan-2-yl}-but-2-enoic acid ethyl ester as a pale yellow oil.

C. 3-{7-[2-(2,2-Difluoroethoxy)-3,5-diisopropylphenyl]-benzo[b]furan-2-yl}-but-2-enoic acid A mixture of 0.450 mmol of 3-{7-[2-(2,2-difluoroethoxy)-3,5-diisopropylphenyl]-benzo[b]furan-2-yl}-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO₄ and after evaporation of the solvents, the crude acid was recrystallized from acetonitrile. 3-{7-[2-(2,2-Difluoroethoxy)-3,5-diisopropylphenyl]-benzo[b]furan-2-yl}-but-2-enoic acid was isolated as a white solid. ¹H-NMR (400 MHz, CDCl₃) δ 7.60 (d, J=7.1 Hz, 1H, Ar—H), 7.57 (d, J=7.4 Hz, 1H, Ar—H), 7.32 (d, J=2.3 Hz, 1H, Ar—H), 7.31 (t, J=7.6 Hz, 1H, Ar—H), 7.18 (d, J=2.2 Hz, 1H, Ar—H), 7.11 (s, 1H, furan-H), 6.58 (s, 1H, C=C—H), 5.54 (tt, J=55.3 Hz, J=4.2 Hz, 1H, O—CH₂—CF₂H), 3.54 (dt, J=13.6 Hz, J=4.2 Hz, 2H, O—CH₂—CF₂H), 3.42 (m, 1H, CH₃—CH—CH₃), 2.96 (m, 1H, CH₃—CH—CH₃), 2.57 (s, 3H, C=C—CH₃), 1.32 (d, J=6.8 Hz, 6H, CH₃—CH—CH₃), 1.31 (d, J=6.8 Hz, 6H, CH₃—CH—CH₃).

Example 10

(E)-2-Fluoro-3-{7-[2-(2,2-difluoroethoxy)-3,5-diisopropylphenyl]-benzo[b]furan-2-yl}-but-2-enoic acid

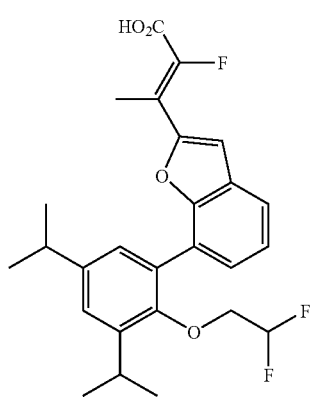

A. 2-Fluoro-3-{7-[2-(2,2-difluoroethoxy)-3,5-diisopropylphenyl]-benzo[b]furan-2-yl}-but-2-enoic acid ethyl ester

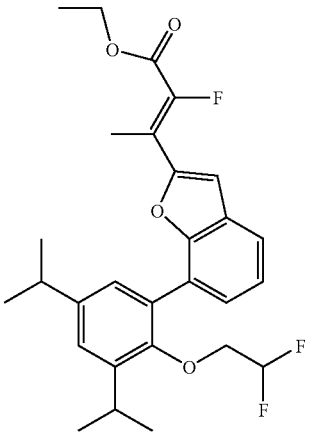

To a slurry of 74 mg (1.54 mmol) of NaH (50% in mineral oil) in 3 mL of dry DMF was added 285.6 mg (1.27 mmol, 2.5 equivalents) of triethyl 2-fluoro-2-phosphonoacetate (diluted in 1 mL of dry DMF) at 0° C. After the gas evolution has ceased, 0.51 mmol of 2-acetyl-7-[3,5-diisopropyl-2-(2,2-difluoroethoxy)phenyl]-benzo[b]furan (see Example 9, step A) diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO₄. After evaporation of the solvents, the crude oil is purified over a short plug of silica gel (eluent: 95/5 hexane/ethyl acetate) to afford 2-fluoro-3-{7-[2-(2,2-difluoroethoxy)-3,5-diisopropylphenyl]-benzo[b]furan-2-yl}-but-2-enoic acid ethyl ester as a pale yellow oil.

B. 2-Fluoro-3-{7-[2-(2,2-difluoroethoxy)-3,5-diisopropylphenyl]-benzo[b]furan-2-yl}-but-2-enoic acid A mixture of 0.450 mmol of 2-fluoro-3-{7-[2-(2,2-difluoroethoxy)-3,5-diisopropylphenyl]-benzo[b]furan-2-yl}-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO₄ and after evaporation of the solvents, the crude acid was recrystallized from acetonitrile. 2-Fluoro-3-{7-[2-(2,2-difluoroethoxy)-3,5-diisopropylphenyl]-benzo[b]furan-2-yl}-but-2-enoic acid was isolated as a white solid. ¹H-NMR (400 MHz, CDCl₃) δ 7.65 (d, J=8.1 Hz, 1H, Ar—H), 7.58 (d, J=7.3 Hz, 1H, Ar—H), 7.41 (d, J=3.0 Hz, 1H, furan-H), 7.34 (t, J=7.6 Hz, 1H, Ar—H), 7.31 (d, J=2.2 Hz, 1H, Ar—H), 7.17 (d, J=2.2 Hz, 1H, Ar—H), 5.52 (tt, J=55.2 Hz, J=4.1 Hz, 1H, O—CH₂—CF₂H), 3.52 (dt, J=13.6 Hz, J=4.1 Hz, 2H, O—CH₂—CF₂H), 3.41 (m, 1H, CH₃—CH—CH₃), 2.95 (m, 1H, CH₃—CH—CH₃), 2.56 (d, J=3.5 Hz, 3H, C=C—CH₃), 1.31 (d, J=6.7 Hz, 6H, CH₃—CH—CH₃), 1.29 (d, J=6.8 Hz, 6H, CH₃—CH—CH₃).

Example 11

(E)-3-{7-[5,5,8,8,-Tetramethyl-3-ethoxy-5,6,7,8-tetrahydronaphth-2-yl]-benzo[b]furan-2-yl}-but-2-enoic acid

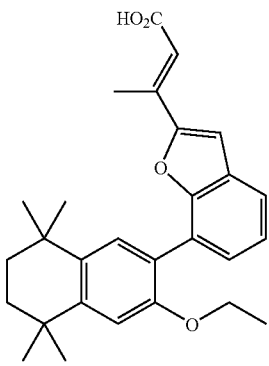

A. 2-Acetyl-7-(5,5,8,8,-tetramethyl-3-ethoxy-5,6,7,8-tetrahydronaphth-2-yl)-benzo[b]furan

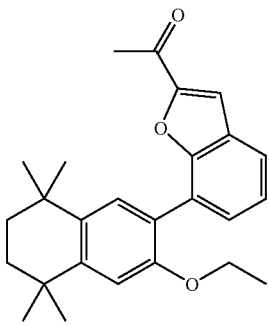

A mixture of 1.08 mmol of (5,5,8,8,-tetramethyl-3-ethoxy-5,6,7,8-tetrahydronaphth-2-yl)-boronic acid, 498 mg (1.62 mmol) of 2-acetyl-7-trifluoromethanesulfonate benzo[b]furan (see Example 4, step A) and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-acetyl-7-(5,5,8,8,-tetramethyl-3-ethoxy-5,6,7,8-tetrahydronaphth-2-yl)-benzo[b]furan as a clear yellow pasty solid.

B. (E)-3-{7-[5,5,8,8,-Tetramethyl-3-ethoxy-5,6,7,8-tetrahydronaphth-2-yl]-benzo[b]furan-2-yl}-but-2-enoic acid ethyl ester

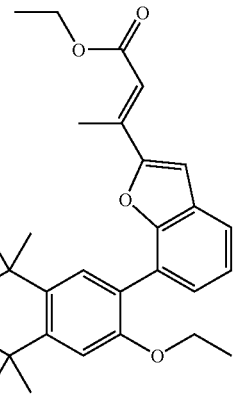

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-7-(5,5,8,8,-tetramethyl-3-ethoxy-5,6,7,8-tetrahydronaphth-2-yl)-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford (E)-3-{7-[5,5,8,8,-tetramethyl-3-ethoxy-5,6,7,8-tetrahydronaphth-2-yl]-benzo[b]furan-2-yl}-but-2-enoic acid ethyl ester as a pale yellow oil.

C. (E)-3-{7-[5,5,8,8,-Tetramethyl-3-ethoxy-5,6,7,8-tetrahydronaphth-2-yl]-benzo[b]furan-2-yl}-but-2-enoic acid A mixture of 0.450 mmol of 3-[7-(2-propoxy-3,5-diisopropylphenyl)-benzo[b]furan-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[7-(2-Propoxy-3,5-diisopropylphenyl)-benzo[b]furan-2-yl]-but-2-enoic acid was isolated as a white solid. $^1$H-NMR (400 MHz, CDCl$_3$) δ 7.55 (m, 2H, Ar—H), 7.54 (s, 1H, Ar—H), 7.28 (t, J=7.6 Hz, 1H, Ar—H), 7.10 (s, 1H, furan-H), 6.94 (s, 1H, Ar—H), 6.62 (s, 1H, C=C—H), 4.06 (q, J=6.9 Hz, 2H, O—CH$_2$—CH$_3$), 2.56 (s, 3H, C=C—CH$_3$), 1.74 (s, 4H, ring-CH$_2$), 1.37 (s, 6H, ring-CH$_3$), 1.33 (s, 6H, ring-CH$_3$), 1.27 (t, J=6.9 Hz, 3H, O—CH$_2$—CH$_3$).

Example 12

3-[7-(2-Ethoxy-3,5-diisopropylphenyl)-benzo[b]thien-2-yl]-but-2-enoic acid

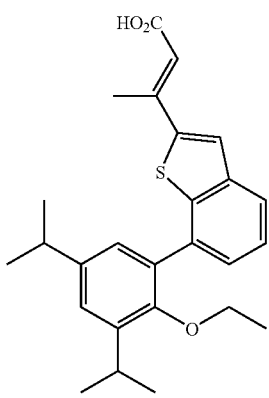

A. 2-Acetyl-7-(2-ethoxy-3,5-diisopropylphenyl)-benzo[b]thiophene

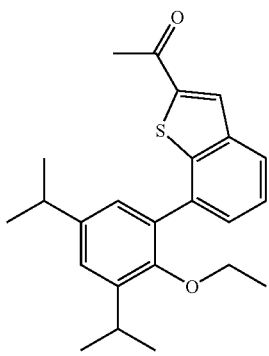

To mixture of 280 mg (0.69 mmol) of ethyl-2-carboxylate-7-(2-ethoxy-3,5-diisopropylphenyl)-benzo[b]thiophene in 5 mL of dry ether was added 0.7 mL of a 1.0 M lithium aluminum hydride solution at 0° C. After complexion of the reaction, the mixture was carefully quenched with 0.5 mL of cold water followed by 1 mL of a 1N aqueous NaOH solution. The precipitate was filtered over celite, washed 2 times with ethyl acetate and the organic layer dried over MgSO$_4$. After filtration and evaporation of the solvents, the crude alcohol was diluted in 3 mL of CH$_2$Cl$_2$ and 121 mg (1.03 mmol) of 4-methylmorpholine N-oxide (NMO) followed by 15 mg of tetrapropylammonium perruthenate (TPAP) (0.04 mmol) were successively added. The dark mixture is stirred at room temperature until complexion (TLC monitoring) and filtrated over silica gel. The gel was washed 2 times with CH$_2$Cl$_2$ and the solvents removed over reduced pressure. The crude aldehyde was dissolved in 5 mL of dry ether and the cooled to 0° C. Methyl magnesium bromide (1 mL, 3 mmol) was then added dropwise. After complexion (TLC monitoring), and work-up, the crude alcohol was oxidized to the ketone using the same protocol previously described (NMO/TPAP in CH$_2$Cl$_2$). Purification over silica gel (eluent: ethyl acetate/hexane: 5/95) gave 125 mg (0.238 mmol, yield: 41% over 5 steps) of 2-acetyl-7-(2-ethoxy-3,5-diisopropylphenyl)-benzo[b]thiophene as orange crystals.

$^1$H-NMR (CDCl$_3$), δ: 8.01 (s, 1H), 7.87 (broad d, J=8.0 Hz, 1H), 7.58 (d, J=7.3 Hz, 1H), 7.48 (t, J=7.6 Hz, 1H), 7.18 (dd, J=6.8, 2.2 Hz, 1H), 3.43 (dt, J=13.8, 6.9 Hz, 1H), 3.33 (dd, J=14.0, 6.9 Hz, 2H), 2.92 (dt, J=13.8, 6.9 Hz, 1H), 2.66 (s, 3H), 1.28 (m, 12H), 0.89 (t, J=7.0 Hz, 3H).

B. 3-[7-(2-Ethoxy-3,5-diisopropylphenyl)-benzo[b]thien-2-yl]-but-2-enoic acid ethyl ester

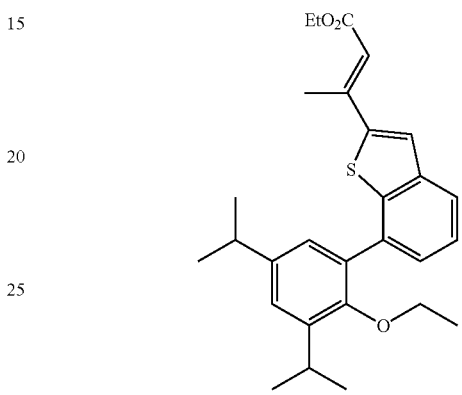

To a mixture of 38 mg (0.79 mmol) of NaH in 1 mL of dry DMF was added dropwise a solution of 148 mg (0.66 mmol, 0.13 mL) of triethylphosphonoacetate at 0° C. After 10 minutes, 125 mg of 2-acetyl-7-(2-ethoxy-3,5-diisopropylphenyl)-benzo[b]thiophene (diluted in 2 mL of dry DMF) was added slowly and the mixture is warmed-up to 40° C. After complexion of the reaction (TLC), and work-up, the crude ester was purified over a short pad of silica gel (eluent: ethyl acetate/hexane: 95/5) to afford 87 mg (0.193 mmol, yield=59%) of 3-[7-(2-ethoxy-3,5-diisopropylphenyl)-benzo[b]thien-2-yl]-but-2-enoic acid ethyl ester (ratio E/Z=85/15)1. $^1$H-NMR (CDCl$_3$), δ: 7.73 (d, J=7.8 Hz, 1H), 7.60 (s, 1H), 7.45 (d, J=1.0 Hz, 1H), 7.43 (t, J=7.9 Hz, 1H), 7.17 (m, 2H), 6.29 (s, 1H), 4.19 (dd, J=14.5, 7.3 z, 2H), 3.44 (dt, J=13.7, 6.9 Hz, 1H), 3.36 (dd, J=14.0, 7.0 Hz, 2H), 2.92 (dt, J=13.7, 6.8 Hz, 1H), 2.66 (s, 3H), 1.28 (m, 12H), 0.90 (t, J=7.0 Hz, 3H).

C. 3-[7-(2-ethoxy-3,5-diisopropylphenyl)-benzo[b]thien-2-yl]-but-2-enoic acid A mixture of 0.450 mmol of 3-[7-2-ethoxy-3,5-diisopropylphenyl)-benzo[b]thien-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile to afford 30 mg (0.07 mmol, yield=40%) 3-[7-(2-ethoxy-3,5-diisopropylphenyl)-benzo[b]thien-2-yl]-but-2-enoic acid was afforded as white solid. $^1$H-NMR (CDCl$_3$), δ: 7.75 (d, J=7.9 Hz, 1H), 7.65 (s, 1H), 7.48 (d, J=6.4 Hz, 1H), 7.42 (t, J=7.7 Hz, 1H), 7.19 (d, J=2.3 Hz, 1H), 7.17 (d, J=2.3 Hz, 1H), 6.32 (s, 1H), 3.43 (dt, J=13.8, 6.9 Hz, 1H), 3.36 (dd, J=14.0, 7.0 Hz, 2H), 2.93 (dt, J=13.8, 6.9 Hz, 1H), 2.69 (s, 3H), 1.28 (m, 12H), 0.92 (t, J=6.9 Hz, 3H).

Example 13

2-Carboxy-4-(2-propoxy-3,5-di-tert-butylphenyl)-benzo[b]thiophene

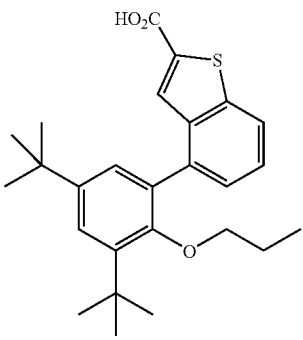

A. 2-(Ethyl carboxylate)-4-(2-hydroxy-3,5-di-tert-butylphenyl)benzo[b]thiophene

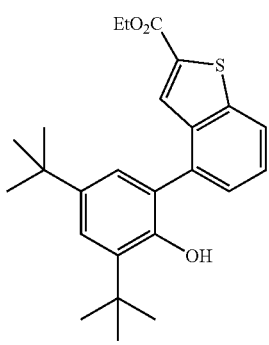

A mixture of 2.42 g (8.22 mmol) of 3,5 di-tert-butyl-2-methoxymethyl phenylboronic acid, 1.52 g (5.0 mmol) of ethyl-4-iodo-benzo[b]thiophene-2-carboxylate, 288 mg (0.25 mmol, 5%) Pd(PPh$_3$)$_4$ diluted in 10 mL of ethanol, 20 mL of toluene and 5 mL of 2N Na$_2$CO$_3$ aqueous solution was refluxed until complexion of the reaction. After workup, the solvents are removed under reduced pressure and the crude product is directly hydrolyzed with aqueous 6N HCl in THF at 40° C. After cooling at room temperature, the mixture was extracted with ethyl acetate and the organic layer dried over MgSO$_4$. After evaporation of the solvents, the crude phenol was recrystallized from ethyl acetate/methanol (ratio: 10/1) to afford 1.23 g (3 mmol, yield: 60%) of 2-(ethyl carboxylate)-4-(2-hydroxy-3,5di-tert-butylphenyl) benzo[b]thiophene as a pale orange powder. $^1$H-NMR (CDCl$_3$), δ: 7.925 (d, J=8.0 Hz, 1H), 7.87 (s, 1H), 7.56 (d, J=7.4 Hz, H), 7.46 (t, J=7.3 Hz, 1H), 7.40 (d, J=2.2 Hz, 1H), 7.12 (d, J=2.4 Hz, 1H), 4.98 (s, 1H), 4.35 (dd, J=14.1, 7.0 Hz, 2H), 1.54 (s, 9H), 1.46 (s, 9H).

B. 2-(Ethyl carboxylate)-4-(2-propoxy-3,5-di-tert-butylphenyl)benzo[b]thiophene

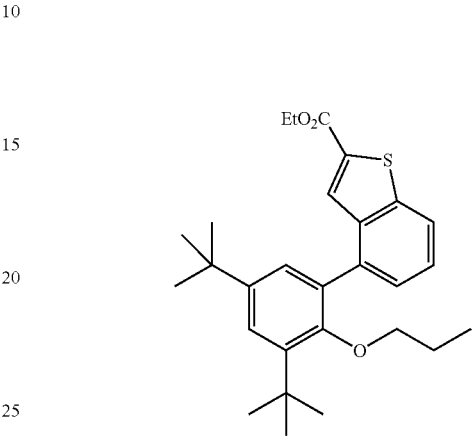

To a mixture of 284 mg (0.691 mmol) of 2-(ethyl carboxylate)-4-(2-hydroxy-3,5 di-tert-butylphenyl) benzo[b]thiophene and 102 mg (0.075 mL, 0.83 mmol) of 1-bromopropane in 2 mL of dry DMF was added 338 mg (1.04 mmol) of Cs$_2$CO$_3$. After complexion of the reaction, 10 mL of a1/9 mixture of ethyl acetate/hexane was added and the solution was filtrated over a short pad of silica gel. The pad was washed 2 times with a1/9 mixture of ethyl acetate/hexane and the solvents were evaporated under reduced pressure to afford 303 mg (0.669 mmol, yield: 97%) of 2-(ethyl carboxylate)-4-(2-propoxy-3,5-di-tert-butylphenyl) benzo[b]thiophene. $^1$H-NMR (CDCl$_3$), δ: 7.95 (s, 1H), 7.83 (d, J=7.8 Hz, 1H), 7.51 (d, J=7.4 Hz, 1H), 7.45 (t, J=7.5 Hz, 1H), 7.41 (d, J=2.5 Hz, 1H), 7.18 (d, J=2.4 Hz, 1H), 4.36 (m, 2H), 3.23 (m, 1H), 3.16 (m, 1H), 1.47 (s, 9H), 1.33 (s, 9H), 1.14 (m, 2H), 0.42 (t, J=7.5 Hz, 3H).

C. 2-Carboxy-4-(2-propoxy-3,5-di-tert-butylphenyl)-benzo[b]thiophene

A mixture of 0.450 mmol of 2-(ethyl carboxylate)-4-(2-propoxy-3,5-di-tert-butylphenyl) benzo[b]thiophene, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile to afford 200 mg (0.47 mmol, yield=70%) of 2-carboxy-4-(2-propoxy-3,5-di-tert-butylphenyl)-benzo[b]thiophene was afforded as white solid. $^1$H-NMR (CDCl$_3$), δ: 8.05 (s, 1H), 7.87 (d, J=7.9 Hz, 1H), 7.55 (t, J=7.4 Hz, 1H), 7.49 (d, J=7.2 Hz, 1H), 7.43 (d, J=2.4 Hz, 1H), 7.18 (d, J=2.4 Hz, 1H), 3.25 (m, 1H), 3.17 (m, 1H), 1.47 (s, 9H), 1.34 (s, 9H), 1.15 (m, 2H), 0.43 (t, J=7.2 Hz, 3H). (LG101564).

Example 14

3-{4-[2-(2,2-Difluoroethoxy)-3,5-di-tert-butylphenyl]-benzo[b]thien-2-yl}-but-2-enoic acid

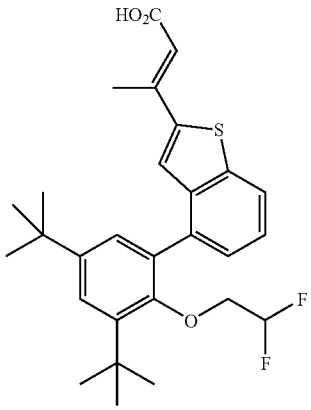

A. 2-Acetyl-4-iodo benzo[b]thiophene

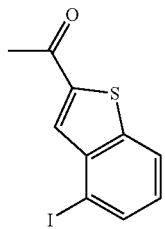

A mixture of 2.53 g (10.1 mmol) of 2-fluoro-6-iodo benzaldehyde, 1.0 g (11.1 mmol) of mercapto-2-propanone and 3.5 mL (2.5 g, 25 mmol) of Et$_3$N in 15 mL of DMSO was heated to 80° C. overnight. After cooling to room temperature, water was added and the mixture was extracted with ethyl acetate. The organic layer was washed with water (2 times), brine and dried over MgSO$_4$. After evaporation of the solvents, the crude product was purified over silica gel column chromatography to afford 1.85 g (6.12 mmol, yield: 61%) of 2-acetyl-4-iodo benzo[b]thiophene as an orange powder. $^1$H-NMR (CDCl$_3$), δ: 7.97 (s, 1H), 7.83 (d, J=7.9 Hz, 2H), 7.16 (t, J=7.9 Hz, 1H), 2.70 (s, 3H).

B. 2-Acetyl-4-(2-methoxymethoxy-3,5-di-tert-butylphenyl)benzo[b]thiophene

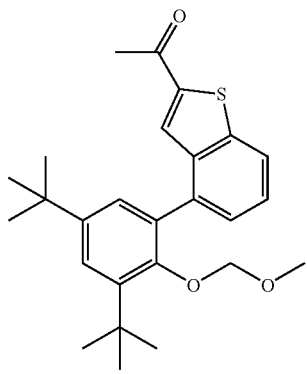

A mixture of 620 mg (2.1 mmol) 3,5-di-tert-butyl-2-methoxymethoxy phenylboronic acid, 377 mg (1.24 mmol) of 2-acetyl-4-iodo benzo[b]thiophene, 72 mg (0.105 mmol, 5%) Pd(PPh$_3$)$_4$ 6 mL of ethanol, 1.25 mL of Na$_2$CO$_3$ in 8 mL of toluene was heated to reflux for 12 hours. After cooling and work-up, the crude product was purified over a short silica gel plug (eluent: ethyl acetate/hexane: 10/90) to give 368.6 mg (0.868 mmol, yield: 70%) of pure 2-acetyl-4-(2-methoxymethoxy-3,5-di-tert-butylphenyl)benzo[b]thiophene as a clear oil. $^1$H-NMR (CDCl$_3$), δ: 7.84 (d, J=7.9 Hz, 1H), 7.79 (s, 1H), 7.53 (t, J=7.4 Hz, 1H), 7.46 (d, J=2.6 Hz, 1H), 7.44 (d, J=2.6 Hz, 1H), 7.19 (d, J=2.5 Hz, 1H), 4.47 (d, J=4.5 Hz, 1H), 4.06 (dd, J=14.2, 7.0 Hz, 2H), 2.81 (s, 3H), 2.54 (s, 3H), 2.02 (s, 3H), 1.49 (s, 9H), 1.33 (s, 9H), 1.23 (t, J=7.3 Hz, 3H).

C. 2-Acetyl-4-(2-hydroxy-3,5-di-tert-butylphenyl)benzo[b]thiophene

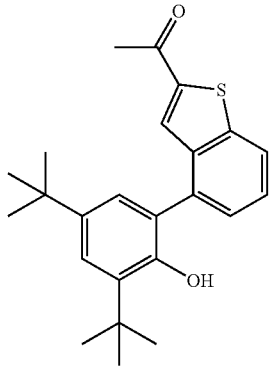

A slurry of 365 mg (0.859 mmol) of 2-acetyl-4-(2-methoxymethoxy-3,5-di-tert-butylphenyl)benzo[b]thiophene into a mixture of 5 mL of THF and 5 mL of aqueous 6N HCl was heated to 50° C. overnight. After cooling, the THF was evaporated and the aqueous solution was extracted with ethyl acetate. The organic layer was dried over MgSO$_4$ and evaporated under reduced pressure. The crude 2-acetyl-4-(2-hydroxy-3,5-di-tert-butylphenyl)benzo[b]thiophene was directly used in the next step. $^1$H-NMR (CDCl$_3$), δ: 7.92 (d, J=8.0 Hz, 1H), 7.73 (s, 1H), 7.58 (t, J=7.4 Hz, 1H), 7.47 (d, J=2.6 Hz, 1H), 7.42 (d, J=2.3 Hz, 1H), 7.14 (d, J=2.4 Hz, 1H), 5.03 (s, 1H), 2.57 (s, 3H), 1.48 (s, 9H), 1.34 (s, 9H).

D. 3-{4-[2-(2,2-Difluoroethoxy)-3,5-di-tert-butylphenyl]-benzo[b]thien-2-yl}-but-2-enoic acid ethyl ester

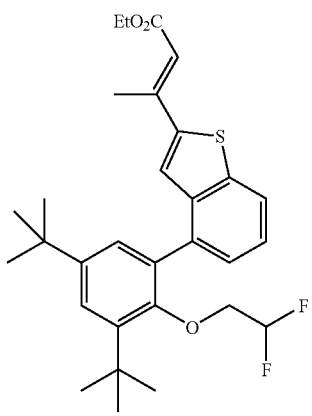

A mixture of the crude 2-acetyl-4-(2-hydroxy-3,5-di-tert-butylphenyl)benzo[b]thiophene, 142.0 mg (1 mmol) of 2-bromo-1,1-difluoroethane and 410 mg (2.7 mmol) of CsF in 10 mL of dry DMF was stirred at room temperature overnight. After work-up the crude oil was filtrated over a short pad of silica gel (eluent: 10/90 ethyl acetate/hexane) to give 2-acetyl-4-[2-(2,2-difluoroethoxy)-3,5-di-tert-butylphenyl]-benzo[b]thiophene as an oil, directly used without further purification. The crude ketone was treated with the anion of triethylphosphonoacetate (previously prepared from 336 mg of triethylphosphonoacetate and 86 mg of NaH in 3 mL of dry DMF) at 60° C. After completion of the reaction (TLC monitored) and work-up, the crude ester was purified over silica gel column (eluent: 5/95 ethyl acetate/hexane) to afford 315 mg (0.65 mmol, yield: 75%, 2 steps) of pure 3-{4-[2-(2,2-difluoroethoxy)-3,5-di-tert-butylphenyl]-benzo[b]thien-2-yl}-but-2-enoic acid ethyl ester as an oil. $^1$H-NMR (CDCl$_3$), δ: 7.80 (dd, J=7.2, 1.6 Hz, 1H), 7.43 (m, 4H), 7.23 (d, J=2.5 Hz, 1H), 6.29 (s, 1H), 5.17 (dt, J=55.4, 4.1 Hz, 1H), 4.21 (dd, J=14.4, 7.2 Hz, 2H), 3.50 (m, 2H), 2.57 (s, 3H), 1.47 (s, 9H), 1.34 (s, 9H), 1.31 (t, J=7.0 Hz).

E. 3-{4-[2-(2,2-Difluoroethoxy)-3,5-di-tert-butylphenyl]-benzo[b]thien-2-yl}-but-2-enoic acid A mixture of 0.450 mmol of 3-{4-[2-(2,2-difluoroethoxy)-3,5-di-tert-butylphenyl]-benzo[b]thien-2-yl}-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, and the crude acid was recrystallized from acetonitrile to afford 192 mg (0.378 mmol, yield: 58%) of 3-{4-[2-(2,2-difluoroethoxy)-3,5-di-tert-butylphenyl]-benzo[b]thien-2-yl}-but-2-enoic acid was isolated as a white solid. $^1$H NMR (CDCl$_3$), δ: 7.81 (dd, J=7.3, 1.5 Hz, 1H), 7.45 (m, 4H), 7.21 (d, J=2.4 Hz, 1H), 6.33 (s, 1H), 5.19 (dt, J=55.5, 4.3 Hz, 1H), 3.51 (m, 2H), 2.59 (s, 3H), 1.48 (s, 9H), 1.35 (s, 9H).

Example 15

(E)-3-[4-2-Propoxy-3,5-di-iso-propylphenyl)-benzo[b]thien-2-yl]-but-2-enoic acid

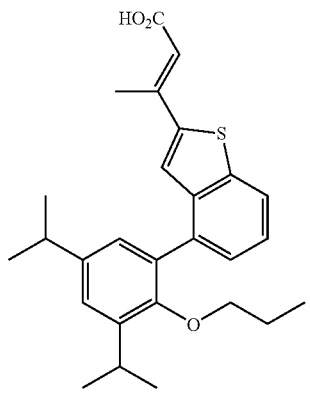

A. 2-Acetyl-4-(2-Propoxy-3,5-di-iso-propylphenyl)-benzo[b]thiophene

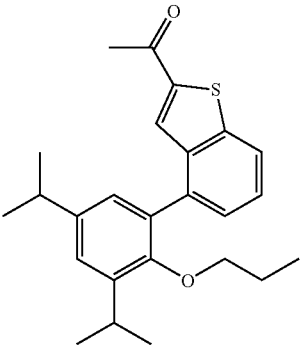

A mixture of 1.08 mmol of 3,5-di-iso-propyl-2-propoxy phenylboronic acid, 1.62 mmol of 2-acetyl-4-iodo benzo[b]thiophene (see Example 14, step A) and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-acetyl-4-(2-propoxy-3,5-di-iso-propylphenyl)-benzo[b]thiophene.

B. 3-[4-(2-Propoxy-3,5-di-iso-propylphenyl)-benzo[b]thien-2-yl]-but-2-enoic acid ethyl ester

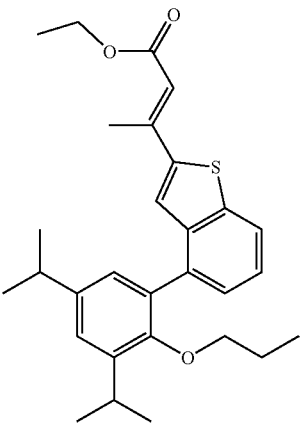

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-4-(2-propoxy-3,5-di-iso-propylphenyl)-benzo[b]thiophene diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent:

95/5 hexane/ethyl acetate) to afford 3-[4-(2-propoxy-3,5-di-iso-propylphenyl)-benzo[b]thien-2-yl]-but-2-enoic acid ethyl ester.

C. 3-[4-(2-Propoxy-3,5-di-iso-propylphenyl)-benzo[b]thien-2-yl]-but-2-enoic acid A mixture of 0.450 mmol of 3-[4-(2-propoxy-3,5-di-iso-propylphenyl)-benzo[b]thien-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[4-(2-Propoxy-3,5-di-iso-propylphenyl)-benzo[b]thien-2-yl]-but-2-enoic acid was isolated as a white solid.

$^1$H NMR (CDCl$_3$), δ: 7.76 (dd, J=5.9, 2.6 Hz, 1H), 7.50 (s, 1H), 7.42 (m, 2H), 7.17 (d, J=2.3 Hz, 1H), 7.05 (d, J=2.2 Hz, 1H), 6.32 (s, 1H), 3.41 (dt, J=13.7, 6.9 Hz 1H), 3.26 (m, 1H), 3.18 (m, 1H), 2.93 (dt, J=13.7, 6.8 Hz, 1H), 2.61 (s, 3H), 1.29 (m, 14H), 0.52 (t, J=7.5 Hz, 3H).

Example 16

(E)-3-[4-(2-Ethoxy-3,5-di-iso-propylphenyl)-benzo[b]thien-2-yl]-but-2-enoic acid

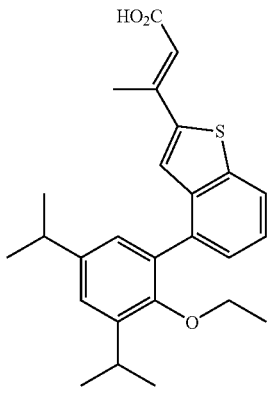

A. 2-Acetyl-4-(2-ethoxy-3,5-di-iso-propylphenyl)-benzo[b]thiophene

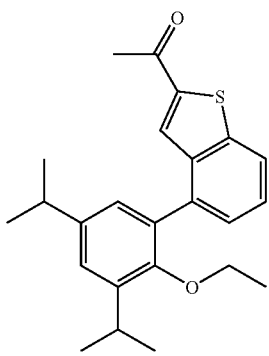

A mixture of 1.08 mmol of 3,5-di-iso-propyl-2-ethoxy phenylboronic acid, 1.62 mmol of 2-acetyl-4-iodo benzo[b]thiophene (see Example 14, step A) and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-acetyl-4-(2-ethoxy-3,5-di-iso-propylphenyl)-benzo[b]thiophene.

B. 3-[4-(2-Ethoxy-3,5-di-iso-propylphenyl)-benzo[b]thien-2-yl]-but-2-enoic acid ethyl ester

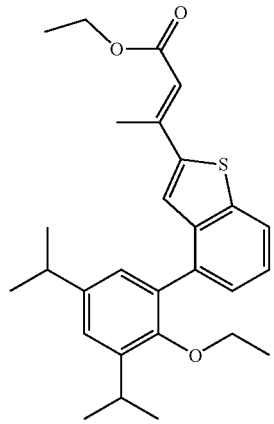

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-4-(2-ethoxy-3,5-di-iso-propylphenyl)-benzo[b]thiophene diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 3-[4-(2-ethoxy-3,5-di-iso-propylphenyl)-benzo[b]thien-2-yl]-but-2-enoic acid ethyl ester.

C. 3-[4-(2-Ethoxy-3,5-di-iso-propylphenyl)-benzo[b]thien-2-yl]-but-2-enoic acid A mixture of 0.450 mmol of 3-[4-(2-ethoxy-3,5-di-iso-propylphenyl)-benzo[b]thien-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[4-(2-Ethoxy-3,5-di-iso-propylphenyl)-benzo[b]thien-2-yl]-but-2-enoic acid was isolated as a white solid. $^1$H NMR (CDCl$_3$), δ: 7.77 (dd, J=5.9, 3.6 Hz, 1H), 7.51 (s, 1H), 7.43 (m, 2H), 7.17 (d, J=2.2 Hz, 1H), 7.05 (d, J=2.3 Hz, 1H), 6.32 (s, 1H), 3.43 (dt, J=13.8, 6.9 Hz, 1H), 3.33 (m, 2H), 2.93 (dt, J=13.7, 6.9 Hz, 1H), 2.61 (s, 3H),1.29 (m, 12H), 0.85 (t, J=7.4 Hz, 3H).

Example 17

(E)-3-[4-(2-n-Butoxy-3,5-di-iso-propylphenyl)-benzo[b]thien-2-yl]-but-2-enoic acid

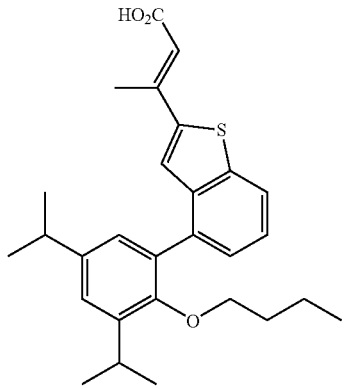

A. 2-n-Butoxy-1-iodo-3,5-diiosopropyl-benzene

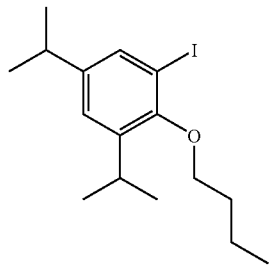

2-Iodo-4,6-diisopropyl-phenol (60.8 g, 0.2 mol), 1-bromobutane (41.1 g, 0.3 mol), and powdered potassium carbonate (55.3 g, 0.4 mol) were combined in ethanol (366 mL). The mixture was heated at reflux for 4 h and then diluted with water (1 L)/hexane (300 mL). The solids were dissolved and the water layer separated and extracted with hexane (150 mL). The hexane portions were combined, dried ($Na_2SO_4$), and concentrated in vacuo to provide 70.63 g (98%) of an orange oil.

$^1$H NMR (250 MHz, $CDCl_3$): δ 7.46 (d, 1H, J=2.1), 7.05 (d, 1H, J=2.1), 3.83, (t, 2H, J=6.6), 3.31 (sep, 1H, J=6.9), 2.81 (sep, 1H, J=6.9), 1.82 (m, 2H), 1.55 (m, 2H), 1.22 (d, 6H, J=6.9), 1.21 (d, 6H, J=6.9).

B. (2-n-Butoxy-3,5-di-iso-propylphenyl)-boronic acid

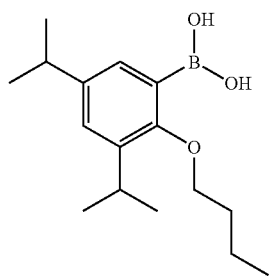

2-n-Butoxy-1-iodo-3,5-diiosopropyl-benzene (20.16 g, 56 mmol) was dissolved in anhydrous THF (250 mL) under nitrogen and cooled to −75° C. to in a dry ice/acetone bath. t-Butyl lithium (72.6 mL, 123 mmol, 1.7 M in pentane) was added over 21 min at −73° C. and the suspension was stirred for 40 min. Trimethyl borate (27.6 mL, 246 mmol) was added at −73° C. The dry ice bath was left in place and the reaction allowed to warm to 12° C. overnight. The reaction was stirred 30 min with 1N $H_2SO_4$ (125 mL) and then diluted into water (125 mL)/ethyl acetate (175 mL). The organic phase was separated and washed with 10% aqueous $NaHCO_3$, dried ($Na_2SO_4$) and concentrated in vacuo to provide 15.7 g of a viscous yellow oil. The oil was passed over a large silica pad with a gradient elution of hexane, (95:5) hexane:ethyl acetate, (9:1) hexane:ethyl acetate and (4:1) hexane:ethyl acetate. The product came off in (95:5) and (9:1) hexane:ethyl acetate providing 11.3 g (73%) of product. Mp: 73-78° C. $^1$H NMR (250 MHz, $CDCl_3$): δ 7.52 (d, 1H, J=2.4), 7.24 (d, 1H, J=2.4), 6.25 (s, 2H), 3.81, (t, 2H, J=6.8), 3.27 (sep, 1H, J=6.9), 2.90 (sep, 1H, J=6.9), 1.83 (m, 2H), 1.54 (m, 2H), 1.26 (d, 6H, J=6.9), 1.25 (d, 6H, J=6.9).

C. 2-Acetyl-4-(2-n-butoxy-3,5-di-iso-propylphenyl)-benzo[b]thiophene

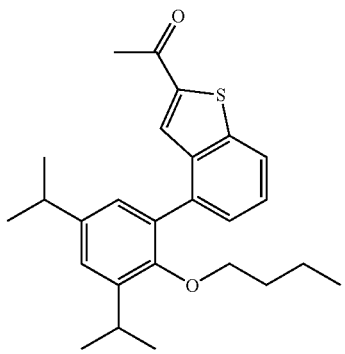

A mixture of 1.08 mmol of 3,5-di-iso-propyl-2-n-butoxy phenylboronic acid, 1.62 mmol of 2-acetyl-4-iodo benzo[b] thiophene (see Example 14, step A) and 62 mg (0.05 mmol) of $Pd(PPh_3)_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over $MgSO_4$ and after evaporation of the solvents, the crude oil was purified over a short silica plug (eluent: 10/90=ethyl acetate/hexane) to afford 2-acetyl-4-(2-n-butoxy-3,5-di-iso-propylphenyl)-benzo[b]thiophene.

D. 3-[4-(2-n-butoxy-3,5-di-iso-propylphenyl)-benzo[b]thien-2-yl]-but-2-enoic acid ethyl ester

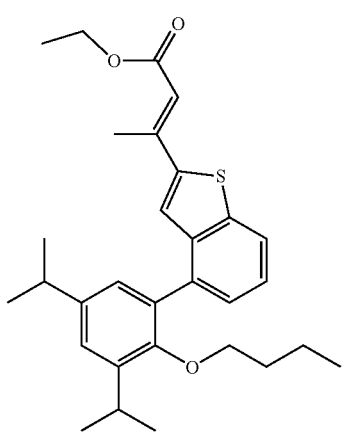

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-4-(2-n-butoxy-3,5-di-iso-propylphenyl)-benzo[b]thiophene diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 3-[4-(2-n-butoxy-3,5-di-iso-propylphenyl)-benzo[b]thien-2-yl]-but-2-enoic acid ethyl ester.

E. 3-[4-(2-n-Butoxy-3,5-di-iso-propylphenyl)-benzo[b]thien-2-yl]-but-2-enoic acid A mixture of 0.450 mmol of 3-[4-(2-n-butoxy-3,5-di-iso-propylphenyl)-benzo[b]thien-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[4-(2-n-butoxy-3,5-di-iso-propylphenyl)-benzo[b]thien-2-yl]-but-2-enoic acid was isolated as a white solid.

$^1$H-NMR (CDCl$_3$), δ: 7.76 (dd, J=6.8, 2.9 Hz, 1H), 7.48 (s, 1H), 7.43 (m, 2H), 7.16 (d, J=2.2 Hz, 1H), 7.04 (d, J=2.2 Hz, 1H), 6.32 (s, 1H), 3.39 (dt, J=13.8, 6.8 Hz, 1H), 3.32 (m, 2H), 2.93 (dt, J=13.7, 6.8 Hz, 1H), 2.60 (s, 3H), 1.29 (m, 14H), 0.95 (m, 2H), 0.57 (t, J=7.5 Hz, 3H).

Example 18

(E)-3-[4-(2-n-Butoxy-3,5-di-iso-propylphenyl)-5-fluorobenzo[b]thien-2-yl]-but-2-enoic acid

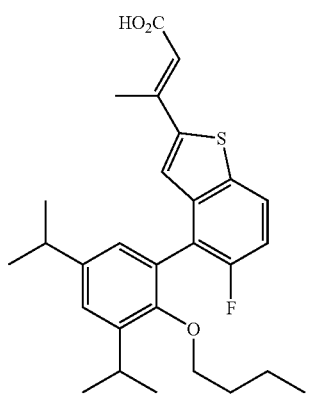

A. 2-Acetyl-4-(2-n-butoxy-3,5-di-iso-propylphenyl)-5-fluorobenzo[b]thiophene

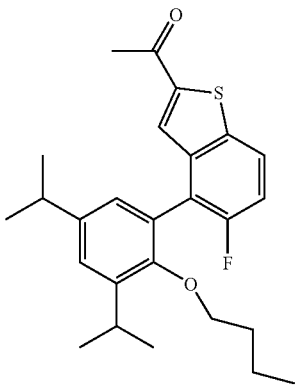

A mixture of 1.08 mmol of 3,5-di-iso-propyl-2-n-butoxy phenylboronic acid, 1.62 mmol of 2-acetyl-4-iodo-5-fluorobenzo[b]thiophene and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-acetyl-4-(2-n-butoxy-3,5-di-iso-propylphenyl)-5-fluorobenzo[b]thiophene.

B. 3-[4-(2-n-butoxy-3,5-di-iso-propylphenyl)-5-fluorobenzo[b]thien-2-yl]-but-2-enoic acid ethyl ester

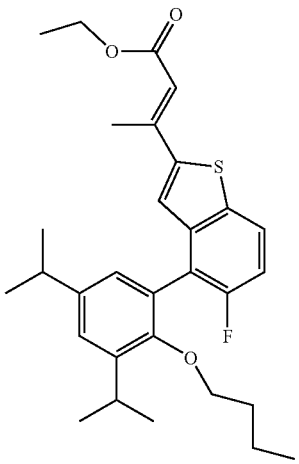

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-4-(2-n-butoxy-3,5-di-iso-propylphenyl)-5-fluorobenzo[b]thiophene diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent:

95/5 hexane/ethyl acetate) to afford 3-[4-(2-n-butoxy-3,5-di-iso-propylphenyl)-5-fluorobenzo[b]thien-2-yl]-but-2-enoic acid ethyl ester.

C. 3-[4-(2-n-Butoxy-3,5-di-iso-propylphenyl)-5-fluorobenzo[b]thien-2-yl]-but-2-enoic acid A mixture of 0.450 mmol of 3-[4-(2-n-butoxy-3,5-di-iso-propylphenyl)-5-fluorobenzo[b]thien-2-yl]-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-[4-(2-n-butoxy-3,5-di-iso-propylphenyl)-5-fluorobenzo[b]thien-2-yl]-but-2-enoic acid was isolated as a white solid. $^1$H-NMR (CDCl$_3$), δ: 7.71 (dd, J=8.7, 4.4 Hz, 1H), 7.26 (t, J=16.7 Hz, 2H), 7.20 (d, J=1.8 Hz, 1H), 7.03 (d, J=1.8 Hz, 1H), 3.39 (dt, J=13.8, 6.9 Hz, 1H), 3.33 (t, J=6.3 Hz, 2H), 2.93 (dt, J=13.7, 6.8 Hz, 1H), 2.57 (s, 3H), 1.28 (m, 12H), 1.22 (m, 2H), 0.96 (m, 2H), 0.57 (t, J=7.2 Hz, 3H).

Example 19

(E) 2-Fluoro-3-[4-(2-n-propoxy-3,5-di-iso-propylphenyl)-benzo[b]thien-2-yl]-prop-2-enoic acid

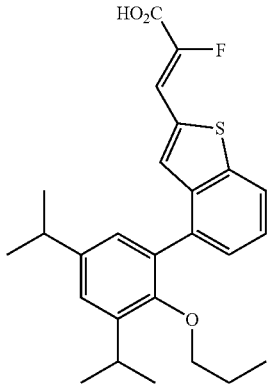

A. 2-Formyl-4-(2-n-propoxy-3,5-di-iso-propylphenyl)-benzo[b]thiophene

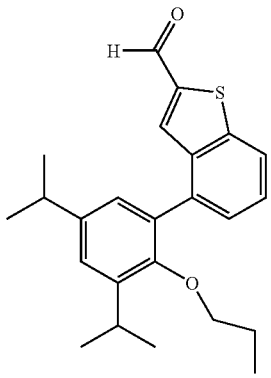

A mixture of 1.08 mmol of 3,5-di-iso-propyl-2-n-propoxy phenylboronic acid, 1.62 mmol of 2-formyl-4-iodo-benzo[b]thiophene and 62 mg (0.05 mmol) of Pd(PPh$_3$)$_4$, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO$_4$ and after evaporation of the solvents, the crude oil was purified over a short silica plug (eluent: 10/90=ethyl acetate/hexane) to afford 2-formyl-4-(2-n-propoxy-3,5-di-iso-propylphenyl)-benzo[b]thiophene.

B. 2-Fluoro-3-[4-(2-n-propoxy-3,5-di-iso-propylphenyl)-benzo[b]thien-2-yl]-prop-2-enoic acid ethyl ester

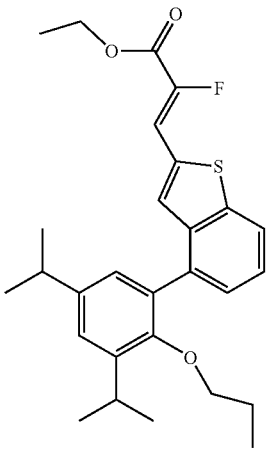

To a slurry of 74 mg (1.54 mmol) of NaH (50% in mineral oil) in 3 mL of dry DMF was added 285.6 mg (1.27 mmol, 2.5 equivalents) of triethyl phosphonofluoroacetate (diluted in 1 mL of dry DMF) at 0° C. After the gas evolution has ceased, 0.51 mmol of 2-formyl-4-(2-n-propoxy-3,5-di-iso-propylphenyl)-benzo[b]thiophene diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 2-fluoro-3-[4-(2-n-propoxy-3,5-di-iso-propylphenyl)-benzo[b]thien-2-yl]-prop-2-enoic acid ethyl ester.

C. (E) 2-Fluoro-3-[4-(2-n-propoxy-3,5-di-iso-propylphenyl)-benzo[b]thien-2-yl]-prop-2-enoic acid A mixture of 0.450 mmol of 2-fluoro-3-[4-(2-n-propoxy-3,5-di-iso-propylphenyl)-benzo[b]thien-2-yl]-prop-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. (E)-2-Fluoro-3-[4-(2-n-propoxy-3,5-di-iso-propylphenyl)-benzo[b]thien-2-yl]-prop-2-enoic acid was isolated as a white solid. $^1$H-NMR (CDCl$_3$), δ: 7.83 (d, J=7.7 Hz, 1H), 7.49 (broad s, 1H), 7.46 (s, 1H), 7.42 (t, J=7.0 Hz, 2H), 7.18 (d, J=2.1 Hz, 1H), 7.00 (d, J=2.1 Hz, 1H), 3.42 (dt, J=13.7, 6.8 Hz, 1H), 3.32 (m, 1H), 3.19 (m, 1H), 2.92 (dt, J=13.8, 6.9 Hz, 1H), 1.29 (m, 14H), 1.22 (m, 2H), 0.45 (t, J=7.3 Hz, 3H).

Example 20

(E) 3-[4-(2-propyloxy-3,5-di-iso-propylphenyl)benzo[b]thien-2-yl]prop-2-enoic acid

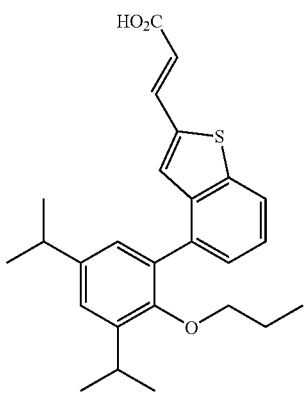

A. 3-[4-(2-n-propoxy-3,5-di-iso-propylphenyl)-benzo[b]thien-2-yl]-prop-2-enoic acid ethyl ester

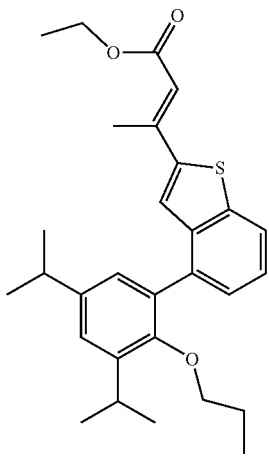

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-formyl-4-(2-n-propoxy-3,5-di-iso-propylphenyl)-benzo[b]thiophene (see Example 19, step A) diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 3-[4-(2-n-propoxy-3,5-di-iso-propylphenyl)-benzo[b]thien-2-yl]-prop-2-enoic acid ethyl ester.

B. (E) 3-[4-(2-n-propoxy-3,5-di-iso-propylphenyl)-benzo[b]thien-2-yl]-prop-2-enoic acid A mixture of 0.450 mmol of 3-[4-(2-n-propoxy-3,5-di-iso-propylphenyl)-benzo[b]thien-2-yl]-prop-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. (E) 3-[4-(2-n-propoxy-3,5-di-iso-propylphenyl)-benzo[b]thien-2-yl]-prop-2-enoic acid was isolated as a white solid.

$^1$H-NMR (CD$_3$COCD$_3$), δ: 7.95 (d, J=7.9 Hz, 1H), 7.92 (d, J=15.9 Hz, 1H), 7.53 (t, J=7.5 Hz, 1H), 7.49 (s, 1H), 7.42 (dd, J=7.4, 1.0 Hz, 1H), 7.29 (d, J=2.3 Hz, 1H), 7.09 (d, J=2.3 Hz, 1H), 6.27 (d, J=15.9 Hz, 1H), 3.45 (dt, J=13.6, 6.8 Hz, 1H), 3.35 (m, 2H), 2.93 (dt, J=13.7, 6.8 Hz, 1H), 2.05 (m, 2H), 1.30 (d, J=6.9 Hz, 6H), ), 1.28 (d, J=6.9 Hz, 6H), 0.49 (t, J=7.2 Hz, 3H).

Example 21

3-{4-[2-(2,2,2-Trifluoroethoxy)-3,5-di-ispropylphenyl]benzo[b]thien-2-yl}-but-2-enoic acid

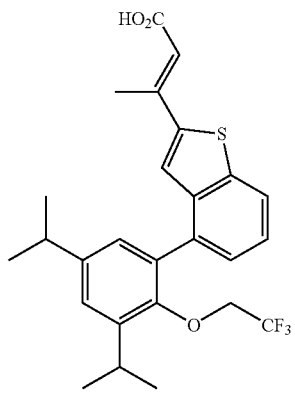

A. 2-Acetyl-4-[2-(2,2,2-trifluoroethoxy)-3,5-di-iso-propylphenyl]-benzo[b]thiophene

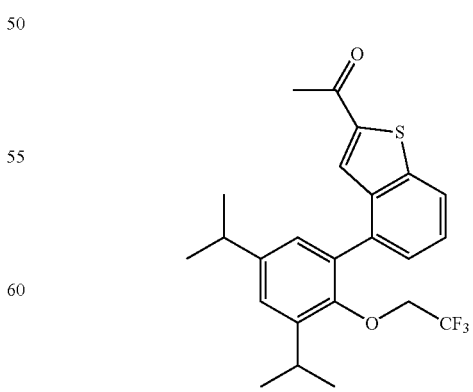

A mixture of 1.08 mmol of 3,5-di-iso-propyl-2-(2,2,2-trifluoroethoxy)-phenylboronic acid, 1.62 mmol of 2-acetyl- 4-iodo-benzo[b]thiophene and 62 mg (0.05 mmol) of Pd(PPh₃)₄, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO₄ and after evaporation of the solvents, the crude oil was purified over a short silica plug (eluent: 10/90=ethyl acetate/hexane) to afford 2-acetyl-4-[2-(2,2,2-trifluoroethoxy)-3,5-di-iso-propylphenyl]-benzo[b]thiophene.

C. 3-{4-[2-(2,2,2-Trifluoroethoxy)-3,5-di-iso-propylphenyl]-benzo[b]thien-2-yl}-but-2-enoic acid ethyl ester

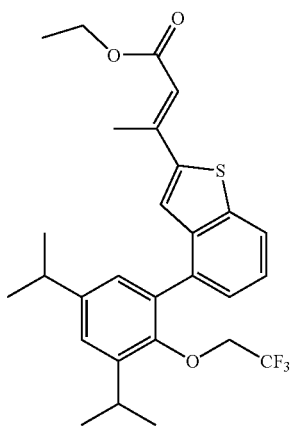

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-4-[2-(2,2,2-trifluoroethoxy)-3,5-di-iso-propylphenyl]-benzo[b]thiophene diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO₄. After evaporation of the solvents, the crude oil is purified over a short plug of silica gel (eluent: 95/5 hexane/ethyl acetate) to afford 3-{4-[2-(2,2,2-trifluoroethoxy)-3,5-di-iso-propylphenyl]-benzo[b]thien-2-yl}-but-2-enoic acid ethyl ester.

C. 3-{4-[2-(2,2,2-Trifluoroethoxy)-3,5-di-iso-propylphenyl]-5-fluorobenzo[b]thien-2-yl}-but-2-enoic acid A mixture of 0.450 mmol of 3-{4-[2-(2,2,2-trifluoroethoxy)-3,5-di-iso-propylphenyl]-benzo[b]thien-2-yl}-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO₄ and after evaporation of the solvents, the crude acid was recrystallized from acetonitrile. 3-{4-[2-(2,2,2-Trifluoroethoxy)-3,5-di-iso-propylphenyl]-5-fluorobenzo[b]thien-2-yl}-but-2-enoic acid was isolated as a white solid. ¹H-NMR (400 MHz, CDCl₃) δ 7.81 (dd, J=8.9 Hz, J=1.7 Hz, 1H), 7.45 (m, 3H), 7.20 (d, J=2.0 Hz, 1H), 7.07 (d, J=2.1 Hz, 1H), 6.34 (s, 1H), 3.51 (m, 2H), 3.45 (m, 1H), 2.94 (m, 1H), 2.61 (s, 3H), 1.31 (d, J=6.9 Hz, 6H), 1.28 (d, J=6.9 Hz, 6H).

Example 22

3-{4-[2-(2,2,2-Trifluoroethoxy)-3,5-di-iso-propylphenyl]benzo[b]furan-2-yl}-but-2-enoic acid

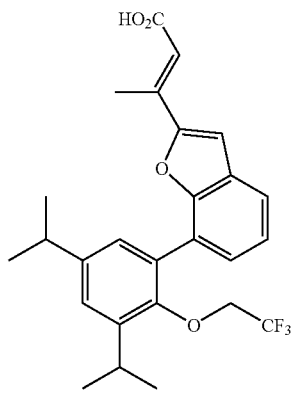

A. 2-Acetyl-4-[2-(2,2,2-trifluoroethoxy)-3,5-di-iso-propylphenyl]-benzo[b]furan

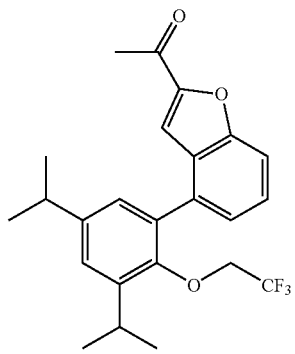

A mixture of 1.08 mmol of 3,5-di-iso-propyl-2-(2,2,2-trifluoroethyoxy)-phenylboronic acid, 1.62 mmol of 2-acetyl-7-trifluoromethanesulfonate benzo[b]furan and 62 mg (0.05 mmol) of Pd(PPh₃)₄, 1 mL of 2N aqueous sodium carbonate in 9 mL of toluene and 4 mL ethanol was heated to reflux. After complexion (TLC), water was added and the solution was extracted with ethyl acetate. The organic layer is dried over MgSO₄ and after evaporation of the solvents, the crude oil was purified over a short silica plug (eluent: 10/90=ethyl acetate/hexane) to afford 2-acetyl-4-[2-(2,2,2-trifluoroethoxy)-3,5-di-iso-propylphenyl]-benzo[b]furan.

B. 3-{4-[2-(2,2,2-Trifluoroethoxy)-3,5-di-iso-propylphenyl]-benzo[b]furan-2-yl}-but-2-enoic acid ethyl ester

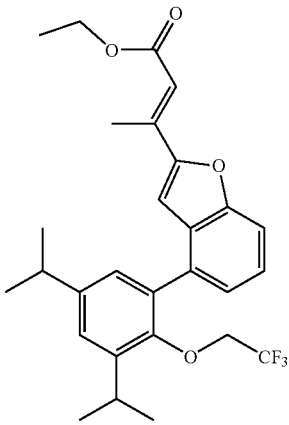

To a slurry of 74 mg (1.54 mmol) of NaH (50% in mineral oil) in 3 mL of dry DMF was added 285.6 mg (1.27 mmol, 2.5 equivalents) of triethyl phosphonoacetate (diluted in 1 mL of dry DMF) at 0° C. After the gas evolution has ceased, 0.51 mmol of 2-acetyl-4-[2-(2,2,2-trifluoroethoxy)-3,5-di-iso-propylphenyl]-benzo[b]furan diluted in 3 mL of dry DMF was added dropwise. The red mixture was slowly heated to 40° C. until complexion. After cooling, water was added and the solution was extracted 2 times with ethyl acetate. The organic layers were combined, washed with water and brine and dried over MgSO$_4$. After evaporation of the solvents, the crude oil is purified over a short plug of silica gel (eluent: 95/5 hexane/ethyl acetate) to afford 3-{4-[2-(2,2,2-trifluoroethoxy)-3,5-di-iso-propylphenyl]-benzo[b]furan-2-yl}-but-2-enoic acid ethyl ester.

C. 3-{4-[2-(2,2,2-Trifluoroethoxy)-3,5-di-iso-propylphenyl]-5-fluorobenzo[b]furan-2-yl}-but-2-enoic acid A mixture of 0.450 mmol of 3-{4-[2-(2,2,2-trifluoroethoxy)-3,5-di-iso-propylphenyl]-benzo[b]furan-2-yl}-but-2-enoic acid ethyl ester, 3 mL of THF, 3 mL of methanol and 1 mL of LiOH (2N aqueous) was refluxed for 2 hours. After cooling at room temperature, the mixture was acidified to pH=2 and extracted with ethyl acetate. The organic layer was dried over MgSO$_4$ and after evaporation of the solvents, the crude acid was recrystallized from acetonitrile. 3-{4-[2-(2,2,2-Trifluoroethoxy)-3,5-di-iso-propylphenyl]-5-fluorobenzo[b]furan-2-yl}-but-2-enoic acid was isolated as a white solid. $^1$H-NMR (400 MHz, CDCl$_3$) δ 7.60 (d, J=6.9 Hz, 1H), 7.58 (d, J=6.2 Hz, 1H), 7.33 (d, J=2.1 Hz, 1H), 7.32 (t, J=7.6 Hz, 1H), 7.19 (d, J=2.1 Hz, 1H), 7.11 (s, 1H), 6.59 (s, 1H), 3.64 (dd, J=8.5 Hz, 2), 3.45 (m, 1H), 2.96 (m, 1H), 2.57 (s, 3H), 1.32 (d, J=6.8 Hz, 6H), 1.31 (d, J=6.7 Hz, 6H).

Example 23

3-{4-[2-(2,2,2-Trifluoroethoxy)-3-tert-butyl-5-methylphenyl]benzo[b]thien-2-yl}but-2-enoic acid

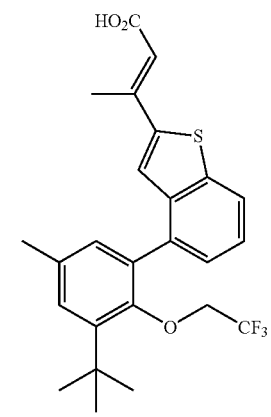

A. 2-Acetyl-4-(4,4,5,5-tetramethyl-1,3,2-dioxaborolane)benzo[b]thiophene

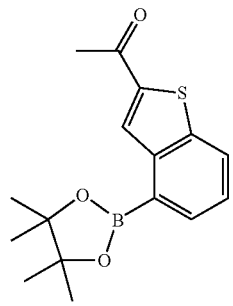

To a mixture of 5.0 g (16.5 mmol) 2-acetyl-4-iodobenzo[b]thiophene and 675 mg (0.82 mmol) of PdCl$_2$dppf in a mixture of 55 mL of dry dioxane and 6.8 mL of dry triethylamine was added dropwise 3.6 mL (3.2 g, 24.8 mmol) of 4,4,5,5-tetramethyl-1,3,2-dioxaborolane. When the vigorous gas evolution has stopped, the mixture was stirred 3 hours at 80° C. When the reaction was complete (TLC monitoring), water (1 mL) was added carefully to hydrolyze the remaining boronate and the solvents were removed under reduced pressure. The remaining brownish solid was disolved in 10 mL of a 1/10 mixture of methylene chloride-hexane and purified over a silica plug (eluent: methylene chloride/hexane, 1/10). After removal of the solvents, the crude boronate was recrystallized from hexanes to afford 3.6 g (11.9 mmol, yield: 74%) of 2-acetyl-4-(4,4,5,5-tetramethyl-1,3,2-dioxaborolane)benzo[b]thiophene as a bright yellow crystal. $^1$H NMR (400 MHz, CDCl$_3$) δ 8.58 (s, 1H), 7.95 (d, J=7.8 Hz, 1H), 7.92 (d, J=7.8 Hz, 1H), 7.45 (t, J=7.8 Hz, 1H), 2.70 (s, 3H), 1.41 (s, 12H).

B. 2-Acetyl-4-(2-hydroxy-3-tert-butyl-5-methylphenyl)benzo[b]thiophene

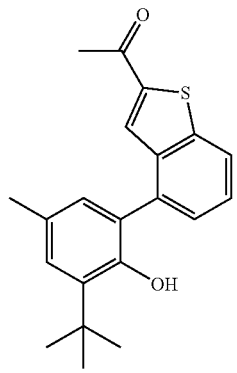

A mixture of 240 mg (0.86 mmol) of 2-tert-butyl-4-methyl-6-iodophenol, 260 mg (0.86 mmol) of 2-acetyl-4-(4,4,5,5-tetramethyl-1,3,2-dioxaborolane)benzo[b]thiophene, 25 mg (0.03 mmol) of PdCl$_2$dppf, 0.9 ml of a 2N Na$_2$CO$_3$ aqueous solution in 6 ml of dry ethylene glycol dimethyl ether was heated to reflux for 5 hours. After cooling at room temperature, the solvents were removed under reduced pressure and the crude phenol was purified using silica gel column chromatography (eluent: 15/85 ethyl acetate/hexanes) to give 211 mg (0.63 mmol, yield: 72%) of 2-acetyl-4-(2-hydroxy-3-tert-butyl-5-methylphenyl)benzo[b]thiophene. $^1$H NMR (400 MHz, CDCl$_3$) δ 7.92 (d, J=7.7 Hz, 1H), 7.71 (s, 1H), 7.57 (t, J=7.7 Hz, 1H), 7.44 (d, J=7.8 Hz, 1H), 7.20 (d, J=1.9 Hz, 1H), 6.95 (d, J=1.9 Hz, 1H), 4.95 (s, 1H), 2.57 (s, 3H), 2.35 (s, 3H), 1.46 (s, 9H).

C. 2-Acetyl-4-[2-(2,2,2-trifluoroethoxy)-3-tert-butyl-5-methylphenyl]benzo[b]thiophene

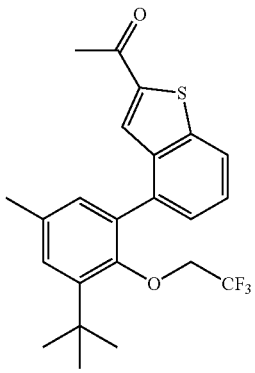

A mixture of 211 mg (0.63 mmol) of 2-acetyl-4-(2-hydroxy-3-tert-butyl-5-methylphenyl)benzo[b]thiophene, 0.1 ml (132 mg, 0.81 mmol) of 1,1,1-trifluoro-2-bromoethane and 304 mg (0.94 mmol) of Cs$_2$CO$_3$ in 2.5 ml of dry DMF was heated at 60° C. in a pressure tube overnight. After cooling at room temperature, 10 mL of a 5/95 ethyl acetate/hexane solution was added and the remaining mixture was stirred for 5 minutes. The solution was filtrated through a silica plug (eluent: 5/95 ethyl acetate/hexane) and the solvents were removed under pressure. 188 mg (0.44 mmol, yield: 71%) of 2-acetyl-4-[2-(2,2,2-trifluoroethoxy)-3-tert-butyl-5-methylphenyl]benzo[b]thiophene was isolated as an oil. $^1$H NMR (400 MHz, CDCl3) δ 7.89 (d, J=7.9 Hz, 1H), 7.75 (s, 1H), 7.54 (t, J=7.8 Hz, 1H), 7.45 (d, J=7.9 Hz, 1H), 7.26 (d, J=1.9 Hz, 1H), 7.06 (d, J=1.9 Hz, 1H), 3.63 (m, 1H), 3.52 (m, 1H), 2.56 (s, 3H), 2.38 (s, 3H), 1.48 (s, 9H).

D. 3-{4-[2-(2,2,2-Trifluoroethoxy)-3-tert-butyl-5-methylphenyl]-benzo[b]thien-2-yl}but-2-enoic acid ethyl ester

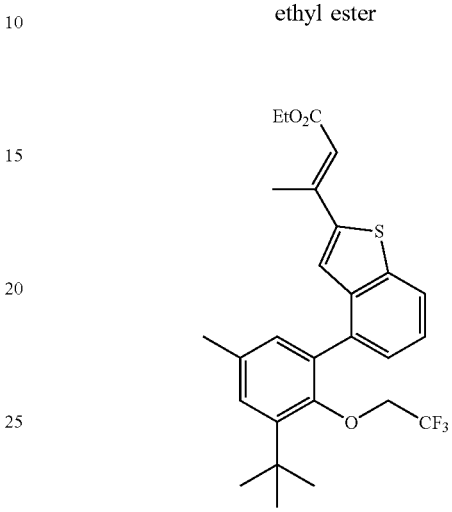

To a mixture of 33 mg (0.79 mmol) of NaH in 2 ml of dry DMF was added dropwise 0.13 mL (148 mg, 0.66 mmol) of triethylphosphonoacetate at 0° C. The solution was stirred for 10 minutes at 0° C., then 185 mg (0.44 mmol) of of 2-acetyl-4-[2-(2,2,2-trifluoroethoxy)-3-tert-butyl-5-methylphenyl]benzo[b]thiophene diluted in 2 ml of dry DMF was added dropwise. The reddish solution was stirred at 60° C. until the reaction was complete (TLC monitoring). After cooling to room temperature and work-up, the crude ester was purified using silica gel column chromatography to afford 198 mg (0.41 mmol, yield: 94%) of 3-{4-[2-(2,2,2-trifluoroethoxy)-3-tert-butyl-5-methylphenyl]-benzo[b]thien-2-yl}but-2-enoic acid ethyl ester as an oil. $^1$H NMR (400 MHz, CDCl$_3$) δ 7.81(d, J=7.9 Hz, 1H), 7.43 (t, J=7.9 Hz, 1H), 7.39 (d, J=7.8 Hz, 1H), 7.37 (s, 1H), 7.24 (d, J=1.6 Hz, 1H), 7.06 (d, J=1.6 Hz, 1H), 6.29 (s, 1H), 4.21 (dd, J=14.1, 7.0 Hz, 2H), 3.64 (m, 1H), 3.51 (m, 1H), 2.57 (s, 3H), 2.37 (s, 3H), 1.47 (s, 9H), 1.32 (t, J=7.2 Hz, 3H).

E. 3-{4-[2-(2,2,2-Trifluoroethoxy)-3-tert-butyl-5-methylphenyl]benzo[b]thien-2-yl}but-2-enoic acid A mixture of 198 mg (0.41 mmol) of 3-{4-[2-(2,2,2-trifluoroethoxy)-3-tert-butyl-5-methylphenyl]benzo[b]thien-2-yl}but-2-enoic acid ethyl ester disolved in 4 mL of methanol, 5 mL of THF and 1 mL of a 2N aqueous solution of LiOH was heated to reflux for 2 hours. After cooling at room temperature and acidic work-up, the crude acid was purified using preparative HPLC (kromosil column, eluent: 8/92 water/methanol+0.1% TFA). Collection of the desired fractions, evaporation of the solvents and recrystallization from acetonitrile affords 110 mg (0.23 mmol, yield: 58%) of 3-{4-[2-(2,2,2-trifluoroethoxy)-3-tert-butyl-5-methylphenyl]benzo[b]thien-2-yl}but-2-enoic acid as a white solid. 1H NMR (400 MHz, CDCl3) d: 7.80 (d, J=8.2 Hz, 1H), 7.43 (t, J=7.7 Hz, 1H), 7.40 (s, 1H), 7.38 (d, J=8.2 Hz, 1H), 7.24 (d, J=1.9 Hz, 1H), 7.06 (d, J=1.9 Hz, 1H), 6.32 (s, 1H), 3.61 (m, 1H), 3.58 (m, 1H), 2.58 (s, 3H), 2.37 (s, 3H), 1.46 (s, 9H).

Examples 24-47 were synthesized using the method described in Example 23.

Example 24

(E) 3-{4-[2-(2,2,2-Trifluoroethoxy)-3,5-di-tert-butylphenyl]-benzo[b]thien-2-yl}but-2-enoic acid

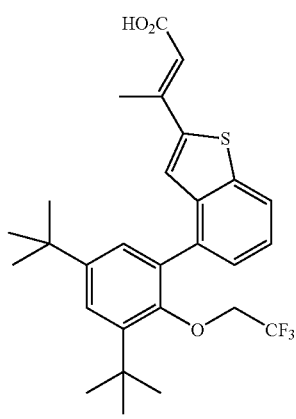

$^1$H NMR (400 MHz, CDCl$_3$) δ: 7.82 (dd, J=6.7, 2.2 Hz, 1H), 7.46 (m, 3H), 7.45 (s, 1H), 7.23 (d, J=2.3 Hz, 1H), 6.33 (s, 1H), 3.60 (m, 2H), 2.59 (s, 3H), 1.48 (s, 3H), 1.33 (s, 9H).

Example 25

(E) 3-{4-[2-(2,2,2-Trifluoroethoxy)-3-tert-butyl-5-ethylphenyl]-benzo[b]thien-2-yl}but-2-enoic acid

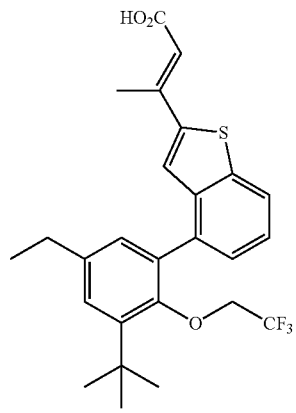

$^1$H NMR (400 MHz, CDCl$_3$) δ: 7.81 (d, J=7.7 Hz, 1H), 7.45 (t, J=7.7 Hz, 1H), 7.43 (s, 1H), 7.42 (d, J=7.7 Hz, 1H), 7.39 (d, J=2.1 Hz, 1H), 7.08 (d, J=2.1 Hz, 1H), 6.32 (s, 1H), 3.62 (m, 1H), 3.55 (m, 1H), 2.65 (dd, J=15.1, 7.5 Hz, 2H), 2.59 (s, 3H), 1.47 (s, 9H), 1.27 (t, J=7.5 Hz, 3H).

Example 26

(E) 3-{4-[2-(3-fluoropropoxy)-3-tert-butyl-5-ethylphenyl]-benzo[b]thien-2-yl}but-2-enoic acid

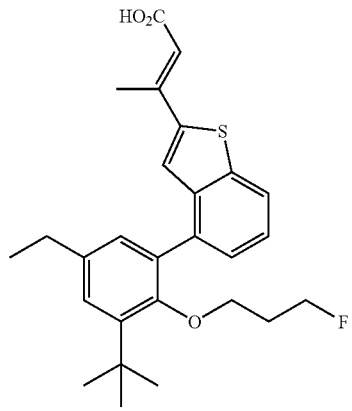

$^1$H NMR (400 MHz, CDCl$_3$) δ: 7.78 (d, J=7.7 Hz, 1H), 7.47 (t, J=7.8 Hz, 1H), 7.43 (s, 1H), 7.42 (d, J=7.7 Hz, 1H), 7.23 (d, J=2.0 Hz, 1H), 7.05 (d, J=2.0 Hz, 1H), 6.32 (s, 1H), 4.12 (m, 1H), 3.95 (m, 1H), 3.47 (m, 1H), 3.35 (m, 1H), 2.67 (dd, J=15.2, 7.6 Hz, 2H), 2.58 (s, 3H), 1.55 (m, 2H), 1.46 (s, 9H), 1.27 (t, J=7.4 Hz, 3H).

Example 27

(E) 3-{4-[2-(2,2-difluoroethoxy)-3-(adamant-1-yl)-5-methylphenyl]benzo[b]thien-2-yl}but-2-enoic acid

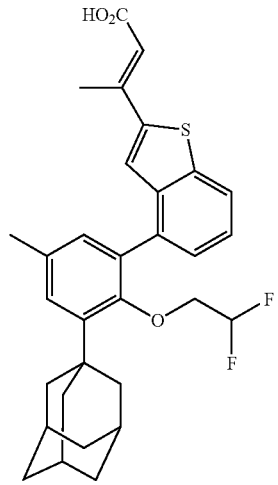

$^1$H NMR (400 MHz, CDCl$_3$) δ: 7.80 (d, J=7.9 Hz, 1H), 7.45 (t, J=7.9 Hz, 1H), 7.41 (s, 1H), 7.40 (d, J=7.9 Hz, 1H), 7.18 (d, J=1.6 Hz, 1H), 7.05 (d, J=1.6 Hz, 1H), 6.33 (s, 1H), 5.17 (dt, J=55.4, 3.8 Hz, 1H), 3.52 (m, 1H), 3.45 (m, 1H), 2.59 (s, 3H), 2.37 (s, 3H), 2.12 (m, 9H), 1.79 (m, 6H).

Example 28

(E) 3-{4-[2-(3,3-difluoropropoxy)-3-tert-butyl-5-ethylphenyl]-benzo[b]thien-2-yl}but-2-enoic acid

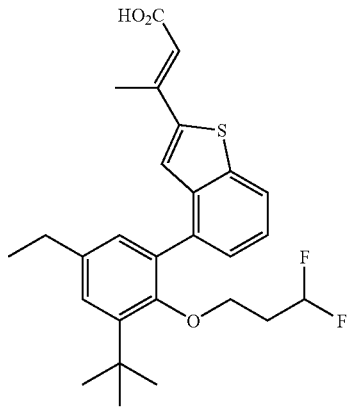

$^1$H NMR (400 MHz, CDCl$_3$) δ: 7.80 (d, J=7.9 Hz, 1H), 7.46 (t, J=7.9 Hz, 1H), 7.42 (s, 1H), 7.41 (d, J=7.9 Hz, 1H), 7.23 (d, J=1.9 Hz, 1H), 7.07 (d, J=1.9 Hz, 1H), 6.33 (s, 1H), 5.35 (dt, J=56.9, 4.7 Hz, 1H), 3.51 (m, 1H), 3.42 (m, 1H), 2.67 (dd, J=15.1, 7.5 Hz, 2H), 2.58 (s, 3H), 1.65 (m, 2H), 1.46 (s, 9H), 1.27 (t, J=7.4 Hz, 3H).

Example 29

(E) 3-{4-[2-(2,2-difluoroethoxy)-3-propyl-5-tert-butylphenyl]-benzo[b]thien-2-yl}but-2-enoic acid

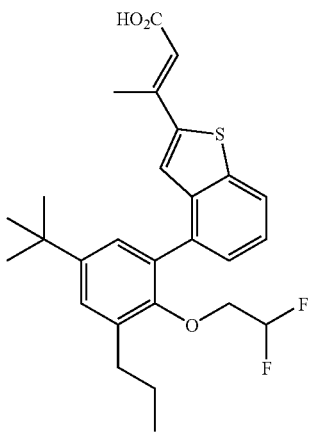

$^1$H NMR (400 MHz, CDCl$_3$) δ: 7.81 (d, J=7.8 Hz, 1H), 7.46 (d, J=7.8 Hz, 1H), 7.45 (s, 1H), 7.42 (t, J=7.8 Hz, 1H), 7.27 (d, J=2.2 Hz, 1H), 7.22 (d, J=2.2 Hz, 1H), 6.33 (s, 1H), 5.43 (dt, J=55.4, 4.2 Hz, 1H), 3.48 (m, 2H), 2.70 (t, J=7.7 Hz, 2H), 2.60 (s, 3H), 1.70 (m, 2H), 1.34 (s, 9H), 1.03 (t, J=7.3 Hz, 3H). (LG101646)

Example 30

(E) 3-{4-[2-(3,3-difluoropropoxy)-3-propyl-5-phenylphenyl]-benzo[b]thien-2-yl}but-2-enoic acid

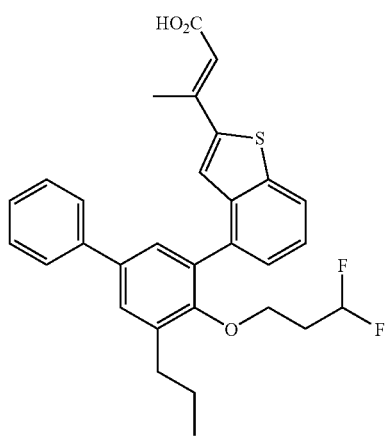

$^1$H NMR (400 MHz, CDCl$_3$) δ: 7.81 (d, J=7.8 Hz, 1H), 7.59 (d, J=8.1 Hz, 2H), 7.50 (d, J=1.8 Hz, 1H), 7.43 (m, 6H), 7.33 (t, J=6.9 Hz, 1H), 6.33 (s, 1H), 5.45 (dt, J=56.9, 4.7 Hz, 1H), 3.55 (m, 1H), 3.42 (m, 1H), 2.73 (t, J=7.7 Hz, 2H), 2.58 (s, 3H), 1.72 (m, 4H), 1.38 (m, 2H), 1.05 (t, J=7.4 Hz, 3H).

Example 31

(E) 3-[4-(2-(2,2,2-trifluoroethoxy)-3-phenyl-5-methylphenyl]-benzo[b]thienyl}but-2-enoic acid

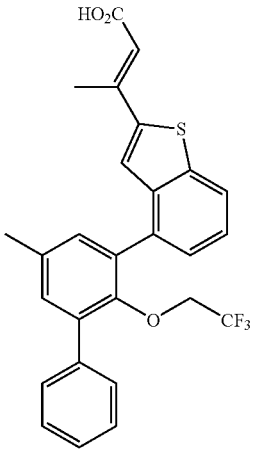

$^1$H NMR (400 MHz, CDCl$_3$) δ: 7.81 (d, J=7.8 Hz, 1H), 7.62 (d, J=7.4 Hz, 2H), 7.52 (s, 1H), 7.45 (td, J=7.5, 2.4 Hz, 2H), 7.39 (m, 3H), 7.28 (d, J=1.8 Hz, 1H), 7.21 (d, J=1.8 Hz, 1H), 6.36 (s, 1H), 2.66 (s, 3H), 2.44 (s, 3H).

Example 32

(E) 3-{4-[2-(2-methylpropoxy)-3-tert-butyl-5-ethylphenyl]-benzo[b]thien-2-yl}but-2-enoic acid

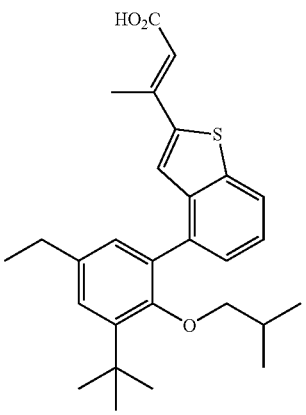

¹H NMR (400 MHz, CDCl₃) δ: 7.77 (d, J=7.7 Hz, 1H), 7.45 (d, J=7.7 Hz, 1H), 7.44 (s, 1H), 7.40 (t, J=7.7 Hz, 1H), 7.22 (d, J=2.0 Hz, 1H), 7.05 (d, J=2.0 Hz, 1H), 6.30 (s, 1H), 3.15 (dd, J=8.9, 6.1 Hz, 1H), 2.95 (dd, J=8.9, 6.1 Hz, 1H), 2.0 Hz, (dd, J=15.1, 7.5 Hz, 2H), 2.59 (s, 3H), 1.27 (s, 9H), 1.41 (m, 1H), 1.27 (t, J=7.7 Hz, 3H), 0.49 (d, J=6.7 Hz, 3H), 0.35 (d, J=6.7 Hz, 3H).

Example 33

(E) 3-{4-[2-(2,2,2-trifluoroethoxy)-4-tert-butylphenyl]-benzo[b]thien-2-yl}but-2-enoic acid

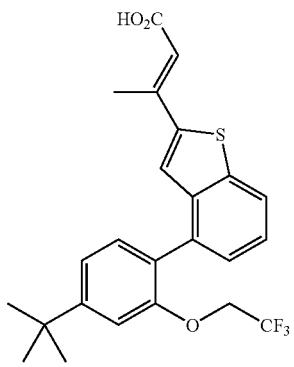

¹H NMR (400 MHz, CDCl₃) δ: 8.52 (d, J=7.9 Hz, 1H), 8.17 (s, 1H), 8.15 (t, J=7.9 Hz, 1H), 8.05 (d, J=7.9 Hz, 2H), 7.99 (s, 1H), 7.97 (dd, J=7.9, 1.4 Hz, 1H), 7.84 (d, J=1.9 Hz, 1H), 7.06 (s, 1H), 4.90 (d, J=8.2 Hz, 1H), 4.86 (d, J=8.2 Hz, 1H), 3.35 (s, 3H), 2.14 (s, 9H).

Example 34

(E) 3-[4-(5-(2,2,2-trifluoroethoxy)-6-tert-butylindan-4-yl)-benzo[b]thien-2-yl]but-2-enoic acid

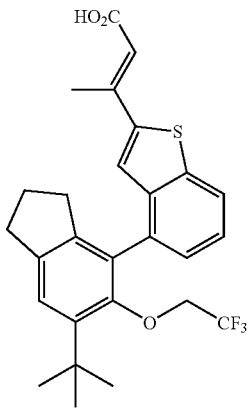

¹H NMR (400 MHz, CDCl₃) δ: 7.81 (d, J=7.9 Hz, 1H), 7.44 (t, J=7.9 Hz, 1H), 7.34 (d, J=7.9 Hz, 1H), 7.33 (s, 1H), 7.25 (s, 1H), 6.32 (s, 1H), 3.61 (m, 2H), 2.96 (t, J=7.4 Hz, 2H), 2.75 (m, 1H), 2.57 (s, 3H), 2.51 (m, 1H), 2.05 (m, 2H), 1.44 (s, 9H).

Example 35

(E) 3-[4-(3,5-di-tert-butylphenyl)-benzo[b]thien-2-yl]but-2-enoic acid

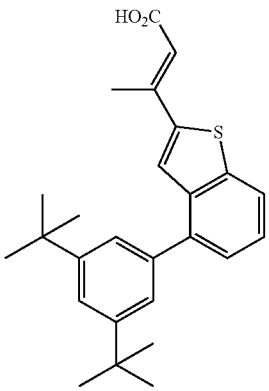

¹H NMR (400 MHz, CDCl₃) δ: 7.76 (m, 2H), 7.44 (m, 5H), 6.34 (s, 3H), 2.62 (s, 3H), 1.40 (s, 18H).

Example 36

(E) 3-{4-[3,5-di-iso-propyl-2-(2,2,2-trifluoroethoxy)phenyl]-5-fluoro-benzo[b]thien-2-yl}but-2-enoic acid

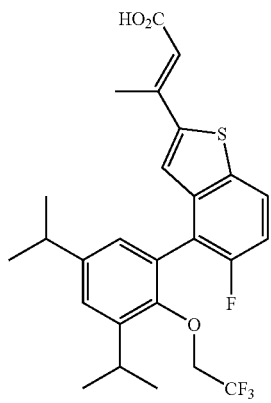

¹H NMR (400 MHz, CDCl₃) δ: 7.77 (m, 1H), 7.25 (m, 4H), 7.06 (d, J=2.3 Hz, 1H), 6.32 (s, 1H), 3.63 (m, 2H), 3.42 (m, 1H), 2.95 (m, 1H), 2.58 (s, 3H), 1.31 (d=6.9 Hz, 6H), 1.28 (d, J=6.8 Hz, 6H).

Example 37

(E) 3-{4-[2-(3-methylbutoxy)-3,5-di-tert-butylphenyl]-benzo[b]thien-2-yl}but-2-enoic acid

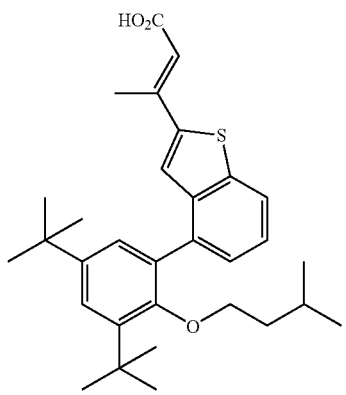

¹H NMR (400 MHz, CDCl₃) δ: 7.76 (d, J=6.9 Hz, 1H), 7.46 (m, 3H), 7.41 (d, J=2.3 Hz, 1H), 7.19 (d, J=2.3 Hz, 1H), 6.31 (s, 1H), 3.29 (m, 2H), 2.59 (s, 3H), 1.47 (s, 9H), 1.34 (s, 9H), 1.21 (m, 1H), 0.99 (q, J=6.7 Hz, 2H), 0.54 (d, J=6.6 Hz, 3H), 0.41 (d, J=6.6 Hz, 3H).

Example 38

(E) 3-{4-[2-(3,3,3-difluoropropoxy)-3,5-di-tert-butylphenyl]-benzo[b]thien-2-yl}but-2-enoic acid

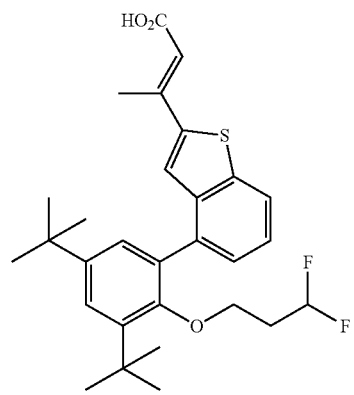

¹H NMR (400 MHz, CDCl₃) δ 7.80 (d, J=7.6 Hz, 1H), 7.45 (m, 4H), 7.21 (d, J=2.4 Hz, 1H), 6.33 (s, 1H), 5.39 (tt, J=56.8 Hz, J=4.7 Hz, 1H), 3.44 (m, 2H), 2.59 (s, 3H), 1.70 (m, 2H), 1.46 (s, 9H), 1.35 (s, 9H).

Example 39

(E) 3-{4-[2-(2-methylpropoxy)-3,5-di-tert-butylphenyl)-benzo[b]thien-2-yl]but-2-enoic acid

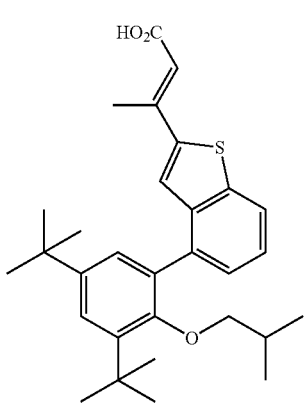

¹H NMR (400 MHz, CDCl₃) δ 7.77 (d, J=7.7 Hz, 1H), 7.43 (m, 4H), 7.19 (d, J=2.4 Hz, 1H), 6.30 (s, 1H), 3.14 (m, 1H), 2.94 (m, 1H), 2.59 (s, 3H), 1.47 (s, 9H), 1.40 (m, 1H), 1.34 (s, 9H), 0.50 (d, J=6.7 Hz, 3H), 0.36 (d, J=6.6 Hz, 3H).

Example 40

(E) 3-{4-[2-(2,2,2-trifluoroethoxy)-3,5-di-(1,1-dimethylpropyl)-phenyl]-benzo[b]thien-2-yl}but-2-enoic acid

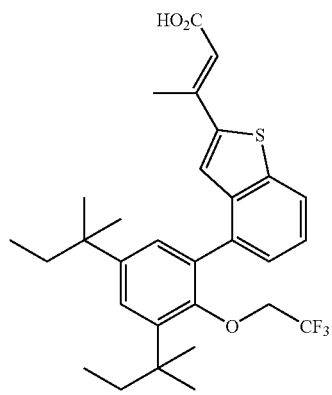

$^{1}$H NMR (400 MHz, CDCl$_3$) δ 7.81 (d, J=7.0 Hz, 1H), 7.45 (m, 3H), 7.31 (d, J=2.4 Hz, 1H), 7.16 (d, J=2.4 Hz, 1H), 6.32 (s, 1H), 3.58 (m, 2H), 2.59 (s, 3H, 1.96 (m, 1H), 1.80 (m, 1H), 1.65 (q, J=7.5 Hz, 2H), 1.45 (s, 3H), 1.43 (s, 3H), 1.31 (s, 3H), 1.30 (s, 3H), 0.75 (t, J=7.5 Hz, 3H), 0.73 (t, J=7.5 Hz, 3H).

Example 41

(E) 3-{4-[2-(2,2-difluoroethoxy)-3,5-di-(1,1-dimethylpropyl)phenyl]-benzo[b]thien-2-yl}but-2-enoic acid

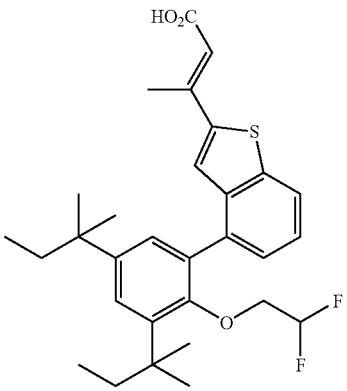

$^{1}$H NMR (400 MHz, CDCl$_3$) δ: 7.81 (d, J=7.6 Hz, 1H), 7.45 (m, 3H), 7.29 (d, J=2.1 Hz, 1H), 7.15 (d, J=2.2 Hz, 1H), 6.33 (s, 1H), 5.13 (tt, J=55.3 Hz, J=4.2 Hz, 1H), 3.49 (m, 2H), 2.59 (s, 3H), 1.93 (m, 1H), 1.81 (m, 1H), 1.64 (q, J=7.4 Hz, 2H), 1.44 (s, 3H), 1.42 (s, 3H), 1.30 (s, 6H), 0.74 (t, J=7.2 Hz, 3H), 0.73 (t, J=7.3 Hz, 3H).

Example 42

(E) 3-{4-[2-(3-fluoropropoxy)-3,5-di-(1,1-dimethylpropyl)phenyl]-benzo[b]thien-2-yl}but-2-enoic acid

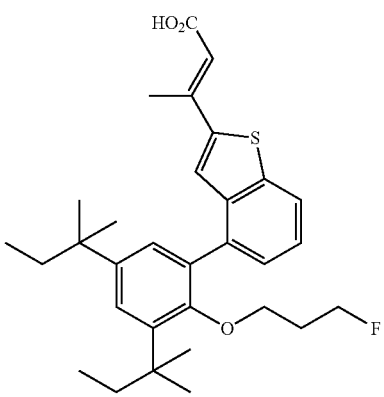

$^{1}$H-NMR (400 MHz, CDCl$_3$) δ: 7.78 (d, J=7.6 Hz, 1H), 7.44 (m, 3H), 7.28 (d, J=2.3 Hz, 1H), 7.13 (d, J=2.3 Hz, 1H), 6.32 (s, 1H), 4.00 (m, 2H), 3.36 (m, 2H), 2.59 (s, 3H), 1.98 (m, 1H), 1.78 (m, 1H), 1.64 (q, J=7.5 Hz, 2H), 1.44 (s, 3H), 1.42 (s, 3H), 1.30 (s, 6H), 0.74 (t, J=7.4 Hz, 3H), 0.72 (t, J=7.4 Hz, 3H).

Example 43

(E) 3-{4-[2-(3-methylbutoxy)-3,5-di-(1,1-dimethylpropyl)phenyl]-benzo[b]thien-2-yl}but-2-enoic acid

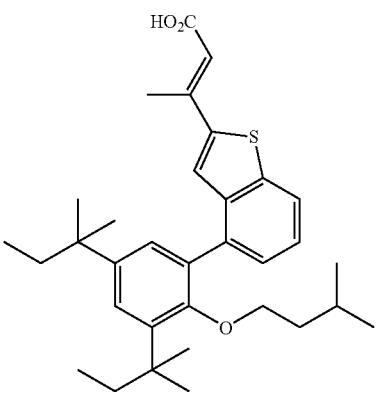

$^{1}$H NMR (400 MHz, CDCl$_3$) δ: 7.76 (d, J=7.4 Hz, 1H), 7.43 (m, 3H), 7.26 (d, J=2.1 Hz, 1H), 7.12 (d, J=2.3 Hz, 1H), 6.31 (s, 1H), 3.26 (m, 2H), 2.59 (s, 3H), 2.00 (m, 1H), 1.78 (m, 1H), 1.64 (q, J=7.4 Hz, 2H), 1.43 (s, 3H), 1.41 (s, 3H), 1.29 (s, 6H), 1.21 (m, 1H), 0.96 (q, J=6.7 Hz, 2H), 0.74 (t, J=7.3 Hz, 3H), 0.72 (t, J=7.3 Hz, 3H), 0.54 (d, J=6.6 Hz, 3H), 0.41 (d, J=6.6 Hz, 3H).

Example 44

(E) 3-{4-[2-(3,3-difluoropropoxy)-3,5-di-(1,1-dimethylpropyl)-phenyl]-benzo[b]thiophene]but-2-enoic acid

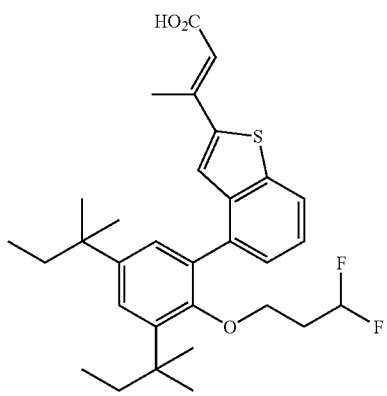

¹H NMR (400 MHz, CDCl₃) δ: 7.80 (d, J=7.9 Hz, 1H), 7.47 (t, J=7.6 Hz, 1H), 7.41 (d, J=6.2 Hz, 1H), 7.40 (s, 1H), 7.28 (d, J=2.3 Hz, 1H), 7.14 (d, J=2.2 Hz, 1H), 6.32 (s, 1H), 5.36 (tt, J=56.8 Hz, J=4.7 Hz, 1H), 3.41 (m, 2H), 2.58 (s, 3H), 1.95 (m, 1H), 1.76 (m, 1H), 1.64 (q, J=7.3 Hz, 2H), 1.52 (m, 2H), 1.43 (s, 3H), 1.41 (s, 3H), 1.30 (s, 6H), 0.74 (t, J=7.5 Hz, 3H), 0.72 (t, J=7.5 Hz, 3H).

Example 45

(E) 3-{4-[2-(2,2-difluoroethoxy)-3,5-di-(dimethylphenylmethyl)phenyl]-benzo[b]thien-2-yl}but-2-enoic acid

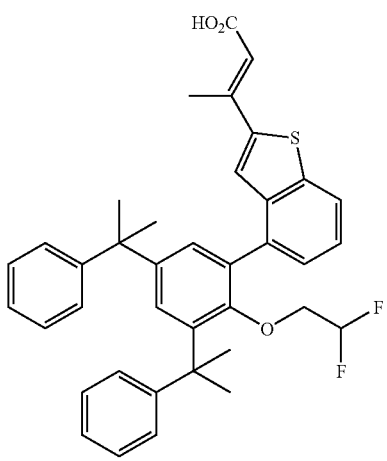

¹H NMR (400 MHz, CDCl₃) δ: 7.73 (d, J=7.9 Hz, 1H), 7.52 (d, J=2.2 Hz, 1H), 7.37 (t, J=7.6 Hz, 1H), 7.32 (m, 5H), 7.24 (m, 6H), 7.14 (m, 2H), 6.28 (s, 1H), 4.34 (tt, J=55.4 Hz, J=4.3 Hz, 1H), 2.55 (s, 3H), 2.36 (m, 1H), 2.25 (m, 1H), 1.77 (s, 9H), 1.67 (s, 3H).

Example 46

(E) 3-{4-[2-(2,2-difluoroethoxy)-3-tert-butyl-5-phenylphenyl]-benzo[b]thien-2-yl]but-2-enoic acid

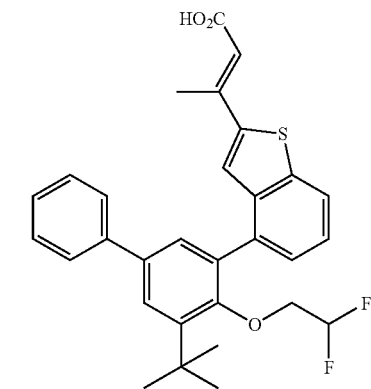

¹H NMR (400 MHz, CDCl₃) δ: 7.84 (dd, J=6.7 Hz, J=2.2 Hz, 1H), 7.65 (d, J=2.3 Hz, 1H), 7.59 (d, J=7.4 Hz, 2H), 7.47 (m, 6H), 7.35 (t, J=7.3 Hz, 1H), 6.34 (s, 1H), 5.19 (tt, J=55.4 Hz, J=4.2 Hz, 1H), 3.54 (m, 2H), 2.60 (s, 3H), 1.53 (s, 9H).

Example 47

(E) 3-{5-[2-(2,2-difluoroethoxy)-3-phenyl-5-tert-butylphenyl]-benzo[b]thien-2-yl}but-2-enoic acid

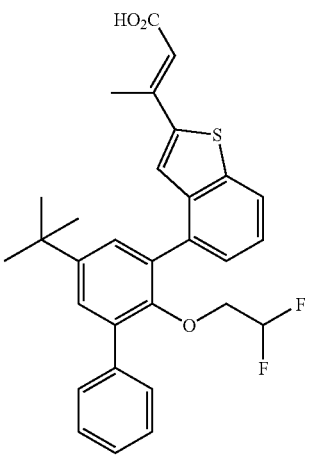

¹H NMR (400 MHz, CDCl₃) δ: 7.83 (m, 1H), 7.62 (d, J=7.4 Hz, 2H), 7.55 (s, 1H), 7.47 (m, 5H), 7.40 (m, 2H), 6.36 (s, 1H), 5.06 (tt, J=55.5 Hz, J=4.2 Hz, 1H), 3.29 (m, 2H), 2.66 (s, 3H), 1.39 (s, 9H).

Example 48

3-[3-(2-Butoxy-3,5-di-iso-propylphenyl)-1H-indol-5-yl]-but-2-enoic acid

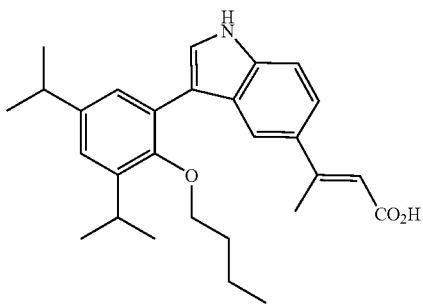

A. 1-Benzenesulfonyl-5-iodo-1H-indole

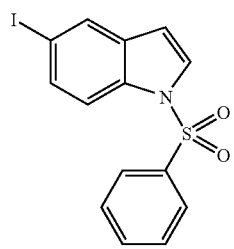

5-Iodoindole (9.72 g, 40 mmol), tetrabutylammonium hydrogen sulfate (1.36 g, 4 mmol) and benzene sulfonyl chloride (5.1 mL, 40 mmol) was dissolved in a biphasic mixture of toluene (240 mL)/2.5 N NaOH (480 mL) and stirred vigorously for 16 h. The two layers were separated and the toluene was washed with water (3×300 mL), brine (250 mL), dried ($Na_2SO_4$), filtered and evaporated in vacuo to provide 14.9 g of a reddish brown oil. The material was passed over a silica pad with (9:1) hexane:ethyl acetate to provide 14.0 g (91%) of a brown gum. $^1$H NMR (250 MHz, $CDCl_3$): δ 7.90-7.86 (m, 3H), 7.79 (d, 1H, J=8.7), 7.63-7.55 (m, 3H), 7.51-7.45 (m, 2H), 6.61 (1H, d, J=3.8).

B. 3-(1-Benzenesulfonyl-1H-indol-5-yl)-but-2-enoic acid methyl ester

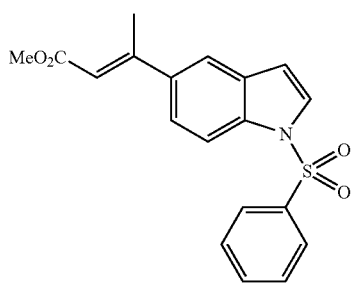

5-Iodo-N-benzenesulfonylindole (18.09 g, 47 mmol), methyl crotonate (40 mL, 378 mmol), triethylamine (145 mL), and palladium acetate (2.65 g, 11.8 mmol) were combined in DMF (600 mL). The reaction was heated at 100° C. for 4 h. TLC (3:1) hexane:ethyl acetate showed iodide still present. Methyl crotonate (25 mL) and dichlorobis(triphenylphosphine) palladium(II) (3.31 g, 4.7 mmol) was added. The reaction was heated for an additional 4 h and then at room temperature for 13 h at which time starting material was virtually gone. The solids were allowed to settle and most of the liquid decanted off. The remaining portion was filtered through a pad of celite to remove the solids and the volume reduced somewhat in vacuo. The solution was diluted with water (1 L) and washed with diethyl ether (3×500 mL). The organic portion was washed with 1N HCl (2×500 mL), brine (2×500 mL), dried ($MgSO_4$), filtered and evaporated in vacuo to provide 18.3 g of a dark brown oil. The material was purified preparatively in two runs on a Waters 2000LC using a gradient elution of (98:2) ethyl acetate:hexane to 66:34 ethyl acetate:hexane to give 6.79 g (40%). Mp: 80-85° C.

$^1$H NMR (250 MHz, $CDCl_3$): δ 7.90 (d, 1H, J=8.7), 7.84-7.81 (m, 2H), 7.57 (d, 1H, J=1.6), 7.52-7.35 (m, 5H), 6.60 (m, 1H), 6.07, (d, 1H, J=1.2), 3.68, (s, 3H), 2.53 (d, 3H, J=1.2). MS [EI+] 356 (M+H)$^+$. Anal. Calcd for $C_{19}H_{17}NO_4S$: C, 64.21; H, 4.82; N, 3.94. Found: C, 64.06; H, 4.63; N, 4.04.

C. 3-(1-Benzenesulfonyl-3-iodo-1H-indol-5-yl)-but-2-enoic acid methyl ester

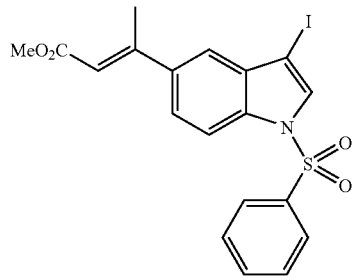

3-(1-Benzenesulfonyl-1H-indol-5-yl)-but-2-enoic acid methyl ester (6.78 g, 19.1 mmol), N-iodosuccinimide (6.45 g, 28.7 mmol) and p-toluenesulfonic acid monohydrate (0.55 g, 2.87 mmol) were dissolved in dichloromethane (50 mL) and stirred for 4 h. The reaction was diluted with diethyl ether (250 mL) and washed with 10% $Na_2S_2O_3$ (2×100 mL). The aqueous layers were combined and backwashed with ether and then the combined organic portions washed with water (200 mL, brine (200 mL), dried ($MgSO_4$), filtered, and evaporated to give 9.56 g reddish foam. The foam was passed over a pad of Florosil in a 2L sintered glass funnel using (9:1) hexane:ethyl acetate. Fractions containing product were concentrated. The reside was redissolved in hexane:ethyl acetate and the volume reduced in vacuo. The resulting solids were filtered and dried to give 4.08 g (44%) of a light pink solid. $^1$H NMR (250 MHz, $CDCl_3$): δ 8.00-7.92 (m, 3H), 7.75 (s, 1H), 7.54-7.48 (m, 5H), 6.20 (d, 1H, J=1.3), 3.79 (s, 3H), 2.65 (d, 3H, J=1.2).

D. 3-[1-Benzenesulfonyl-3-(2-butoxy-3,5-diisopropyl-phenyl)-1H-indol-5-yl]-but-2-enoic acid methyl ester

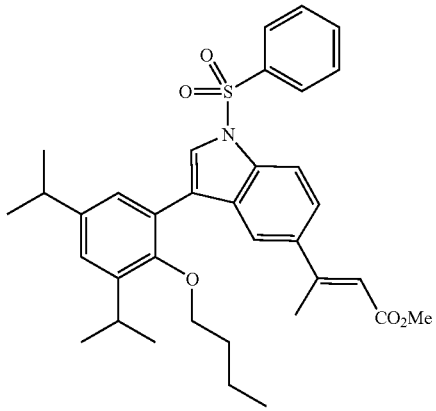

3-(1-Benzenesulfonyl-3-iodo-1H-indol-5-yl)-but-2-enoic acid methyl ester (653 mg, 1.35 mmol) and (2-butoxy-3,5-diisopropylphenyl)-boronic acid (415 mg, 1.49 mmol) were dissolved in toluene (8 mL) under a nitrogen atmosphere. Tetrakis(triphenylphosphine) palladium (172 mg, 0.15 mmol) and 2N $Na_2CO_3$ (2.7 mL) was added and the biphasic mixture stirred at 80° C. for 6 h. The reaction was judged complete by TLC (9:1) in hexane:ethyl acetate but was allowed to stir overnight at room temperature. The reaction was diluted with water (5 mL)/ethyl acetate (15 mL). The layers were separated and the aqueous washed with ethyl acetate (10 mL). The organic portions were passed through a pad of Celite, dried ($MgSO_4$), filtered and concentrated in vacuo to provide 1.20 g of a dark brown oil. Chromatography ($SiO_2$, hexanes/ethyl acetate) provided 294 mg (37%) of a yellow foam. $^1$H NMR (250 MHz, $CDCl_3$): δ 8.06 (d, 1H, J=8.7), 7.94 (m, 2H), 7.80 (s, 1H), 7.75 (d, 1H, J=1.7), 7.56-7.45 (m, 4H), 7.13 (m, 2H), 6.14 (d, 1H, J=1.2), 3.75 (s, 3H), 3.39 (sep, 1H, J=6.9), 3.29 (t, 2H, J=6.3), 2.93 (sep, 1H, J=6.9), 2.60 (d, 3H, J=1.2), 1.29 (d, 7H, J=6.9), 1.27 (d, 7H, J=6.9), 1.22 (m, 2H), 0.62 (t, 3H, J=7.2). MS [EI+] 588 $(M+H)^+$.

E. 3-[3-(2-butoxy-3,5-diisopropyl-phenyl)-1H-indol-5-yl]-but-2-enoic acid

3-[1-Benzenesulfonyl-3-(2-butoxy-3,5-diisopropyl-phenyl)-1H-indol-5-yl]-but-2-enoic acid methyl ester (130 mg, 0.22 mmol) was dissolved in methanol (3.5 mL)/dioxane (3.5 mL) and treated with 2.5N KOH (2.5 mL) at 60° C. for 8 h. Diluted with 1N HCl (10 mL) and extracted with ethyl acetate (3×10 mL). The combined organic portions were washed with water, brine, dried ($MgSO_4$), filtered and concentrated in vacuo to provide 151 mg of a yellow oil. The material was purified using radial chromatography by elution with hexane/ethyl acetate gradient to provide 51 mg (54%) of a yellow foam. $^1$H NMR (250 MHz, $CDCl_3$): δ 8.32 (bs, 1H), 8.02 (s, 1H), 7.55 (d, 1H, J=2.3), 7.40 (s, 2H), 7.28 (d, 1H, J=2.2), 7.09 (d, 1H, J=2.2), 6.26 (d, 1H, J=1.0), 3.44 (m, 3H), 2.95 (sep, 1H, J=6.9), 2.70 (d, 3H, J=0.9), 1.41 (m, 2H), 1.32-1.19 (m, 14H), 0.75 (t, 3H, J=7.3). MS [EI+] 434 $(M+H)^+$ [EI–] 432 $(M-H)^+$. HPLC [MetaSil AQ C18 (0.46×15 cm) 5-90% $CH_3CN$(0.1% TFA) in $H_2O$(0.1% TFA)], 21.973 min. >99%.

Example 49

3-[3-(2-Butoxy-3,5-diisopropylphenyl)-1-methyl-1H-indol-5-yl]-but-2-enoic acid

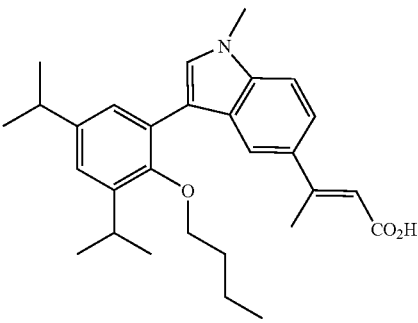

A. 3-[3-(2-Butoxy-3,5-diisopropylphenyl)-1-methyl-1H-indol-5-yl]-but-2-enoic acid methyl ester

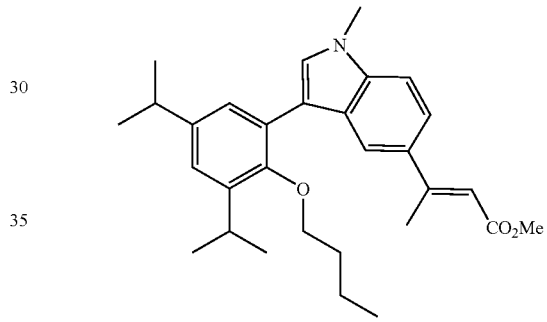

3-[3-(2-Butoxy-3,5-diisopropyl-phenyl)-1H-indol-5-yl]-but-2-enoic acid (129 mg, 0.30 mmol), cesium carbonate (293 mg, 0.90 mmol), and iodomethane (0.041 mL, 65 mmol) were combined in DMF (6 mL) and heated at 40° C. for 2 h. The reaction was diluted with water and extracted with ethyl acetate (2×). The organic portions were combined and washed with brine, dried ($MgSO_4$), filtered and concentrated in vacuo to provide 139 mg of a yellow oil. The material was purified using radial chromatography by elution with (95:5) hexane:ethyl acetate to provide 119 mg (86%) of product.

$^1$H NMR (250 MHz, $CDCl_3$): δ 8.00 (d, 1H, J=1.4), 7.45 (dd, 1H, J=1.7, 8.7), 7.41 (s, 1H), 7.34 (d, 1H, J=8.7), 7.28 (d, 1H, J=2.3), 7.07 (d, 1H, J=2.3), 6.22 (d, 1H, J=1.2), 3.86 (s, 3H), 3.76 (s, 3H), 3.44 (m, 3H), 2.94 (sep, 1H, J=6.9), 2.68 (d, 3H, J=1.0), 1.44 (m, 2H), 1.30-1.19 (m, 14H), 0.76 (t, 3H, 7.3). MS [EI+] 462 $(M+H)^+$.

B. 3-[3-(2-Butoxy-3,5-diisopropylphenyl)-1-methyl-1H-indol-5-yl]-but-2-enoic acid 3-[3-(2-Butoxy-3,5-diisopropylphenyl)-1-methyl-1H-indol-5-yl]-but-2-enoic acid methyl ester (119 mg, 0.26 mmol) was dissolved in methanol (2.5 mL)/dioxane (2.5 mL) and treated with 1N NaOH (2.5 mL) at 60° C. for 3 h. The reaction was diluted with 1N HCl (3 mL) and extracted with ethyl acetate (3×10 mL). The combined organic portions were washed with brine, dried (MgSO₄), filtered and concentrated in vacuo to provide 134 mg of residue. The material was purified using radial chromatography by elution with hexane:ethyl acetate gradient to provide 60 mg (52%) of a light yellow solid. $^1$H NMR (250 MHz, CDCl$_3$): δ 8.05 (d, 1H, J=1.4), 7.49 (dd, 1H, J=1.6, 8.7), 7.44 (s, 1H), 7.38 (d, 1H, J=8.7), 7.07 (d, J=2.3), 7.30 (d, 1H, J=2.2), 7.10 (d, 1H, J=2.2), 3.89 (s, 3H), 3.47 (m, 3H), 2.97 (sep, 2H, J=6.9), 2.73 (s, 3H), 1.46 (m, 2H), 1.34-1.22 (m, 14H), 0.78 (t, 3H, J=7.3). MS [EI+] 448 (M+H)⁺[EI−] 446. Anal. Calcd for C$_{29}$H$_{37}$NO$_3$: C, 77.82; H, 8.33; N, 3.13. Found: C, 77.50; H, 8.28; N, 3.15.

Example 50

3-[3-(2-Ethoxy-3,5-diisopropyl-phenyl)-1H-indol-5-yl]-but-2-enoic acid

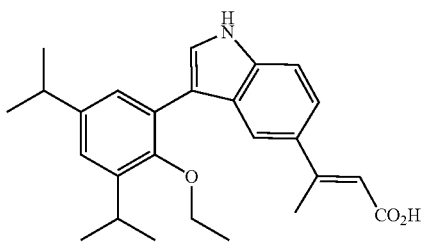

A. 3-[3-(2-ethoxy-3,5-diisopropyl-phenyl)-1H-indol-5-yl]-but-2-enoic acid methyl ester

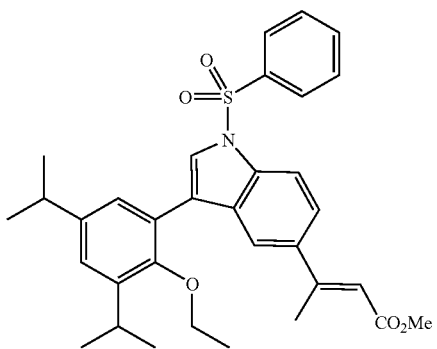

3-(1-Benzenesulfonyl-3-iodo-1H-indol-5-yl)-but-2-enoic acid methyl ester (226 mg, 0.47 mmol) (see Example 23, step C), (2-ethoxy-3,5-diiosopropylphenyl)-boronic acid (129 mg, 0.52 mmol) and tetrakis(triphenylphosphine) palladium (54 mg, 0.05 mmol) were combined in toluene (3 mL)/2N Na₂CO₃ (1 mL) and heated at 80° C. After 4.5 h, the reaction was diluted with water/ethyl acetate and the layers were separated. The aqueous layer was washed with ethyl acetate. The organic portions were combined washed with brine, dried (MgSO₄), filtered and evaporated in vacuo to provide 337 mg as a dark brown oil. The material was purified by column chromatagraphy using (9:1) hexane:ethyl acetate. Further purification was accomplished by radial chromatography using (99:1) hexane:ethyl acetate and (95:5) hexane:ethyl acetate to provide 93 mg (35%) of a yellow solid. $^1$H NMR (250 Mz, CDCl$_3$): δ 8.08 (d, 1H, J=8.7), 7.93 (m, 2H), 7.92 (s, 1H), 7.78 (d, 1H, J=1.7), 7.56-7.45 (m, 4H), 7.14 (s, 2H), 6.15 (d, 1H, J=1.2), 3.74 (s, 3H), 3.38 (m, 3H), 2.92 (sep, 1H, J=6.9), 2.60 (d, 3H, J=1.2), 1.29 (d, 7H, J=6.9), 1.27 (d, 6H, J=6.9), 0.91 (t, 3H, J=7.0). MS [EI+] 560 (M+H)⁺.

B. 3-[3-(2-ethoxy-3,5-diisopropyl-phenyl)-1H-indol-5-yl]-but-2-enoic acid

3-[3-(2-Ethoxy-3,5-diisopropyl-phenyl)-1H-indol-5-yl]-but-2-enoic acid methyl ester (77 mg, 0.14 mmol) was dissolved in methanol (1 mL)/dioxane (1 mL) and treated with 1N NaOH (1 mL) at 55° C. for 5 h. Diluted with 1N HCl (3 mL)/water (10 mL) and extracted with ethyl acetate (3×10 mL). The combined organic portions were washed with brine (2×10 mL), dried (MgSO₄), filtered and concentrated in vacuo to provide 68 mg. The material was purified by radial chromatography using a hexane/ethyl acetate gradient to provide 34 mg (62%) of a yellow foam. $^1$H NMR (250 MHz, CDCl$_3$): δ 8.33 (bs, 1H), 8.04 (s, 1H), 7.58 (d, 1H, J=2.4), 7.44 (s, 1H), 7.29 (d, 1H, J=2.2), 7.09 (d, 1H, J=2.2), 6.27 (s, 1H), 3.56-3.38 (m, 3H), 2.95 (sep, 1H, J=6.9), 2.70 (s, 3H), 1.32 (s, 12H, J=6.9), 1.08 (t, 3H, J=7.0). MS [EI−] 404 (M−H)⁺.

Example 51

3-[3-(2-Butoxy-3,5-di-tert-butyl-phenyl)-1H-indol-5-yl]-but-2-enoic acid

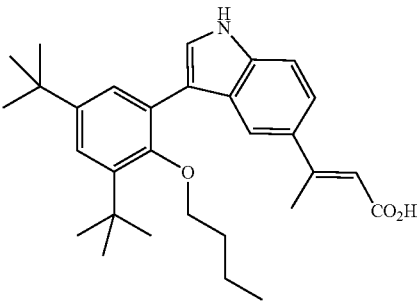

A. 1-Butoxy-2,4-di-tert-butyl-benzene

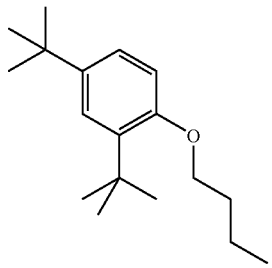

2,4-Di-tert-butylphenol (10.3 g, 50 mmol), cesium carbonate (32.6 g, 100 mmol) and 1-iodobutane (6 ml, 52.5 mmol) were combined and stirred in dimethylformamide (250 mL) at room temperature for 24 h. The reaction was diluted with water (250 mL) and washed with 50% hexane/diethyl ether (400 mL, 2×200 mL). The organic portions were combined, washed with water (2×250 mL), dried MgSO₄), filtered and evaporated in vacuo to provide 12.2 g of a yellow oil. The material was passed over a silica pad with hexane to give 11.26 g (86%) of a clear oil. ¹H NMR (250 MHz, CDCl₃): δ 7.38 (d, 1H, J=2.5), 7.22 (dd, 1H, J=2.6, J=8.5), 6.84 (d, J=8.5), 4.02 (t, 2H, J=6.4), 1.87 (m, 2H), 1.59 (m, 2H), 1.46 (s, 9H), 1.36 (s, 9H), 1.04 (t, 3H, J=7.3).

B. 2-Butoxy-1,5-di-tert-butyl-3-iodo-benzene

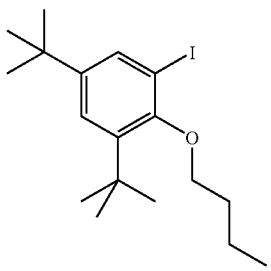

1-Butoxy-2,4-di-tert-butyl-benzene (11.21 g, 42.7 mmol), N-iodosuccinimide (11.53 g, 51.2 mmol) and p-toluenesulfonic acid monohydrate (1.62 g, 8.5 mmol) were combined in dichloromethane (100 mL) and stirred at room temperature for 62 h. TLC (hexane) showed the reaction was not yet complete. Additional N-iodosuccinimide (4.8 g, 21.3 mmol) and p-toluenesulfonic acid monohydrate (1.62 g, 8.5 mmol) were added and the reaction stirred at 35° C. for 6 h. TLC showed the reaction was completed. It was washed with a 10% Na₂S₂O₃ solution (3×100 mL).

The aqueous was backwashed with dichloromethane (100 mL) and then the combined organic portions washed with water (100 mL) dried (MgSO₄), filtered and evaporated in vacuo to provide 16.42 g yellow oil. The material was passed over a silica pad with hexane and 99 hexane/1 ethyl acetate to provide 15.93 g (96%) of a pale yellow oil. ¹H NMR (250 MHz, CDCl₃): δ 7.68 (d, 1H, J=2.4), 7.36 (d, 1H, J=72.4), 4.00 (t, 2H, J=6.8), 1.92 (m, 2H), 1.58 (m, 2H), 1.42 (s, 9H), 1.31 (s, 9H), 1.04 (t, 3H, J=7.3). MS [EI+] 275 (M+H)⁺(−2 tBu).

C. (2-Butoxy-3,5-di-tert-butylphenyl)-boronic acid

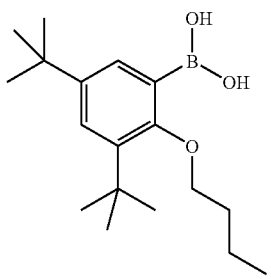

2-Butoxy-1,5-di-tert-butyl-3-iodo-benzene (3.88 g, 10 mmol) was dissolved in anhydrous 1,2-dimethoxy-ethane (55 mL under a nitrogen atmosphere. The solution was cooled to −75° C. and t-butyl lithium (14.7 mL, 25 mmol, 1.7M in pentane) was added dropwise over 20-25 min at −72° C. to −69° C. The reaction was stirred at −72° C. for 45 min and then treated with trimethyl borate (5.7 mL, 50 mmol). The reaction was kept cold for 1 h and then the bath was removed and the reaction allowed to warm to room temperature over 24 h. It was treated with 1N hydrochloric acid (35 mL) and stirred for 30 min. The reaction was then diluted with water (200 mL) and extracted with ethyl acetate (150 mL, 2×100 mL). The combined organic portions were washed with bicarbonate solution (100 mL), water (150 mL), brine (150 mL), dried (Na₂SO₄), filtered and evaporated in vacuo to provide 3.0 g of an oil. The material was purified by flash chromatography (eluet: (9:1) hexane:ethyl acetate and (4:1) hexane:ethyl acetate) to provide 2.04 g (67%) of a white solid. Mp: 82-91° C. ¹H NMR (250 MHz, CDCl₃): δ 7.66 (d, 1H, J=2.6), 7.48 (d, 1H, J=2.6), 5.75 (s, 1H), 3.84 (t, 2H, J=7.1), 1.84 (m, 2H), 1.47 (m, 2H), 1.42 (s, 9H), 1.33 (s, 9H), 2.66 (t, 3H, J=7.3). MS [EI+] 307 (M+H)⁺[EI−] 305 (M−H)⁺.

C. 3-[1-Benzenesulfonyl-3-(2-butoxy-3,5-di-tert-butyl-phenyl)-1H-indol-5-yl]-but-2-enoic acid methyl ester

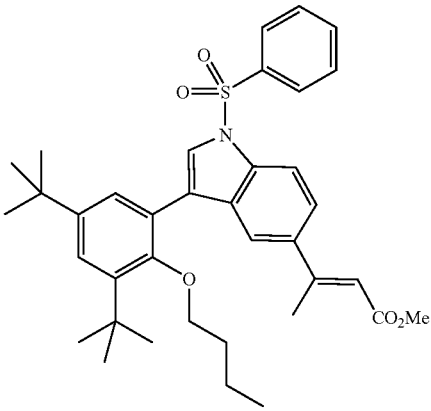

3-(1-Benzenesulfonyl-3-iodo-1H-indol-5-yl)-but-2-enoic acid methyl ester (400 mg, 0.83 mmol) (see Example 23, step C) and (2-butoxy-3,5-di-tert-butylphenyl)-boronic acid (415 mg, 1.49 mmol) were dissolved in toluene (6 mL) under a nitrogen atmosphere. Tetrakis(triphenylphosphine) palladium (96 mg, 0.083 mmol) and 2N Na₂CO₃ (2.0 mL) were added and the biphasic mixture stirred at 80 ° C. for 5 h. TLC (9 hexane/1 EtOAc, 3×) showed the iodide still present and additional palladium catalyst (90 mg) was added and the reaction stirred at 80° C. for 18 h. The reaction was allowed to cool to room temperature and the aqueous layer was washed with ethyl acetate. The layers were separated and the aqueous washed with EtOAc (2×10 mL). The organic portions were washed with brine, dried (MgSO₄), filtered and concentrated in vacuo to provide 750 mg of a residue. The material was purified by column and radial chromatography (SiO₂, hexane/ethyl acetate gradient) to provide 192 mg (31%) of a yellow foam. ¹H NMR (250 MHz, CDCl₃): δ 8.07 (d, 1H, J=8.7), 7.95 (m, 2H), 7.71 (m, 2H), 7.53-7.39 (m, 5H), 7.22 (d, 1H, J=2.5), 6.15 (d, 1H, J=1.2), 3.75 (s, 3H), 3.27 (t, 2H, J=6.4), 2.58 (d, 3H, J=1.1), 1.45 (s, 9H), 1.34 (s, 9H), 1.09 (m, 2H), 0.83 (m, 2H), 0.47 (t, 3H). MS [EI+] 616 (M+H)⁺.

D. 3-[3-(2-butoxy-3,5-di-tert-butyl-phenyl)-1H-indol-5-yl]-but-2-enoic acid

3-[1-Benzenesulfonyl-3-(2-butoxy-3,5-di-tert-butyl-phenyl)-1H-indol-5-yl]-but-2-enoic acid methyl ester (187 mg, 0.3 mmol) was dissolved in methanol (2 mL)/dioxane (3.5 mL) and treated with 1N NaOH (2 mL) at 60° C. for 4 h. Diluted with 1N HCl (3 mL) and extracted with ethyl acetate (3×10 mL). The combined organic portions were washed with water (10 mL), brine (10 mL), dried (MgSO$_4$), filtered and concentrated in vacuo to provide 160 mg of an orange solid. The material was purified using radial chromatography (eluet: hexane/ethyl acetate gradient) to provide 85 mg (62%) of a yellow foam. $^1$H NMR (250 MHz, CDCl$_3$): δ 8.24 (bs, 1H), 7.88 (s, 1H), 7.40-7.35 (m, 3H), 7.28 (d, 2H), 6.18 (s, 1H), 3.37 (t, 2H, J=6.5), 2.61 (s, 3H), 1.41 (s, 9H), 1.28 (s, 9H), 1.19-0.98 (m, 4H), 0.56 (t, 3H, J=7.2). MS [EI+] 462 M+H)$^+$, [EI−] 460 (M−H)$^+$. Anal. Calcd for C$_{30}$H$_{39}$NO$_3$: C, 78.05; H, 8.52; N, 3.03. Found: C, 78.10; H, 8.30; N, 3.02.

Example 52

3-[4-(2-Butoxy-3,5-diisopropylphenyl)-1H-indol-2-yl]-but-2-enoic acid

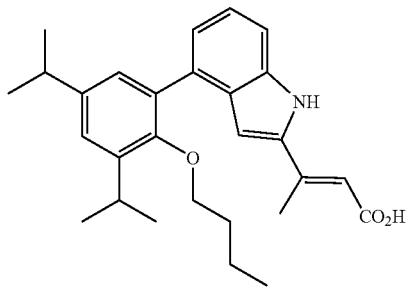

A. 1-Benzenesulfonyl-4-bromo-1H-indole

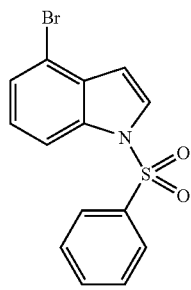

5-Bromoindole (9.76 g, 50 mmol), tetrabutylammonium hydrogen sulfate (1.70 g, 5 mmol) and benzene sulfonyl chloride (6.7 mL, 50 mmol) was dissolved in a biphasic mixture of toluene (300 mL)/2.5 N NaOH (600 mL) and stirred vigorously for 2.5 h. The aqueous layer was separated and washed with ethyl acetate (2×250 mL). All organic portions were combined and washed with water (3×250 mL), brine (250 mL), dried over MgSO$_4$, filtered and evaporated in vacuo to provide 16.5 g of crude product. The crude product was triturated in diethyl ether and filtered to give 12.49 g of a light pink solid. The filtrate was concentrated and triturated in hexane to give 2.10 g of a brick red solid for a combined yield of 87%. $^1$H NMR (250 MHz, CDCl$_3$): δ 7.98 (dl, 1H, J=8.3), 7.90 (m, 2H), 7.66 (d, 1H), 7.56-7.41 (m; 4H), 7.24 (t, 1H, J=8.0) 6.76 (1H, d, J=3.8). MS [EI+] 335, 337 (M)$^+$.

B. 1-Benzenesulfonyl-4-bromo2-trimethylsilanyl-1H-indole

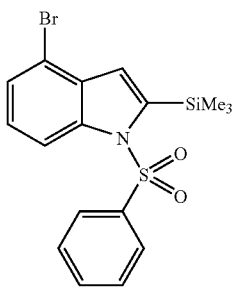

Anhydrous THF (12 mL) was placed in an oven-dried 3-neck, reaction flask under nitrogen and cooled to −73° C. in a dry ice/acetone bath. Lithium diisopropylamide (2.0 M, 3.0 mL, 6 mmol) was added followed by addition of a solution of 4-bromo-benzenesulfonylindole (1.92 g, 5.7 mmol) in anhydrous THF (10 mL) over a period of 10 min at −73° C. to −70° C. The reaction was stirred at −73° C. for 1.5 h and then placed in an ice/brine bath and allowed to warm to −5° C. over 50 min. Chlorotrimethylsilane (3.0 mL, 1.2 mmol) was dissolved in anhydrous THF (10 mL) in a separate 3-neck roundbottom flask under nitrogen and cooled to −73° C. with a dry ice/acetone bath. The indolyl lithium species was cooled back down to −73° C. and cannulated into the chlorotrimethyl silane while the temperature was maintained at −72° C. to −68° C. After the addition was complete, the bath was left in place, and the reaction allowed to gradually warm to room temperature overnight The reaction was poured slowly into ethyl acetate (150 mL) and washed with 3-5% aqueous NaHCO$_3$ solution (50 mL). The organic layer was washed with more aqueous NaHCO$_3$ (50 mL) and then the bicarbonate layer was backwashed with ethyl acetate (50 mL). The combined organic layers were washed with water (100 mL), brine (100 mL), dried over MgSO$_4$, filtered and evaporated in vacuo to provide 2.27 g of a yellow oil. The material was purified chromatographically using (99:1) hexane:ethyl acetate followed by (9:1) hexane:ethyl acetate to elute the product. Obtained 1.56 g (67%) of a clear oil. $^1$H NMR (250 MHz, CDCl$_3$): δ 7.83 (d, 1H, J=8.4), 7.65 (m, 2H), 7.53 (m, 1H), 7.51-7.35 (m, 3H), 7.10 (t, 1H, J=8.2), 7.00 (s, 1H), 0.48 (s, 9H). MS [EI+] 408, 410 (M+H)$^+$, [EI−] 407, 408.

C. 1-(1-Benzenesulfonyl-4-bromo-1H-indol-2-yl)-ethanone

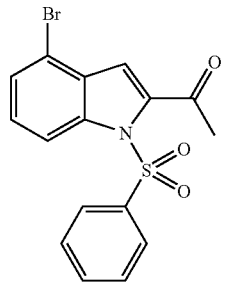

To a suspension of aluminum chloride (3.04 g, 22.8 mmol) in anhydrous CH$_2$Cl$_2$ 25 mL) under nitrogen was added acetic anhydride (1.1 mL, 11.4 mmol). The mixture was stirred for 20 min and then cooled in an ice bath. A solution of 2-trimethylsilyl-4-bromo-benzenesulfonylindole (1.55 g, 3.8 mmol) in CH$_2$Cl$_2$ was added slowly. The ice bath was removed after 5 min and the reaction allowed to warm to room temperature. After 1 h the reaction was judged complete by TLC (9:1) hexane:ethyl acetate. Ice was added, the biphasic mixture stirred for 20 min and then diluted into water (25 mL)/CH$_2$Cl$_2$. The layers were separated and the aqueous layer was washed with CH$_2$Cl$_2$ (2×50 mL). The combined organic portions were washed with saturated NaHCO$_3$ solution (100 mL), brine (100 mL), dried over MgSO$_4$, filtered and evaporated in vacuo to provide 1.28 g of a pink solid.

The material was purified by column chromatography using (99:1) hexane:ethyl acetate followed by (5:1) hexane:ethyl acetate to provide 1.15 g (yield=80%) of product as an off-white solid. Mp: 142-146° C. $^1$H NMR (250 MHz, CDCl$_3$): δ 8.16 (d, 1H, J=8.5), 8.02 (m, 2H), 7.63-7.48 (m, 4H), 7.35 (t, 1H, J=8.3), 7.22 (s, 1H), 2.69 (s, 3H). MS [EI+] 378, 380 (M+H)$^+$.

D. 3-(1-Benzenesulfonyl-4-bromo-1H-indol-2-yl)-but-2-enoic acid methyl ester

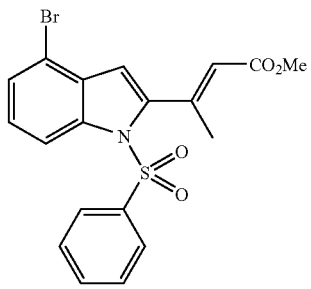

Methyldiethylphosphonoacetate (366 mg, 0.97 mmol) was dissolved in DMF (8 mL) under nitrogen, cooled in an ice bath, and treated with potassium t-butoxide (434 mg, 3.87 mmol). The ice bath was removed and allowed to warm to room temperature over 30 min. 1-(1-Benzenesulfonyl-4-bromo-1H-indol-2-yl)ethanone (366 mg, 0.97 mmol) dissolved in DMF (4 mL) was added and the reaction heated at 50° C. for 1.5 h. The reaction was allowed to cool and poured into ethyl acetate/saturated ammonium chloride solution. The aqueous was washed with more ethyl acetate. Then the pH was lowered and the aqueous washed a third time with ethyl acetate. The organic portions were washed with brine, dried (MgSO$_4$), filtered and evaporated to give 3.24 g brown oil. The material was purified by column chromatography using (5:1) hexane:ethyl acetate to give 207 mg (28%) of a crude foam. The material was used without further purification. MS [EI+] 434, 436 (M+H)$^+$.

E. 3-[1-Benzenesulfonyl-4-(2-butoxy-3,5-diisopropyl-phenyl)-1H-indol-2-yl]-but-2-enoic acid methyl ester

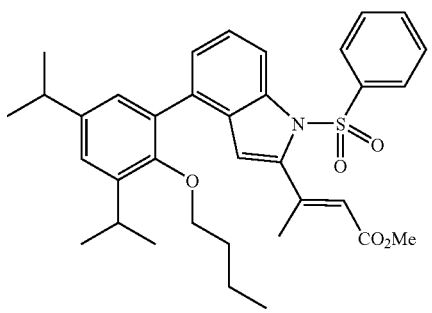

3-(1-Benzenesulfonyl-4-bromo-1H-indol-2-yl)-but-2-enoic acid methyl ester (117 mg, 0.27 mmol) and 2-butoxy-3,5-diisopropylphenyl-boronic acid (150 mg, 54 mmol) (see Example 17, step B) were dissolved in toluene (2 mL) under a nitrogen atmosphere. Tetrakis(triphenylphosphine) palladium (31 mg, 0.027 mmol) and 2N Na$_2$CO$_3$ (0.7 mL) were added and the biphasic mixture stirred at 75° C. for 16 h. The reaction was diluted with water/ethyl acetate. The layers were separated and the aqueous layer was washed with ethyl acetate. The organic portions were passed through a pad of Celite, dried (MgSO$_4$), filtered and concentrated in vacuo to provide 243 mg of a crude black oil. Radial chromatography using (99:1) hexane:ethyl acetate provided 76 mg (48%) of product. $^1$H NMR (250 MHz, CDCl$_3$): δ 8.15 (d, 1H, 8.2), 7.66 (m, 2H), 7.46-7.27 (m, 5H), 7.11 (d, 1H, J=2.2), 6.90 (d, 1H, J=2.2), 6.54 (s, 1H), 6.05 (d, 1H, J=1.2), 3.80 (s, 3H), 3.36 (sep, 1H, J=6.9), 3.04 (t, 2H, J=6.0), 2.88 (sep, 1H, J=6.9), 2.61 (d, 3H, J=1.2), 1.25 (d, 6H, J=6.9), 1.24 (d, 6H, J=6.9), 1.08-0.87 (m, 4H), 0.62 (t, 3H, J=7.0). MS [EI+] 588 (M+H)$^+$ [EI−] 586 (M−H)$^+$.

F. 3-[1-Benzenesulfonyl-4-(2-butoxy-3,5-diisopropyl-phenyl)-1H-indol-2-yl]-but-2-enoic acid

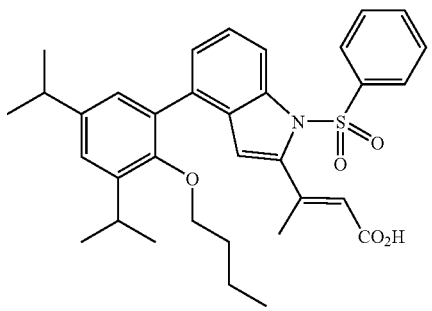

3-[1-Benzenesulfonyl-4-(2-butoxy-3,5-diisopropyl-phenyl)-1H-indol-2-yl]-but-2-enoic acid methyl ester (74 mg, 0.126 mmol) was dissolved in methanol (1 mL)/dioxane (1 mL) and treated with 1N NaOH (1 mL, 1 mmol) at 60° C. for 2 h. The reaction was diluted with 1N HCl (3 mL)/water (10 mL) and extracted with ethyl acetate (3×10 mL). The organic portions were washed with water (10 mL), brine (10 mL), dried (MgSO$_4$), filtered and evaporated in vacuo to provide 78 mg of a yellow oil. The material was purified using radial chromatgraphy with a gradient of hexane/ethyl acetate to provide 42 mg (58%) of a yellow amorphous foam. $^1$H NMR (250 MHz, CDCl$_3$): δ 8.08 (d, 1H, 8.2), 7.58 (m, 2H), 7.42-7.21 (m, 5H), 7.03 (d, 1H, J=2.2), 6.82 (d, 1H, J=2.2), 6.49 (s, 1H), 6.00 (bs, 1H), 3.28 (sep, 1H, J=6.9), 2.96 (t, 2H, J=6.0), 2.81 (sep, 1H, J=6.9), 1.18 (d 6H, J=6.9), 1.17 (d, 6H, J=6.9). MS [EI+] 574, (M+H)$^+$, [EI−] 572 (M−H)$^+$.

G. 3-[4-(2-butoxy-3,5-diisopropyl-phenyl)-1H-indol-2-yl]-but-2-enoic acid

3-[1-Benzenesulfonyl-4-(2-butoxy-3,5-diisopropyl-phenyl)-1H-indol-2-yl]-but-2-enoic acid (32 mg, 0.056 mmol) was dissolved in ethanol (1 mL)/dioxane (1 mL) and treated with 2.5N KOH (1 mL, 1 mmol) at 70-75° C. for 24 h. The reaction was neutralized with 1N HCl and extracted with ethyl acetate (3×10 mL). The organic portions were washed with water (10 mL), brine (10 mL), dried over MgSO$_4$, filtered and evaporated in vacuo to provide 25 mg of a residue. The material was purified using radial chromatography with a gradient of hexane/ethyl acetate to provide 13 mg (53%) of a yellow amorphous foam. $^1$H NMR (250 MHz, CDCl$_3$): δ 8.26 (bs, 1H), 7.26-7.15 (m, 3H), 7.06 (m, 2H), 6.83 (s, 1H), 6.11 (s, 1H), 3.37 (m, 1H), 3.22 (t, 2H, J=6.3), 2.86 (m, 1H), 2.55 (s, 3H), 1.23 (m, 14H), 0.95 (m, 2H), 0.54 (t, 3H, J=7.2). MS [EI+] 434, (M+H)$^+$, [EI−] 432 (M−H)$^+$.

Example 53

3-[1-(2-Butoxy-3,5-diisopropyl-phenyl)-isoquinolin-7-yl]-but-2(E)-enoic acid

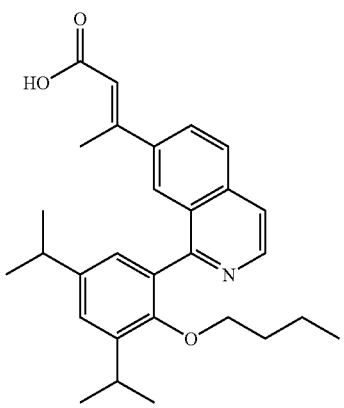

A. 3-(1-Oxo-1,2-dihydro-isoquinolin-7-yl)-but-2(E)-enoic acid methyl ester

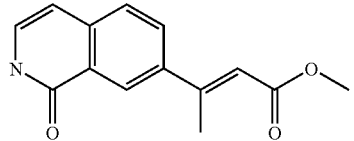

To a solution of 7-bromo-2H-isoquinolin-1-one (272 mg, 1.21 mmol) in DMF (4.0 mL) was added trans-methylcrotonate (0.40 mL, 3.8 mmol), triethylamine (0.70 mL, 5.04 mmol), and palladium acetate (79 mg, 0.35 mmol). The solution was sparged with N$_2$ for 5 min then stirred overnight at 90° C. under N$_2$ atm. Additional trans-methylcrotonate (0.40 mL, 3.8 mmol) and dichlorobis(triphenylphospine) palladium(II) (180 mg, 0.26 mmol) were added, and the mixture was stirred at 100° C. for 6 h under N$_2$ atm. The mixture was cooled to room temperature, diluted with H$_2$O, and extracted with ethyl acetate (50 mL). The organic layer was separated and washed with H$_2$O (2×25 mL), saturated NaHCO$_3$ (25 mL) and brine (25 mL) then dried, filtered, and concentrated. The crude material was purified by flash chromatography (50% to 75% ethyl acetate/hexanes) to give 3-(1-oxo-1,2-dihydro-isoquinolin-7-yl)-but-2(E)-enoic acid methyl ester (112 mg, 38% yield) as a white solid. $^1$H NMR (400 MHz, CDCl$_3$): δ 11.42 (br s, 1H), 8.53 (d, 1H, J=1.5), 8.40 (d, 1H, J=8.3), 7.78 (dd, 1H, J=2.0, 8.3), 7.55 d (d, 1H, J=8.3), 6.56 (d, 1H, J=6.8), 6.28 (d, 1H, J=1.0), 3.76 (s, 3H), 2.66 (d, 3H, J=1.0). MS [EI+] 244 (M+H)$^+$, [EI−]242 (M−H)$^−$.

B. 3-(1-Trifluoromethanesulfonyloxy-isoquinolin-7-yl)-but-2(E)-enoic acid methyl ester

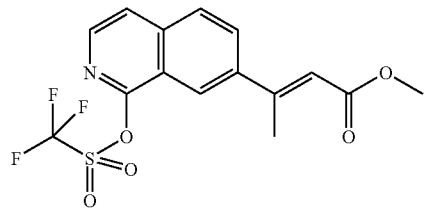

To a 0° C. solution of 3-(1-oxo-1,2-dihydro-isoquinolin-7-yl)-but-2(E)-enoic acid methyl ester (112 mg, 0.46 mmol) in (2:1) CH$_2$Cl$_2$:pyridine (3 mL) was added trifluoromethanesulfonic anhydride (0.09 mL, 0.6 mmol). The solution was stirred at 0° C. for 2 h then poured into brine (25 mL) and extracted with ethyl acetate (30 mL). The organic layer was separated and dried, filtered, and concentrated to give crude material which was purified by flash chromatography to give 3-(1-trifluoromethanesulfonyl-oxy-isoquinolin-7-yl)-but-2(E)-enoic acid methyl ester (98 mg, 56% yield) as a white solid. $^1$H NMR (400 MHz, CDCl$_3$): δ 8.21 (d, 1H, J=8.3), 8.15 (s, 1H), 7.90 (m, 2H), 7.70 (dd, 1H, J=1.1, 8.3), 6.26 (m, 1H), 3.78 (s, 3H), 2.67 (d, 3H, J=1.5). MS [EI+] 376 (M+H)$^+$.

C. 3-[1-(2-Butoxy-3,5-diisopropyl-phenyl)-isoquinolin-7-yl]-but-2(E)-enoic acid methyl ester

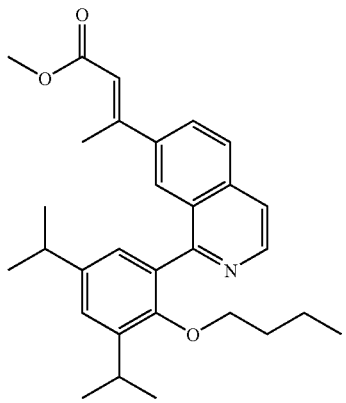

To a solution of 3-(1-trifluoromethanesulfonyl-oxy-isoquinolin-7-yl)-but-2(E)-enoic acid methyl ester (96 mg, 0.26 mmol) and (2-butoxy-3,5-diisopropyl-phenyl)-boronic acid (97 mg, 0.35 mmol) (see Example 17, step B) in toluene (3 mL) was added 2N $Na_2CO_3$ (0.58 mmol) and tetrakis(triphenylphosphine)palladium(0) (80 mg, 0.069 mmol). The mixture was stirred at 80° C. for 1.5 h under $N_2$ atm. The mixture was then poured into brine (25 mL) and extracted with ethyl acetate (30 mL). The organic phase was dried, filtered, and concentrated. The crude material was purified by flash chromatography (0 to 10% ethyl acetate:hexanes) to give 3-[1-(2-butoxy-3,5-diisopropyl-phenyl)-isoquinolin-7-yl]-but-2(E)-enoic acid methyl ester (66 mg, 55% yield) as a white solid. $^1$H NMR (400 MHz, $CDCl_3$): δ 8.62 (d, 1H, J=5.9), 7.93 (m, 1H), 7.82 (d, 1H, J=8.8), 7.75 (d, 1H, J=8.8), 7.62 (d, 1H, J=5.9), 7.22 (d, 1H, J=2.4), 7.16 (d, 1H, J=2.4), 6.20 (d, 1H, J=1.5), 3.72 (s, 3H), 3.37 (m, 2H), 3.07 (m, 1H), 2.93 (m, 1H), 2.54 (d, 3H, J=1.5), 1.27 (m, 12H), 1.01 (m, 2H), 0.70 (m, 2H), 0.43 (t, 3H, J=7.8). $^{13}$C NMR (63 MHz): δ 167.1, 160.6, 155.0, 152.4, 144.3, 143.0, 141.6, 140.1, 136.2, 132.1, 131.3, 127.8, 127.2, 126.7, 126.6, 125.5, 119.4, 117.6, 73.9, 51.1, 33.8, 31.8, 27.0, 24.4, 24.1, 23.9, 23.1, 18.5, 17.8, 13.4. MS (EI+) 460 (M+H)$^+$.

D. 3-[1-(2-Butoxy-3,5-diisopropyl-phenyl)-isoquinolin-7-yl]-but-2(E)-enoic acid To a solution of 3-[1-(2-butoxy-3,5-diisopropyl-phenyl)-isoquinolin-7-yl]-but-2(E)-enoic acid methyl ester (66 mg, 0.14 mmol) in methanol (1.0 mL) was added 1N NaOH (0.58 mL). The solution was stirred at 45° C. overnight. The solution was neutralized with 1N HCl solution, diluted with $H_2O$ (20 mL) and extracted with ethyl acetate (3×20 mL). The organic layers were combined and washed with brine (20 mL), dried, filtered, and concentrated. The crude material was purified by flash chromatography (20% to 40% ethyl acetate:hexanes) to give 3-[1-(2-butoxy-3,5-diisopropyl-phenyl)-isoquinolin-7-yl]-but-2(E)-enoic acid (37 mg, 58% yield) as a white solid. mp 149.8° C. $^1$H NMR (400 MHz, $CDCl_3$): δ 8.65 (d, 1H, J=5.9), 7.95 (s, 1H), 7.84 (d, 1H, J=8.8), 7.77 (d, 1H, J=7.3), 7.65 (d, 1H, J=5.4), 7.22 (d, 1H, J=2.0), 7.17 (s, 1H), 6.22 (s, 1H), 3.37 (m, 2H), 3.0 6(m, 1H), 2.93 (m, 1H), 2.56 (s, 3H), 1.27 (m, 12H), 1.02 (m, 2H), 0.75 (m, 2H), 0.44 (t, 3H, J=7.3). $^{13}$C NMR (63 MHz): δ 171.0, 160.5, 156.3, 152.4, 144.3, 142.5, 141.6, 140.2, 136.4, 131.6, 128.1, 127.4, 126.9, 126.7, 125.6, 119.7, 117.9, 74.0, 33.8, 31.8, 27.0, 24.4, 24.3, 24.0, 23.0, 18.5, 18.0, 13.4. MS [EI+] 446 (M+H)$^+$. Analytical ($C_{29}H_{35}NO_3$): Calculated C, 78.17; H, 7.92; N, 3.14. Found: C, 78.12; H, 8.14; N, 3.13.

Example 54

3-[4-(2-Butoxy-3,5-diisopropyl-phenyl)quinolin-6-yl]-but-2(E)-enoic acid

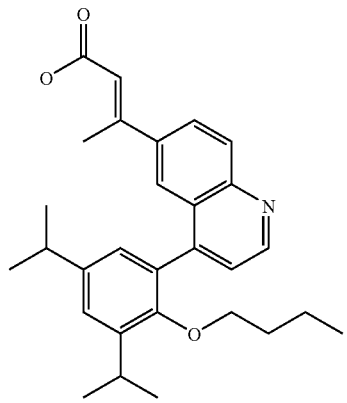

A. Trifluoro-methanesulfonic acid 6-acetyl-quinolin4-yl ester

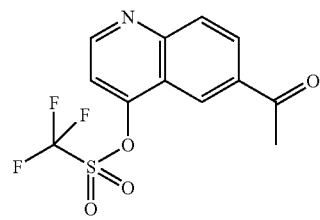

To a 0° C. solution of 6-acetyl-1H-quinolin-4-one [1] (507 mg, 2.71 mmol) in (7:3) $CH_2Cl_2$:pyridine (10 mL) was added trifluoromethane-sulfonic anhydride (0.55 mL, 3.27 mmol). The solution was stirred at 0° C. for 2 h under $N_2$ atm. The solution was quenched by addition of saturated $NaHCO_3$ (50 mL). The mixture was extracted with ethyl acetate (50 mL) and the organic phase was washed with brine (50 mL) then dried, filtered, and concentrated. The crude trifluoro-methanesulfonic acid 6-acetyl-quinolin-4-yl ester (648 mg, 75% yield) was used without further purification in the subsequent step. Mp 94.0° C.

[1] 6-Acetyl-1H-quinolin-4-one was prepared according to Cassis, et al., *Synthetic Communications* (1985), 15(2):125.

B. 1-[4-(2-Butoxy-3,5-diisopropyl-phenyl)-quinolin-6-yl]-ethanone

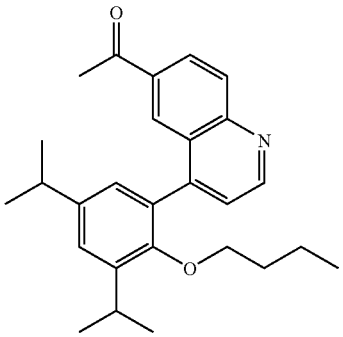

To a solution of trifluoro-methanesulfonic acid 6-acetyl-quinolin-4-yl ester (321.7 mg, 1.008 mmol) and (2-butoxy-3,5-diisopropyl-phenyl)-boronic acid (315.3 mg, 1.133 mmol) (see Example 17, step B) in toluene (10 mL) was added 2N $Na_2CO_3$ (1.1 mL) and $Pd(PPh_3)_4$ (117.1 mg, 0.101 mmol). The solution was stirred at 80° C. for 2 h under $N_2$ atm. The mixture was poured into brine (30 mL) and extracted with ethyl acetate (30 mL). The organic phase was dried, filtered, and concentrated. The crude material was purified by flash chromatography (2:8) ethyl acetate:hexanes to give 1-[4-(2-butoxy-3,5-diisopropyl-phenyl)quinolin-6-yl]-ethanone (378 mg, 93% yield) as a light yellow crystalline solid. Mp 132.8° C. $^1$H NMR (400 MHz, DMSO-$d_6$): δ 9.01 (d, 1H, J=4.4), 8.40 (d, 1H, J=2.0), 8.25 (2d, 1H, J=2.0, 8.8), 8.16 (d, 1H, J=8.8), 7.50 (d, 1H, J=4.4), 7.24 (m, 1H), 7.00 (d, 1H, J=2.4), 3.36 (m, 1H), 3.26 (m, 1H), 3.16 (m, 1H), 2.94 (m, 1H), 2.58 (s, 3H), 1.29 (m, 12H), 1.10 (m, 2H), 0.79 (m, 2H), 0.47 (t, 3H, J=7.3). $^{13}$C NMR (75 MHz, DMSO-$d_6$): δ 197.1, 152.3, 151.6, 149.6, 147.2, 144.2, 141.6, 134.0, 129.7, 128.5, 127.2, 126.5, 125.4, 123.0, 73.0, 33.0, 31.1, 26.4, 24.0, 23.9, 23.8, 23.0, 17.9, 12.9. IR (CHCl$_3$, cm$^{-1}$): 2963, 2934, 2872, 1681. MS [EI+] 404 (M+H)$^+$. Analytical ($C_{27}H_{33}NO_2$): Calculated C, 80.36; H, 8.24; N, 3.47. Found: C, 79.98; H, 8.57; N, 3.46.

C. 3-[4-(2-Butoxy-3,5-diisopropyl-phenyl)-quinolin-6-yl]-but-2(E)-enoic acid methyl ester

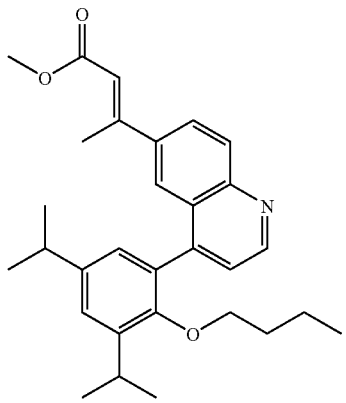

To a solution of 1,1-difluoroethylene (4.5 mL, 0.5M in 8:2 TEF:Et$_2$O) at −100° C. was added dropwise a solution of sec-butyl lithium (1.1 mL, 1.3 M in cyclohexane) via syringe. The solution was stirred at −100° C. for 10 min. A solution of 1-[4-(2-butoxy-3,5-diisopropyl-phenyl)-quinolin-6-yl]-ethanone (426 mg, 1.06 mmol) in (8:2) THF:Et$_2$O (5 ml) was added to the above solution via cannula. The reaction solution was stirred at −100° C. for 10 min then warmed to −78° C. for 15 min. The reaction was quenched by addition of a few drops of saturated NaHCO$_3$. The mixture was diluted with additional saturated NaHCO$_3$ and extracted with diethyl ether (2×30 mL). The organic phases were combined, dried, and concentrated to give an oil which was dissolved in methanol (10 mL) and 4 drops of concentrated H$_2$SO$_4$. The yellow solution was stirred at room temperature for 1 h then poured into saturated NaHCO$_3$ (30 mL) and extracted with ethyl acetate (3×25 mL). The organic phases were combined, washed with brine (20 mL) then dried, filtered, and concentrated to give 3-[4-(2-butoxy-3,5-diisopropyl-phenyl)-quinolin-6-yl]-but-2(E)-enoic acid methyl ester (430 mg, 89% yield) which was used without further purification. Mp 104.7° C. $^1$H NMR(400 MHz, CDCl$_3$): δ 8.92 (d, 1H, J=4.4), 8.11 (d, 1H, J=8.8), 7.88 (d, 1H, J=2.0), 7.80 (dd, 1H, J=2.0, 8.8), 7.45 (d, 1H, J=4.4), 7.22 (dd, 1H, J=2.0, 4.4), 6.99 (d, 1H, J=2.4), 6.21 (m, 1H), 3.72 (s, 3H), 3.36 (q, 1H, J=6.8), 3.24 (m, 1H), 3.17 (m, 1H), 2.92 (q, 1H, J=6.8), 2.56 (d, 3H, J=1.5), 1.27 (m, 12H), 1.11 (m, 2H), 0.81 (m, 2H), 0.48 (t, 3H, J=7.3). $^{13}$C NMR (75 MHz): δ 167.1, 155.1, 152.2, 150.3, 148.6, 147.3, 144.3, 142.2, 139.5, 130.2, 129.6, 127.2, 126.6, 125.4, 125.2, 122.6, 117.6, 73.6, 51.0, 33.8, 31.8, 29.6, 26.9, 24.2, 24.0, 23.3, 18.5, 17.8, 13.3. IR (CHCl$_3$, cm$^{-1}$): 2963, 2934, 2872, 1712. MS [EI+] 460 (M+H)$^+$. Analytical ($C_{30}H_{37}NO_3$): Calculated C, 78.40; H, 8.11; N, 3.05. Found: C, 78.64; H, 8.46; N, 3.13.

E. 3-[4-(2-Butoxy-3,5-diisopropyl-phenyl)-quinolin-6-yl]-but-2(E)-enoic acid To a solution of 3-[4-(2-butoxy-3,5-diisopropyl-phenyl)-quinolin-6-yl]-but-2(E)-enoic acid methyl ester (349 mg, 0.759 mmol) in methanol (6 mL) at room temperature was added aqueous 1N NaOH (3 mL, 3 mmol). The white suspension was stirred at room temperature for 1 h then at 45° C. overnight The clear solution was concentrated, diluted with water (25 mL) and treated with aqueous 1N HCl until solution achieved pH 2. The resulting mixture was extracted with ethyl acetate (3×30 mL). The organic phases were combined and washed with brine (30 mL) then dried, filtered, and concentrated. The crude material was purified by flash chromatography twice (1:1) ethyl acetate:hexanes) to give 3-[4-(2-butoxy-3,5-diisopropyl-phenyl)-quinolin-6-yl]-but-2(E)-enoic acid (250 mg, 74%) as a white amorphous solid. Mp 195.3° C. $^1$H NMR (400 MHz, CDCl$_3$): δ 8.96 (s, 1H), 8.15 (d, 1H, J=8.8), 7.92 (s, 1H), 7.83 (d, 1H, J=8.8), 7.48 (d, 1H, J=3.4), 7.23 (m, 1H), 7.00 (s, 1H), 6.27 (s, 1H), 3.37 (m, 1H), 3.25 (m, 1H), 3.20 (m, 1H), 2.93 (m, 1H), 2.60 (s, 3H), 1.29 (m, 12H), 1.26 (m, 2H), 0.83 (m, 2H), 0.49 (t, 3H, J=7.3). $^{13}$C NMR (63 MHz): δ 170.0, 157.0, 152.2, 150.3, 148.4, 147.7, 144.4, 142.3, 139.6, 130.2, 129.4, 127.4, 126.7, 125.6, 125.4, 122.7, 117.4, 73.6, 33.8, 31.9, 27.0, 24.3, 24.1, 24.0, 23.4, 18.6, 18.1, 13.4. IR (CHCl$_3$, cm$^{-1}$): 2963, 2934, 2872, 1689. MS [EI+] 446 (M+H)$^+$, [EI−] 444 (M−H)$^−$. Analytical ($C_{29}H_{35}NO_3$): Calculated C, 78.17; H, 7.92; N, 3.14. Found C, 77.87; H, 8.09; N, 3.17.

Example 55

3-{3-[2-(3-Fluoropropoxy)-3,5-di-iso-propylphenyl]-benzo[b]thien-5-yl}-but-2-enoic acid

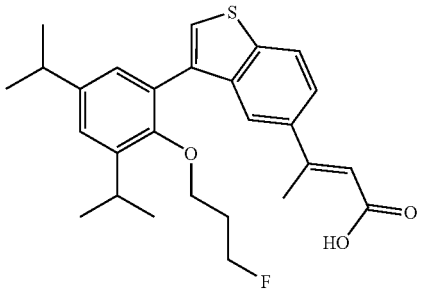

A. (4-Acetyl-phenylsulfanyl)-acetic acid methyl ester

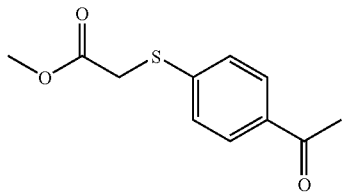

Methyl thioglycolate was dissolved in DMF (10 ml) and this mixture was cooled to 0° C. under an atmosphere of nitrogen. NaH (750 mg of 60% mineral oil dispersion, 18.1 mmol) was then added in one portion. After 5 min., the ice bath was removed and p-fluoroacetophenone (1 ml, 8.2 mmol) was added in one portion. The reaction mixture stirred at ambient temperature for 1 hr then diluted with ethyl acetate (50 ml) and washed with water. The aqueous layer was extracted with ethyl acetate (2×50 ml) and the combined organics dried over MgSO$_4$ and concentrated in vacuo to yield (4-acetyl-phenylsulfanyl)-acetic acid methyl ester, as a white waxy solid (1.48 g, 80%). $^1$H NMR (250 MHz, CDCl$_3$): δ 7.80 (d, 2H, J=9.4), 7.32 (d, 2H, J=9.4), 3.71 (s, 2H), 3.67 (s, 3H), 2.50 (s, 3H). MS [EI+] 225 (M+H)$^+$.

B. (4-Acetyl-phenylsulfanyl)-acetic acid

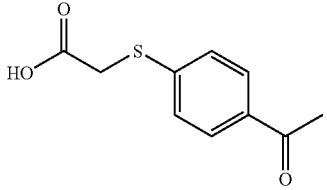

(4-Acetyl-phenylsulfanyl)-acetic acid methyl ester (1.48 g, 6.6 mmol) is dissolved in THF (40 ml). To this solution is added LiOH (415 mg, 9.9 mmol) in water (10 ml), and the mixture was stirred at ambient temperature overnight. The mixture was acidified to pH 5 using 1N HCl and then extracted with ethyl acetate (3×25 ml). The combined organic layers were dried over MgSO$_4$ and concentrated in vacuo to yield (4-acetyl-phenylsulfanyl)-acetic acid as a white solid (1.27 g, 91%).

$^1$H NMR (250 MHz, DMSO): δ 7.89 (d, 2H, J=9.4), 7.41 (d, 2H, J=9.4),3.96 (s, 2H), 2.55 (s, 3H). MS [EI−] 209 (M−H)$^−$.

C. 5-Acetyl-benzo[b]thiophen-3-one

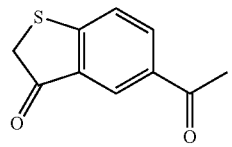

(4-Acetyl-phenylsulfanyl)-acetic acid (1.0 g, 4.8 mmol) is suspended in dichloroethane, under nitrogen at ambient temperature. To this is added thionyl chloride (0.694 ml, 9.6 mmol) followed immediately by 1 drop of DMF. After maintaining the reaction mixture at 50° C. for 30 min., the mixture became homogenous. After cooling to ambient temperature, nitrogen was bubbled into the mixture to remove any trace gasses (10 min.), then aluminum trichloride (1.9 g, 14.4 mmol) was added in 4 portions which caused the reaction temperature to raise to 40° C. After the reaction had cooled to ambient temperature (2 hr), the reaction mixture was poured into 200 mL of and ice/water mixture and extracted with dichloromethane (3×100 ml). The combined organic layers were washed with saturated bicarbonate solution, and brine, then dried over MgSO$_4$, filtered and concentrated in vacuo to yield 5-acetyl-benzo[b]thiophen-3-one as a red brown solid (720 mg, 79%). This material was used without further purification. $^1$H NMR (250 MHz, CDCl$_3$): δ 8.23 (d, 1H, J=2.1), 8.15 (dd, 1H, J=7.5,J=2.1), 7.48 (d, 1H, J=7.5), 3.83 (s, 2H), 2.56 (s, 3H). MS [EI+] 193 (M+H)$^+$, [EI−] 191 (M−H)$^−$.

D. Trifluoro-methanesulfonic acid 5-acetyl-benzo[b]thiophen-3-yl ester

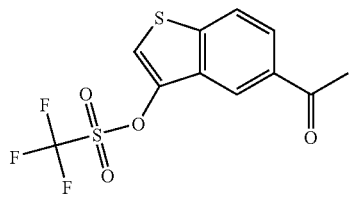

5-Acetyl-benzo[b]thiophen-3-one (720 mg, 3.7 mmol) was dissolved in THF under nitrogen and cooled to −78° C. with a dry ice acetone bath. 2.8 ml of a 2M lithium diisopropylamide solution (5.6 mmol) was added to this mixture. After 30 min., N-phenyltrifluoromethane-sulfonimide (2.68 g, 7.5 mmol) was added. The dry ice acetone bath was removed and after 1 hr the reaction had warmed to ambient temperature and was and concentrated in vacuo. The residue was then purified by chromatography (chromatotron, 4µ plate, 0-10% ethyl acetate in hexanes) to provide trifluoro-methanesulfonic acid 5-acetyl-benzo[b]thiophen- 3-yl ester as a clear oil (788 mg, 65%). ¹HNMR (250 MHz, CDCl₃): δ 8.29 (d, 1H, J=1.2), 8.01 (dd, 1H, J=7.8, J=1.2), 7.85 (d, 1H, J=7.8), 7.44 (s, 1H), 2.64 (s, 3H).

E. 1-[3-(3,5-Diisopropyl-2-methoxymethoxy-phenyl)-benzo[b]thiophen-5-yl]-ethanone

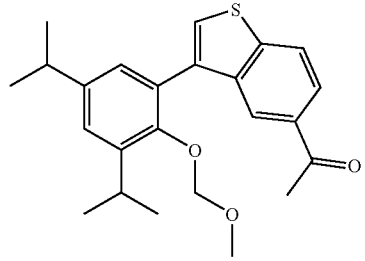

3,5-Diisopropyl-2-methoxymethoxy-phenyl-boronic acid (470 mg, 1.8 mmol) was dissolved in toluene (15 ml) and ethanol (15 ml). Trifluoro-methanesulfonic acid 5-acetyl-benzo[b]thiophen-3-yl ester (320 mg, 0.99 mmol), tetrakis(triphenylphosphine)palladium(0) (114 mg, 0.1 mmol) followed by some 2M sodium carbonate solution (1.98 mmol) was added to this solution. The reaction was then heated overnight, then poured into brine (20 ml) and extracted with ethyl acetate (2×20 ml). The organic layers were then dried over MgSO₄ and concentrated in vacuo. The residue was purified by chromatography (chromatotron, 4μ plate, 0-10% ethyl acetate in hexanes) to give 1-[3-(3,5-diisopropyl-2-methoxymethoxy-phenyl)-benzo[b]thiophen-5-yl]-ethanone as a yellow oil (228 mg, 58%). An analytical sample was obtained by preparatory thin layer chromatography (5% ethyl acetate in hexanes). ¹HNMR (250 MHz, CDCl₃): δ 8.23 (s, 1H), 7.85-7.97 (m, 2H), 7.48 (s, 1H), 7.14 (d, 1H, J=1.2), 7.04 (d, 1H, J=1.2), 4.41 (s, 2H), 3.40 (m, 1H), 2.95 (s, 3H), 2.86 (m, 1H), 2.55 (s, 3H), 1.26 (s, 3H), 1.23 (s, 3H), 1.21, (s, 3H), 1.18 (s, 3H).

F. 3-[3-(3,5-Di-iso-propyl-2-methoxymethoxyphenyl)-benzo[b]thien-5-yl]-but-2-enoic acid methyl ester

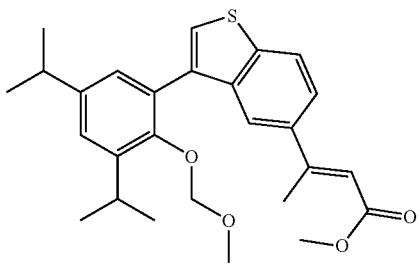

Sodium hydride (13 mg, 60% mineral oil dispersion, 0.33 mmol) was suspended in dry DMF (5 ml) at 0° C. under nitrogen atmosphere. Methyl diethyl phophonoacetate (0.061 ml, 0.33 mmol) was added, and the reaction was stirred for 30 min., then time 1-[3-(3,5-diisopropyl-2-methoxymethoxy-phenyl)-benzo[b]thiophen-5-yl]-ethanone (110 mg, 0.28 mmol) was added. The ice bath was removed, and after 1 h the reaction was heated to 50° C. After 5 h, the reaction was quenched with saturated ammonium chloride solution and extracted with ethyl acetate (2×5 ml). The residue was then purified by chromatography (chromatotron, 2μ plate, 0-10% ethyl acetate in hexanes) to give 3-[3-(3,5-di-iso-propyl-2-methoxymethoxyphenyl)-benzo[b]thien-5-yl]-but-2-enoic acid methyl ester as a white solid (33.2 mg, 26%). ¹H NMR (250 MHz, CDCl₃): δ 7.78 (d, 1H, J=7.2), 7.74 (d, 1H, J=0.6), 7.37-7.45 (m, 2H), 7:10 (d, 1H, J=1.2), 7.02 (d, 1H, J=1.2), 6.11 (d, 1H, J=0.5), 4.38 (s, 2H), 3.66 (s, 3H), 3.40 (m, 1 h), 2.96 (s, 3H), 2.87 (m, 1H), 2.54 (d, 3H, J=0.5), 1.25 (s, 3H), 1.23 (s, 3H), 1.21 (s, 3H), 1.19 (s, 3H). MS [EI+] 470 (M+H₂O)⁺.

G. 3-[3-(2-Hydroxy-3,5-di-iso-propylphenyl)-benzo[b]thien-5-yl]-but-2-enoic acid methyl ester

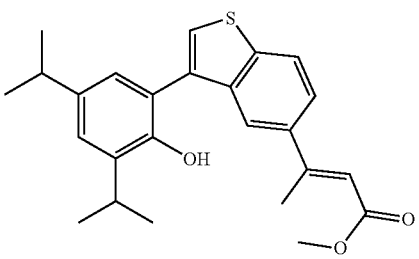

3-[3-(3,5-Di-iso-propyl-2-methoxymethoxy-phenyl)-benzo[b]thien-5-yl]-but-2-enoic acid methyl ester (15 mg, 0.033 mmol) was dissolved in methanol (5 ml) and 2 drops of concentrated HCl was added. This mixture was stirred at ambient temperature for 4 h then concentrated in vacuo. The residue was passed over a silica gel plug (50% ethyl acetate in hexane) to yield a quatitative amount of 3-[3-(2-hydroxy-3,5-di-iso-propylphenyl)-benzo[b]thien-5-yl]-but-2-enoic acid methyl ester as a white solid which was used without further purification. ¹H NMR (250 MHz, CDCl₃): δ 7.96 (d, 1H, J=11.2), 7.77 (d, 1H, J=0.6), 7.75-7.61 (m, 2H), 7.18 (d, 1H, J=3.1), 7.05 (d, 1H, J=3.1), 6.20 (d, 1H, J=1.2), 5.05 (bs, 1H), 3.77 (s, 3H), 3.38 (m, 1H), 2.94 (m, 1H), 2.62 (d, 3H, J=1.2), 1.36 (s, 3H), 1.34 (s, 3H), 1.33 (s, 3H), 1.31 (s 3H). MS [EI+] 426 (M+H₂O)⁺, [EI−] 407 (M−1)⁻.

H. 3-{3-[2-(3-Fluoropropoxy)-3,5-di-iso-propylphenyl]-benzo[b]thien-5-yl}but-2-enoic acid methyl ester

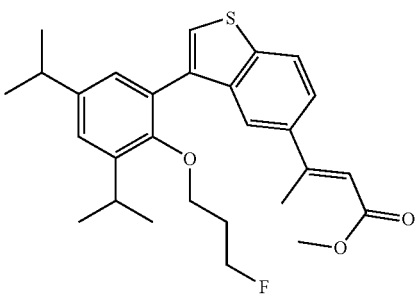

3-[3-(2-Hydroxy-3,5-di-iso-propylphenyl)-benzo[b] thien-5-yl]-but-2-enoic acid methyl ester (15 mg, 0.037 mmol) was dissolved in 1 ml of DMF. Cesium fluoride (22.3 mg, 0.14 mmol), followed by 1-bromo-3-fluoropropane (0.004 ml, 0.044 mmol) was added, and the reaction was stirred under a nitrogen atmosphere at ambient temperature overnight. Then 2 mL of water was added, and the mixture extracted with ethyl acetate (2×5 ml). The combined organics were washed with brine, then dried over MgSO₄ and concentrated in vacuo to yield 3-{3-[2-(3-fluoropropoxy)-3,5-iso-propylphenyl]-benzo[b]thien-5-yl}but-2-enoic acid methyl ester as a white solid (14.8 mg, 83%). ¹H NMR (250 MHz, CDCl₃): δ 7.81 (d, 1H, J=10.0), 7.74 (d, 1H, J=1.2), 7.45 (s, 1H), 7.43 (dd, 1H, J=7.5, J=1.2), 7.11 (d, 1H, J=3.1), 7.04 (d, 1H, J=3.1), 6.12 (d, 1H, J=0.62), 4.10 (dt, 2H, J=50.0, J=6.25), 3.68 (s, 3H), 3.38 (t, 2H, J=6.25), 3.30 (m, 1H), 2.86 (m, 1H), 2.55 (d, 3H, J=0.62), 1.58 (dq, 2H, J=25.0, J=6.25), 1.25 (s, 3H), 1.22 (s, 6H), 1.20 (s, 3H).

I. 3-{3-[2-(3-Fluoropropoxy)-3,5-di-iso-propylphenyl]-benzo[b]thien-5-yl}-but-2-enoic acid 3-{3-[2-(3-Fluoropropoxy)-3,5-di-iso-propylphenyl]-benzo[b]thien-5-yl}-but-2-enoic acid methyl ester (14.8 mg, 0.031 mmol) was dissolved in methanol (1 ml) and 1N NaOH solution (1 ml), then heated to 60° C. for 2 h. The reaction was brought to pH=4 with 1N HCl solution, then extracted with ethyl acetate (3×5 ml). The combined organic layers were washed with brine, then dried over MgSO₄ and concentrated in vacuo to yield a white solid (13.7 mg, 96%). ¹H NMR (250 MHz, CDCl₃): δ 7.81 (d, 1H, J=10.0), 7.74 (d, 1H, J=1.2), 7.45 (s, 1H), 7.43 (dd, 1H, J=7.5, J=1.2), 7.11 (d, 1H, J=3.1), 7.04 (d, 1H, J=3.1), 6.12 (d, 1H, J=0.62), 4.10 (dt, 2H, J=50.0, J=6.25), 3.38 (t, 2H, J=6.25), 3.30 (m, 1H), 2.86 (m, 1H), 2.55 (d, 3H, J=0.62), 1.58 (dq, 2H, J=25.0, J=6.25), 1.25 (s, 3H), 1.22 (s, 6H), 1.20 (s, 3H). MS [EI+] 437 (M+H–H₂O)⁺, [EI–] 453 (M–1)⁻. HPLC [MetaSil AQ C18 (0.46×25 cm) 95% CH₃CN(0.1% TFA) in H₂O (0.1% TFA)] 5.262 min.

Example 56

3-[3-(2-Hydroxy-3,5-di-iso-propylphenyl)-benzo[b]thien-5-yl]-but-2-enoic acid

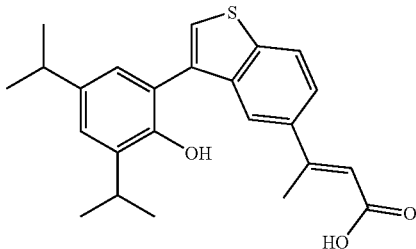

3-[3-(3,5-Di-iso-propyl-2-methoxymethoxyphenyl)-benzo[b]thien-5-yl]-but-2-enoic acid methyl ester (15 mg, 0.033 mmol) (see Example 55, step F) was dissolved in MeOH (2 ml) and 1N NaOH (2 ml). The mixture was then stirred at 60° C. for 2 h, then cooled to ambient temperature and brought to pH 2 with 1N HCl. The reaction mixture was allowed to stir for 1 h, it was extracted with ethyl acetate (3×5 mL) and the organic layers were dried over MgSO₄ and concentrated in vacuo. The residue was purified by silica gel chromatography (10% ethyl acetate in hexanes) to give 3-[3-(2-hydroxy-3,5-diisopropyl-phenyl)-benzo[b]thien-5-yl]-but-2-enoic acid as a white solid (11.7 mg, 89%). ¹H NMR (250 MHz, CDCl₃): δ 7.89 (d, 1H, J=8.75), 7.70 (d, 1H, J=0.62), 7.50 (m, 2H), 7.08 (d, 1H, J=1.2), 6.95 (d, 1H, J=1.2), 6.14 (bs, 1H), 3.29 (m, 1H), 2.85 (m, 1H), 2.55 (s, 3H), 1.27 (s, 3H), 1.25 (s, 3H), 1.23 (s, 3H), 1.20 (s, 3H). MS [EI+] 395 (M+H–H₂O)+, [EI–] 393 (M–1)⁻. HPLC [MetaSil AQ C18 (0.46×25 cm) 95% CH₃CN(0.1% TFA) in H₂O(0.1% TFA)] 4.388 min.

Example 57

3-[3-(3,5-Di-iso-propyl-2-methoxyphenyl)-benzo[b]thien-5-yl]-but-2-enoic acid

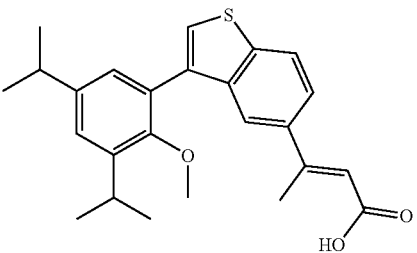

A. 3-[3-(3,5-Di-iso-propyl-2-methoxyphenyl)-benzo[b]thien-5-yl]-but-2-enoic acid methyl ester

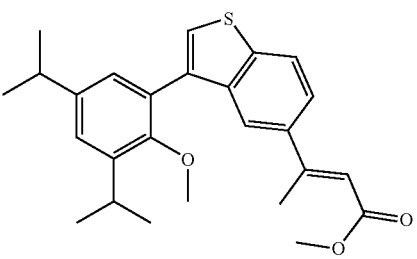

3-[3-(2-Hydroxy-3,5-di-iso-propylphenyl)-benzo[b]thien-5-yl]-but-2-enoic acid methyl ester (100 mg, 0.24 mmol) was dissolved in DMF (5 ml), and iodomethane (0.0183 ml, 0.29 mmol) and cesium fluoride (149 mg, 0.98 mmol) were added to this solution. The reaction was stirred at ambient temperature under nitrogen overnight, then water (2 ml) was added and the mixture extracted with ethyl acetate (2×5 mL). The combined organics were washed with brine, then dried over MgSO₄ and concentrated in vacuo to yield 3-[3-(3,5-di-iso-propyl-2-methoxyphenyl)-benzo[b]thien-5-yl]but-2-enoic acid methyl ester as a pale yellow solid (101 mg, 98%). ¹H NMR (250 MHz, CDCl₃): δ 7.85 (d, 1H, J=6.2), 7.80 (s, 1H), 7.46 (s, 1H), 7.40 (dd, 1H, J=0.6, J=8.8), 7.09 (d, 1H, J=1.2), 7.03 (d, 1H, J=1.2), 6.12 (d, 1H, J=0.6), 3.65 (s, 3H), 3.32 (m, 1H), 3.18 (s, 3H), 2.85 (m, 1H), 2.53 (d, 3H, J=0.6), 1.24 (s, 3H), 1.22 (s, 6H), 1.18 (s, 3H).

B. 3-[3-(3,5-Di-iso-propyl-2-methoxyphenyl)-benzo[b]thien-5-yl]-but-2-enoic acid 3-[3-(3,5-Di-iso-propyl-2-methoxyphenyl)-benzo[b]thien-5-yl]-but-2-enoic acid methyl ester (100 mg, 0.24 mmol) was dissolved in methanol (5 ml) and 1N NaOH solution (5 ml), then heated to 60° C. for 2 h. The reaction was brought to pH 6 with 1N HCl solution, then extracted with ethyl acetate (3×10 mL). The combined organics were washed with brine, then dried over MgSO₄ and concentrated in vacuo. The residue was purified by silica gel chromatography (10% ethyl acetate in hexanes) to yield a white solid (59.5 mg, 59%). ¹HNMR (250 MHz, CDCl₃): δ 7.82 (d, 1H, J=6.2), 7.80 (s, 1H), 7.48 (s, 1H), 7.44 (dd, 1H, J=0.6, J=8.8), 7.10 (d, 1H, J=1.2), 7.04 (d, 1H, J=1.2), 6.16 (d, 1H, J=0.6), 3.34 (m, 1H), 3.21 (s, 3H), 2.87 (m, 1H), 2.56 (d, 3H, J=0.6), 1.26 (s, 3H), 1.23 (s, 6H), 1.20 (s, 3H). MS [EI+] 409 (M+H−H$_2$O)$^+$, [EI−] 407 (M−1)$^−$. HPLC [MetaSil AQ C18 (0.46×25 cm) 95% CH$_3$CN(0.1% TFA) in H$_2$O(0.1% TFA)] 5.695 min.

Example 58

3-[3-(2-Ethoxy-3,5-diisopropyl-phenyl)-thieno[2,3-c]pyridin-5-yl]-but-2-enoic acid

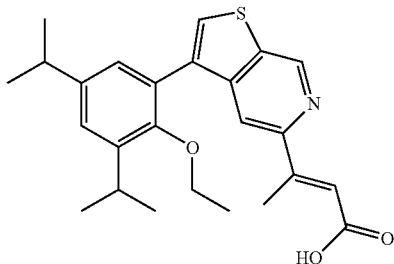

A. 1-Thieno[2,3-c]pyridin-5-yl]ethanone

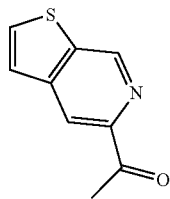

A solution of 2,3-thiophenedicarboxaldehyde (600 mg, 4.28 mmol) in dichloromethane (50 ml) was cooled to 0° C. under an atmosphere of nitrogen. (1-Acetylamino-2-oxo-propyl)-phosphonic acid dimethyl ester (1.05 g, 4.70 mmol) was added [literature procedure: Kitamura, et al. *Tet. Lett.*, 36(32), 1995, pp. 5769-5772], followed by DBU (0.471 ml, 4.70 mmol), and the mixture allowed to warm to ambient temperature overnight, then concentrated in vacuo, and the residue was then purified by flash chromatography (0-50% ethyl acetate in hexanes) to provide 1-thieno[2,3-c]pyridin-5-yl-ethanone as a white solid (326 mg, 43%). $^1$HNMR (250 MHz, CDCl$_3$): δ 9.20 (s, 1H), 8.50 (d, 1H, J=1.02), 7.80 (d, 1H, J=5.36), 7.51 (d, 1H, J=5.36), 2.81 (s, 3H).

B. 1-(3-Bromo-thieno[2,3-c]pyridin-5-yl)-ethanone

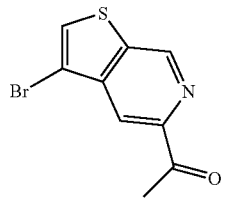

An aqueous saturated sodium bicarbonate solution (10 ml) and water (10 ml) was added to a solution of 1-thieno [2,3-c]pyridin-5-yl-ethanone (600 mg, 3.39 mmol) in carbon tetrachloride (5 ml). Bromine (0.523 ml, 10.2 mmol) was added and the reaction was stirred overnight. The biphasic mixture was allowed to separate and the organic layer was diluted with dichloromethane (25 ml) and washed with 10% sodium sulfide (in ammonium hydroxide) (1×20 mL), and brine (1×20 mL). The organic layer was dried over MgSO$_4$ and concentrated in vacuo. The residue was then purified by chromatography (chromatotron, 4μ plate, 0-200% ethyl acetate in hexanes) to yield 1-(3-bromo-thieno[2,3-c]pyridin-5-yl)-ethanone as a white solid (311.3 mg, 36%). $^1$H NMR (250 MHz, CDCl$_3$): δ 9.20 (s, 1H), 8.54 (s, 1H), 7.30 (s, 1H), 7.30 (s, 1H), 2.85 (s, 3H). MS [E+] 255 & 257 (M+H)$^+$.

C. 1-[3-(2-Ethoxy-3,5-diisopropyl-phenyl)-thieno[2,3-c]pyridin-5-yl]-ethanone

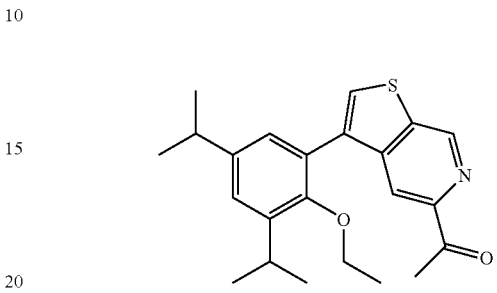

2-Ethoxy-3,5-diisopropyl-phenyl-boronic acid (586 mg, 2.34 mmol) was dissolved in toluene (10 ml). 1-(3-Bromo-thieno[2,3-c]pyridin-5-yl)-ethanone (310 mg, 1.21 mmol), and tetrakis(triphenylphosphine)palladium(0) (140 mg, 0.12 mmol) followed by 2M sodium carbonate solution (2.34 ml) was added to this solution. This mixture was then heated to 90° C. overnight, then poured into brine (20 ml) and extracted with ethyl acetate (2×20 mL). The organic layers were dried over MgSO$_4$ and concentrated in vacuo. The residue was then purified by chromatography (chromatotron, 4μ plate, 10% ethyl acetate in hexanes) to give a 1-[3-(2-ethoxy-3,5-diisopropyl-phenyl)-thieno[2,3-c]pyridin-5-yl]-ethanone as a white solid (422.2 mg, 91%). $^1$H NMR (250 MHz, CDCl$_3$): δ 9.14 (s, 1H), 8.38 (s, 1H), 7.80 (s, 1H), 7.13 (d, 1H, J=1.9), 6.98 (d, 1H, J=1.9), 3.33 (m, 1H), 3.28 (q, 2H, J=7.5), 2.87 (m, 1H), 2.74 (s, 3H), 1.25 (s, 3H), 1.23 (s, 3H), 1.22 (s, 3H), 1.20 (s, 3H), 0.85 (t, 3H, J=7.5). MS [EI+] 382 (M+H)$^+$.

D. 3-[3-(2-Ethoxy-3,5-diisopropyl-phenyl)-thieno[2,3-c]pyridin-5-yl]-but-2-enoic acid methyl ester

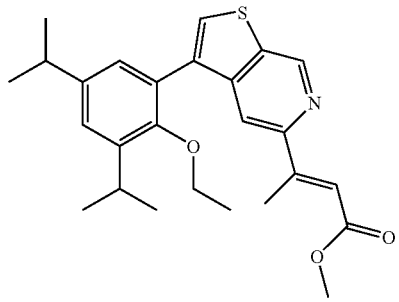

Methyl diethyl phophonoacetate (0.606 ml, 3.3 mmol) was added to a suspension of sodium hydride (132 mg, 60% mineral oil dispersion, 3.3 mmol) in dry DMF (10 ml) under nitrogen atmosphere which was maintained at 0° C. After the suspension had stirred for 30 min., 1-[3-(2-ethoxy-3,5-diisopropyl-phenyl)-thieno[2,3-c]pyridin-5-yl]-ethanone (420 mg, 1.1 mmol) was added and the cold bath removed. The reaction was allowed to stir overnight at room temperature, then was quenched with saturated ammonium chloride solution and extracted with ethyl acetate (2×10 mL). The residue was then purified by chromatography (chromatotron, 4μ plate, 0-10% ethyl acetate in hexanes) to give 3-[3-(2-ethoxy-3,5-diisopropyl-phenyl)-thieno[2,3-c]pyridin-5-yl]-but-2-enoic acid methyl ester as a white solid (294.9 mg, 61%). ¹H NMR (250 MHz, CDCl₃): δ 9.06 (s, 1H), 7.36 (s, 1H), 7.23 (s, 1H), 7.10 (d, 1H, J=6.2), 7.00 (d, 1H, J=6.2), 6.80 (d, 1H, J=0.12), 3.67 (s, 3H), 3.35 (m, 1H), 3.28 (q, 2H, J=8.8), 2.36 (m, 1H), 2.58 (d, 3H, J=0.12), 1.24 (s, 3H), 1.21 (s, 3H), 1.20 (s, 3H), 1.18 (s, 3H), 0.83 (t, 3H, J=8.75). MS [EI+] 438 (M+H)⁺.

E. 3-[3-(2-Ethoxy-3,5-diisopropyl-phenyl)-thieno[2,3-c]pyridin-5-yl]-but-2-enoic acid A solution of 3-[3-(2-ethoxy-3,5-diisopropyl-phenyl)-thieno[2,3-c]pyridin-5-yl]-but-2-enoic acid methyl ester (295 mg, 0.675 mmol) in methanol (5 ml) and 1N NaOH solution (5 ml) was heated to 60° C. for 2 h, then brought to pH=4 with 1N HCl solution and extracted with ethyl acetate (3×5 mL). The combined organic layers were washed with brine, then dried over MgSO₄ and concentrated i71 vacuo to yield a white crystals (203.4 mg, 71%). ¹H NMR (250 MHz, CDCl₃): δ 9.24 (d, 1H, J=0.62), 8.00 (d, 1H, J=0.62), 7.86 (s, 1H), 7.23 (d, 1H, J=1.2), 7.13 (d, 1H, J=1.2), 6.94 (d, 1H, J=0;62), 3.45 (m, 1H), 3.40 (q, 2H, J=7.5), 3.00 (m, 1H), 2.72 (d, 3H), J=0.62), 1.36 (s, 3H), 1.34 (s, 3H), 1.33, (s, 3H), 1.31 (s, 3H), 0.97 (t, 3H, J=7.5). MS [EI+] 424 (M+H)⁺. HPLC [YMC ODS-A (0.46×50 mm) 5%-95% CH₃CN(0.1% TFA) in H₂O(0.1% TFA) in 12 min.] 10.068 min.

Example 59

3-[3-(2-Ethoxy-3,5-diisopropyl-phenyl)-benzo[d]isoxazol-5-yl]-but-2-enoic acid

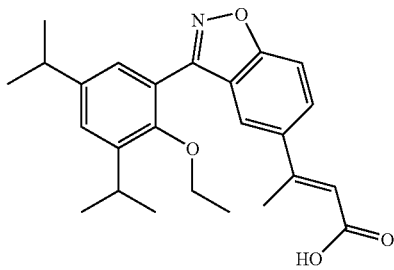

A. (5-Bromo-2-fluoro-phenyl)-(2-ethoxy-3,5-diisopropyl-phenyl)-methanol

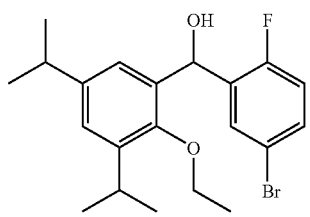

1-Bromo-2-ethoxy-3,5-diisopropyl-benzene (2.0 g, 7.01 mmol) was dissolved in ethylene glycol dimethyl ether (20 ml) and the mixture cooled to −78° C. t-Butyl lithium (8.66 ml, 1.7M, 14.7 mmol) dropwise to the mixture over 30 min., then the reaction was stirred for an additional 30 min. before 5-bromo-2-fluorobenzaldehyde (1.57 g, 7.71 mmol) was added in one portion. The reaction was allowed to warm to ambient temperature, then stirred overnight The mixture was poured into saturated ammonium chloride solution (100 mL), and extracted with ethyl acetate (3×50 mL). The combined organic layers were dried over MgSO₄ and concentrated in vacuo. The residue was purified flash column (5% ethyl acetate in hexanes) to give (5-bromo-2-fluoro-phenyl)-(2-ethoxy-3,5-diisopropyl-phenyl)-methanol, as a pale yellow oil (1.88 g, 66%). ¹H NMR (250 MHz, CDCl₃): δ 7.73 (dd, 1H, J=1.2, J=7.5), 7.42 (m, 1H), 7.11 (d, 1H, J=1.2), 6.95 (t, 1H, J=7.5), 6.85 (d, 1H, J=1.2), 6.35 (d, 1H, J=6.2), 3.84 (q, 2H, J=6.9), 3.30 (m, 1H), 3.07 (d, 1H, J=6.2), 2.85 (m, 1H), 1.47 (t, 3H, J=6.9), 1.25 (s, 6H), 1.20 (s, 6H). MS [EI+] 431, 433 (M+Na)⁺.

B. (5-Bromo-2-fluoro-phenyl)-(2-ethoxy-3,5-diisopropyl-phenyl)-methanone

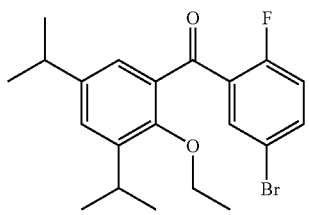

(5-Bromo-2-fluoro-phenyl)-(2-ethoxy-3,5-diisopropyl-phenyl)-methanol (1.88 g, 4.6 mmol) was dissolved in dichloromethane (5 ml) and added to a suspension of pyridinium chlorochromate (1.1 g, 5.1 mmol) in dichloromethane (20 ml). After stirring at ambient temperature under and atmosphere of nitrogen for 4 h the reaction was diluted with ether (50 mL) and filtered through a plug of florosil. The remaining solvent was evaporated to yield (5-bromo-2-fluoro-phenyl)-(2-ethoxy-3,5-diisopropyl-phenyl)-methanone as yellow crystals (1.75 g, 94%). ¹H NMR (250 MHz, CDCl₃): δ 7.81 (dd, 1H, J=3.1, J=6.9), 7.62 (m, 1H), 7.33 (d, 1H, J=2.5), 7.28 (d, 1H, J=2.5), 7.02 (dd, 1H, J=11.2, J=9.4), 3.67 (q, 2H, J=6.9), 3.34 (m, 1H), 2.95 (m, 1H), 1.31 (s, 3H), 1.28 (s, 6H), 1.25 (s, 3H), 1.02 (t, 3H, J=6.9). MS [EI+] 407, 409 (M+H)⁺.

C. 5-Bromo-3-(2-ethoxy-3,5-diisopropyl-phenyl)-benzo[d]isoxazole

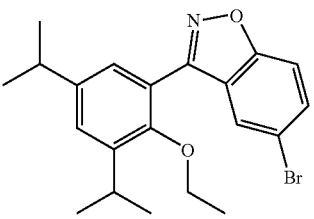

Acetone oxime (172 mg, 2.35 mmol) was added to a solution of potassium t-butoxide (264 mg, 2.35 mmol) in 10 ml of THF. This was stirred for 30 min. at ambient temperature under a nitrogen atmosphere, then a solution of (5-bromo-2-fluoro-phenyl)-(2-ethoxy-3,5-diisopropyl-phenyl)-methanone (800 mg, 1.96 mmol) in THF was added. After 2 hrs., the reaction was quenched with saturated ammonium chloride solution (20 mL) and extracted with ether (2×20 mL). The organic layers were combined, dried over MgSO$_4$ and evaporated. The residue was dissolved in ethanol (10 mL) and 1N HCl solution (10 mL) and refluxed for 1 h. The reaction mixture was portioned between ether and water after cooling to room temperature. The organic layer was dried over MgSO$_4$ and evaporated. The residue was purified by silica gel column (10% ethyl acetate in hexanes) to give 5-bromo-3-(2-ethoxy-3,5-diisopropyl-phenyl)-benzo[d]isoxazole as a clear oil (313.2 mg, 40%).

$^1$H NMR (250 MHz, CDCl$_3$): δ 7.97 (d, 1H, J=2.5), 7.60 (dd, 1H, J=2.5, J=9.4), 7.45 (d, 1H, J=9.4), 7.27 (d, 1H, J=1.2), 7.24 (d, 1H, J=1.2), 3.49 (q, 2H, J=7.5), 3.38 (m, 1H), 2.88 (m, 1H), 1.25 (s, 3H), 1.23 (s, 6H), 1.20 (s, 3H), 0.95 (t, 3H, J=7.5). MS [EI+] 402, 404 (M+)$^+$.

D. 3-[3-(2-Ethoxy-3,5-diisopropyl-phenyl)-benzo[d]isoxazol-5-yl]-but-2-enoic acid methyl ester

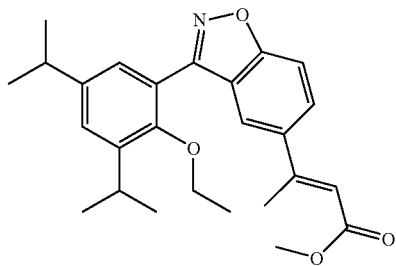

Methyl crotonate (0.087 ml, 0.82 mmol), tris(dibenzylideneacetone)-dipalladium(0) (6.8 mg, 0.007 mmol), tri-o-tolylphosphine (91 mg, 0.30 mmol), and triethyl amine (0.208 ml, 1.5 mmol) was added to a solution of 5-bromo-3-(2-ethoxy-3,5-diisopropyl-phenyl)-benzo[d]isoxazole (300 mg, 0.75 mmol) in DMF (5 ml). The reaction mixture was then heated to 120° C. under an atmosphere of nitrogen. After 12 h, the reaction was cooled and poured into brine, then extracted with ethyl acetate (2×10 mL). The organic layer was dried over MgSO$_4$ and evaporated to a residue. The residue was purified by silica gel chromatography (5% ethyl acetate in hexanes) to give 3-[3-(2-ethoxy-3,5-diisopropyl-phenyl)-benzo[d]isoxazol-5-yl]-but-2-enoic acid methyl ester as a clear oil (99.6 mg, 32%).

$^1$H NMR (250 MHz, CDCl$_3$): δ 7.89 (d, 1H, J=0.62), 7.61 (dd, 1H, J=2.5, J=9.4) 7.51 (d, 1H, J=9.4), 7.28 (d, 1H, J=1.2), 7.23 (d, 1H, J=1.2), 6.07 (d, 1H, J=0.62), 3.67 (s, 3H), 3.48 (q, 2H, J=7.5), 3.37 (m, 1H), 2.87 (m, 1H), 2.54 (d, 3H, J=0.62), 1.25 (s, 3H), 1.22 (s, 6H), 1.19 (s, 3H), 0.90 (t, 3H, J=7.5). MS [EI+] 422 (+H)$^+$.

E. 3-[3-(2-Ethoxy-3,5-diisopropyl-phenyl)-benzo[d]isoxazol-5-yl]-but-2-enoic acid A solution of 3-[3-(2-ethoxy-3,5-diisopropyl-phenyl)-benzo[d]isoxazol-5-yl]-but-2-enoic acid methyl ester (99.6 mg, 0.24 mmol) in 2 mL of methanol and 2 ml of 1N NaOH solution was heated this mixture to 60° C. for 3 h, then cooled and brought to pH 2 with 1N HCl. The reaction mixture was extracted with ethyl acetate (2×10 mL), and the organic layers were dried over MgSO$_4$ and evaporated to a residue. The residue was purified by silica gel chromatography (50% ethyl acetate in hexanes) to give a clear oil, which solidified upon standing to a waxy solid (12.1 mg, 13%).

$^1$H NMR (250 MHz, CDCl$_3$): δ 7.92 (d, 1H, J=0.62), 7.65 (dd, 1H, J=2.1, J=9.4), 7.55 (d, 1H, J=9.4), 7.30 (d, 1H, J=1.2), 7.24 (d, 1H, J=1.2), 6.12 (bs, 1H), 3.50 (q, 2H, J=7.5), 3.39 (m, 1H), 2.90 (m, 1H), 2.58 (bs, 3H), 1.26 (s, 3H), 1.23 (s, 6H), 1.20 (s, 3H), 0.90 (t, 3H, J=7.5). MS [EI+] 408 (M+H)$^+$ MS [EI−] 406 (M−H)$^−$.

Example 60

3-[3-(2-Ethoxy-3,5-diisopropyl-phenyl)-1H-indazol-5-yl]-but-2-enoic acid

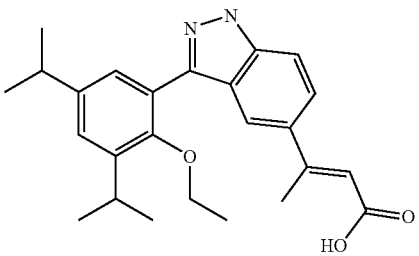

A. 5-Bromo-3-(2-ethoxy-3,5-diisopropyl-phenyl)-1H-indazole

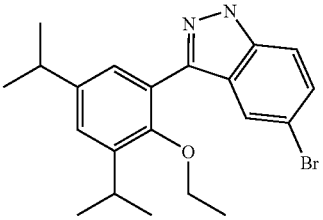

Benzophenone hydrazone (232 mg, 1.2 mmol) was added to a solution of potassium t-butoxide (132 mg, 1.2 mmol) in 10 ml of THF. After stirring for 30 min. at ambient temperature under a nitrogen atmosphere, a solution of (5-bromo-2-fluoro-phenyl)-(2-ethoxy-3,5-diisopropyl-phenyl)-methanone (400 mg, 1.0 mmol) in THF (10 mL) was added and the reaction was stirred for 12 h, then quenched with saturated ammonium chloride solution (20 mL) and extracted with ether (2×20 mL). The organic layers were combined, dried over MgSO$_4$ and evaporated to a residue. The residue was dissolved in ethanol (10 mL) and 1N HCl solution (10 mL) and refluxed for 1 h. After cooling, the reaction was partitioned between ether and water. The organic layer was dried over MgSO$_4$ and evaporated to a residue. The residue was purified by silica gel column (10% ethyl acetate in hexanes) to give 5-bromo-3-(2-ethoxy-3,5-diisopropyl-phenyl)-1H-indazole as a clear oil (61.8 mg, 16%). $^1$H NMR (250 MHz, CDCl$_3$): δ 7.87 (bs, 1H), 7.22-7.02 (m, 3H), 6.55 (bd, 1H, J=9.4), 3.32 (m, 1H), 3.26 (q, 2H, J=7.5), 2.73 (m, 1H), 1.05 (s, 6H), 1.03 (s, 6H), 0.77 (t, 3H, J=7.5). MS [EI+] 401, 403 (M+H)$^+$.

B. 3-[3-(2-Ethoxy-3,5-diisopropyl-phenyl)-1H-indazol-5-yl]-but-2-enoic acid methyl ester

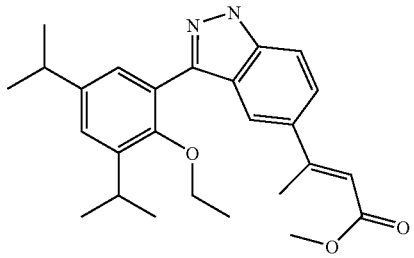

Methyl crotonate (0.017 mL, 0.17 mmol), tris(dibenzylideneacetone)-dipalladium(0) (1.3 mg, 0.001 mmol), tri-o-tolylphosphine (18.2 mg, 0.06 mmol), and triethyl amine (0.042 mL, 0.30 mmol) were added to a solution of 5-bromo-3-(2-ethoxy-3,5-diisopropyl-phenyl)-1H-indazole (60 mg, 0.15 mmol) in DMF (1 mL). The reaction mixture was then heated to 120° C. under an atmosphere of nitrogen for 12 hrs., then cooled, poured into brine and extracted with ethyl acetate (2×5 mL). The organic was dried over $MgSO_4$ and evaporated to give 3-[3-(2-ethoxy-3,5-diisopropyl-phenyl)-1H-indazol-5-yl]-but-2-enoic acid methyl ester as a clear oil which was used without further purification. MS [EI+] 421 (M+H)$^+$ MS [EI−] 419 (M−H)$^−$.

C. 3-[3-(2-Ethoxy-3,5-diisopropyl-phenyl)-1H-indazol-5-yl]-but-2-enoic acid

A solution of 3-[3-(2-ethoxy-3,5-diisopropyl-phenyl)-1H-indazol-5-yl]-but-2-enoic acid methyl ester in 2 ml of methanol and 2 ml of 1N NaOH solution was heated to 60° C. for 3 h, then cooled and brought to pH 7 with 1N HCl. The reaction mixture was extracted with ethyl acetate (2×10 mL), and the organic layers were dried over $MgSO_4$ and evaporated to a residue. The residue was purifed by silica gel chromatography (50% ethyl acetate in hexanes) to give a white solid (6.1 mg, 10%).

$^1$H NMR (250 MHz, CDCl$_3$): δ 7.97 (bs, 1H), 7.60-6.90 (m, 4H), 6.12 (d, 1H, J=0.62), 3.32 (q, 2H, J=6.9), 3.27 (m, 1H), 2.80 (m, 1H), 2.51 (d, 3H, J=0.62), 1.20 (s, 3H), 1.16 (s, 3H), 1.15 (s, 3H), 1.11 (s, 3H), 0.80 (t, 3H, J=6.9). MS [EI+] 407 (M+H)$^+$ MS [EI−] 405 (M−H)$^−$.

Example 61

3-[3-(2-Ethoxy-3,5-diisopropyl-phenyl)-imidazo[1,2-a]pyridin-6-yl]-but-2-enoic acid

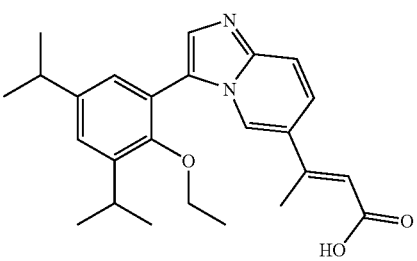

A. 3-(6-Amino-pyridin-3-yl)-but-2-enoic acid methyl ester

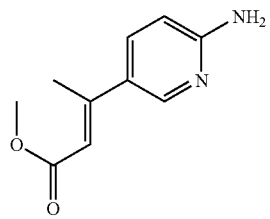

Methyl crotonate (1.35 ml, 12.8 mmol), tris(dibenzylideneacetone)-dipalladium(0) (106 mg, 0.12 mmol), tri-o-tolylphosphine (1.41 g, 4.6 mmol), and triethylamine (3.22 ml, 23.1 mmol) were added to a solution of $^2$-amino-5-bromo pyridine (2 g, 11.6 mmol) in DMF (25 mL). The reaction mixture was heated to 120° C. in a nitrogen atmosphere overnight, then cooled to ambient temperature and diluted with ethyl acetate (50 mL). The reaction was filtered, then washed with saturated ammonium chloride solution (2×25 mL), and the organic layer dried over $MgSO_4$ and concentrated in vacuo. The residue was then purified by flash column (2% methanol in dichloromethane) to give 3-(6-amino-pyridin-3-yl)-but-2-enoic acid methyl ester as a yellow solid (904.7 mg, 41%). $^1$H NMR (250 MHz, DMSO): δ 8.22 (d, 1H, J=3.1), 7.68 (dd, 1H, J=7.5, J=3.1), 6.46 (d, 1H, J=7.5), 6.40 (bs, 2H), 6.11 (d, 1H, J=0.62), 3.65 (s, 3H), 2.48 (d, 3H, J=0.62). MS [EI+] 193 (M+H)$^+$.

B. 3-Imidazo[1,2-a]pyridin-6-yl-but-2-enoic acid methyl ester

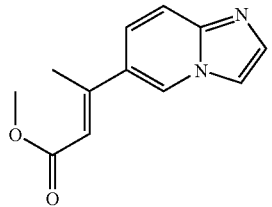

Bromoacetaldehyde dimethyl acetal (0.692 mL, 5.85 mmol) was refluxed in a solution of water (10 mL) and concentrated HCl (0.1 mL) for 30 min. The reaction was cooled to ambient temperature, and sodium bicarbonate (629 mg, 7.49 mmol) was added in several portions. After the addition was complete, 3-(6-amino-pyridin-3-yl)-but-2-enoic acid methyl ester (900 mg, 4.68 mmol) was added, and the reaction stirred overnight. During this time, the reaction became homogenous. After extracting the reaction mixture with ethyl acetate (3×20 mL), the organic layers were combined, dried over $MgSO_4$ and concentrated in vacuo. The residue was purified by chromatography (chromatotron, 4μ plate, 50% ethyl acetate in hexanes) to yield 3-imidazo[1,2-a]pyridin-6-yl-but-2-enoic acid methyl ester as an off white solid (223.3 mg, 22%). $^1$H NMR (250 MHz, CDCl$_3$): δ 8.32 (bs, 1H), 7.58-7.70 (m, 3H), 7.35 (dd, 1H, J=7.5, J=3.1), 6.24 (d, 1H, J=0.62), 3.31 (s, 3H), 2.64 (d, 3H, J=0.62). MS [EI+] 217 (M+H)$^+$.

C. 3-(3-Iodo-imidazo[1,2-a]pyridin-6-yl)-but-2-enoic acid methyl ester

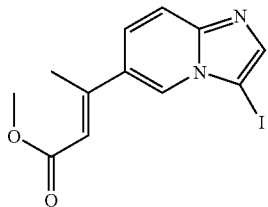

N-iodosuccinimide (252 mg, 1.12 mmol) was added to a mixture of 3-imidazo[1,2-a]pyridin-6-yl-but-2-enoic acid methyl ester (220 mg, 1.02 mmol) in acetonitrile (10 mL) which had been cooled to 0° C. under nitrogen atmosphere. The mixture was stirred for 1 h, then diluted with ethyl acetate (30 mL) and washed with saturated sodium bicarbonate solution (2×10 mL), and brine (1×15 mL). The organic layers were combined, dried over MgSO$_4$ and concentrated in vacuo. The residue was purified by chromatography (chromatotron, 4μ plate, 50% ethyl acetate in hexanes) to yield 3-(3-iodo-imidazo[1,2-a]pyridin-6-yl)-but-2-enoic acid methyl ester as a pale yellow solid (168.1 mg, 48%). $^1$H NMR (250 MHz, CDCl$_3$): δ 8.27 (bs, 1H), 7.77 (s, 1H), 7.64 (d, 1H, J=9.4), 7.41 (dd, 1H, J=9.4, J=1.6), 6.27 (d, 1H, J=0.62), 3.84 (s, 3H), 2.68 (d, 3H, J=0.62). MS [EI+] 343 (M+H)$^+$.

D. 3-[3-(2-Ethoxy-3,5-diisopropyl-phenyl)-imidazo[1,2-a]pyridin-6-yl]-but-2-enoic acid methyl ester

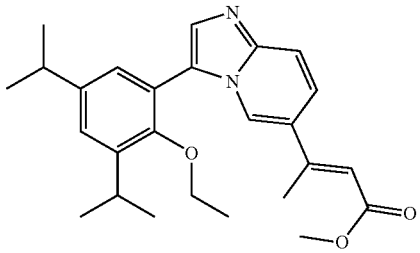

3-(3-Iodo-imidazo[1,2-a]pyridin-6-yl)-but-2-enoic acid methyl ester (168 mg, 0.49 mmol), tetrakis(triphenylphosphine)palladium(0) (57 mg, 0.05 mmol), followed by 2M sodium carbonate solution (1 ml) were added to a solution of 2-ethoxy-3,5-diisopropyl-phenyl-boronic acid (246 mg, 0.98 mmol) (see Example 5, step B) in toluene (10 mL). The reaction mixture was heated to 90° C. overnight, then poured into brine (20 mL) and extracted with ethyl acetate (2×20 mL). The organic layers were combined, dried over MgSO$_4$ and concentrated in vacuo. The residue was purified by chromatography (chromatotron, 2μ plate, 50% ethyl acetate in hexanes) to give a 3-[3-(2-ethoxy-3,5-diisopropyl-phenyl)-imidazo[1,2-a]pyridin-6-yl]-but-2-enoic acid methyl ester as a yellow oil (157.5 mg, 76%). $^1$H NMR (250 MHz, CDCl$_3$): δ 8.19 (bs, 1H), 7.75 (s, 1H), 7.68 (d, 1H, J=9.4), 7.42 (dd, 1H, J=9.4, J=1.2), 7.25 (d, 1H, J=2.5), 7.15 (d, 1H, J=2.5), 6.24 (d, 1H, J=0.62), 3.28 (s, 3H), 3.44 (m, 1H), 3.35 (q, 2H, J=8.1), 2.97 (m, 1H), 2.59 (d, 3H, J=0.62), 1.35 (s, 3H), 1.33 (s, 3H), 1.32 (s, 3H), 1.30 (s, 3H), 1.29 (t, 3H, J=8.1). MS [EI+] 421 (M+1)$^+$.

E. 3-[3-(2-Ethoxy-3,5-diisopropyl-phenyl)-imidazo[1,2-a]pyridin-6-yl]-but-2-enoic acid A solution of 3-[3-(2-ethoxy-3,5-diisopropyl-phenyl)-imidazo[1,2-a]pyridin-6-yl]-but-2-enoic acid methyl ester (157 mg, 0.37 mmol) in methanol (2 mL) and 1N NaOH solution (2 ml) was heated to 40° C. for 2 hrs. The reaction was brought to pH=7.5 with 1N HCl solution, then extracted with ethyl acetate (3×5 mL). The combined organic layers were washed with brine, then dried over MgSO$_4$ and concentrated in vacuo. The residue was then purified by chromatography (chromatotron, 2μ plate, 20% methanol in dichloromethane) to yield a white solid (118.1 mg, 78%). $^1$H NMR (250 MHz, CDCl$_3$): δ 8.19 (bs, 1H), 7.75 (s, 1H), 7.68 (d, 1H, J=9.4), 7.42 (dd, 1H, J=9.4, J=1.2), 7.25 (d, 1H, J=2.5), 7.15 (d, 1H, J=2.5), 6.24 (d, 1H, J=0.62), 3.44 (m, 1H), 3.35 (q, 2H, J=8.1), 2.97 (m, 1H), 2.59 (d, 3H, J=0.62), 1.35 (s, 3H), 1.33 (s, 3H), 1.32 (s, 3H), 1.30 (s, 3H), 1.29 (t, 3H, J=8.1). MS [EI+] 407 (M+1)$^+$, [EI−] 405 (M−1)$^-$. HPLC [YMC ODS-A (0.46×50 mm) 5%-95% CH$_3$CN(0.1% TFA) in H$_2$O(0.1% TFA) in 12 min.] 7.857 min.

Example 62

3-[3-(2-Ethoxy-3,5-diisopropyl-phenyl)-imidazo[1,2-a]pyridin-6-yl]-acrylic acid

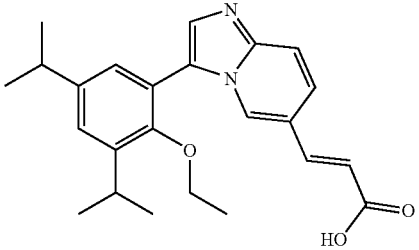

A. Imidazo[1,2-a]pyridine-6-carboxylic acid

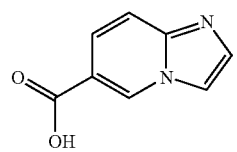

Concentrated HCL (1.5 mL) was added to a solution of bromoacetaldehyde dimethylacetal in water (50 mL), and the reaction refluxed for 30 min. The reaction mixture was then cooled in an ice bath, and sodium bicarbonate (10 g, 0.12 mol) was added slowly. After the addition was complete, 6-aminonicotinic acid (10 g, 0.072 mol) was added, and the reaction stirred at ambient temperature overnight. The reaction was then filtered, and the solid washed with water, and dried in vaccuo to give imidazo[1,2-a]pyridine-6-carboxylic acid as a white solid (2.61 g, 22%). $^1$H NMR (250 MHz, DMSO): δ 9.30 (s, 1H), 8.13 (s, 1H), 7.68 (s, 1H), 7.64 (s, 2H).

B. Imidazo[1,2-a]pyridine-6-carboxylic acid methyl ester

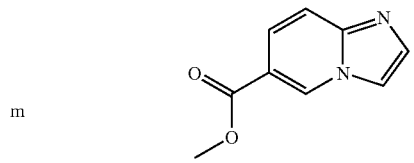

Cesium carbonate (15.7 g, 48.2 mmol) and iodomethane (1.50 ml, 24.2 mmol) were added to a solution of imidazo[1,2-a]pyridine-6-carboxylic acid (2.61 g, 16.1 mmol) in DMF (100 ml). The reaction was stirred at ambient temperature overnight, then poured into brine (100 ml) and extracted with ethyl acetate (3×100 mL). The combined organics were washed with saturated sodium bicarbonate solution (25 mL), and a 1N HCl solution (25 mL) then dried over MgSO$_4$ and evaporated to give imidazo[1,2-a]pyridine-6-carboxylic acid methyl ester as a yellow solid (1.1 g, 39%). $^1$H NMR (250 MHz, CDCl$_3$): δ 8.96 (s, 1H), 7.8-7.6 (m, 4H), 3.98 (s, 3H). MS [EI+] 177 (M+H)$^+$.

C. 3-Iodo-imidazo[1,2-a]pyridine-6-carboxylic acid methyl ester

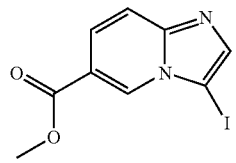

N-iodosuccinamide (1.55 g, 6.89 mmol) was added to a solution of imidazo[1,2-a]pyridine-6-carboxylic acid methyl ester (1.1 g, 6.24 mmol) in acetonitrile (50 mL) which had been cooled to 0° C. under a nitrogen atmosphere. The reaction stirred for 1 hr, then concentrated in vaccuo to a residue. The residue was dissolved in ethyl acetate (50 mL) and washed with 10% sodium bisulfate (2×10 ml) and brine (1×20 mL), then the organic layers were dried over MgSO$_4$ and evaporated to give 3-iodo-imidazo[1,2-a]pyridine-6-carboxylic acid methyl ester as a pale yellow solid (1.79 g, 95%). $^1$H NMR (250 MHz, CDCl$_3$): δ 8.91 (s, 1H), 7.85 (dd, 1H, J=2.5, J=10), 7.80 (s, 1H), 7.69 (d, 1H, J=10), 4.01 (s, 3H).

D. 3-(2-Ethoxy-3,5-diisopropyl-phenyl)-imidazo[1,2-a]pyridine-6-carboxylic acid methyl ester

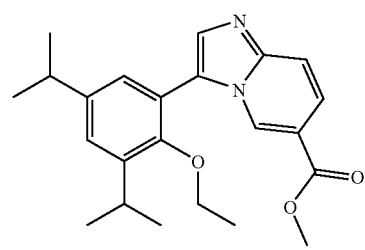

3,5-Diisopropyl-2-methoxymethoxy-phenyl-boronic acid (455 mg, 1.83 mmol), followed by tetrakis(triphenylphosphine)palladium(0) (191 mg, 0.16 mmol), and 2M sodium carbonate solution (3.31 ml, 3.32 mmol) were added to a solution of 3-iodo-imidazo[1,2-a]pyridine-6-carboxylic acid methyl ester (500 mg, 1.66 mmol) in toluene (10 mL). This reaction was then heated to 80° C. overnight, then cooled to ambient temperature and partitioned between brine (10 mL) and ethyl acetate (50 mL). The organic layer was dried over MgSO$_4$ and evaporated to a residue. The residue was purified by silica gel chromatography (5% MeOH in dichlorometlane) to yield 3-(2-ethoxy-3,5-diisopropyl-phenyl)-imidazo[1,2-a]pyridine-6-carboxylic acid methyl ester as a yellow solid (411 mg, 65%). $^1$H NMR (250 MHz, CDCl$_3$): δ 8.71 (s, 1H), 7.70 (m, 1H), 7.62 (m, 1H), 7.41 (m 1H), 7.19 (d, 1H, J=1.2), 7.08 (d, 1H, J=1.2), 3.85 (s, 3H), 3.38 (m, 1H), 3.29 (q, 2H, J=6.8),2.90 (m, 1H), 1.28 (s, 3H), 1.26 (s, 6H), 1.24 (s, 3H), 0.75 (t, 3H, J=6.8). MS [EI+] 381 (M+H)$^+$.

E. [3-(2-Ethoxy-3,5-diisopropyl-phenyl)-imidazo[1,2-a]pyridin-6-yl]-methanol

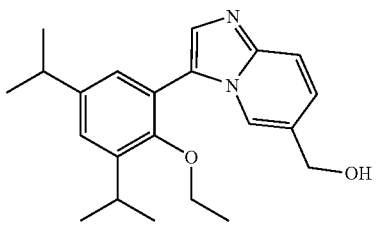

Diisobutylaluminum hydride (2.4 ml, 1M soln., 2.4 mmol) was added dropwise to a solution of 3-(2-ethoxy-3,5-diisopropyl-phenyl)-imidazo[1,2-a]pyridine-6-carboxylic acid methyl ester (300 mg, 0.79 mmol) in dichloromethane (10 mL) which had been cooled to −78° C. under a nitrogen atmosphere. After the addition was complete, the reaction was kept at −78° C. for 4 h, then quenched with with methanol (10 mL). After addition of the methanol, the mixture was poured into water, filtered and the solution evaporated to a residue. The residue was purified by silica gel chromatography (2.5% MeOH in dichloromethane) to give [3-(2-ethoxy-3,5-diisopropyl-phenyl)-imidazo[1,2-a]pyridin-6-yl]-methanol as a clear glass (102 mg, 38%). $^1$H NMR (250 MHz, CDCl$_3$): δ 8.01 (s, 1H), 7.70 (bs, 1H), 7.64 (d, 1H, J=9.4), 7.24 (m, 2H), 7.12 (d, 1H, J=0.62), 4.73 (s, 1H), 3.45 (m, 1H), 3.35 (q, 2H, J=7.0), 1.34 (s, 3H), 1.31 (s, 3H), 1.30 (s, 3H), 1.29 (s, 3H), 0.84 (t, 3H, J=7.0), MS [EI+] 353 (M+H)$^+$.

F. 3-(2-Ethoxy-3,5-diisopropyl-phenyl)-imidazo[1,2-a]pyridine-6-carbaldehyde

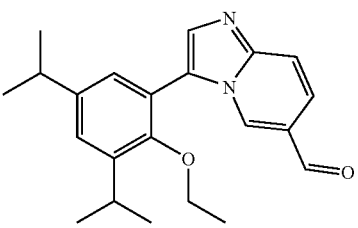

Tetrapropylammonium perruthenate (24 mg, 0.07 mmol) and 4-methylmorpholine N-oxide (239.3 mg, 2.04 mmol) were added to a solution of [3-(2-ethoxy-3,5-diisopropylphenyl)-imidazo[1,2-a]pyridin-6-yl]-methanol (480 mg, 1.36 mmol) in dichloromethane under an atmosphere of nitrogen. After 3 h, the reaction was filtered through celite and evaporated. The residue used without further purification.

G. 3-[3-(2-Ethoxy-3,5-diisopropyl-phenyl)-imidazo[1,2-a]pyridin-6-yl]-acrylic acid methyl ester

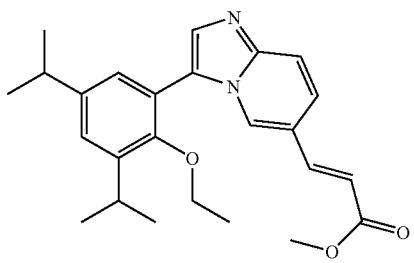

Sodium hydride (163.3 mg, 4.1 mmol) was added to a solution of methyl diethyl phosphoacetate (0.75 ml, 4.1 mmol) in DMF (10 ml) which had been cooled to 0° C. under a nitrogen atmosphere. The reaction stirred for 30 min., then 3-(2-ethoxy-3,5-diisopropyl-phenyl)-imidazo[1,2-a]pyridine-6-carbaldehyde (477 mg, 1.4 mmol) was added, and the reaction was allowed to stir at ambient temperature overnight. The reaction was then poured into brine (30 mL) and extracted with ethyl acetate (3×10 mL). The combined organic layers were dried over MgSO$_4$ and evaporated to a residue. The residue was purified by silica gel chromatography to give 3-[3-(2-ethoxy-3,5-diisopropyl-phenyl)-imidazo[1,2-a]pyridin-6-yl]-acrylic acid methyl ester as a pale yellow solid (288 mg, 52%). $^1$H NMR (250 MHz, CDCl$_3$): δ 8.02 (s, 1H), 7.64 (d, 2H, J=0.6), 7.57 (d, 1H, J=7.5), 7.39 (dd, 1H, J=0.6, J=7.5), 7.17 (d, 1H, J=1.2), 7.04 (d, 1H, J=1.2), 6.35 (d, 1H, J=16.9), 3.74 (s, 3H), 3.37 (m, 1H), 3.26 (q, 2H, J=7.2), 2.88 (m, 1H), 1.26 (s, 3H), 1.23 (s, 6H), 1.20 (s, 3H), 0.72 (t, 3H, J=7.2).

H. 3-[3-(2-Ethoxy-3,5-diisopropyl-phenyl)-imidazo[1,2-a]pyridin-6-yl]-acrylic acid A solution of 3-[3-(2-ethoxy-3,5-diisopropyl-phenyl)-imidazo[1,2-a]pyridin-6-yl]-acrylic acid methyl ester (288 mg, 0.71 mmol) in MeOH (5 ml) and 1N NaOH (5 ml) was heated to 40° C. for 2 h. The reaction was cooled, then brought to pH 7.5 with solid ammonium chloride and extracted with ethyl acetate (2×10 mL). The combined organic layers were then dried over MgSO$_4$ and evaporated to a residue. The residue was purified by silica gel chromatography (10% MeOH in dichloromethane) to give 3-[3-(2-ethoxy-3,5-diisopropyl-phenyl)-imidazo[1,2-a]pyridin-6-yl]-acrylic acid as a white solid (65 mg, 23%). $^1$H NMR (250 MHz, CDCl$_3$): δ 8.02 (s, 1H), 7.64 (m, 2H), 7.57 (d, 1H, J=7.5),7.39 (m, 1H), 7.17 (d, 1H), J=1.2), 7.04 (d, 1H, J=1.2), 6.35 (d, 1H, J=16.9), 3.37 (m, 1H), 3.26 (q, 2H, J=7.2), 2.88 (m, 1H), 1.26 (s, 3H), 1.23 (s, 6H), 1.20 (s, 3H), 0.72 (t, 3H, J=7.2). MS [EI+] 393 (M+H)$^+$.

Example 63

3-[3-(3,5-Di-tert-butyl-2-propoxy-phenyl)-1H-indol-5-yl]-but-2-enoic acid

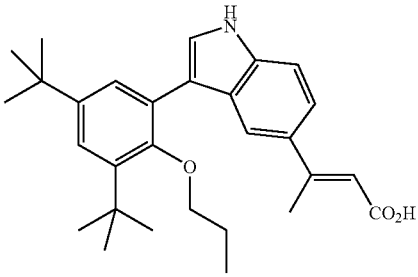

A. 1-Bromo-3,5-di-tert-butyl-2-propoxy-benzene

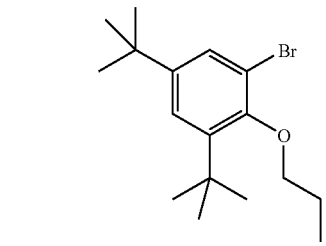

A solution of 2-bromo-4,6-di-tert-butyl-phenol (18.58 g, 65 mmol) in DMF (200 mL) was added to a stirred slurry of sodium hydride in anhydrous DMF (500 mL) precooled to −7° C. over 15 min. The resulting reaction mixture was stirred at <0° C. for 0.5 h. n-Propyl iodide was added and stirring of the olive green reaction mixture was continued for 18 h. after removal of the ice bath. The reaction was quenched with de-ionized water (2.5 L), 1 M HCl (250 mL) and 5% LiCl solution (250 mL). The resulting mixture was extracted with ethyl acetate (2×250 mL). Sodium chloride (q.s. to saturation) was added to facilitate the separation. The aqueous layer was extracted with hexane (200 mL). The combined organic layers were washed with 5% LiCl (2×200 mL) dried (MgSO$_4$) and filtered. The solvent was removed under vacuum to give a viscous oil which was a 2:1 ration of product to DMF. The residue was dissolved in hexane (100 mL) and the solution was washed with 5% LiCl solution (3×30 mL). The hexane solution was dried (MgSO$_4$), filtered, and the hexane was removed under vacuum to give a light brown oil which crystallized on standing to give a tan solid (21.23 g, 99%). The product may be purified by sublimation at 150° C. at 0.5 torr to give a light yellow solid. NMR (250 Mz, CDCl$_3$): δ 7.32 (d, 1H, J=2.4 Hz), 7.20 (d, 1H, J=2.4), 3.92 (t, 2H, J=6.8), 1.82 (sex, 2H), 1.00 (t, 3H, J=7.4). MS [EI+] 326, 328 (M+H)$^+$.

B. (2-Propoxy-3,5-di-tert-butylphenyl)-boronic acid

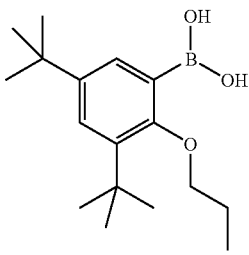

1-Bromo-3,5-di-tert-butyl-2-propoxy-benzene (6.55 g, 20 mmol) was dissolved in anhydrous 1,2-dimethoxy-ethane (125 mL under a nitrogen atmosphere. The solution was cooled to −75° C. and t-butyl lithium (30 mL, 50 mmol, 1.7M in pentane) was added dropwise over 20 min at −73° C. to −68° C. The reaction was stirred at −74° C. for 1 h and then treated with trimethyl borate (11.4 mL, 100 mmol). The reaction was kept cold for 1 h and then the bath was removed and the reaction allowed to warm to room temperature over 24 h. It was treated with 1N hydrochloric acid (70 mL) and stirred for 30 min. The reaction was then diluted with water (150 mL) and extracted with ethyl acetate (300 mL, 2×150 mL). The combined organic portions were washed with bicarbonate solution (150 mL), water (150 mL), brine (2×150 mL), dried ($Na_2SO_4$), filtered and evaporated in vacuo to provide 6.33 g of a yellow semi-solid. The material was purified by flash chromatography (eluet:(9:1)hexane: ethyl acetate and (3:1) hexane:ethyl acetate) to provide 3.34 g (57%) of a white solid. $^1$H NMR (250 MHz, $CDCl_3$): δ 7.67 (d, 1H, J=2.6), 7.49 (d, 1H, J=2.6), 5.91 (m, 1H), 3.82 (t, 2H, J=7.1), 1.89 (m, 2H), 1.42 (s, 9H), 1.33 (s, 9H), 2.63 (t, 3H, J=7.4). MS [EI+] 293 (M+H)$^+$ [EI−] 291 (M−H)$^+$.

C. 3-[1-Benzenesulfonyl-3-(3,5-di-tert-butyl-2-propoxy-phenyl)-1H-indol-5-yl]-but-2-enoic acid methyl ester

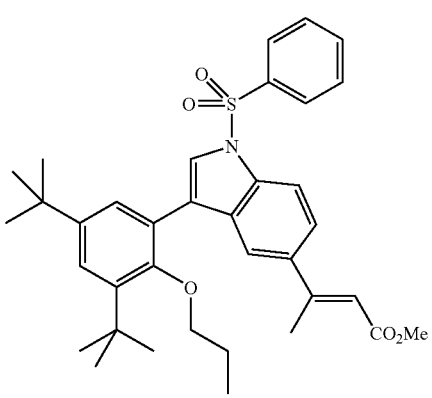

3-(1-Benzenesulfonyl-3-iodo-1H-indol-5-yl)-but-2-enoic acid methyl ester (722 mg, 1.5 mmol) (see Example 23, step C) and (2-propoxy-3,5-di-tert-butylphenyl)-boronic acid (526 mg, 1.8 mmol) were dissolved in toluene (15 mL) under a nitrogen atmosphere. Tetrakis(triphenylphosphine)palladium (347 mg, 0.3 mmol) and 2N $Na_2CO_3$ (10 mL) were added and the biphasic mixture stirred at 80° C. for 24 h. The reaction was allowed to cool to room temperature and the toluene portion was passed through a pad of celite, washing liberally with ethyl acetate. The aqueous portion was washed with ethyl acetate (2×) and the combined organics dried ($Na_2SO_4$), filtered, and evaporated in vacuo to give a black oil. The material was passed over a silica pad with (4:1) hexane:ethyl acetate to give 875 mg of a brown oil and then purified further by column chromatography (eluet: (9:1) hexane:ethyl acetate and (4:1) hexane:ethyl acetate) to provide 183 mg (20%) of a yellow oil.
$^1$H NMR (250 MHz, $CDCl_3$): δ 8.07 (d, 1H, 8.7), 7.94 (m, 2H) 7.72 (m, 2H), 7.53-7.39 (m, 5H), 7.21 (d, 1H, J=2.5), 6.15 (d, 1H, J=1.2), 3.74 (s, 3H), 3.22 (t, 2H, J=6.5) 2.57 (d, 3H, J=1.1), 1.45 (s, 9H), 1.34 (s, 9H), 1.02 (m, 2H) 0.39 (t, 3H, J=7.4). MS [EI+] 602 (M+H)$^+$.

D. 3-[3-(3,5-Di-tert-butyl-2-propoxy-phenyl)-1H-indol-5-yl]-but-2-enoic acid 3-[1-Benzenesulfonyl-3-(3,5-di-tert-butyl-2-propoxy-phenyl)-1H-indol-5-yl]-but-2-enoic acid methyl ester (171 mg, 0.28 mmol) was dissolved in methanol (1.5 mL)/dioxane (3 mL) and treated with 1N NaOH (2 mL) at 60° C. for 4 h. The reaction was diluted with 1N HCl (10 mL) and extracted with ethyl acetate (3×15 mL). The combined organic portions were washed with water (10 mL), brine (10 mL), dried ($MgSO_4$), filtered and concentrated in vacuo to provide 160 mg of a brown solid. The material was purified using radial chromatography (eluent:hexane/ethyl acetate gradient) to provide 73 mg (58%) of a yellow foam. Mp. 105-115° C. $^1$H NMR (250 MHz, $CDCl_3$): δ 8.31 (bs, 1H), 7.98 (bs, 1H, 8.7), 7.92 (m, 2H) 7.70 (m, 2I), 7.47-7.35 (m, 5H), 6.27 (bs, 1H), 3.42 (t, 2H, J=6.4) 2.68 (d, 3H, J=1.0), 1.49 (s, 9H), 1.37 (s, 9H), 1.32 (m, 2H) 0.68 (t, 3H, J=7.4). MS [EI+] 448 (M+E)$^+$, [EI−] 446 (M−H)$^+$. Analytical ($C_{29}H_{37}NO_3$): Calculated C, 77.81; H, 8.33; N, 3.13. Found: C, 77.89; H, 8.68; N, 2.94.

Example 64

3-{3-[3,5-Di-tert-butyl-2-(2,2-difluro-ethoxy)-phenyl]-1H-indol-5-yl}-but-2-enoic acid

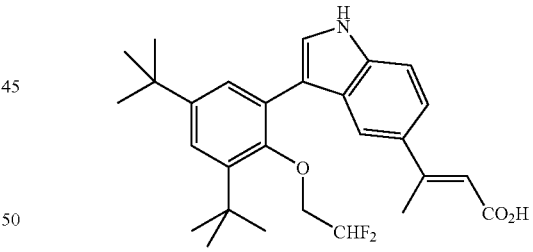

A. 2,4-Di-tert-butyl-1-(2,2-difluoro-ethoxy)-benzene

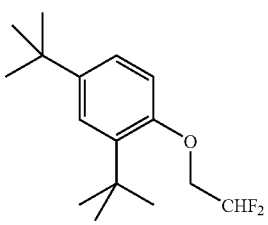

2,4-Di-tert-butylphenol (6.72 g, 32.6 mmol), cesium carbonate (21.2 g, 65.2 mmol) and methanesulfonic acid 2,2-difluoro ethyl ester (5.72 g, 35.8 mmol) were combined and stirrred in dimethylformamide (100 mL) at room temperature for 2 days. The reaction was diluted with water (100 mL) and washed with 50% hexane/diethyl ether (3×100 mL). The organic portions were washed with water (200 mL), dried (MgSO$_4$), filtered and evaporated in vacuo to provide 7.93 g of a yellow oil. The oil was passed over a silica pad with 1% ethyl acetate/hexane to provide 6.84 g (78%) of a clear oil. $^1$H NMR (250 MHz, CDCl$_3$): δ 7.37 (d, 1H, J=2.5 Hz), 7.19 (dd, 1H, J=8.5, J=2.5), 6.74 (d, 1H, J=8.5), 6.16 (tt, 1H, J=55.3, J=4.1), 4.20 (td, 2H, J=13.2, J=4.1), 1.40 (s, 9H), 1.29 (s, 9H).

B. 1,5-Di-tert-butyl-2-(2,2-difluoro-ethoxy)-3-iodo-benzene

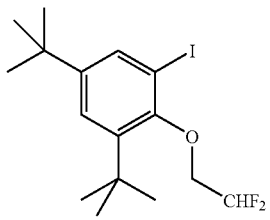

2,4-Di-tert-butyl-1-(2,2-difluoro-ethoxy)-benzene (6.75 g, 25 mmol), N-iodosuccinimide (6.74 g, 30 mmol) and p-toluenesulfonic acid monohydrate (1.90 g, 10 mmol) were combined in dichloromethane (75 mL) and heated at 38° C. for 7 h. TLC (hexanes) indicated a small amount of starting material still present and the reaction was treated with additional N-iodosuccinimde (0.33 g). After 4 h the reaction was washed with 10% Na$_2$SO$_2$O$_3$ solution (50 mL). The aqueous was backwashed with dichloromethane (100 mL) and then the combined organic portions washed with water (75 mL) and the combined organic portions washed with water (100 mL), dried (MgSO$_4$), filtered and evaporated in vacuo to provide an orange oil (9.92 g). The material was purified by flash chromatography using hexane to give 8.88 g (90%) of a light pink oil which solidified over time. $^1$H NMR (250 MHz, CDCl$_3$): δ 7.66 (d, 1H, J=2.4), 7.36 (d, 1H, =2.4), 6.29 (tt, 1H, J=55.3, J=4.3), 4.24 (td, 2H, J=13.2, J=4.3), 1.40 (s, 9H), 1.29 (s, 9H).

C. 2-(2,2-difluoro-ethoxy)-3,5-di-tert-butylphenyl)-boronic acid

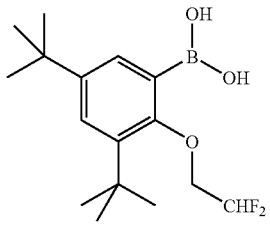

1,5-Di-tert-butyl-2-(2,2-difluoro-ethoxy)-3-iodo-benzene (3.96 g, 10 mmol)was dissolved in anhydrous diethyl ether (100 mL) in an oven-dried flask under nitrogen. N,N,N',N'-Tetramethyl ethylenediamine (2.3 mL, 15 mmol) was added and the reaction cooled in a dry ice/acetone bath. At −76° C. to −73° C. was added over 5 min n-butyl lithium (6 mL, 15 mmol, 2.5M in hexane). The reaction was stirred at −75° C. for 15 min and then treated slowly with trimethyl borate (3.4 mL, 30 mmol). The reaction was stirred at −75° C. for 1 h. The dry ice/acetone bath was replace with an ice bath and the reaction was allowed to warm to 0° C. over 40 min. 1N hydrochloric acid (50 mL) was added and after 5 min the ice bath was removed and stirring allowed to continue for 1 h. The aqueous and organic layers were separated and the aqueous layer was washed with ethyl acetate (2×150 mL). The combined organic portion was washed with brine (150 mL), dried (MgSO$_4$), filtered and evaporated in vacuo to provide an oil (4.01 g). The material was purified by flash chromatography using (9:1) hexane:ethyl acetate and (4:1) hexane:ethyl acetate to give 1.32 g (42%) of a white solid. $^1$H NMR (250 MHz, CDCl$_3$): δ 7.69 (d, 1H, J=2.6), 7.53 (d, 1H, J=2.6), 6.29 (tt, 1H, J=55.3, J=4.3), 4.24 (td, 2H, J=13.2, J=4.3), 1.40 (s, 9H), 1.29 (s, 9H). MS [EI−] 313 (M−H)$^+$.

D. 3-{1-Benzenesulfonyl-3-[3,5-di-tert-butyl-2-(2,2-difluro-ethoxy)-phenyl]-1H-indol-5-yl}-but-2-enoic acid methyl ester

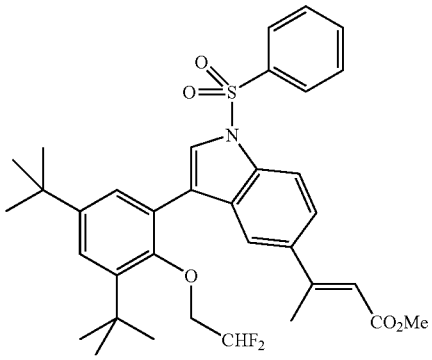

3-(1-Benzenesulfonyl-3-iodo-1H-indol-5-yl)-but-2-enoic acid methyl ester (400 mg, 0.83 mmol) (see Example 23, step C) and 2-(2,2-difluoro-ethoxy)-3,5-di-tert-butylphenyl)-boronic acid (565 mg, 1.8 mmol) were dissolved in toluene (15 mL) under a nitrogen atmosphere. Tetrakis (triphenylphosphine)palladium (173 mg, 0.15 mmol) and 2N Na$_2$CO$_3$ (15 mL) were added and the biphasic mixture stirred at 80° C. for 5 h. The layers were separated and the aqueous washed with EtOAc (2×25 mL). The organic portions were washed with brine, dried (MgSO$_4$), filtered and concentrated in vacuo to provide 1.31 g of a black oil. The material was purified by flash chromatography using (9:1) hexane:ethyl acetate and (4:1) hexane:ethyl acetate to give 543 mg (58%) of an oil. $^1$H NMR (250 MHz, CDCl$_3$): δ 8.09 (d, 1H, J=8.7), 7.93 (m, 2H) 7.76 (s, 1H), 7.67 (d, 1H, J=1.6), 7.54-7.42 (m, 5H), 7.24 (d, 1H, J=2.5), 6.15 (d, 1H, J=1.2), 5.26 (tt, 1H, J=55.3, J=4.3), 3.74 (s, 3H), 3.53 (td, 2H, J=13.5, J=4.2), 2.58 (d, 3H, J=1.1), 1.46 (s, 9H), 1.34 (s, 9H). MS [EI+] 624 (M+H)$^+$.

E. 3-{3-[3,5-Di-tert-butyl-2-(2,2-difluro-ethoxy)-phenyl]-1H-indol-5-yl}-but-2-enoic acid 3-{1-Benzenesulfonyl-3-[3,5-di-tert-butyl-2-(2,2-difluro-ethoxy)-phenyl]-1H-indol-5-yl}-but-2-enoic acid methyl ester (493 mg, 0.79 mmol) was dissolved in methanol (4 mL)/dioxane (8 mL) and treated with 1N NaOH (5.5 mL) at 60° C. for 4 h. Diluted with 1N HCl (25 mL) and extracted with ethyl acetate (3×25 mL). The combined organic portions were washed with water (50 mL), brine (50 mL), dried (MgSO$_4$), filtered and concentrated in vacuo to provide crude material. The material was purified using radial chromatography by elution with hexane/ethyl acetate gradient to provide 158 mg (43%) of a lightyellow solid. Mp. 135-145° C. $^1$H NMR (250 MHz, CDCl$_3$): δ 8.40 (bs, 1H), 7.92 (s, 1H), 7.47 (m, 3H), 7.39 (m, 2H), 6.26 (d, J=1.1), 5.49 (tt, 1H, J=55.3, J=4.3), 3.69 (td, 2H, J=14.0, J=4.0), 2.68 (d, 3H, J=1.0), 1.50 (s, 9H), 1.37 (s, 9H). MS [EI−] 468 (M−H)$^+$. Analytical (C$_{28}$H$_{33}$NO$_3$): Calculated C, 71.62; H, 7.08; N, 2.98. Found: C, 69.95; H, 7.38; N, 2.70.

Example 65

3-{3-[3,5-Di-tert-butyl-2-(2,2,2-trifluoro-ethoxy)-phenyl]-1H-indol-5-yl}-but-2-enoic acid

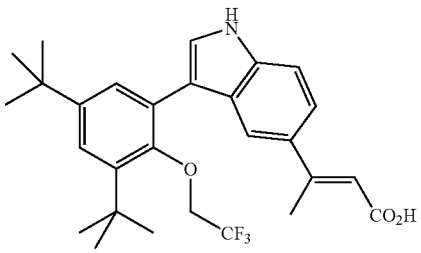

A. 2,4-Di-tert-butyl-1-(2,2,2-trifluoro-ethoxy)-benzene

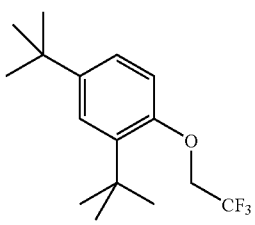

2,4-Di-tert-butylphenol (6.19 g, 30 mmol), cesium carbonate (19.5 g, 60 mmol) and 2-bromo-1,1,1-trifluoroethane (7.3 mL, 60 mmol) were combined and stirred in anhydrous dimethylformamide (75 mL) at 50° C. for 2 days. The reaction was judged to be incomplete by TLC (hexane) and additional 2-bromo-1,1,1-trifluoroethane (4.8 mL, 53 mmol) was added and stirring continued at 50° C. for 12 h. At that time there was still a minor amount of unreacted phenol. The reaction was diluted with water (100 mL) and washed with 50% hexane/diethyl ether (3×150 mL). The organic portions were washed with water (100 mL), dried (Na$_2$SO$_4$), filtered and evaporated in vacuo to provide 8.15 g of a yellow oil. The oil was passed over a silica pad with hexane to provide 5.17 g (60%) of a clear oil. $^1$H NMR (250 MHz, CDCl$_3$): δ 7.39 (d, 1H, J=2.5 Hz), 7.20 (dd, 1H, J=8.5, J=2.5), 6.70 (d, 1H, J=8.5), 4.35 (q, 2H, J=8.2), 1.41 (s, 9H), 1.32 (s, 9H).

B. 1,5-Di-tert-butyl-3-iodo-2-(2,2,2-trifluoro-ethoxy)-benzene

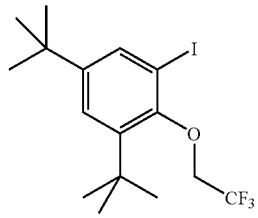

2,4-Di-tert-butyl-1-(2,2,2-trifluoro-ethoxy)-benzene (5.06 g, 17.5 mmol), N-iodosuccinimide (4.74 g, 21 mmol) and p-toluenesulfonic acid monohydrate (1.33 g, 7 mmol) were combined in dichloromethane (50 mL) and heated at 38° C. for 19 h. The reaction was washed with 10% Na$_2$S$_2$O$_3$ solution (2×40 mL). The aqueous was backwashed with dichloromethane (70 mL) and then the combined organic portions washed with water (75 mL) and the combined organic portions washed with water (100 mL), dried (MgSO$_4$), filtered and evaporated in vacuo to provide a yellow oil (6.96 g). The material was purified by flash chromatography using hexane to give 5.85 g (81%) of a light pink oil. $^1$HNMR (250 MHz, CDCl$_3$): δ 7.67 (d, 1H, J=2.4), 7.37 (d, 1H, J=2.4), 4.45 (q, 2H, J=8.2), 1.40 (s, 9H), 1.30 (s, 9H).

C. 2-(2,2,2-Trifluoro-ethoxy)-3,5-di-tert-butylphenyl-boronic acid

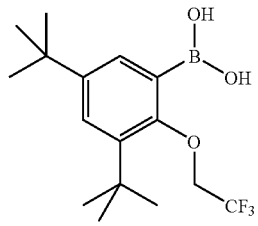

1,5-Di-tert-butyl-3-iodo-2-(2,2,2-trifluoro-ethoxy)-benzene (3.17 g, 7.7 mmol) was dissolved in anhydrous diethyl ether (75 mL) in an oven-dried flask under nitrogen. N,N,N',N'-Tetramethyl ethylenediamine (1.73 mL, 11.5 mmol) was added and the reaction cooled in a dry ice/acetone bath. At −76° C. to −73° C. was added over 5 min n-butyl lithium (4.6 mL, 11.5 mmol, 2.5M in hexane). The reaction was stirred at −75° C. for 15 min and then treated slowly with trimethyl borate (2.6 mL, 23 mmol). The reaction was stirred at −75° C. for 1 h. The dry ice/acetone bath was replace with an ice bath and the reaction was allowed to warm to 0° C. over 40 min. 1N hydrochloric acid (50 mL) was added and after 5 min the ice bath was removed and stirring allowed to continue for 1 h. The aqueous and organic layers were separated and the aqueous layer was washed with ethyl acetate (2×75 mL). The combined organic portion was washed with brine (100 mL), dried (MgSO$_4$), filtered and evaporated in vacuo to provide a yellow gum. The material was purified by flash chromatography using (9:1) hexane:ethyl acetate and then (4:1) hexane:ethyl acetate to give 1.28 g (50%) of an off-white solid.
$^1$H NMR (250 MHz, CDCl$_3$): δ 7.65 (d, 1H, J=2.6), 7.51 (d, 1H, J=2.6), 5.34 (bs, 1H), 4.24 (2H, J=8.2), 1.42 (s, 9H), 1.33 (s, 9H). MS [EI−] 331 (M−H)$^+$. MS [EI−] 331 (M−H)$^+$.

D. 3-{1-Benzenesulfonyl-3-[3,5-di-tert-butyl-2-(2,2, 2-trifluoro-ethoxy)-phenyl]-1H-indol-5-yl}-but-2-enoic acid methyl ester

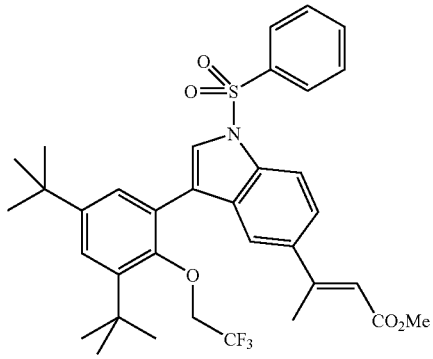

3-(1-Benzenesulfonyl-3-iodo-1H-indol-5-yl)-but-2-enoic acid methyl ester (587 mg, 1.22 mmol) (see Example 23, step C) and 2-(2,2,2-trifluoro-ethoxy)-3,5-di-tert-butylphenyl-boronic acid (445 mg, 1.34 mmol) were dissolved in toluene (12 mL) under a nitrogen atmosphere. Tetrakis (triphenylphosphine)palladium (282 mg, 0.24 mmol) and 2N $Na_2CO_3$ (8 mL) were added and the biphasic mixture stirred at 80° C. for 6 h. The layers were separated and the aqueous washed with EtOAc (2×25 mL). The organic portions were washed with brine, dried ($MgSO_4$), filtered and concentrated in vacuo to provide 1.20 g of a black oil. The material was purified by flash chromatography (eluent: (9:1) hexane:ethyl acetate and (4:1) hexane:ethyl acetate) to provide 195 mg (25%) of a yellow gum.

$^1$H NMR (250 MHz, $CDCl_3$): δ 8.08 (d, 1H, J=8.7), 7.93 (m, 2H), 7.78 (s, 1H), 7.66 (d, 1H, J=1.6), 7.55-7.43 (m, 5H), 7.25 (d, 1H, J=2.5), 6.14 (d, 1H, J=1.2), 3.74 (s, 3H), 3.65 (q, 2H, J=8.4), 2.58 (d, 3H, J=1.2), 1.47 (s, 9H), 1.34 (s, 9H). MS [EI+] 642 (M+H)$^+$.

E. 3-{3-[3,5-Di-tert-butyl-2-(2,2,2-trifluoro-ethoxy)-phenyl]-1H-indol-5-yl}-but-2-enoic acid 3-{1-Benzenesulfonyl-3-[3,5-di-tert-butyl-2-(2,2,2-trifluoro-ethoxy)-phenyl]-1H-indol-5-yl}-but-2-enoic acid methyl ester was dissolved in methanol (1.5 mL)/dioxane (3 mL) and treated with 1N NaOH (2.0 mL) at 60° C. for 2.5 h. Diluted with 1N HCl (15 mL) and extracted with ethyl acetate (3×15 mL). The combined organic portions were washed with water (30 mL), brine (30 mL), dried ($MgSO_4$), filtered and concentrated in vacuo to provide 145 mg of crude material. The material was purified using radial chromatography by (eluet: hexane/ethyl acetate gradient) to provide 72 mg (53%) of a pale yellow solid. Mp. 146-153° C. $^1$H NMR (250 MHz, $CDCl_3$): δ 8.43 (bs, 1H), 7.95 (s, 1H), 7.53 (d, 1H, J=2.4), 7.46 (m, 3H), 7.38 (d, 1H, J=2.5), 6.26 (d, 1H, J=1.1), 3.86 (q, 2H, J=8.6), 2.69 (d, 3H, J=1.0), 1.49 (s, 9H), 1.37 (s, 9H). MS [EI+] 488 (M+H)$^+$, [EI−] 486 (M−H)$^+$. Analytical ($C_{29}H_{37}NO_3$): Calculated C, 68.98; H, 6.62; N, 2.87. Found: C, 66.45; H, 6.85; N, 2.59.

Example 66

Evaluation of Activity In Vivo

Rodents that are genetically defective in the leptin pathway are commonly used as animal models of non-insulin dependant diabetes mellitus (NIDDM. db/db mice and ZDF rats develop frank diabetes that progresses to include β-cell failure and the accompanying precipitous drop in plasma insulin levels. Both strains are profoundly obese, hyperglycemic, hyperinsulinemic, and hypertriglyceridemic. fa/fa rats, on the other hand, are obese and insulin resistant but do not develop frank diabetes and the associated hyperglycemia. All three rodent models were used to examine the efficacy of oral dosing with compounds of the invention on diabetes, insulin sensitivity, food consumption and body weight gain.

All animal experiments were conducted in a United States Department of Agriculture registered facility in accordance with NIH guidelines for the care and use of laboratory animals. Mice (obtained from Jackson Laboratory), ZDF rats (obtained from Genetic Models Inc.) and fa/fa rats (obtained from either Charles River, or Harlan) were maintained on 12-hour light/dark cycle. Mice (age 28-42 days) were caged in groups of 5-6. Rats (age 7 weeks) were housed individually. All animals were allowed ad libitum access to water and food (urina 5015 for mice and 5008 for rats). Compounds were administered at the specified doses by oral gavage on the morning of each day of any experiment. Blood samples were obtained 3 hours after dosing from fed animals under anesthesia and collected into heparinized capillary tubes from the tail vein.

Mice transgenic for the human apolipoprotein A-I gene (obtained from Jackson Laboratory) were used to evaluate PPARα mediated effects on high density lipoprotein (HDL) cholesterol. The mice were handled as described above for db/db mice, except that they were fed Purina 5001.

Compounds that are full agonists at the RXR homodimer, such as LG100268, are efficacious insulin sensitizers in rodent models of NIDDM and, thus, lower blood glucose levels. However, such compounds raise triglycerides and suppress the thyroid hormone axis in these animals. On the other hand, full antagonists have no effect on glucose, triglycerides or the thyroid status in these same model systems. We have identified a specific subset of rexinoids that maintain the desirable insulin sensitizing activity and eliminate both the suppression of the thyroid axis and triglyceride elevations (see Table 1 for glucose and triglyceride data for animals treated with a compound of the invention compared to animals treated with LG100268). These compounds are heterodimer selective modulators of RXR activity. They bind to RXR with high affinity ($K_i$<55 nM) and produce potent synergistic activation of the RXR: PPARγ heterodimer. This synergistic activation of PPARγ in vitro is presumably a major determinant of the antidiabetic efficacy of compounds in vivo. To eliminate the undesirable increases in triglycerides and suppression of T4, the modulators must not significantly activate RXR:RAR heterodimers and must have substantial RXR:RAR antagonist activity. Examples 14, 15, 5, and 18 in Table 1 clearly demonstrate that compounds of the invention do not activate RXR:RAR heterodimers.

When administered to obese, insulin resistant db/db mice (100 mg/kg by daily oral gavage for 14 days), compounds of the invention lower plasma glucose. However, unlike full agonists (e.g., LG100268), they do not increase triglycerides.

Four week old db/db mice are essentially normoglycemic, they have not yet developed hyperglycemia. Treatment of such mice with a compound of the invention (30 mg/kg by daily oral gavage) prevents the development of hyperglycemia. This treatment is expected to successfully control plasma glucose levels for up to 11 weeks (when the mice are 15 weeks old).

Treatment of 7 week old db/db mice with metformin (300 mg/kg by daily oral gavage) lowers plasma glucose. However the maximum effect is seen following the first week of treatment. Over 3 subsequent weeks the efficacy of metformin decreases. At this point, treatment with metformin plus the addition of a compound of the invention (100 mg/kg by daily oral gavage) is expected to lowered plasma glucose to the level of age matched lean. Thus, the RXR modulator could be efficacious in cases of secondary failure of metformin.

To determine whether compounds of the invention produce insulin sensitization, compounds of the invention can be administered to insulin resistant fa/fa rats (100 mg/Kg by daily oral gavage for 14 days. In response to the oral glucose challenge, both insulin and glucose is expected to rise significantly less in animals treated with a compound of the invention than in untreated control animals. Animals treated with a compound of the invention are expected to consume the same amount of food and gain the same amount of weight as vehicle treated control animals. When fa/fa animals are treated with a thiazolinedione insulin sensitizer, they consume significantly more food and gain significantly more weight than control animals. In contrast, animals treated with a combination of the thiazolidinedione and a compound of the invention are expected to consume the same amount of food and gain the same amount of weight as the control animals. Compounds of the invention are expected to block the thiazolidinedione induced increases in both food consumption and body weight gain.

When administered to transgenic mice carrying the human apo A-I gene, compounds of the invention are expected to increase HDL cholesterol. However, unlike LG100268 which also raises triglycerides, compounds of the invention do not raise triglycerides (see Examples 14, 15, 5, and 18 of Table 1). Compounds of the invention that are not RXR:RAR heterodimer agonist and have greater than 50% RXR:RAR antagonists activity do not raise triglycerides in the transgenic mouse model, consistent with their heterodimer selectivity. This effect is consistent with activation of PPARα and, in fact, in vivo these compounds synergize with the weak PPARα agonist fenofibrate.

TABLE 1

Modulation of RXR activity using compounds of the invention.

| Compound | Bind RXR α K$_i$ (nM) | PPARγ CV-1 (%) Synergy | RXR:RXR CV-1 (%) Ag | RXR:RXR CV-1 (%) Antag | RXR:RAR CV-1 (%) Ag. | db/db mouse Glu. (D 7) | db/db mouse Trigs. (D 3) |
|---|---|---|---|---|---|---|---|
| LG100268 | 3 | 183 | 73 | — | 6 | 73 | 195 |
| Ex. 14 | 12 | 67 | 1 | 79 | 2 | 35 | 139 |
| Ex. 15 | 14 | 109 | 4 | 81 | 6 | 20 | 98 |
| Ex. 5 | 22 | 140 | 33 | 10 | 3 | 17 | 104 |
| Ex. 18 | 54 | 40 | 1 | 86 | 4 | 38 | 105 |

NC: "no change"
NT: "not tested"
K$_i$ = Determined from IC$_{50}$ values by the Cheng-Prussof equation using tritiated LGD1069.
Synergy = Efficacy calculated as the maximal response in presence of 100 nM BRL49653 (RXR:PPARγ) relative to maximal response of BRL49653 alone.
Ag. = Efficacy calculated as the maximal response relative to maximal response of ATRA.
Antag. = Efficacy calculated as the maximal repression (100%) in the presence of 32 nM LGD1069 (RXR:RXR) or 10 nM TTNPB (RXR:RAR).
Glu. = Plasma glucose as a % correction relative to lean values on day 7 of treatment with 30 mg/kg/day.
Trigs. = Plasma triglycerides as a % of control values on day 3 of treatment with 30 mg/kg/day.

Example 67

Evaluation of Teratogenicity In Vivo

Teratogenicity is commonly evaluated by examination of fetuses obtained by cesarean section from pregnant mice dosed daily with test compound between gestation days 6-18. A blind study can be conducted using time-mated female Crl:CD-1® (ICR)BR mice to evaluate potential developmental toxicity (teratogenicity) following administration of a compound of the invention at either 30 or 200 mg/kg-day by daily oral gavage for the specified 12 days of gestation. Each test group consists of 7-8 pregnant females and produced approximately 100 live fetuses per test group. As a positive control, pregnant female mice are treated with the retinoid LG100268 at a dose of either 30 mg/kg-day or 100 mg/kg-day. Teratogenicity can be observed in fetuses from mice treated with the LG100268 at both dosage groups. In contrast, no teratogenic effects are expected to be observed in fetuses from mice treated with a compound of the invention. Compared to controls dosed with vehicle, no effects are expected to be observed on the number of Corpora lutea, implantation sites, live or dead fetuses, early or late resorptions, fetal weight or sex, gross external morphology or visceral morphology of the cranial region in fetuses from mice treated with a compound of the invention at either dose. The highest dose of a compound of the invention tested (200 mg/kg-day) is twice the dose required to produce maximum antidiabetic activity in db/db mice (100 mg/kg-day).

EQUIVALENTS

While this invention has been particularly shown and described with references to preferred embodiments thereof, it will be understood by those skilled in the art that various changes in details may be made therein without departing from the scope of the invention encompassed by the appended claims.

What is claimed is:
1. A compound represented by the following structural formula:

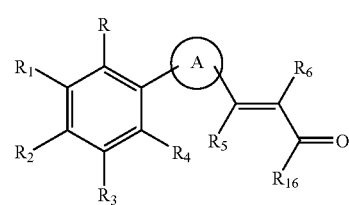

or a pharmaceutically acceptable salt, solvate or hydrate thereof, wherein:
R is H, F, Cl, Br, I, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;
$R_1$ and $R_2$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy; or $R_1$ and $R_2$ taken together with the carbon atoms to which they are attached form a five or six membered carbocyclic ring which is optionally substituted with one or more halo or $C_1$-$C_6$ alkyl groups; or R and $R_1$ taken together with the carbon atoms to which they are attached form an aryl, a heteroaryl, a $C_5$-$C_8$ cycloalkyl or $C_5$-$C_8$ cycloalkenyl ring wherein the aryl, heteroaryl, cycloalkyl and cyclolkenyl are optionally substituted with one or more halo, $C_1$-$C_3$ alkyl, $C_1$-$C_3$ haloalkyl or $C_1$-$C_3$ alkoxy substituents; and $R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy;

$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$; or $R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents; and $R_5$ is H, a halo, or a $C_1$-$C_3$ alkyl group which is optionally substituted with one or more halo;

$R_6$ is H or halo;

$R_{14}$ and $R_{15}$ are each, independently, H, a $C_1$-$C_6$ alkyl, or taken together with the nitrogen they are attached to can form a 5 to 8 membered heterocycle;

$R_{16}$ is $OR_{17}$, $OCH(R_{17})OC(O)R_{18}$, —$NR_{19}R_{20}$, or an aminoalkyl;

$R_{17}$, $R_{19}$ and $R_{20}$ are each, independently, H or a $C_1$-$C_6$ alkyl;

$R_{18}$ is a $C_1$-$C_6$ alkyl;

wherein ring A is a benzofuryl of formula

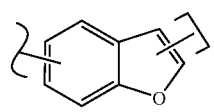

further optionally substituted with one or more substituents selected from a halo, a $C_1$-$C_6$ alkyl, or a $C_1$-$C_6$ alkoxy, wherein:

the symbol "$\zeta$" indicates a single bond connecting ring A to the phenyl group; and the symbol "[" indicates a single bond connecting ring A to the α,β-unsaturated carbonyl group.

2. The compound of claim 1 wherein ring A is selected from the group consisting of:

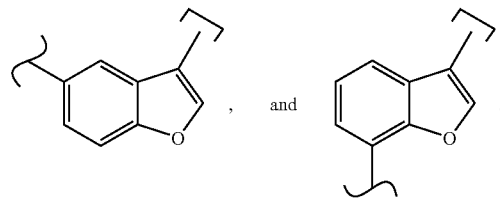

3. The compound of claim 1, wherein $R_4$ is a $C_2$-$C_5$ alkoxy group which is optionally substituted with one or more fluoro.

4. The compound of claim 1, wherein $R_5$ is methyl and $R_6$ is H.

5. The compound of claim 1, wherein $R_5$ is methyl and $R_6$ is fluoro.

6. The compound of claim 1, wherein:
$R_1$ and $R_3$ are both isopropyl; and
$R_2$ is H.

7. The compound of claim 1, wherein:
$R_1$ and $R_3$ are both t-butyl; and
$R_2$ is H.

8. The compound of claim 1, wherein the compound is represented by the following structure:

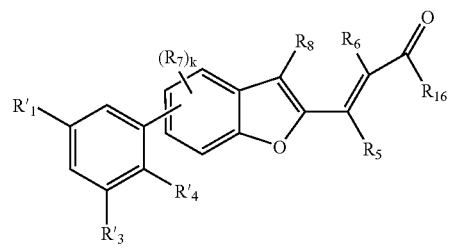

or a pharmaceutically acceptable salt, solvate or hydrate thereof wherein:

$R_1'$ and $R_3'$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl, or $C_1$-$C_3$ alkoxy;

$R_4'$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$;

each $R_7$ is, independently, a halo or a $C_1$-$C_6$ alkyl group;
$R_8$ is H, a halo or a $C_1$-$C_6$ alkyl group; and
k is 0, 1, 2 or 3.

9. The compound of claim 8, wherein:
$R'_1$ and R'3 are both isopropyl; and
$R_5$ is methyl.

10. The compound of claim 9, wherein $R'_4$ is a $C_2$-$C_5$ alkoxy group which is optionally substituted with one or more fluoro.

11. A compound selected from the group consisting of:
3-[5-(2-hydroxy-3-tert-butyl-5-ethylphenyl)-benzo[b]furan-2-yl]-but-2-enoic acid;
2-fluoro-3-[5-(2-methoxy-3,5-di-iso-propylphenyl)-benzo[b]furan-2-yl]-but-2-enoic acid;
2-fluoro-3-[7-(2-propoxy-3-tert-butyl-5-ethylphenyl)-benzo[b]furan-2-yl]-but-2-enoic acid ethyl ester;
3-[7-(2-ethoxy-3,5-di-tert-butylphenyl)-benzo[b]furan-2-yl]-but-2-enoic acid;
3-[7-(2-ethoxy-3,5-di-iso-propylphenyl)-benzo[b]furan-2-yl]-but-2-enoic acid;
3-[7-(2-propoxy-3,5-di-iso-propylphenyl)-benzo[b]furan-2-yl]-but-2-enoic acid;
3-{7-[2-(3-fluoropropoxy)-3,5-di-iso-propylphenyl]-benzo[b]furan-2-yl}-but-2-enoic acid;
3-{7-[2-(2,2-difluoroethoxy)-3,5-di-iso-propylphenyl]-benzo[b]furan-2-yl}-but-2-enoic acid;
(E)-2-fluoro-3-{7-[2-(2,2-difluoroethoxy)-3,5-di-iso-propylphenyl]-benzo[b]furan-2-yl}-but-2-enoic acid;
(E)-3-{7-[5,5,8,8-tetramethyl-3-ethoxy-5,6,7,8-tetrahydronaphth-2-yl]-benzo[b]furan-2-yl}-but-2-enoic acid;
or a pharmaceutically acceptable salt, solvate or hydrate thereof.

12. A pharmaceutical composition, comprising a pharmaceutically acceptable carrier and at least one compound represented by the following structural formula:

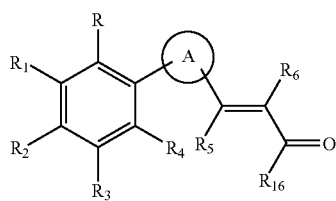

or a pharmaceutically acceptable salt, solvate or hydrate thereof, wherein:

R is H, F, Cl, Br, I, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;

$R_1$ and $R_2$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy; or $R_1$ and $R_2$ taken together with the carbon atoms to which they are attached form a five or six membered carbocyclic ring which is optionally substituted with one or more halo or $C_1$-$C_6$ alkyl groups; or R and $R_1$ taken together with the carbon atoms to which they are attached form an aryl, a heteroaryl, a $C_5$-$C_8$ cycloalkyl or $C_5$-$C_8$ cycloalkenyl ring wherein the aryl, heteroaryl, cycloalkyl and cyclolkenyl are optionally substituted with one or more halo, $C_1$-$C_3$ alkyl, $C_1$-$C_3$ haloalkyl or $C_1$-$C_3$ alkoxy substituents; and $R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy;

$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$; or $R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents; and $R_5$ is H, a halo, or a $C_1$-$C_3$ alkyl group which is optionally substituted with one or more halo;

$R_6$ is H or halo;

$R_{14}$ and $R_{15}$ are each, independently, H, a $C_1$-$C_6$ alkyl, or taken together with the nitrogen they are attached to can form a 5 to 8 membered heterocycle;

$R_{16}$ is $OR_{17}$, $OCH(R_{17})OC(O)R_{18}$, —$NR_{19}R_{20}$, or an aminoalkyl;

$R_{17}$, $R_{19}$ and $R_{20}$ are each, independently, H or a $C_1$-$C_6$ alkyl;

$R_{18}$ is a $C_1$-$C_6$ alkyl;

wherein ring A is a benzofuryl of formula

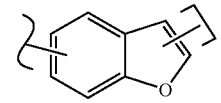

further optionally substituted with one or more substituents selected from a halo, a $C_1$-$C_6$ alkyl, or a $C_1$-$C_6$ alkoxy, wherein:

the symbol "⟨" indicates a single bond connecting ring A to the phenyl group; and the symbol "[" indicates a single bond connecting ring A to the α,β-unsaturated carbonyl group.

13. The pharmaceutical composition of claim 12, wherein ring A is selected from the group consisting of:

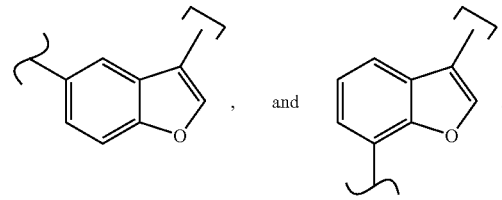

14. The pharmaceutical composition of claim 12, wherein $R_4$ is a $C_2$-$C_5$ alkoxy group which is optionally substituted with one or more fluoro.

15. The pharmaceutical composition of claim 12, wherein $R_5$ is methyl and $R_6$ is H.

16. The pharmaceutical composition of claim 12, wherein $R_5$ is methyl and $R_6$ is fluoro.

17. The pharmaceutical composition of claim 12, wherein:
$R_1$ and $R_3$ are both isopropyl; and
$R_2$ is H.

18. The pharmaceutical composition of claim 12, wherein:
$R_1$ and $R_3$ are both t-butyl; and
$R_2$ is H.

19. The pharmaceutical composition of claim 12, wherein the compound is represented by the following structure:

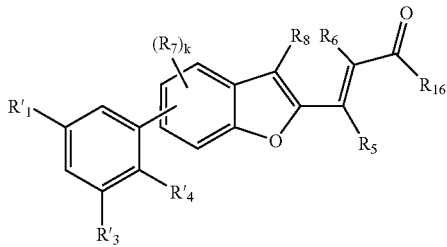

or a pharmaceutically acceptable salt, solvate or hydrate thereof, wherein:

$R_1'$ and $R_3'$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl, or $C_1$-$C_3$ alkoxy;

$R_4'$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$;

each $R_7$ is, independently, a halo or a $C_1$-$C_6$ alkyl group;

$R_8$ is H, a halo or a $C_1$-$C_6$ alkyl group; and k is 0, 1, 2 or 3.

20. The pharmaceutical composition of claim 19, wherein:

$R_1'$ and $R_3'$ are both isopropyl; and $R_5$ is methyl.

21. The pharmaceutical composition of claim 19, wherein $R_4'$ is a $C_2$-$C_5$ alkoxy group which is optionally substituted with one or more fluoro.

22. The pharmaceutical composition of claim 19, wherein the compound is selected from the group consisting of:

3-[5-(2-hydroxy-3-tert-butyl-5-ethylphenyl)-benzo[b]furan-2-yl]-but-2-enoic acid;

2-fluoro-3-[5-(2-methoxy-3,5-diisopropylphenyl)-benzo[b]furan-2-yl]-but-2-enoic acid;

2-fluoro-3-[7-(2-propoxy-3-tert-butyl-5-ethylphenyl)-benzo[b]furan-2-yl]-but-2-enoic acid ethyl ester;

3-[7-(2-ethoxy-3,5-di-tert-butylphenyl)-benzo[b]furan-2-yl]-but-2-enoic acid;

3-[7-(2-ethoxy-3,5-diisopropylphenyl)-benzo[b]furan-2-yl]-but-2-enoic acid;

3-[7-(2-propoxy-3,5-diisopropylphenyl)-benzo [b]furan-2-yl]-but-2-enoic acid;

3-{7-[2-(3-fluoropropoxy)-3,5-diisopropylphenyl]-benzo[b]furan-2-yl}- but-2-enoic acid;

3-{7-[2-(2,2-difluoroethoxy)-3,5-diisopropylphenyl]-benzo[b]furan-2-yl}-but-2-enoic acid;

(E)-2-fluoro-3- {7-[2-(2,2-difluoroethoxy)-3,5-diisopropylphenyl]-benzo[b]furan-2-yl}-but-2-enoic acid;

(E)-3-{7- [5,5,8,8,-tetramethyl-3-ethoxy-5,6,7,8-tetrahydronaphth-2-yl]-benzo[b]furan-2-yl}-but-2-enoic acid;

3-{4-[2-(2,2,2-trifluoroethoxy)-3,5-di-iso-propylphenyl]-benzo[b]furan-2-yl}-but-2-enoic acid; or a pharmaceutically acceptable salt, solvate or hydrate thereof.

23. A method for increasing HDL cholesterol levels and reducing triglyceride levels in a mammal comprising administering to said mammal a pharmaceutically effective amount of at least one compound represented by the following structural formula:

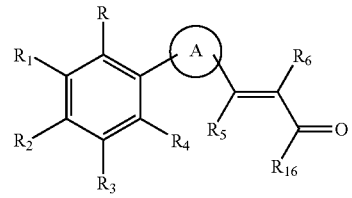

or a pharmaceutically acceptable salt, solvate or hydrate thereof, wherein:

R is H, F, Cl, Br, I, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;

$R_1$ and $R_2$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy; or $R_1$ and $R_2$ taken together with the carbon atoms to which they are attached form a five or six membered carbocyclic ring which is optionally substituted with one or more halo or $C_1$-$C_6$ alkyl groups; or R and $R_1$ taken together with the carbon atoms to which they are attached form an aryl, a heteroaryl, a $C_5$-$C_8$ cycloalkyl or $C_5$-$C_8$ cycloalkenyl ring wherein the aryl, heteroaryl, cycloalkyl and cyclolkenyl are optionally substituted with one or more halo, $C_1$-$C_3$ alkyl, $C_1$-$C_3$ haloalkyl or $C_1$-$C_3$ alkoxy substituents; and $R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy;

$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$; or $R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents; and $R_5$ is H, a halo, or a $C_1$-$C_3$ alkyl group which is optionally substituted with one or more halo;

$R_6$ is H or halo;

$R_{14}$ and $R_{15}$ are each, independently, H, a $C_1$-$C_6$ alkyl, or taken together with the nitrogen they are attached to can form a 5 to 8 membered heterocycle;

$R_{16}$ is $OR_{17}$, $OCH(R_{17})OC(O)R_{18}$, $-NR_{19}R_{20}$, or an aminoalkyl;

$R_{17}$, $R_{19}$ and $R_{20}$ are each, independently, H or a $C_1$-$C_6$ alkyl;

$R_{18}$ is a $C_1$-$C_6$ alkyl;

wherein ring A is a benzofuryl of formula

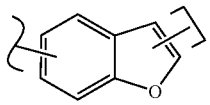

further optionally substituted with one or more substituents selected from a halo, a $C_1$-$C_6$ alkyl, or a $C_1$-$C_6$ alkoxy,
wherein:
the symbol $\varsigma$ indicates a single bond connecting ring A to the phenyl group; and
the symbol "[" indicates a single bond connecting ring A to the α,β-unsaturated carbonyl group.

24. The method of claim 23, further comprising the step of administering to said mammal a PPARγ agonist.

25. The method of claim 23, wherein $R_4$ is a $C_2$-$C_5$ alkoxy group which is optionally substituted with one or more fluoro.

26. The method of claim 23, wherein the compound is represented by the following structure:

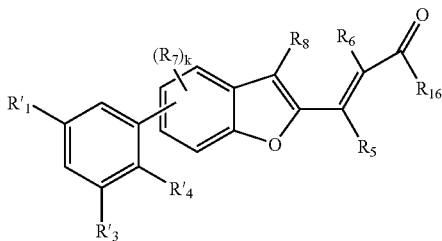

or a pharmaceutically acceptable salt, solvate or hydrate thereof, wherein:
$R_1'$ and $R_3'$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl, or $C_1$-$C_3$ alkoxy;
$R_4'$ is H, a halo, an aryl-$C_1$-$C_6$-alkyl, a $C_1$-$C_{10}$ alkyl or a C1-C10 alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$;
each $R_7$ is, independently, a halo or a $C_1$-$C_6$ alkyl group;
$R_8$ is H, a halo or a $C_1$-$C_6$ alkyl group; and
k is 0, 1, 2 or 3.

27. The method of claim 26, wherein the compound is selected from the group consisting of:
3- [5 -(2-hydroxy-3 -ter-butyl-5-ethylphenyl)-benzo [b]furan-2-yl]-but-2-enoic acid;
2-fluoro-3 -[5 -(2-methoxy-3 ,5-diisopropylphenyl)-benzo [b]furan-2-yl]- but-2-enoic acid;
2-fluoro-3 - [7-(2-propoxy-3 -tert-butyl-5-ethylphenyl)-benzo [b]furan-2-yl]-but-2-enoic acid ethyl ester;
3- [7-(2-ethoxy-3 , 5 -di-ert-butylphenyl)-benzo [b]furan-2-yl]-but-2-enoic acid;
3- [7-(2-ethoxy-3 ,5 -diisopropylphenyl)-benzo [b]furan-2-yl]-but-2-enoic acid;
3- [7-(2-propoxy-3 ,5-diisopropylphenyl)-benzo [b]furan-2-yl]-but-2-enoic acid;
3- {7- [2-(3 -fluoropropoxy)-3 ,5-diisopropylphenyl]-benzo [b]furan-2-yl }- but-2-enoic acid;
3- {7- [2-(2,2-difluoroethoxy)-3,5-diisopropylphenyl]-benzo[b]furan-2-yl }-but-2-enoic acid;
(E)-2-fluoro-3- {7-[2-(2,2-difluoroethoxy)-3,5-diisopropylphenyl]- benzo[b]furan-2-yl }-but-2-enoic acid;
(E)-3- {7-[5,5,8,8,-tetramethyl-3-ethoxy-5,6,7,8-tetrahydronaphth-2-yl]-benzo [b]furan-2-yl}-but-2-enoic acid;
3-{4-[2-(2,2,2-trifluoroethoxy)-3,5-di-*iso*-propylphenyl]-benzo[b]furan-2-yl}-but-2-enoic acid; or
a pharmaceutically acceptable salt, solvate or hydrate thereof.

28. A method for modulating lipid metabolism in a mammal comprising administering to said mammal a pharmaceutically effective amount of at least one compound represented by the following structural formula:

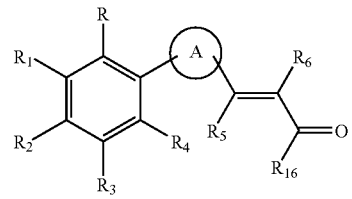

or a pharmaceutically acceptable salt, solvate and hydrate thereof, wherein:
R is H, F, Cl, Br, I, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;
$R_1$ and $R_2$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy; or
$R_1$ and $R_2$ taken together with the carbon atoms to which they are attached form a five or six membered carbocyclic ring which is optionally substituted with one or more halo or $C_1$-$C_6$ alkyl groups; or
R and $R_1$ taken together with the carbon atoms to which they are attached form an aryl, a heteroaryl, a $C_5$-$C_8$ cycloalkyl or $C_5$-$C_8$ cycloalkenyl ring wherein the aryl, heteroaryl, cycloalkyl and cyclolkenyl are optionally substituted with one or more halo, $C_1$-$C_3$ alkyl, $C_1$-$C_3$ haloalkyl or $C_1$-$C_3$ alkoxy substituents; and
$R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy;
$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$; or
$R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents; and
$R_5$ is H, a halo, or a $C_1$-$C_3$ alkyl group which is optionally substituted with one or more halo;
$R_6$ is H or halo;

$R_{14}$ and $R_{15}$ are each, independently, H, a $C_1$-$C_6$ alkyl, or taken together with the nitrogen they are attached to can form a 5 to 8 membered heterocycle;

$R_{16}$ is $OR_{17}$, $OCH(R_{17})OC(O)R_{18}$, $-NR_{19}R_{20}$, or an aminoalkyl;

$R_{17}$, $R_{19}$ and $R_{20}$ are each, independently, H or a $C_1$-$C_6$ alkyl; $R_{18}$ is a $C_1$-$C_6$ alkyl;

wherein ring A is a benzofuryl of formula

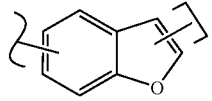

further optionally substituted with one or more substituents selected from a halo, a $C_1$-$C_6$ alkyl, or a $C_1$-$C_6$ alkoxy, wherein:

the symbol $\S$ indicates a single bond connecting ring A to the phenyl group; and the symbol "[" indicates a single bond connecting ring A to the α,β-unsaturated carbonyl group.

29. The method of claim 28, wherein $R_4$ is a $C_2$-$C_5$ alkoxy group which is optionally substituted with one or more fluoro.

30. The method of claim 28, wherein the compound is represented by the following structure:

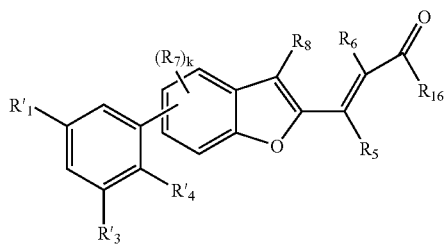

or a pharmaceutically acceptable salt, solvate or hydrate thereof, wherein:

$R_1'$ and $R_3'$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl, or $C_1$-$C_3$ alkoxy;

$R_4'$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$;

each $R_7$ is, independently, a halo or a $C_1$-$C_6$ alkyl group;

$R_8$ is H, a halo or a $C_1$-$C_6$ alkyl group; and k is 0, 1, 2 or 3.

31. The method of claim 30, wherein the compound is selected from the group consisting of:

3- [5-(2-hydroxy-3-*tert*-butyl-5-ethylphenyl)-benzo[b]furan-2-yl]-but-2-enoic acid;

2-fluoro-3-[5-(2-methoxy-3,5-diisopropylphenyl)-benzo[b]furan-2-yl]-but-2-enoic acid;

2-fluoro-3-[7-(2-propoxy-3-*tert*-butyl-5-ethylphenyl)-benzo[b]furan-2-yl]-but-2-enoic acid ethyl ester;

3-[7-(2-ethoxy-3,5-di-*tert*-butylphenyl)-benzo[b]furan-2-yl]-but-2-enoic acid;

3-[7-(2-ethoxy-3,5-diisopropylphenyl)-benzo[b]furan-2-yl]-but-2-enoic acid;

3-[7-(2-propoxy-3,5-diisopropylphenyl)-benzo[b]furan-2-yl]-but-2-enoic acid;

3-{7-[2-(3-fluoropropoxy)-3,5-diisopropylphenyl]-benzo[b]furan-2-yl}-but-2-enoic acid;

3-{7-[2-(2,2-difluoroethoxy)-3,5-diisopropylphenyl]-benzo[b]furan-2-yl}-but-2-enoic acid;

(E)-2-fluoro-3- {7-[2-(2,2-difluoroethoxy)-3,5-diisopropylphenyl]- benzo[b]furan-2-yl }-but-2-enoic acid;

(E)-3- {7-[5,5,8,8,-tetramethyl-3-ethoxy-5,6,7,8-tetrahydronaphth-2-yl]-benzo [b]furan-2-yl}-but-2-enoic acid;

3-{4-[2-(2,2,2-trifluoroethoxy)-3,5-di-*iso*-propylphenyl]-benzo[b]furan-2-yl}-but-2-enoic acid; or a pharmaceutically acceptable salt solvate or hydrate thereof.

32. A method for lowering blood glucose levels without altering serum triglyceride levels in a mammal comprising administering to said mammal a pharmaceutically effective amount of at least one compound represented by the following structural formula:

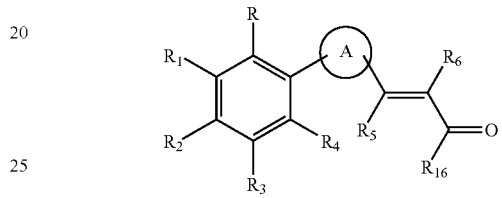

or a pharmaceutically acceptable salt, solvate or hydrate thereof, wherein:

R is H, F, Cl, Br, I, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;

$R_1$ and $R_2$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy; or $R_1$ and $R_2$ taken together with the carbon atoms to which they are attached form a five or six membered carbocyclic ring which is optionally substituted with one or more halo or $C_1$-$C_6$ alkyl groups; or R and $R_1$ taken together with the carbon atoms to which they are attached form an aryl, a heteroaryl, a $C_5$-$C_8$ cycloalkyl or $C_5$-$C_8$ cycloalkenyl ring wherein the aryl, heteroaryl, cycloalkyl and cyclolkenyl are optionally substituted with one or more halo, $C_1$-$C_3$ alkyl, $C_1$-$C_3$ haloalkyl or $C_1$-$C_3$ alkoxy substituents; and $R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy;

$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$; or $R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents; and $R_5$ is H, a halo, or a $C_1$-$C_3$ alkyl group which is optionally substituted with one or more halo;

$R_6$ is H or halo;

$R_{14}$ and $R_{15}$ are each, independently, H, a $C_1$-$C_6$ alkyl, or taken together with the nitrogen they are attached to can form a 5 to 8 membered heterocycle;

$R_{16}$ is $OR_{17}$, $OCH(R_{17})OC(O)R_{18}$, $-NR_{19}R_{20}$, or an aminoalkyl;

$R_{17}$, $R_{19}$ and $R_{20}$ are each, independently, H or a $C_1$-$C_6$ alkyl;

$R_{18}$ is a $C_1$-$C_6$ alkyl;

wherein ring A is a benzofuryl of formula

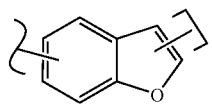

further optionally substituted with one or more substituents selected from a halo, a $C_1$-$C_6$ alkyl, or a $C_1$-$C_6$ alkoxy, wherein:

the symbol ʂ indicates a single bond connecting ring A to the phenyl group; and the symbol "ʃ" indicates a single bond connecting ring A to the α,β-unsaturated carbonyl group.

33. The method of claim 32, wherein $R_4$ is a $C_2$-$C_5$ alkoxy group which is optionally substituted with one or more fluoro.

34. The method of claim 32, wherein the compund is represented by the following structure:

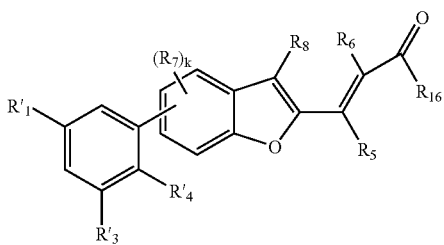

or a pharmaceutically acceptable salt, solvate or hydrate thereof, wherein:

$R_1'$ and $R_3'$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl, or $C_1$-$C_3$ alkoxy;

$R_4'$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$;

each $R_7$ is, independently, a halo or a $C_1$-$C_6$ alkyl group;

$R_8$ is H, a halo or a $C_1$-$C_6$ alkyl group; and k is 0, 1, 2 or 3.

35. The method of claim 34, wherein the compound is selected from the group consisting of:

3-[5-(2-hydroxy-3-*tert*-butyl-5-ethylphenyl)-benzo[b]furan-2-yl]-but-2-enoic acid;

2-fluoro-3-[5-(2-methoxy-3,5 -diisopropylphenyl)-benzo[b]furan-2-yl]-but-2-enoic acid;

2-fluoro-3-[7-(2-propoxy-3-*tert*-butyl-5-ethylphenyl)-benzo[b]furan-2-yl]-but-2-enoic acid ethyl ester;

3-[7-(2-ethoxy-3,5-di-*tert*-butylphenyl)-benzo[b]furan-2-yl]-but-2-enoic acid;

3-[7-(2-ethoxy-3,5-diisopropylphenyl)-benzo[b]furan-2-yl]-but-2-enoic acid;

3-[7-(2-propoxy-3,5-diisopropylphenyl)-benzo[b]furan-2-yl -but-2-enoic acid;

3-{7-[2-(3-fluoropropoxy)-3,5-diisopropylphenyl]-benzo[b]furan-2-yl}-but-2-enoic acid;

3-{7-[2-(2,2-difluoroethoxy)-3,5-diisopropylphenyl]-benzo[b]furan-2-yl}-but-2-enoic acid;

(E)-2-fluoro-3- {7-[2-(2,2-difluoroethoxy)-3,5-diisopropylphenyl]- benzo[b]furan-2-yl }-but-2-enoic acid;

(E)-3- {7-[5,5,8,8,-tetramethyl-3-ethoxy-5,6,7,8-tetrahydronaphth-2-yl]-benzo [b]furan-2-yl}-but-2-enoic acid;

3-{4-[2-(2,2,2-trifluoroethoxy)-3,5-di-*iso*-propylphenyl]-benzo[b]furan-2-yl}-but-2-enoic acid; or a pharmaceutically acceptable salt, solvate or hydrate thereof.

36. A method of preparing a benzo[b]furanyl RXR modulator represented by the following structural formula:

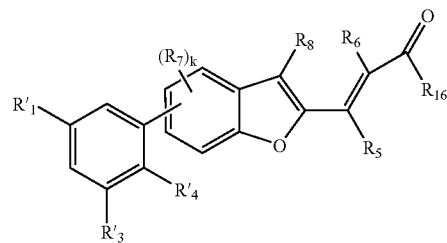

wherein:

R is H, F, Cl, Br, I, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C_2$-$C_3$ haloalkynyl, and $C_1$-$C_3$ alkoxy, wherein said alkyl, haloalkyl, alkenyl, haloalkenyl, alkynyl, haloalkynyl, and alkoxy groups may be optionally substituted;

$R_1$ and $R_2$ are each, independently, H, a halo, a $C_1$-$C_{10}$ alkyl, a $C_3$-$C_{10}$ cycloalkyl, a $C_5$-$C_{10}$ cycloalkenyl, a 6 to 10 membered aryl, a 5 to 10 membered heteroaryl, an aryl-$C_1$-$C_6$-alkyl, or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy; or $R_1$ and $R_2$ taken together with the carbon atoms to which they are attached form a five or six membered carbocyclic ring which is optionally substituted with one or more halo or $C_1$-$C_6$ alkyl groups; or R and $R_1$ taken together with the carbon atoms to which they are attached form an aryl, a heteroaryl, a $C_5$-$C_8$ cycloalkyl or $C_5$-$C_8$ cycloalkenyl ring wherein the aryl, heteroaryl, cycloalkyl and cyclolkenyl are optionally substituted with one or more halo, $C_1$-$C_3$ alkyl, $C_1$-$C_3$ haloalkyl or $C_1$-$C_3$ alkoxy substituents; and $R_3$ is H, a halo, a $C_1$-$C_{10}$ alkyl, a $C_3$-$C_{10}$ cycloalkyl, $C_5$-$C_{10}$ cycloalkenyl, a 6 to 10 membered aryl, a 5 to 10 membered heteroaryl, an aryl-$C_1$-$C_6$-alkyl or an amino group represented by the formula $NR_{14}R_{15}$, wherein the alkyl, cycloalkyl, cycloalkenyl, aryl, heteroaryl and arylalkyl are optionally substituted with one or more halo, $C_1$-$C_3$ alkyl, $C_1$-$C_3$ haloalkyl or $C_1$-$C_3$ alkoxy;

$R_4$ is H, a halo, an aryl-$C_1$-$C_6$-alkyl, a $C_1$-$C_{10}$ alkyl or a $C_1$-$C_{10}$ alkoxy group wherein the arylalkyl, alkyl and alkoxy groups are optionally substituted with one or more substituents selected from halo, $C_1$-$C_6$ alkyl, aryl, heteroaryl, a $C_1$-$C_6$ alkoxy, an amino group represented by the formula $NR_{14}R_{15}$; or $R_3$ and $R_4$ taken together with the carbon atoms to which they are attached form an aryl, an heteroaryl, a $C_5$-$C_8$ cycloalkyl or $C_5$-$C_8$ cycloalkenyl ring wherein the aryl, heteroaryl, cycloalkyl and cycloalkenyl are optionally substituted with one or more halo, $C_1$-$C_3$ alkyl, $C_1$-$C_3$ haloalkyl or $C_1$-$C_3$ alkoxy substituents; and $R_5$ is H, a halo, or a $C_1$-$C_3$ alkyl group which is optionally substituted with one or more halo;

$R_6$ is H or halo;

$R_{14}$ and $R_{15}$ are each, independently, H, a $C_1$-$C_6$ alkyl, or taken together with the nitrogen they are attached to can form a 5 to 8 membered heterocycle; and $R_x$ is a $C_1$-$C_6$ alkyl, comprising the steps of:

a) reacting in the presence of tetrakis(triphenylphosphine)palladium(0) and a base a halosalicyaldehyde represented by the following structural formula:

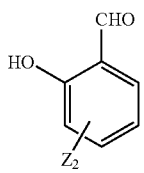

wherein:

$Z_2$ is a halo, with a substituted phenylboronic acid represented by the following structural formula:

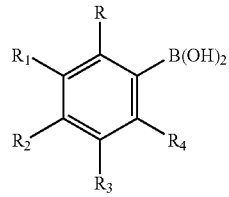

to form a (substituted phenyl)-salicyaldehyde represented by the following structural formula:

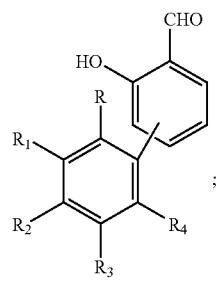

b) reacting the (substituted phenyl)-salicyaldehyde with an β-halocarbonyl compound represented by the following structural formula:

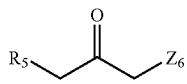

wherein:

$Z_6$ is a halo; to form a (substituted phenyl)-2-carbonylbenzo[b]furan represented by the following structural formula:

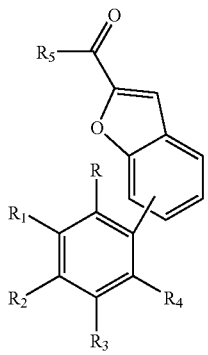

c) forming an enol anion of a trialkyl phosphonoacetate by treating with a base the trialkyl phosphonoacetate, wherein the trialkyl phosphonoacetate is represented by the following structural formula:

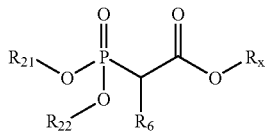

wherein $R_{21}$ and $R_{22}$ are each, independently, a $C_1$-$C_6$ alkyl; and d) reacting the trialkyl phosphonoacetate anion with the (substituted phenyl)-2- carbonylbenzo[b]furan, thereby forming said benzo[b]furanyl RXR modulator.

37. The method of claim 36, further comprising the step of treating the benzo[b]furanyl RXR modulator with an alkali metal hydroxide to form a carboxylic acid represented by the following structural formula:

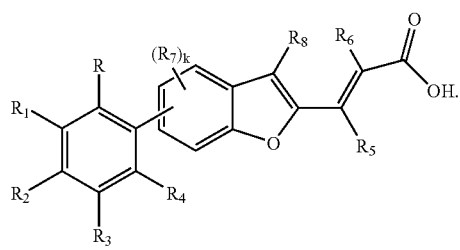

* * * * *